United States Patent
Baker et al.

(10) Patent No.: US 11,464,749 B2
(45) Date of Patent: Oct. 11, 2022

(54) BISMUTH-THIOL COMPOSITIONS AND METHODS OF USE

(71) Applicant: Microbion Corporation, Bozeman, MT (US)

(72) Inventors: Brett Hugh James Baker, Bozeman, MT (US); Jeffrey W. Millard, Bozeman, MT (US)

(73) Assignee: MICROBION CORPORATION, Bozeman, MT (US)

( * ) Notice: Subject to any disclaimer, the term of this patent is extended or adjusted under 35 U.S.C. 154(b) by 0 days.

(21) Appl. No.: 16/528,145

(22) Filed: Jul. 31, 2019

(65) Prior Publication Data

US 2020/0046650 A1     Feb. 13, 2020

Related U.S. Application Data

(60) Provisional application No. 62/800,925, filed on Feb. 4, 2019, provisional application No. 62/712,563, filed on Jul. 31, 2018.

(51) Int. Cl.
*A61K 31/095* (2006.01)
*A61P 31/04* (2006.01)
*A61K 9/00* (2006.01)

(52) U.S. Cl.
CPC .......... *A61K 31/095* (2013.01); *A61K 9/0073* (2013.01); *A61P 31/04* (2018.01)

(58) Field of Classification Search
CPC ...... A61K 31/095; A61K 9/0073; A61P 31/04
See application file for complete search history.

(56) References Cited

U.S. PATENT DOCUMENTS

| | | | |
|---|---|---|---|
| 2,809,971 A | 10/1957 | Bernstein et al. | |
| 3,523,121 A | 8/1970 | Lewis et al. | |
| RE29,409 E | 9/1977 | Yeager | |
| 4,410,642 A | 10/1983 | Layton | |
| 4,596,724 A | 6/1986 | Lane et al. | |
| 4,788,302 A | 11/1988 | Costlow et al. | |
| 5,028,664 A | 7/1991 | Ohmura et al. | |
| 5,045,555 A | 9/1991 | Matsumoto et al. | |
| 5,194,248 A | 3/1993 | Holick | |
| 5,229,124 A | 7/1993 | Rei et al. | |
| 5,384,176 A | 1/1995 | Zimmerman et al. | |
| 5,470,586 A | 11/1995 | Gerhart | |
| 5,928,671 A | 7/1999 | Domenico | |
| 6,071,528 A | 6/2000 | Jensen | |
| 6,086,921 A | 7/2000 | Domenico | |
| 6,162,487 A | 12/2000 | Darouiche | |
| 6,248,371 B1 | 6/2001 | Domenico | |
| 6,261,539 B1 | 7/2001 | Adjei et al. | |
| 6,380,248 B1 | 4/2002 | Domenico et al. | |
| 6,384,040 B1 | 5/2002 | Walter | |
| RE37,793 E | 7/2002 | Domenico | |
| 6,448,306 B1 | 9/2002 | Lever et al. | |
| 6,455,031 B1 | 9/2002 | Davies et al. | |
| 6,488,912 B1 | 12/2002 | Pfirrmann et al. | |
| 6,552,056 B2 | 4/2003 | Assmann et al. | |
| 6,555,599 B2 | 4/2003 | Lever et al. | |
| 6,579,513 B1 | 6/2003 | Tashjian et al. | |
| 6,582,719 B2 | 6/2003 | Modak et al. | |
| 6,638,993 B2 | 10/2003 | Patel et al. | |
| 6,726,898 B2 | 4/2004 | Jernberg | |
| 6,730,324 B2 | 5/2004 | Troczynski et al. | |
| 6,811,767 B1 | 11/2004 | Bosch et al. | |
| 6,848,871 B1 | 2/2005 | Cottrell | |
| 6,852,782 B2 | 2/2005 | Patel et al. | |
| 6,861,049 B2 | 3/2005 | Harwood | |
| 6,875,453 B2 | 4/2005 | Viamonte, Jr. | |
| 6,943,205 B2 | 9/2005 | Patel et al. | |
| 7,060,739 B2 | 6/2006 | Patel et al. | |
| 7,074,391 B1 | 7/2006 | Alvarez Hernandez | |
| 7,419,681 B2 | 9/2008 | Tormala et al. | |
| 7,507,281 B2 | 3/2009 | Ong et al. | |
| 7,547,433 B2 | 6/2009 | Jacob et al. | |
| 8,389,021 B2 | 3/2013 | Baker | |
| 9,028,878 B2 | 5/2015 | Baker | |
| 2002/0136780 A1 | 9/2002 | Batarseh | |
| 2002/0155144 A1 | 10/2002 | Troczynski et al. | |
| 2002/0197282 A1 | 12/2002 | Mohseni et al. | |
| 2006/0205838 A1 | 9/2006 | Velamakanni et al. | |
| 2007/0125703 A1 | 6/2007 | Chapman et al. | |

(Continued)

FOREIGN PATENT DOCUMENTS

| | | |
|---|---|---|
| AU | 2003 204 105 | 11/2005 |
| CA | 2751386 A1 | 8/2010 |

(Continued)

OTHER PUBLICATIONS

Veloira et al. In vitro activity and synergy of bismuth thiols and tobramycin against Burkholderia cepacia complex. Journal of Antimicrobial Chemotherapy (2003) 52, 915-919. (Year: 2003).*
Wu et al. Subinhibitory Bismuth-Thiols Reduce Virulence of Pseudomonas aeruginosa. Am. J. Respir. Cell Mol. Biol. vol. 26, pp. 731-738, 2002. (Year: 2002).*
Dhanani et al. Fundamentals of aerosol therapy in critical care. Critical Care (2016) 20:269. (Year: 2016).*
Agocs et al., "Spectroscopic, Structural, and Mass Spectrometric Studies on Two Systematic Series of Dithiabismuth (III) Heterocycles: Identification of Bismuthenium Cations and Their Solvent Complexes," J. Am. Chem. Soc. 118:3225-3232, 1996.

(Continued)

*Primary Examiner* — Robert A Wax
*Assistant Examiner* — Olga V. Tcherkasskaya
(74) *Attorney, Agent, or Firm* — Cooley LLP

(57) ABSTRACT

The invention relates to Bis-thiol compounds and pharmaceutical preparations thereof. The invention further relates to methods of treating, managing or lessening the severity of pulmonary infections in a subject, the method comprising administering to the subject a bismuth-thiol (BT) composition that comprises at least one BT compound.

22 Claims, 43 Drawing Sheets

(56) References Cited

U.S. PATENT DOCUMENTS

| | | |
|---|---|---|
| 2007/0281096 A1 | 12/2007 | Ong et al. |
| 2008/0181950 A1 | 7/2008 | Bates et al. |
| 2008/0260697 A1 | 10/2008 | Murthy et al. |
| 2008/0292673 A1 | 11/2008 | Crudden |
| 2009/0043388 A1 | 2/2009 | Hsu |
| 2009/0191254 A1 | 7/2009 | Curtin et al. |
| 2009/0196930 A1 | 8/2009 | Surber et al. |
| 2009/0197003 A1 | 8/2009 | Shira |
| 2009/0202610 A1 | 8/2009 | Wilson |
| 2011/0003001 A1 | 1/2011 | Baker |
| 2016/0375034 A1 | 12/2016 | Baker et al. |
| 2017/0150724 A1 | 6/2017 | Baker |
| 2020/0038361 A1 | 2/2020 | Baker |
| 2020/0138033 A1* | 5/2020 | Baker ............... A01N 59/16 |

FOREIGN PATENT DOCUMENTS

| | | |
|---|---|---|
| CN | 1283996 A | 2/2001 |
| EP | 1 363 679 B1 | 10/2004 |
| EP | 1 468 607 A2 | 10/2004 |
| JP | 4-325569 A | 11/1992 |
| JP | 11-158328 A | 6/1999 |
| JP | 2001-516359 A | 9/2001 |
| JP | 2001-516539 A | 9/2001 |
| JP | 2002-510677 A | 4/2002 |
| JP | 2002-526053 A | 8/2002 |
| JP | 2004-500227 A | 1/2004 |
| JP | 2004-137241 A | 5/2004 |
| JP | 2007-181571 A | 7/2007 |
| JP | 2007-332040 A | 12/2007 |
| JP | 2008-517899 A | 5/2008 |
| JP | 2010-534266 A | 11/2010 |
| WO | WO 98/41505 A1 | 9/1998 |
| WO | WO 99/21568 A1 | 5/1999 |
| WO | WO 99/39707 A1 | 8/1999 |
| WO | WO 99/51578 A1 | 10/1999 |
| WO | WO 00/16624 A1 | 3/2000 |
| WO | WO 01/64644 A1 | 9/2001 |
| WO | WO 02/077095 A2 | 10/2002 |
| WO | WO 2008/035085 A1 | 3/2008 |
| WO | WO 2008/043175 A1 | 4/2008 |
| WO | WO 2008/092011 A2 | 7/2008 |
| WO | WO 2008/150375 A1 | 12/2008 |
| WO | WO 2009/014549 A1 | 1/2009 |
| WO | WO 2009/154819 A2 | 12/2009 |
| WO | WO 2010/091124 A2 | 8/2010 |
| WO | WO 2011/097347 A2 | 8/2011 |
| WO | WO 2012/021754 A2 | 2/2012 |

OTHER PUBLICATIONS

Agocs et al., "The Structurally Flexible Bicyclic Bis(2-hydroxyethanethiolato)bismuth(III) Complex: A Model for Asymmetric Monoanionic Chelation of Bismuth(III)," Inorg. Chem. 36:2855-2860, 1997.

Alexander et al., "Association of Inhalation Toxicologists (AIT) Working Party Recommendation for Standard Delivered Dose Calculation and Expression in Non-Clinical Aerosol Inhalation Toxicology Studies with Pharmaceuticals," Inhal Toxicol. 2008; 20(13):1179-89.

Alhariri et al., "Efficacy of Liposomal Bismuth-Ethanedithiol-Loaded Tobramycin after Intratracheal Administration in Rats with Pulmonary Pseudomonas aeruginosa Infection," Antimicrobial Agents and Chemotherapy, Jan. 2013, vol. 57, No. 1, pp. 569-578.

Alt et al., "In Vitro Testing of Antimicrobial Activity of Bone Cement," Antimicrobial Agents and Chemotherapy 48(11):4084-4088, 2004.

Avni et al., "Prophylactic antibiotics for burns patients: systematic review and meta-analysis," BMJ 2010, 340:c241, 10 pages.

Badireddy et al., "Bismuth Dimercaptopropanol (BisBAL) Inhibits the Expression of Extracellular Polysaccharides and Proteins by Brevundimonas diminuta: Implications for Membrane Microfiltration," Biotechnology and Bioengineering 99(3):634-643, 2008.

Badireddy et al., "Spectroscopic Characterization of Extracellular Polymeric Substances from Escherichia coli and Serratia marcescens: Suppression Using Sub-Inhibitory Concentrations of Bismuth Thiols," Biomacromolecules 9:3079-3089, 2008.

Barzilai et al., "Isolation of group A streptococci from children with perianal cellulitis and from their siblings," The Pediatric Infectious Disease Journal 1998, 17(4):358-360, 7 pages.

Bayston et al., "An antimicrobial modified silicone peritoneal catheter with activity against both Gram positive and Gram negative bacteria," Biomaterials 30:3167-3173, 2009.

Bernstein et al., "Combination of Subatmospheric Pressure Dressing and Gravity Feed Antibiotic Instillation in the Treatment of Post-Surgical Dia," Wounds, 2005, 17(2):37-48.

Bisno et al., "Streptococcal Infections of Skin and Soft Tissues," N Engl J Med, Jan. 1996, vol. 334, No. 4, pp. 240-245.

Blume et al., "Comparison of Negative Pressure Wound Therapy Using Vacuum-Assisted Closure With Advanced Moist Wound Therapy in the Treatment of Diabetic Foot Ulcers. A multicenter randomized controlled trial," Diabetes Care, 2008 31: 631-636.

Bohner et al., "Gentamicin-Loaded Hydraulic Calcium Phosphate Bone Cement as Antibiotic Delivery System," Journal of Pharmaceutical Sciences 86(5):565-572, May 1997.

Bowling et al., "MRSA and diabetic foot wounds: contaminating or infecting organisms?" Curr Diab Rep, 2009 9(6):440-444.

Brem, et al., "Cellular and molecular basis of wound healing in diabetes," J. Clinical Invest., 2007, 117(5):1219-1222.

Brogan et al., "Bismuth-dithiol inhibition of the Escherichia coli rho transcription termination factor," Journal of Inorganic Biochemistry 99:841-851, 2005.

Bueno et al., "Study of the bismuth oxide concentration required to provide Portland cement with adequate radiopacity for endodontic," Oral Surg. Oral Med. Oral Pathol. Oral Radial. Endod. 107:e65-e69, 2009.

Cape et al., "Preparation of Active Proteins, Vaccines and Pharmaceuticals as Fine Powders using Supercritical or Near-Critical Fluids," Pharmaceutical Research 25(9):1967-1990, 2008.

Chandler et al., "Mechanism of the Antimicrobial Action of Pyrithione: Effects on Membrane Transport, ATP Levels, and Protein Synthesis," Antimicrobial Agents and Chemotherapy 14(1):60-68, 1978.

Chartier et al., "Erysipelas: an update," Int J Dermatol, 1996, 35:779-781.

Chim et al., "Five-year review of infections in a burn intensive care unit: High incidence of Acinetobacter baumannii in a tropical climate," Burns, 2007, 33:1008-1014.

Chuard et al., "Susceptibility of Staphylococcus aureus Growing on Fibronectin-Coated Surfaces to Bactericidal Antibiotics," Antimicrobial Agents and Chemotherapy 37(4):625-632, 1993.

Codony et al., "Assessment of bismuth thiols and conventional disinfectants on drinking water biofilms," Journal of Applied Microbiology 95:288-293, 2003.

Cooksey, "Genetics of Bactericide Resistance in Plant Pathogenic Bacteria," Annu. Rev. Phytopathol 28:201-219, 1990.

Costerton et al., "Bacterial Biofilms: A Common Cause of Persistent Infections," Science, May 1999, vol. 284, pp. 1318-1322.

Crane et al., "Efficacy of Colistin-Impregnated Beads to Prevent Multidrug-Resistant A. Baumannii Implant-Associated Osteomyelitis," Journal of Orthopaedic Research 27:1008-1015, Aug. 2009.

Database WPI, Thomson Scientific, London, GB, May 13, 2004 (abstract), 6 pages.

De Lalla, "Antibiotic Prophylaxis in Orthopedic Prosthetic Surgery," Journal of Chemotherapy 13(1):48-53, 2001.

De Smet et al., "Decontamination of the Digestive Tract and Oropharynx in ICU Patients," N Engl J Med Jan. 2009, 360(1):20-31.

Den Hollander et al., "Use of Pharmacodynamic Parameters To Predict Efficacy of Combination Therapy by Using Fractional Inhibitory Concentration Kinetics," Antimicrobial Agents and Chemotherapy 42(4):744-748, 1998.

Domenico et al., "Activities of Bismuth Thiols against Staphylococci and Staphylococcal Biofilms," Antimicrobial Agents and Chemotherapy 45(5):1417-1421, 2001.

(56) References Cited

OTHER PUBLICATIONS

Domenico et al., "Antimicrobial Activity of Novel Antimicrobial Agents: Pyrithione Enhanced Antimicrobial Activity of Bismuth," Antibiotics for Clinicians 9:291-297, 2005.
Domenico et al., "BisEDT and RIP act in synergy to prevent graft infections by resistant staphylococci," Peptides 25:2047-2053, 2004.
Domenico et al., "Bismuth Modulation of Antibiotic Activity Against Gastrointestinal Bacterial Pathogens," Med. Microbial. Lett. 3:114-119, 1994.
Domenico et al., "Combating Antibiotic Resistance with Bismuth-Thiols," Res. Adv. In Antimicrob. Agents & Chemother. 3:79-85, 2003.
Domenico et al., "Differential Effects of Bismuth and Salicylate Salts on the Antibiotic Susceptibility of Pseudomonas aeruginosa," Eur. J. Clin. Microbial. Infect. Dis. 11: 170-175, 1992.
Domenico et al., "Efficacy/Toxicity of Bismuth-Dimercaprol (BisBAL) in a Burn Wound Sepsis Model," Abstracts of the General Meeting of the American Society for Microbiology, the Society, Washington, DC, US, Abstract A-10, 96:135, Jan. 1, 1996.
Domenico et al., "Enhancement of Bismuth Antibacterial Activity with Lipophilic Thiol Chelators," Antimicrobial Agents and Chemotherapy 41(8):1697-1703, 1997.
Domenico et al., "Extracellular polysaccharide production by Klebsiella pneumoniae and its relationship to virulence," Can. J. Microbial. 31:472-478, 1985.
Domenico et al., "Polysaccharide Capsule-Mediated Resistance to Opsonophagocytosis in Klebsiella pneumoniae," Infection and Immunity 62(10):4495-4499, 1994.
Domenico et al., "Reduction of capsular polysaccharide and potentiation of aminoglycoside inhibition in Gram-negative bacteria by bismuth subsalicylate," Journal of Antimicrobial Chemotherapy 28:801-810, 1991.
Domenico et al., "Resistance to bismuth among Gram-negative bacteria is dependent upon iron and its uptake," Journal of Antimicrobial Chemotherapy 38:1031-1040, 1996.
Domenico et al., "Salicylate or Bismuth Salts Enhance Opsonophagocytosis of Klebsiella pneumoniae," Infection 20:66-72, 1992.
Domenico et al., "Subinhibitory Bismuth Ethanedithiol (BisEDT) Sensitizes Resistant *Staphylococcus aureus* to Nafcillin or Gentamicin," Annual meeting ASM, Salt Lake, City, UT, Abstract A-147, 2003, pp. 27-28.
Domenico et al., "Surface Antigen Exposure by Bismuth Dimercaprol Suppression of Klebsiella pneumoniae Capsular Polysaccharide," Infection and Immunity 67(2):664-669, 1999.
Domenico et al., "The Potential of Bismuth-Thiols for Treatment and Prevention of Infection," Infect. Med. 17(2):123-127, 2000.
Drosou et al., "Antiseptics on Wounds: an Area of Controversy," Wounds 15(6):1-27, 2003.
El-Feky et al., "Effect of Ciprofloxacin and N-acetylcysteine on Bacterial Adherence and Biofilm Formation on Ureteral Stent Surfaces," Polish Journal of Microbiology 58(3):261-267, 2009.
Ellis Simonsen et al., "Cellulitis incidence in a defined population," Epidemiol Infect., 2006, 134(2):293-299.
Eriksson et al., "Erysipelas: clinical and bacteriologic spectrum and serological aspects," Clin Infect Dis, 1996, 23:1091-1098.
Expert, "Withholding and Exchanging Iron: Interactions Between *Erwinia* spp. And Their Plant Hosts," Annu. Rev. Phytopathol 37:307-334, 1999.
Fitzwater et al., "The Risk Factors and Time Course of Sepsis and Organ Dysfunction after Burn Trauma," The Journal of Trauma: Injury, Infection, and Critical Care, 2003, 54:959-966.
Fonder et al., "Treating the chronic wound: A practical approach to the care of nonhealing wounds and wound care dressings," Journal of the American Academy of Dermatology, 2012, 58(2): 185-206.
Gamelli et al., "Macrophage mediated suppression of granulocyte and macrophage growth after burn wound infection reversal by means of anti-PGE2," J Burn Care Rehabil, 2000, 21:64-69.
Gerry et al., "Silver-impregnated vacuum-assisted closure in the treatment of recalcitrant venous stasis ulcers," Ann Plast Surg, 2007, 59(1):58-62.
Halwani et al., "Bismuth-thiol incorporation enhances biological activities of liposomal tobramycin against bacterial biofilm and quorum sensing molecules production by Pseudomonas aeruginosa," International Journal of Pharmaceutics 373:141-146, 2009.
Halwani et al., "Liposomal bismuth-ethanedithiol formulation enhances antimicrobial activity of tobramycin," International Journal of Pharmaceutics 358:278-284, 2008.
Harsha et al., "ADAM12: a potential target for the treatment of chronic wounds," Journal of Molecular Medicine, 2008, 86(8): 961-969.
Herndon, et al., "Is bacterial translocation a clinically relevant phenomenon in burns?" Crit Care Med, 2000, 28:1682-1683.
Holleman et al., Lehrbuch der Anorganischen Chemie, Walter de Gruyter, New York, vol. 91-100, p. 1003, 1985.
Huang et al., "Reduction of polysaccharide production in Pseudomonas aeruginosa biofilms by bismuth dimercaprol (BisBAL) treatment," Journal of Antimicrobial Chemotherapy 44:601-605, 1999.
Huang, S et al., "A novel in vitro cell model of the human airway epithelium" 3R-Info-Bulletin, No. 41, Oct. 2009, 2 pages.
Huang, S., et al., "The Use of In Vitro 3D Cell Models in Drug Development for Respiratory Diseases," Drug Discovery and Development—Present and Future (Ed. Dr. Izet Kapetanović), 2011, Chapter 8, pp. 169-190.
Hunt et al., "The Effector Component of the Cytotoxic T-Lymphocyte Response Has a Biphasic Pattern after Burn Injury," J Surg Res, 1998, 80:243-251.
Hwang et al., "Chemical composition, radiopacity, and biocompatibility of Portland cement with bismuth oxide," Oral Surg. Oral Med. Oral Pathol. Oral Radial. Endod. 107:e96-e102, 2009.
Imazato, "Antibacterial properties of resin composites and dentin bonding systems," Dental Materials 19:449-457, 2003.
Jeffcoate et al., "Diabetic foot ulcers," Lancet, 2003, 361:1545-1551.
Johnson et al., "Dominance of EMRSA-15 and -16 among MRSA causing nosocomial bacteraemia in the UK: analysis of isolates from the European Antimicrobial Resistance Surveillance System (EARSS)," J. of Antimicrobial Chemotherapy, 2001, 48: 143-144.
King et al., "In Vitro Pharmacodynamics of Levofloxacin and Other Aerosolized Antibiotics under Multiple Conditions Relevant to Chronic Pulmonary Infection in Cystic Fibrosis," Antimicrob Agents Chemother, Jan. 2010, vol. 54, No. 1, pp. 143-148.
Kosinski et al., "Current medical management of diabetic foot infections," Expert Rev Anti-Infect Ther., 2010, 8(11):1293-1305.
Kuvshinova et al., "Reaction of Bismuth Nitrate with Sodium Citrate in Water-Glycerol Solutions," Russian Journal of Inorganic Chemistry 54(11):1816-1819, 2009.
Lambert et al., "The actions of bismuth in the treatment of Helicobacter pylori infection," Aliment Pharmacol Ther 11(Suppl 1):27-33, 1997.
Lee et al., "Inhibition of Methicillin-Resistant *Staphylococcus aureus* Biofilm Formation with Bismuth-Thiol Compounds," Abstracts of the General Meeting of the American Society for Microbiology, the Society, Washington, DC, US, Abstract B-446, 104:111, 2004.
Lepow et al., "Bioengineered tissues in wound healing: a progress report," Expert Rev Dermatol., 2011, 6(3):255-262.
Lipsky et al., "2012 Infectious Diseases Society of America Clinical Practice Guideline for the Diagnosis and Treatment of Diabetic Foot Infections," CID, 2012, 54:e132-e173.
Lipsky et al., "Diagnosis and Treatment of Diabetic Foot Infections," Clin Infect Dis., Oct. 2004, 39:885-910.
Lipsky et al., "Topical Antimicrobial Therapy for Treating Chronic Wounds," Clin Infect Dis., Nov. 2009, 49:1541-1549.
Margolis et al., "Venous leg ulcer: Incidence and prevalence in the elderly," Journal of the American Academy of Dermatology, 2002, 46(3): 381-386.
Martin et al., "Micronization processes with supercritical fluids: Fundamentals and mechanisms," Advanced Drug Delivery Reviews 60:339-350, 2008.
McManus et al., "Antibiotic Use in Plant Agriculture," Annu. Rev. Phytopathol. 40:443-465, 2002.

(56) References Cited

OTHER PUBLICATIONS

Meletiadis et al., "Assessing in vitro combinations of antifungal drugs against yeasts and filamentous fungi: comparison of different drug interaction models," Medical Mycology 43:133-152, 2005.
Mendes et al., "Clinical and bacteriological survey of diabetic foot infections in Lisbon," Diabetes Res Clin Pract., 2012, 95(1):153-161.
Moribe et al., "Supercritical carbon dioxide processing of active pharmaceutical ingredients for polymorphic control and for complex formation," Advanced Drug Delivery Reviews 60:328-338, 2008.
Nelson et al., "Systematic review of antimicrobial treatments for diabetic foot ulcers," Diabet Med, 2006, 23:348-359.
Nguyen et al., "Active starvation responses mediate antibiotic tolerance in biofilms and nutrient-limited bacteria," Science, Nov. 2011, 334(6058): 982-986.
Odds, "Synergy, antagonism, and what the chequerboard puts between them," Journal of Antimicrobial Chemotherapy 52:1, 2003, 1 page.
Pasquaroli et al., "Antibiotic pressure can induce the viable but non-culturable state in *Staphylococcus aureus* growing in biofilms," J Antimicrob Chemother 2013; 68: 1812-1817.
Pereira-Lachataignerais et al., "Study and formation of vesicle systems with low polydispersity index by ultrasound method," Chem Phys Lipids 140(1-2)88-97, 2006, (Abstract Only).
Peterson et al., "Therapeutic Role for Bismuth Compounds in TNBS-Induced Colitis in the Rat," Digestive Diseases and Sciences 45(3):466-473, 2000.
Rasenack et al., "Micron-Size Drug Particles: Common and Novel Micronization Techniques," Pharmaceutical Development and Technology 9(1):1-13, 2004.
Ressner et al., "Outcomes of Bacteremia in Burn Patients Involved in Combat Operations Overseas," J Am Coll Surg, 2008, 206:439-444.
Romanelli M., "Amelogenin: extracellular matrix protein for the treatment of hard-to-heal wounds," Wounds UK, 2010, 6(2):47-52.
Rupp et al., "Effect of subinhibitory concentrations of vancomycin, cefazolin, ofloxacin, L-ofloxacin and D-ofloxacin on adherence to intravascular catheters and biofilm formation by *Staphylococcus epidermidis*," J of Antimicrobial Chemotherapy 41:155-161, 1998.
Sadler et al., "Coordination chemistry of metals in medicine: target sites for bismuth," Coordination Chemistry Reviews 185-186:689-709, 1999.
Saha et al., "Cytokine Modulation by Bismuth-ethanedithiol in Experimental Sepsis," 10th Intl. Conf. Inflamm. Res., Hot Spring, VA. One page.
Salo et al., "Salicylate-Enhanced Exposure of Klebsiella pneumoniae Subcapsular Components," Infection 23(6):371-377, 1995.
Schaper NC, "Diabetic foot ulcer classification system for research purposes: a progress report on criteria for including patients in research studies," Diabetes Metab Res Rev, 2004, 20(Suppl 1):S90-95.
Shankar et al., "Bacterial etiology of diabetic foot infections in South India, 2005," European Journal of Internal Medicine, vol. 16, pp. 567-570. (Year: 2005).
Sharma BR., "Infection in Patients with Severe Burns: Causes and Prevention Thereof," Infect Dis Clin North Am 2007, 21:745-59; ix.
Shoup et al., "Mechanisms of neutropenia involving myeloid maturation arrest in burn sepsis," Ann Surg, 1998, 228:112-122.
Silvestri et al., "Selective decontamination of the digestive tract reduces bacterial bloodstream infection and mortality in critically ill patients. Systematic review of randomized, controlled trials," J Hosp Infect, 2007, 65:187-203.
Smith et al., "Bismuth compounds as fungicides," International Pest Control, pp. 144-145, 1985, 2 pages (+English abstract).
Soothill et al., "The IC50: an exactly defined measure of antibiotic sensitivity," Journal of Antimicrobial Chemotherapy 29:137-139, 1992.
Tascini et al., "Microbiology at first visit of moderate-to-severe diabetic foot infection with antimicrobial activity and a survey of quinolone monotherapy," Diabetes Res Clin Pract., 2011, 94(1):133-139.
Tepper et al., "Symposium Summary: "Breath In, Breath Out, Its Easy: What You Need to Know About Developing Inhaled Drugs, Int. J. Toxicol. 2016, 35(4) 376-392.
Thorsteinsdottir et al., "Abdominal wall cellulitis in the morbidly obese," Scand J Infect Dis. 2005, 37(8):605-608.
Veloira et al., "In vitro activity and synergy of bismuth thiols and tobramycin against Burkholderia cevacia complex," Journal of Antimicrobial Chemotherapy 52:915-919, 2003.
Walker et al., "*Pseudomonas aeruginosa*—Plant Root Interactions. Pathogenicity, Biofilm Formation, and Root Exudation," Plant Physiol., 2004, vol. 134, pp. 320-331.
Weber et al., "Metal-1,4-Dithio-2,3-dihydroxybutane Chelates: Novel Inhibitors of the Rho Transcription Termination Factor," Biochemistry 42(30):9121-9126, 2003.
Wibbenmeyer et al., "Prospective analysis of nosocomial infection rates, antibiotic use, and patterns of resistance in a burn population," J Burn Care Res, 2006, 27:152-160.
Widmer et al., "Killing of Nongrowing and Adherent *Escherichia coli* Determines Drug Efficacy in Device-Related Infections," Antimicrobial Agents and Chemotherapy 35(4):741-746, 1991.
Wolcott et al., "Biofilm maturity studies indicate sharp debridement opens a time-dependent therapeutic window," J Wound Care, 2010, 19:320-328.
Wolcott et al., "Regular debridement is the main tool for maintaining a healthy wound bed in most chronic wounds," J Wound Care, 2009, 18(2):54-6.
Wu et al., "Subinhibitory Bismuth-Thiols Reduce Virulence of Pseudomonas aeruginosa," Am. J. Respir. Cell Mol. Biol. 26:731-738, 2002.
Zhang et al., "Inhibition of Bacterial Adherence on the Surface of Stents and Bacterial Growth in Bile by Bismuth Dimercaprol," Digestive Diseases and Sciences 50(6):1046-1051, 2005.
Extended European Search Report for European Application No. 19843994.5, dated Jul. 6, 2022, 12 pages.

\* cited by examiner

Fig. 2

CASCADE IMPACTOR MASS DISTRIBUTION

2.5 mg/ml
0.5% Tween-80
10mm Sodium Phosphate
PH = 7.4

Gravimetric Size Data
MMAD = 0.97 μm
GSD = 3.02
$R^2$ = 0.50 y-axis: $dM/M_0/d \ln d_{ae}$ aerodynamic diameter (micrometers)

Bismuth-thiol: MB-1B3 – Current Clinical Stage Drug Candidate

| Strain | 2.50 | 1.25 | 0.63 | 0.31 | 0.16 | 0.08 | 0.04 | 0.02 | 0.01 | 0.00 | +control | -control | MIC (mcg/mL) |
|---|---|---|---|---|---|---|---|---|---|---|---|---|---|
| AG1 (Aminoglycoside resistant PA) | - | - | - | + | + | + | + | + | + | + | + | - | 0.63 |
| AG14 (Aminoglycoside resistant PA) | - | - | - | + | + | + | + | + | + | + | + | - | 0.31 |
| AU197 (B. cenocepacia) | - | - | - | - | + | + | + | + | + | + | + | - | 0.16 |
| AX7 (Achromobacter spp.) | - | - | - | - | - | + | + | + | + | + | + | - | 0.08 |
| MR14 (Multi-resistant PA) | - | - | - | + | + | + | + | + | + | + | + | - | 0.63 |
| SM21 (S. maltophilia) | - | - | - | + | + | + | + | + | + | + | + | - | 0.31 |
| 25922 (Control Strain E. coli) | - | - | + | + | + | + | + | + | + | + | + | - | 1.25 |
| 29213 (Control Strain S. aureus) | - | - | - | - | - | - | - | + | + | + | + | - | 0.02 |

Bismuth-thiol: MB-6 – Current Pre-Clinical Stage Drug Candidate

| Strain | 2.50 | 1.25 | 0.63 | 0.31 | 0.16 | 0.08 | 0.04 | 0.02 | 0.01 | 0.00 | +control | -control | MIC (mcg/mL) |
|---|---|---|---|---|---|---|---|---|---|---|---|---|---|
| AG1 (Aminoglycoside resistant PA) | - | - | - | + | + | + | + | + | + | + | + | - | 0.63 |
| AG14 (Aminoglycoside resistant PA) | - | - | - | + | + | + | + | + | + | + | + | - | 0.63 |
| AU197 (B. cenocepacia) | - | - | - | + | + | + | + | + | + | + | + | - | 0.31 |
| AX7 (Achromobacter spp.) | - | - | - | - | + | + | + | + | + | + | + | - | 0.16 |
| MR14 (Multi-resistant PA) | - | - | - | + | + | + | + | + | + | + | + | - | 0.31 |
| SM21 (S. maltophilia) | - | - | - | - | - | + | + | + | + | + | + | - | 0.08 |
| 25922 (Control Strain E. coli) | - | - | - | + | + | + | + | + | + | + | + | - | 0.31 |
| 29213 (Control Strain S. aureus) | - | - | - | - | - | - | + | + | + | + | + | - | 0.04 |

Fig. 39

CASCADE IMPACTOR MASS DISTRIBUTION

Tobramycin (60 mg/mL)

MMAD: 2.81
GSD: 1.87
R2: 0.87

Fig. 42
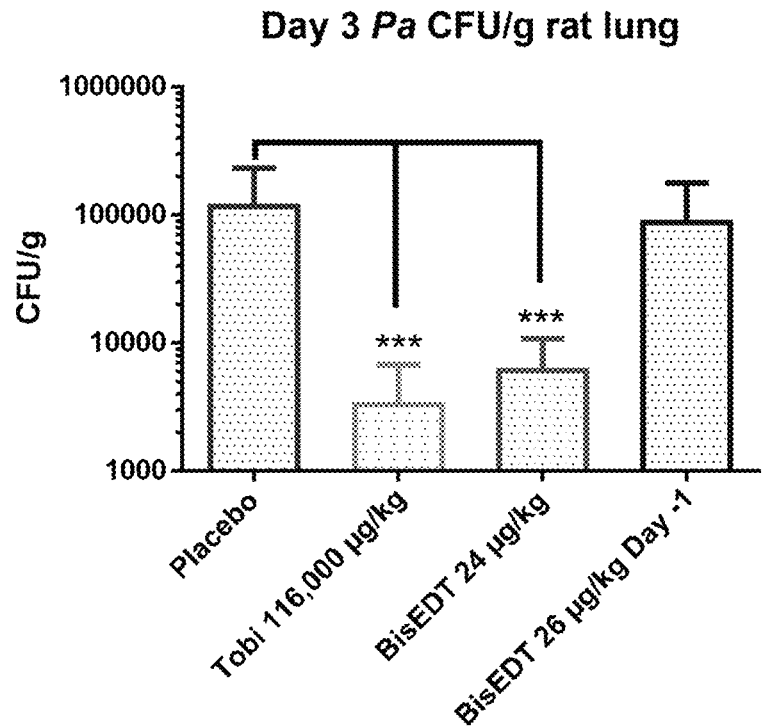
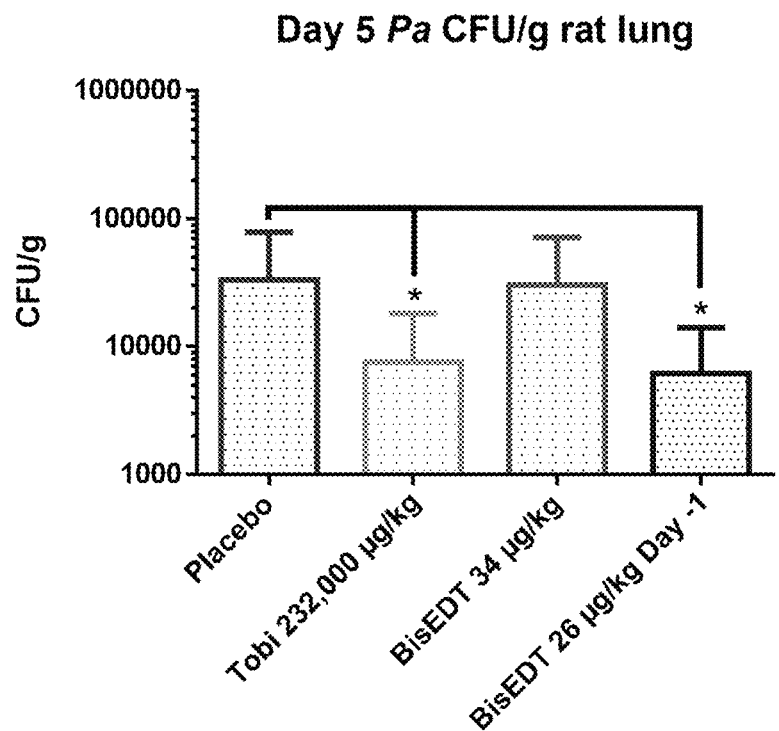

Fig. 43

| Org: | | Combination Agent | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Test Agent | A | 64/.5 | 32/.5 | 16/.5 | 8/.5 | 4/.5 | 2/.5 | 1/.5 | .5/.5 | .25/.5 | .12/.5 | .06/.5 | 0/.5 |
| | B | 64/.25 | 32/.25 | 16/.25 | 8/.25 | 4/.25 | 2/.25 | 1/.25 | .5/.25 | .25/.25 | .12/.25 | .06/.25 | 0/.25 |
| | C | 64/.12 | 32/.12 | 16/.12 | 8/.12 | 4/.12 | 2/.12 | 1/.12 | .5/.12 | .25/.12 | .12/.12 | .06/.12 | 0/.12 |
| | D | 64/.06 | 32/.06 | 16/.06 | 8/.06 | 4/.06 | 2/.06 | 1/.06 | .5/.06 | .25/.06 | .12/.06 | .06/.06 | 0/.06 |
| | E | 64/.03 | 32/.03 | 16/.03 | 8/.03 | 4/.03 | 2/.03 | 1/.03 | .5/.03 | .25/.03 | .12/.03 | .06/.03 | 0/.03 |
| | F | 64/.015 | 32/.015 | 16/.015 | 8/.015 | 4/.015 | 2/.015 | 1/.015 | .5/.015 | .25/.015 | .12/.015 | .06/.015 | 0/.015 |
| | G | 64/.008 | 32/.008 | 16/.008 | 8/.008 | 4/.008 | 2/.008 | 1/.008 | .5/.008 | .25/.008 | .12/.008 | .06/.008 | 0/.008 |
| | H | 64/0 | 32/0 | 16/0 | 8/0 | 4/0 | 2/0 | 1/0 | .5/0 | .25/0 | .12/0 | .06/0 | 0/0 |

BISMUTH-THIOL COMPOSITIONS AND METHODS OF USE

CROSS REFERENCE TO RELATED APPLICATIONS

This application claims the benefit of U.S. Provisional Application No. 62/712,563, filed Jul. 31, 2018 and of U.S. Provisional Application No. 62/800,925, filed Feb. 4, 2019, the contents of which are incorporated herein by reference in their entireties.

BACKGROUND

Cystic fibrosis (CF) manifests as a clinical syndrome characterized by chronic pulmonary infection as well as by gastrointestinal, nutritional, and other abnormalities. The genetic basis for CF is a well-characterized, severe monogenic recessive disorder that arises from mutations in the cystic fibrosis transmembrane conductance regulator (CFTR) gene. Patients often have chronic pulmonary infections, such as with *Pseudomonas aeruginosa*. Ultimately, 80 to 95% of patients with CF succumb to respiratory failure brought on by chronic bacterial infection and concomitant airway inflammation.

Lungs of CF patients are often colonized or infected in infancy and early childhood with organisms, such as *Staphylococcus aureus* and *Haemophilus influenzae*, that may damage the epithelial surfaces, leading to increased attachment of, and eventual replacement by, *P. aeruginosa*. Chronic infection with *P. aeruginosa* is the main proven perpetrator of lung function decline and ultimate mortality in CF patients. Chronic *P. aeruginosa* infection leads to epithelial surface damage and airway plugging, progressively impairing airway conductance, which results in a decline in pulmonary function. *P. aeruginosa* also develops resistance to many common antibiotics which makes eradication of the infection quite difficult. One factor in developing resistance is the tendency of *P. aeruginosa* and other CF associated lung pathogens to form biofilms tendency to create biofilms that are more difficult for antibiotics to penetrate. In addition, the prevalent use of antibiotics in treating infections in general has led to multi-drug resistant (MDR) strains of bacteria, such as *P. aeruginosa*, and *Staphylococcus aureus*.

Long-term inhaled antibiotic therapy is now standard of care for chronic maintenance treatment in stable patients. Effective antibiotic concentrations can be achieved in the airways by nebulization, avoiding side effects of intravenous antibiotics. Colistimethate sodium, amikacin, aztreonam and tobramycin have been administered to patients by inhalation. However, there is an unmet need for treatment of pulmonary microbial (e.g. bacterial or fungal) infections in CF patients that is broad spectrum, durable and potent against even the most resistant of microbial (e.g. bacterial or fungal) species.

SUMMARY

Disclosed herein are methods of treating, managing or lessening the severity of cystic fibrosis (CF) symptoms and infections in a subject, the method comprising administering to the subject a bismuth-thiol (BT) composition that comprises at least one BT compound.

In certain embodiments, the present disclosure provides a pharmaceutical composition suitable for use in a subject for treating, managing or lessening the severity of cystic fibrosis (CF) symptoms and infections, comprising an effective amount of any of the compounds described herein (e.g., a compound of the disclosure, such as a bismuth-thiol compound, or a pharmaceutically acceptable salt thereof), and one or more pharmaceutically acceptable excipients.

In certain embodiments, the present disclosure provides an aerosol comprising a plurality of dispersed liquid droplets in a gas, said liquid droplets comprising a BT composition comprising at least one BT compound suspended therein, wherein the BT compound comprises bismuth and/or a bismuth salt and a thiol-containing compound; and wherein at least 60%, 65%, 70, 75%, 80%, 90%, or 95% of the liquid droplets have a mass median aerodynamic diameter (MMAD) from about of from about 0.4 µm to about 5 µm.

In certain embodiments, the present disclosure provides a method of treating, managing or lessening the severity of cystic fibrosis (CF) symptoms and infections in a subject, the method comprising administering to the subject a bismuth-thiol (BT) composition that comprises at least one BT compound, wherein the composition is a suspension of microparticles having a volumetric mean diameter (VMD) from about 0.4 µm to about 5 µm and/or a mass median aerodynamic diameter (MMAD) from about 0.4 µm to about 5 µm.

In certain embodiments, the present disclosure provides a method of treating, managing or lessening the severity of symptoms and infections associated with one or more pulmonary diseases or infections in a subject, the method comprising administering to the subject a bismuth-thiol (BT) composition that comprises at least one BT compound.

BRIEF DESCRIPTION OF THE DRAWINGS

FIG. 2 shows an aerosol particle size distribution of a 2.5 mg/mL solution of BisEDT.

Figure 4:
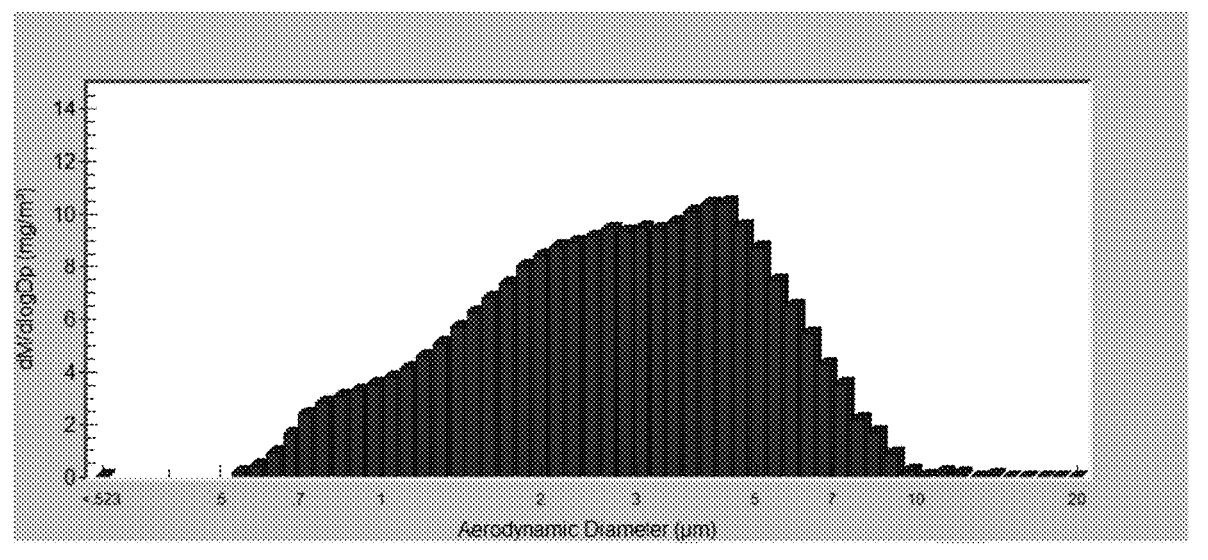

FIG. 4 shows an aerosol particle size distribution of a 50 mg/mL solution of BisEDT.

Figure 6:
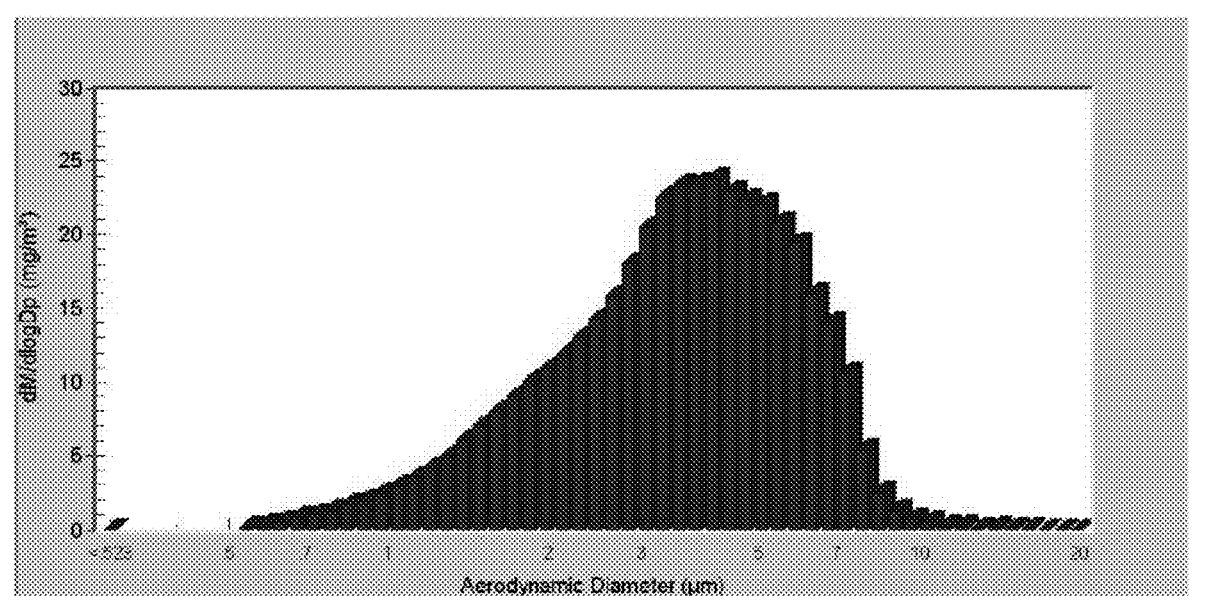

FIG. 6 shows an aerosol particle size distribution of a 100 mg/mL solution of BisEDT.

Figure 7:
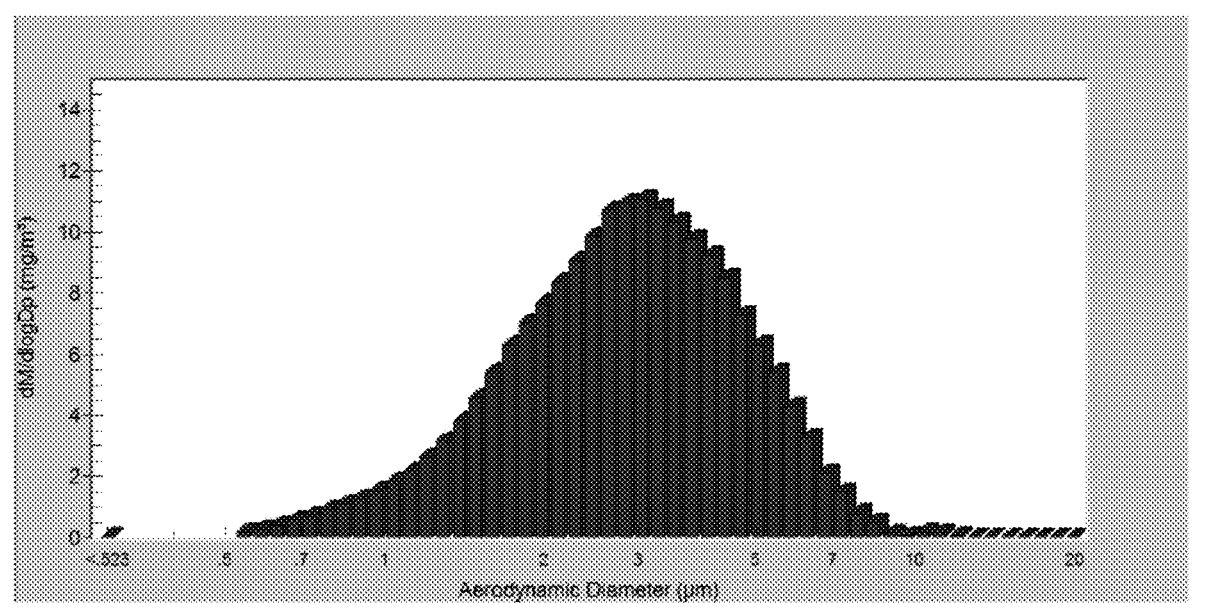

FIG. 7 shows an aerosol particle size distribution of a 100 mg/mL BisEDT in 300 mOsmolality phosphate buffer solution.

Figure 9:
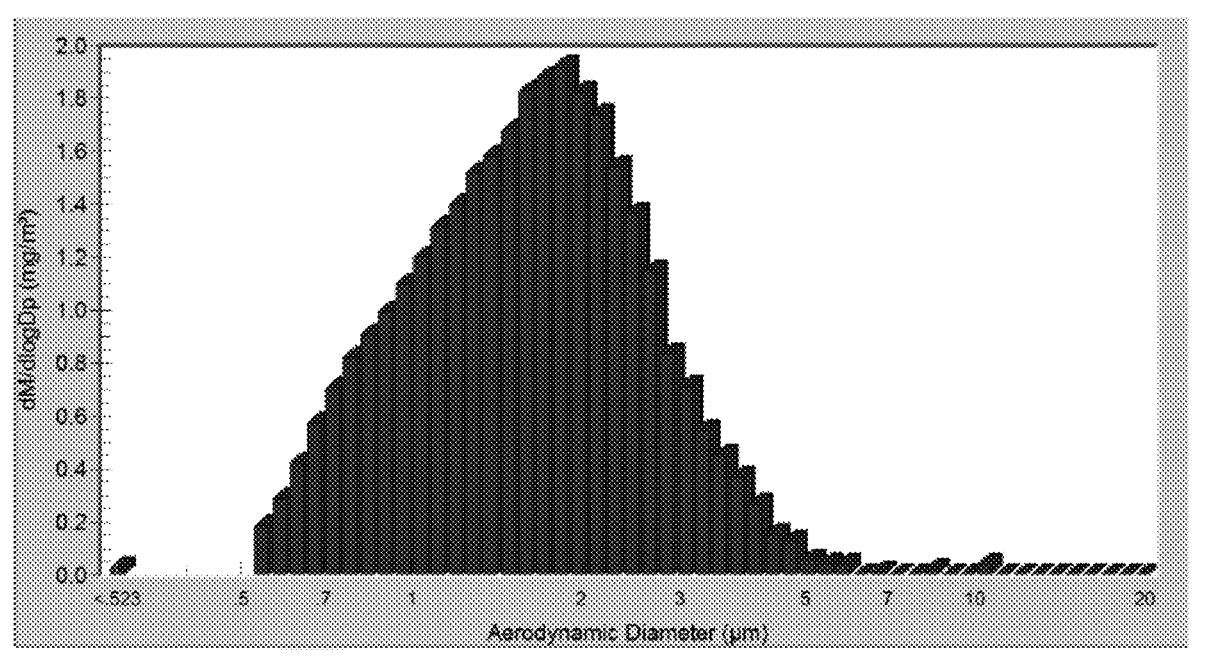

FIG. 9 shows an aerosol particle size distribution of a 10 mg/mL BisEDT in 300 mOsmolality phosphate buffer solution.

FIG. 12 shows the results of MIC testing of BisEDT against a variety of clinically relevant CF isolates.

FIG. 39 shows Particle Size Distribution for Tobramycin.

FIG. 42 shows rat efficacy figures showing cumulative (total) administered dose (lung deposited) at days 3 and 5.

FIG. 43 shows a representative checkerboard assay where each compound is tested alone (Column 12 and Row H) and in combination at varying ratios of drug concentration.

DETAILED DESCRIPTION

Definitions

Figure 1:
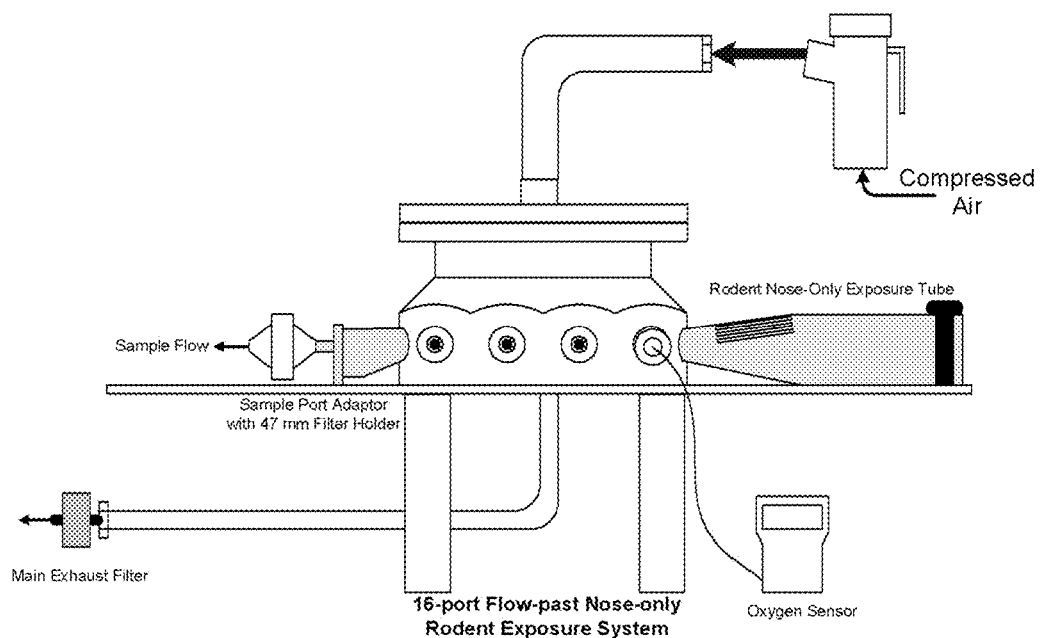
FIG. 1 shows a representative inhalation exposure schematic.
Figure 3:
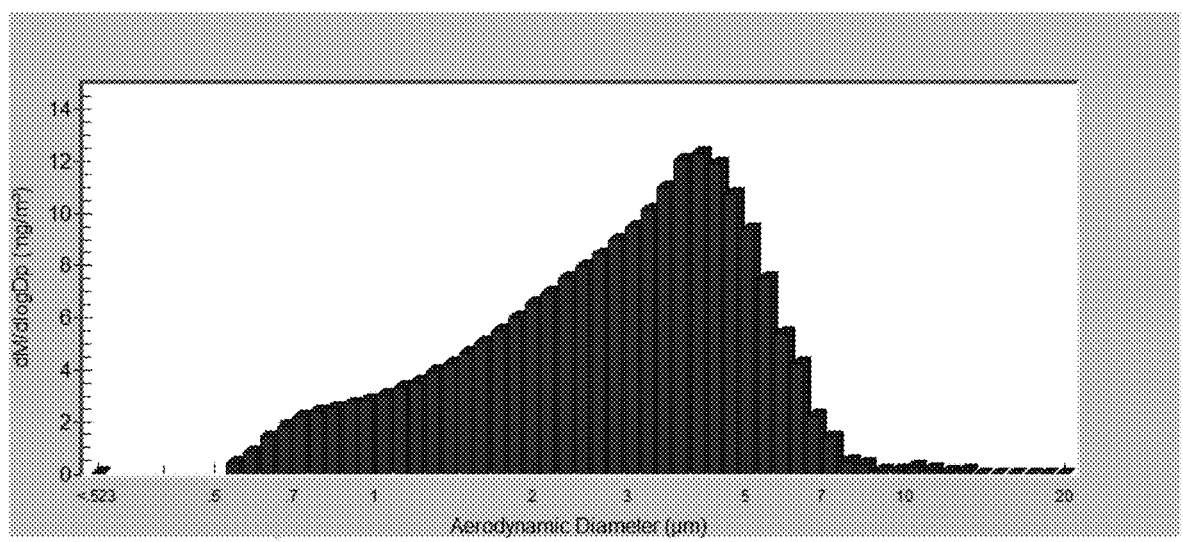
FIG. 3 shows an aerosol particle size distribution of a 25 mg/mL solution of BisEDT.
Figure 5:
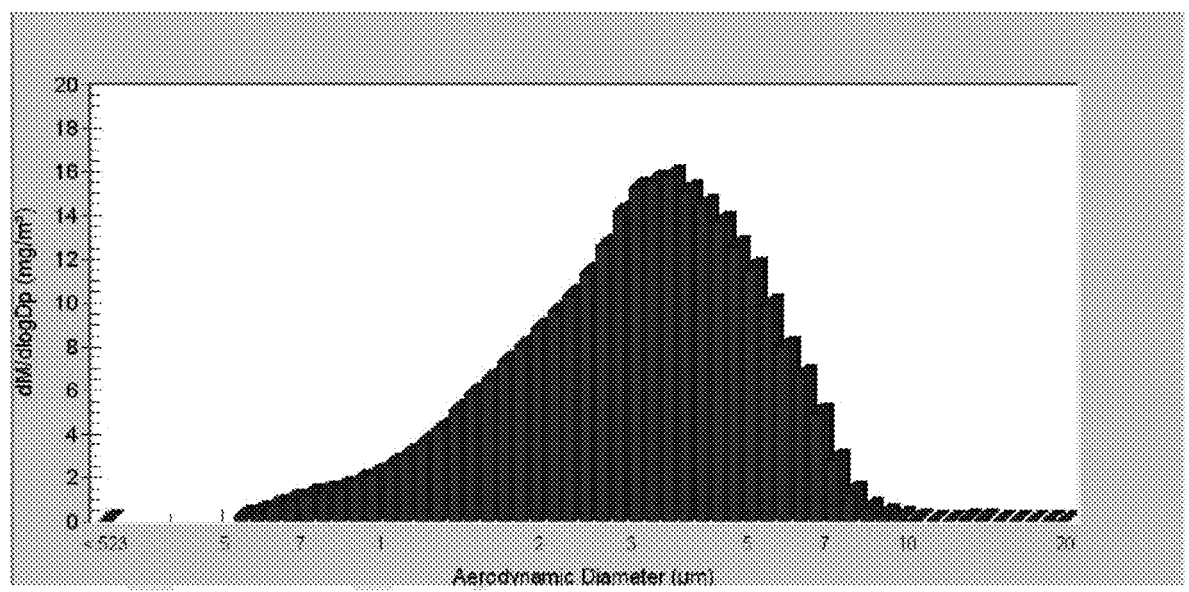
FIG. 5 shows an aerosol particle size distribution of a 75 mg/mL solution of BisEDT.
Figure 8:
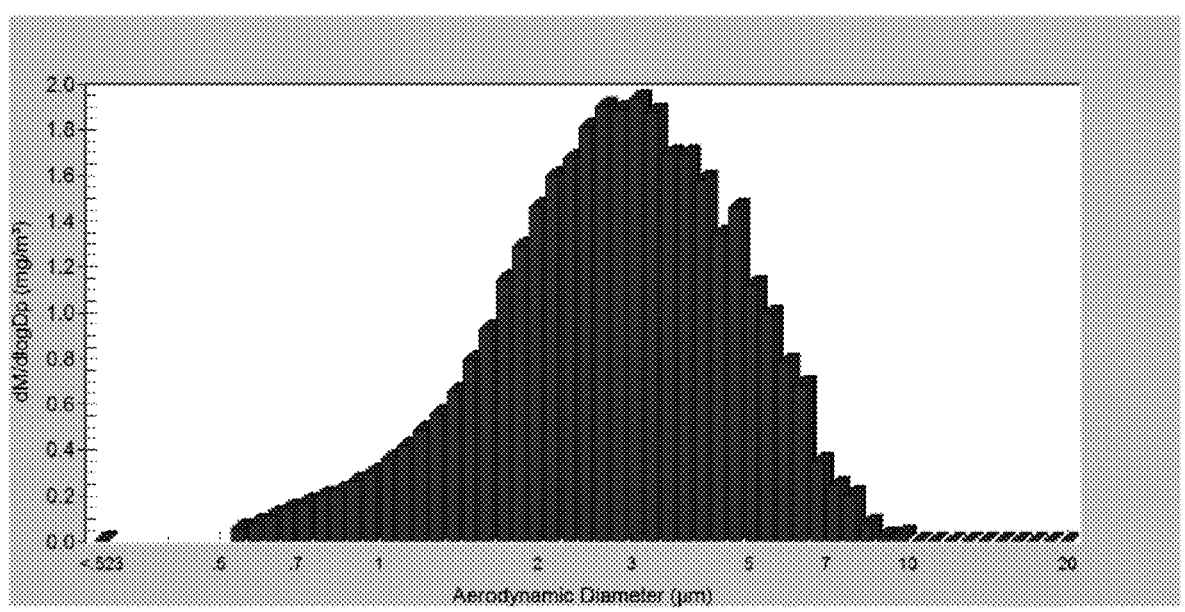
FIG. 8 shows an aerosol particle size distribution of a 50 mg/mL BisEDT in 300 mOsmolality phosphate buffer solution.
Figure 10:
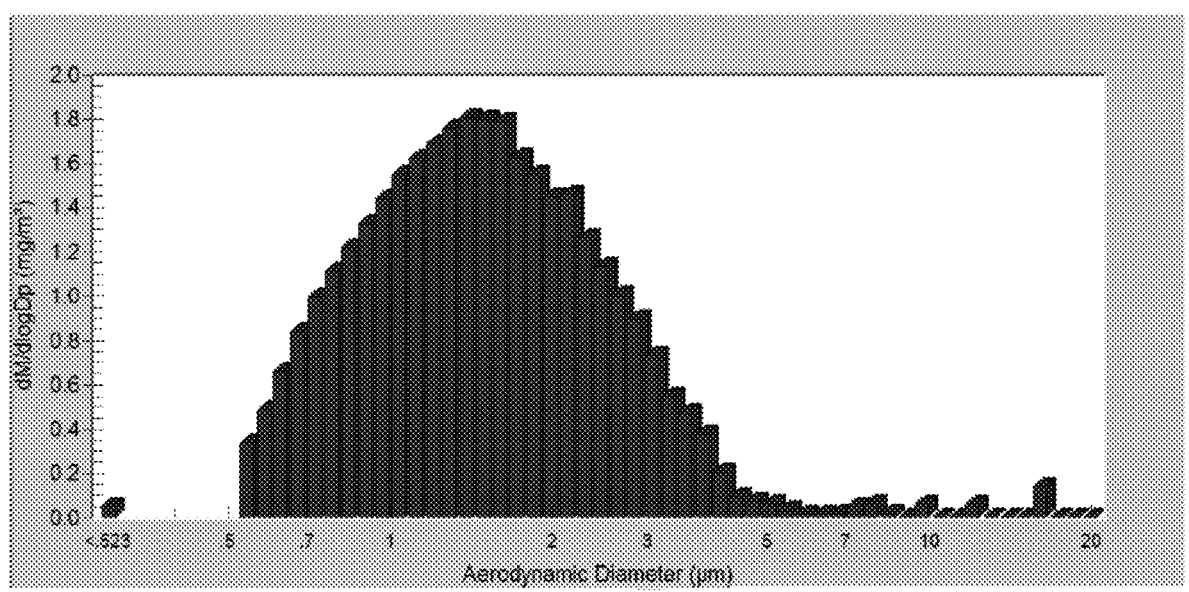
FIG. 10 shows an aerosol particle size distribution of a 2.5 mg/mL BisEDT in 300 mOsmolality phosphate buffer solution.
Figure 11:
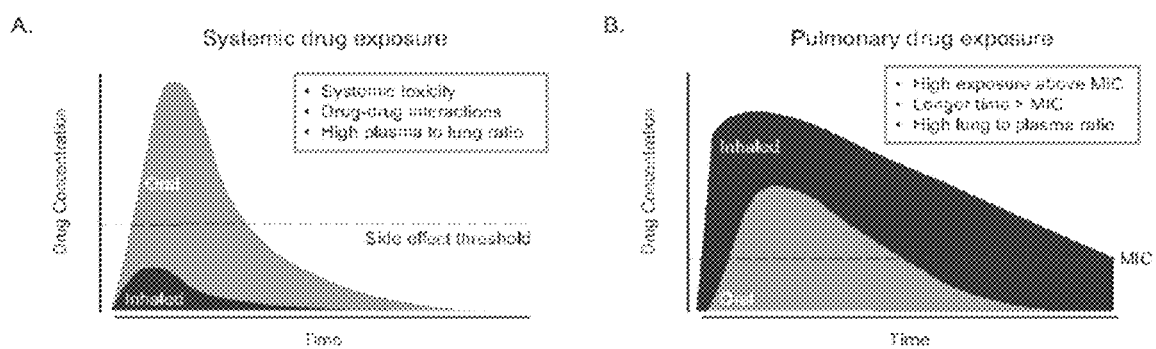
FIG. 11 shows that inhaled drug delivery of an antibiotic increases lung exposure (B) while reducing systemic exposure (A) of the corresponding side effects.

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the verb "comprise" as is used in this description and in the claims and its conjugations are used in its non-limiting sense to mean that items following the word are included, but items not specifically mentioned are not excluded. The present disclosure may suitably "comprise", "consist of", or "consist essentially of", the steps, elements, and/or reagents described in the claims.

Unless specifically stated or obvious from context, as used herein, the term "or" is understood to be inclusive. Unless specifically stated or obvious from context, as used herein, the terms "a", "an", and "the" are understood to be singular or plural.

Throughout the present specification, the terms "about" and/or "approximately" may be used in conjunction with numerical values and/or ranges. The term "about" is understood to mean those values near to a recited value. Furthermore, the phrases "less than about [a value]" or "greater than about [a value]" should be understood in view of the definition of the term "about" provided herein. The terms "about" and "approximately" may be used interchangeably.

An "alkyl" group or "alkane" is a straight chained or branched non-aromatic hydrocarbon which is completely saturated. Typically, a straight chained or branched alkyl group has from 1 to about 20 carbon atoms, e.g. from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A C1-C6 straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl can include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like. Exemplary substituted alkyls are described below. Cycloalkyls can be further substituted with alkyls, alkenyls, alkoxys, alkylthios, aminoalkyls, carbonyl-substituted alkyls, —CF3, —CN, and the like.

The term "Cx-y" when used in conjunction with a chemical moiety, such as, acyl, acyloxy, alkyl, alkenyl, alkynyl, or alkoxy is meant to include groups that contain from x to y carbons in the chain. For example, the term "Cx-yalkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. C0 alkyl indicates a hydrogen where the group is in a terminal position, a bond if internal. The terms "C2-yalkenyl" and "C2-yalkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and can be represented by the general formula alkylS—.

The terms "amine" and "amino" are art-recognized and refer to both unsubstituted and substituted amines and salts thereof, e.g., a moiety that can be represented by

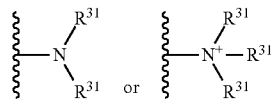

wherein each $R^{31}$ independently represents a hydrogen or a hydrocarbyl group, or two $R^{31}$ are taken together with the N atom to which they are attached complete a heterocycle having from 4 to 8 atoms in the ring structure. The term "aminoalkyl", as used herein, refers to an alkyl group substituted with an amino group.

The term "aryl" as used herein include substituted or unsubstituted single-ring aromatic groups in which each atom of the ring is carbon. In some embodiments, the ring is a 5- to 7-membered ring, e.g. a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "bismuth" refers to the 83$^{rd}$ element of the periodic table, or atoms or ions thereof. Bismuth can occur in the metallic state or in the ionized state, such as in the III or V oxidation state. Bismuth ions can form complexes with anions, either to make bismuth salts, or to form complex anions which are then further complexed with one or more additional cation(s). Bismuth can also form covalent bonds to other atoms, such as sulfur.

As disclosed herein, a "bismuth-thiol compound" or "BT compound" is a compound that has a bismuth atom covalently bound to one, two or three other sulfur atoms present on one or more thiol compounds. The term "thiol" refers to a carbon-containing compound, or fragment thereof, containing an —SH group and can be represented by the general formula R—SH. These thiol compounds include compounds with one, two, three or more S atoms. Thiol compounds can have other functionality, such as alkyl, hydroxyl, carbocyclyl, heterocyclyl, aryl, heteroaryl, amino, and other substituents. Thiol compounds having two or more S atoms can chelate the bismuth atom, such that two S atoms from the same molecule covalently bond with the bismuth atom. Exemplary bismuth-thiol compounds are shown below:

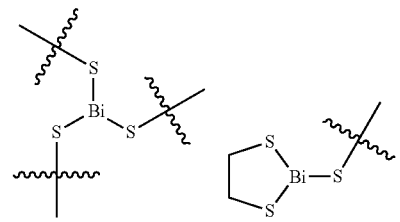

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle can be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle can be selected from saturated, unsaturated and aromatic rings. In an exemplary embodiment, an aromatic ring, e.g., phenyl, can be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" can be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl can be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl can be selected from saturated, unsaturated and aromatic rings. A "cycloalkenyl" group is a cyclic hydrocarbon containing one or more double bonds.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, for example 5- to 7-membered rings, e.g. 5- to 6-membered rings, whose ring structures include at least one heteroatom, for example one to four heteroatoms, e.g. one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, for example, 3- to 10-membered rings, more e.g. 3- to 7-membered rings, whose ring structures include at least one heteroatom, e.g. one to four heteroatoms, e.g. one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but can optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, for example, six or fewer. A "lower alkyl", for example, refers to an alkyl group that contains ten or fewer carbon atoms, e.g. six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, e.g. from 5 to 7.

The term "N-oxide" refers to a zwitterionic group containing a nitrogen atom in the +1 oxidaton state bound to an oxygen atom in the −1 oxidation state. An non-limiting example of an N-oxide is pyridium N-oxide shown below. As used herein, the term "N-oxide" encompasses substituents of other groups having this functionality.

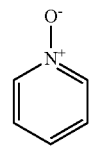

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen can have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "thioalkyl", as used herein, refers to an alkyl group substituted with a thiol group. A "thiol compound" as discussed above can include a thioalkyl as a substituent on the compound structure. A thiol compound can have, for example, one, two, three or more thioalkyl groups.

The term "thioether", as used herein, is equivalent to an ether, wherein the oxygen is replaced with a sulfur.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week.

"Coadministration" refers to the administration of the two agents in any manner in which the pharmacological effects of both agents are manifest in the patient at the same time. Thus, concomitant administration does not require that a single pharmaceutical composition, the same dosage form, or even the same route of administration be used for administration of both agents or that the two agents be administered at precisely the same time. However, in some situations, coadministration will be accomplished most conveniently by the same dosage form and the same route of administration, at substantially the same time.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" means one or more of relieving, alleviating, delaying, reducing, improving, or managing at least one symptom of a condition in a subject. The term "treating" may also mean one or more of arresting, delaying the onset (i.e., the period prior to clinical manifestation of the condition) or reducing the risk of developing or worsening a condition.

The term "managing" includes therapeutic treatments as defined above. Managing includes achieving a steady state level of infection as determined by known methods in the art. The steady state can include evaluation of one or more of the severity of the infection(s), the size and location of the infection(s), the number of different microbial pathogens present in the infection(s), the level of antibiotic tolerant or resistant microbial pathogens, the degree of response to treatment, such as with a BT composition disclosed herein, the degree of biofilm formation and reduction, and the side effects experienced by the subject. During management of an infection, the infection may fluctuate from increasing to lessening in severity, in the amount or extent of infection, amount of side effects experienced by the subject, or other subject outcome indicia. Over a period of time, such as days, month, or years, the degree of management of the infection can be determined by evaluation of the above factors to assess whether the clinical course of infection has improved, is bacteriostatic, or has worsened. In some embodiments, managing an infection include successful treatment of microbial pathogen(s) that are otherwise drug tolerant or drug resistant.

The term "lessen the severity" of infection(s) refers to an improvement in the clinical course of the infection on any measurable basis. Such basis can include measurable indices such as reducing the extent of infection (s), whether the infection(s) are considered acute, the number and identity of microbial pathogens causing the infection(s), the extent of microbial (e.g. bacterial or fungal) biofilms, and side effects experienced by the subject. In some embodiments, lessening the severity of an infection is determined by measurements such as reduction in sputum infection counts (e.g. a reduction in CFU in the sputum). In some embodiments, lessening the severity involves halting a steady decline in outcome to achieve stabilized infection(s), resulting in the subject entering successful management of the infection(s). In other embodiments, lessening the severity can result in substantial to complete treatment of the infection(s). In some embodiments, lessening the severity refers to a lessening of exacerbations associated with the disease or infection (for example by a 1%-99% decrease in exacerbations). In some embodiments, lessening the severity can refer to an increase in lung function (for example by a 1%-99% increase in lung function).

As used herein, the term "exacerbation" refers to an increase in the severity of symptoms during a course of a disease which is mostly associated with a worsening of quality of life. Exacerbations are quite frequent in patients with chronic lung diseases such as CF. By definition, exacerbations are simply a worsening and/or increase in symptoms.

In some embodiments, lessening the severity of infections and/or symptoms can relate to patient-reported outcomes ("PROSs"). A PRO instrument is defined as any measure of a subject's health status that is elicited from the patient and determines how the patient "feels or functions with respect to his or her health condition." PROs are particularly useful in reporting outcomes in CF and whether the severity of symptoms has been reduced or lessened. Such symptoms can be observable events, behaviors, or feelings (e.g., ability to walk quickly, lack of appetite, expressions of anger), or unobservable outcomes that are known only to the patient (e.g., perceptions of pain, feelings of depression).

An "effective amount", as used herein, refers to an amount that is sufficient to achieve a desired biological effect. A "therapeutically effective amount", as used herein refers to an amount that is sufficient to achieve a desired therapeutic effect. For example, a therapeutically effective amount can refer to an amount that is sufficient to improve at least one sign or symptom of infection (e.g. respiratory infection).

A "response" to a method of treatment can include a decrease in or amelioration of negative symptoms, a decrease in the progression of an infection or symptoms thereof, an increase in beneficial symptoms or clinical outcomes, a lessening of side effects, stabilization of the infection, and partial or complete remedy of infection, among others.

"Antibiotic susceptibility or sensitivity" refers to whether a bacteria will be successfully treated by a given antibiotic. Similarly, "Antifungal susceptibility or sensitivity" refers to whether a fungi will be successfully treated by a given antibiotic. Testing for susceptibility can be performed by methods known in the art such as the Kirby-Bauer method, the Stokes method and Agar Broth dilution methods. The effectiveness of an antibiotic in killing the bacteria or preventing bacteria from multiplying can be observed as areas of reduced or stable amount, respectively, of bacterial growth on a medium such as a wafer, agar, or broth culture.

"Antimicrobial tolerance" refers to the ability of a microbe, such as bacteria or fungi, to naturally resist being killed by antibiotics. It is not caused by mutant microbes but rather by microbial cells that exist in a transient, dormant, non-dividing state. Antibiotic or drug tolerance is caused by a small subpopulation of microbial cells termed persisters. Persisters are not mutants, but rather are dormant cells that can survive the antimicrobial treatments that kill the majority of their genetically identical siblings. Persister cells have entered a non- or extremely slow-growing physiological state which makes them insensitive (refractory or tolerant) to the action of antimicrobial drugs. Similarly, "antibiotic tolerance" refers to the ability of a bacteria to naturally resist being killed by antibiotics and "antifungal tolerance" refers to the ability of a fungi to naturally resist being killed by antibiotics.

"Antimicrobial resistance" refers to the ability of a microbe to resist the effects of medication that once could successfully treat the microbe. Microbes resistant to multiple antimicrobials are called multidrug resistant (MDR). Resistance arises through one of three mechanisms: natural resistance in certain types of bacteria, genetic mutation, or by one species acquiring resistance from another. Mutations can lead to drug inactivation, alteration of the drug's binding site, alteration of metabolic pathways and decreasing drug permeability.

As used herein, the terms "antibacterial activity", "antifungal activity" and "antimicrobial activity", with reference to a BT composition of the present disclosure, refers to the ability to kill and/or inhibit the growth or reproduction of a particular microorganism. In certain embodiments, antibacterial or antimicrobial activity is assessed by culturing bacteria, e.g., Gram-positive bacteria (e.g., *S. aureus*), Gram-negative bacteria (e.g., *A. baumannii, E. coli*, and/or *P. aeruginosa*) or bacteria not classified as either Gram-positive or Gram-negative, or fungi according to standard techniques (e.g., in liquid culture or on agar plates), contacting the culture with a BT composition of the present disclosure and monitoring cell growth after said contacting. For example, in a liquid culture, bacteria may be grown to an optical density ("OD") representative of a mid-point in exponential growth of the culture; the culture is exposed to one or more concentrations of one or more BT compounds of the present disclosure, or variants thereof, and the OD is monitored relative to a control culture. Decreased OD relative to a control culture is representative of antibacterial activity (e.g., exhibits lytic killing activity). Similarly, bacterial colonies can be allowed to form on an agar plate, the plate exposed to a BT composition of the present disclosure, or variants thereof, and subsequent growth of the colonies evaluated related to control plates. Decreased size of colonies, or decreased total numbers of colonies, indicate antibacterial activity.

"Biofilm" refers any syntrophic consortium of microorganisms in which cells stick to each other and often also to a surface. These adherent cells become embedded within a slimy extracellular matrix that is composed of extracellular polymeric substances (EPS). Upon formation of biofilms, microbial resistance to antibiotics is up to 1000 times greater compared to that of planktonic bacteria. Bacterial aggregates are clusters of laterally aligned cells can initiate biofilm development, which has a more complex and denser 3-D structure. In some embodiments, the biofilm may comprise one or more species of bacteria (e.g., *Pseudomonas aeruginosa* and *Staphylococcus aureus*) and/or one or more different phyla (e.g., bacteria, virus and fungi).

As used herein, discussion of bacterial or fungal pathogens also encompass any microbe (bacteria and/or fungi) that contributes to the pathological state in the lungs. This includes both recognized and unrecognized microbes, and may also include bacteria or fungi that are not pathogens, but that simply facilitate the activity and presence of pathogens and their biofilms. As an example, embodiments directed to the inhibition of cell viability or cell growth of planktonic cells of the bacterial or fungal pathogen also extend to the inhibition of cell viability or cell growth of planktonic cells of the bacterial and/or fungal microbes that simply facilitate the activity and presence of pathogens and their biofilms.

"Airway surface" and "pulmonary surface," as used herein, include pulmonary airway surfaces such as the bronchi and bronchioles, alveolar surfaces, and nasal and sinus surfaces.

"Saline" as used herein refers to a solution comprised of, consisting of, or consisting essentially of sodium chloride in water. Saline can be hypertonic, isotonic, or hypotonic. In some embodiments, saline can comprise sodium chloride in an amount of from about 0.1% to about 40% by weight, or any range therein, such as, but not limited to, about 0.1% to about 10%, about 0.5% to about 15%, about 1% to about 20%, about 5% to about 25%, about 10% to about 40%, or about 15% to about 35% by weight (in mg/100 mL). In certain embodiments, sodium chloride is included in a solution in an amount of about 0.1%, 0.2%, 0.3%, 0.4%, 0.5%, 0.6%, 0.7% 0.8% 0.9% 1%, 2%, 3% 4% 5% 6% 7% 8%, 9%10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40% by weight (in mg/100 mL), or any range therein.

"Hypertonic saline" as used herein refers to a solution comprised of, consisting of, or consisting essentially of greater than 0.9 wt % sodium chloride in water. In general, the sodium chloride is included in the solution in an amount of from about 0.9% to about 40% by weight, or any range therein, such as, but not limited to, about 1% to about 15%, about 5% to about 20%, about 5% to about 25%, about 10% to about 40%, or about 15% to about 35% by weight. In certain embodiments, sodium chloride is included in the solution in an amount of about 0.9%, 1%, 2%, 3% 4% 5% 6% 7% 8% 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40% by weight, or any range therein.

"Hypotonic saline" as used herein refers to a solution comprised of, consisting of, or consisting essentially of less than 0.9 wt % sodium chloride in water. In some embodiments, sodium chloride is included in the solution in an amount of about 0.9%, 0.8%, 0.7%, 0.6%, 0.5%, 0.4%, 0.3%, 0.2%, 0.1% by weight, or any range therein.

"Isotonic saline" as used herein refers to a solution comprised of, consisting of, or consisting essentially of 0.9 wt % sodium chloride in water.

According to some embodiments, saline (e.g., hypertonic saline) can include an excipient. An excipient can be a pharmaceutically acceptable excipient. "Pharmaceutically acceptable" as used herein means that the compound or composition is suitable for administration to a subject to achieve the treatments described herein, without unduly deleterious side effects in light of the severity of the disease and necessity of the treatment. Exemplary excipients include, but are not limited to, a buffer and/or a buffering agent (e.g., an anion, a cation, an organic compound, a salt, etc.). Exemplary buffers include, but are not limited to, carbonic acid/carbonate/bicarbonate-based buffers, disodium hydrogen phthalate/sodium dihydrogen orthophosphate-based buffers, tris(hydroxymethyl)aminomethane/hydrochloric acid-based buffers, barbitone sodium/hydrochloric acid-based buffers, and any combination thereof. Exemplary buffering agents include, but are not limited to, carbonic acid, carbonate, bicarbonate, disodium hydrogen phthalate, sodium dihydrogen orthophosphate, tris(hydroxymethyl)aminomethane, hydrochloric acid, barbitone sodium, dissolved $CO_2$ (e.g., $CO_2$ formulated at a pH of greater than 6.6), and any combination thereof. In certain embodiments, saline comprises a bicarbonate buffer excipient, such as a bicarbonate anion ($HCO_3$). In some embodiments, hypertonic saline can include sodium bicarbonate, sodium carbonate, carbonic acid, and/or dissolved $CO_2$ formulated at a pH of greater than 6.5. Additional ingredients can be included as desired depending upon the particular condition being treated, as discussed further below.

As used herein, the term "volumetric median diameter" or "VMD" of an aerosol is the particle size diameter identified such that half of the mass of the aerosol particles is contained in particles with larger diameter than the VMD, and half of the mass of the aerosol particles is contained in particles with smaller diameter than the VMD. VMD is typically measured by laser diffraction.

"Mass median aerodynamic diameter" or "MMAD" is a measure of the aerodynamic size of a dispersed aerosol particle. The aerodynamic diameter is used to describe an aerosolized particle in terms of its settling behavior, and is the diameter of a unit density sphere having the same settling velocity, generally in air, as the particle in question. The aerodynamic diameter encompasses particle shape, density and physical size of a particle. As used herein, MMAD refers to the midpoint or median of the aerodynamic particle size distribution of an aerosolized particle determined by cascade impaction and/or laser time of flight and/or cascade impactor.

"Mass median diameter" or "MMD" is a measure of mean particle size. Any number of commonly employed techniques can be used for measuring mean particle size.

As used herein, "D90" refers to the 90% value of particle diameter (either the microparticle or aerosolized particle). For example if D90=1 µm, 90% of the particles are smaller than 1 µm. Similarly, "D80" refers to the 80% value of particle diameter (either the microparticle or aerosolized particle), "D70" refers to the 70% value of particle diameter (either the microparticle or aerosolized particle), "D60" refers to the 60% value of particle diameter (either the microparticle or aerosolized particle), "D50" refers to the 50% value of particle diameter (either the microparticle or aerosolized particle), "D40" refers to the 40% value of particle diameter (either the microparticle or aerosolized particle), "D30" refers to the 30% value of particle diameter (either the microparticle or aerosolized particle), "D20" refers to the 20% value of particle diameter (either the microparticle or aerosolized particle), "D10" refers to the 10% value of particle diameter (either the microparticle or aerosolized particle).

As used herein, "monodisperse" refers to a collection of particles (bulk or aerosol dispersion) comprising particles of a substantially uniform MMD and/or MMAD and/or VMD.

As used herein, the term "deposition efficiency" refers to the percentage of the delivered dose that is deposited into the area of interest. Thus, the deposition efficiency of a method and/or system for delivering an aerosolized medicament into the lungs is the amount by mass of the aerosol deposited into the lungs divided by the total amount of the aerosol delivered by the system to the nares.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" other active agents would either completely lack other active agents, or so nearly completely lack other active agents that the effect would be the same as if it completely lacked other active agents. In other words, a composition that is "substantially free of" an ingredient or element or another active agent may still contain such an item as long as there is no measurable effect thereof.

Methods of Use

Cystic fibrosis (CF), an autosomal recessive disorder, is caused by functional deficiency of the cAMP-activated plasma membrane chloride channel, cystic fibrosis transmembrane conductance regulator (CFTR), which results in pulmonary and other complications.

In cystic fibrosis patients, the absence or dysfunction of CFTR leads to exocrine gland dysfunction and a multisystem disease, characterized by pancreatic insufficiency and malabsorption, as well as abnormal mucociliary clearance in the lung, mucostasis, chronic lung infection and inflammation, decreased lung function and ultimately respiratory failure.

The loss of a functional CFTR channel at the plasma membrane disrupts ionic homeostasis and airway surface hydration leading to reduced lung function. Reduced periciliary liquid volume and increased mucus viscosity impede mucociliary clearance resulting in chronic infection and inflammation.

In healthy individuals, clearance of lung bacteria relies on the concerted action of two anatomic features: (i) the ciliated apical surface of the airway epithelium and (ii) a mucus layer that lines the airway lumen. The airway cilia beat synchronously, creating a steady current that continually moves the mucus layer upward toward the nasopharynx. The mucus layer is biphasic, consisting of an upper, viscous layer that serves to trap particulates and microorganisms and a lower, more fluid layer in which the cilia beat. When functioning normally, this clearance system traps foreign bodies in the mucus and subsequently carries them to the nasopharynx, where they are expectorated and swallowed.

However, abnormal secretory characteristics of the CF airway cells due to the ion imbalance caused by the mutant CFTR protein alter the viscosity of the airway fluid, such that the normally serous "periciliary" layer becomes thicker, inhibiting escalator action that clears foreign bodies. Bacteria are trapped in the mucous and result in an ongoing infection in the lungs.

CF patients routinely produce sputum from the lungs through coughing, aided by other physical therapies designed to free mucous from the lungs. Many of the organisms that are isolated from CF sputum are pathogens that often benignly colonize the upper respiratory tract (e.g., non-typeable *H. influenzae*) or the nose (e.g., *S. aureus*) or are common environmental organisms that behave as pathogens only under certain opportunistic situations (e.g., *P. aeruginosa*). Different bacteria and the level of infection in the lungs can be determinative of a CF patient's symptoms and outcome. For example, the presence of *S. aureus* and the absence of *P. aeruginosa* predicts long term survival in CF patients after the age of 18 years. In addition, the potential for increasing *P. aeruginosa* colonization as a consequence of suppression of *S. aureus* infection may be relevant for some patients.

Of all the bacteria that can colonize in the lungs of CF patients, chronic *P. aeruginosa* airway infection and the accompanying inflammatory response are the major clinical problems for CF patients today. While antibiotic chemotherapy and chemoprophylaxis have reduced the morbidity and early mortality of CF patients from this infection, the intrinsic ability of *P. aeruginosa* to develop resistance to many commonly used antibiotics probably contributes to the inability to eradicate *P. aeruginosa* from CF patients' lung and ultimately allows this microbe to be highly problematic for these patients.

CF patients can acquire *P. aeruginosa* in their respiratory tracts at any time, with most studies indicating that 70 to 80% CF patients are infected by their teen years. *P. aeruginosa* infection probably initially occurs within the first 3 years of life. After the onset of chronic infection, patients experience episodic exacerbations that can benefit from antibiotic chemotherapy. Infection may result from social contacts or may be hospital acquired, but the diversity of *P. aeruginosa* clones isolated from CF patients suggests that most clinical isolates originate in the environment. CF patients chronically infected by *P. aeruginosa* show a steeper lung function decline (expressed as forced expired volume in 1 second (FEV1) decline over time), a higher number of pulmonary exacerbations, more hospital admissions and higher mortality than *P. aeruginosa*-free patients. The effects of *P. aeruginosa* are more severe if chronic infection develops early.

*P. aeruginosa* infections can change over time to develop a mucoid phenotype, which can initiate the chronic-infection stage of cystic fibrosis. The mucoid phenotype results from bacterial production of a polysaccharide known as both alginate and mucoid exopolysaccharide (MEP) and plays an important role in bacterial evasion of the host immune response. The MEP/alginate itself is able to promote bacterial survival in the face of host immune effectors. Alginate overproduction by *P. aeruginosa* correlates with the onset of significant deterioration in lung function. In addition, *P. aeruginosa* can grow as a biofilm, which increases bacterial resistance to phagocytic action and antibiotic efficacy.

Bacterial biofilms are a matrix of cells that adhere to each other and often a surface, such as lung mucosa. The bacterial cells become embedded within an extracellular matrix formed from extracellular polymeric substances, such as polysaccharides, proteins, lipids and DNA. Biofilm bacterial cells are physiologically different than planktonic cells in which a large number of genes are differentially regulated. Biofilms can also be more resistant to antibiotics given the shelter provided by the matrix. Biofilms of *P. aeruginosa* and other bacteria that are present in the lungs of CF patients increase the difficulty of successful infection management and reduction. Combinations of CF-relevant bacteria forming multispecies biofilms containing *P. aeruginosa* have demonstrated greater resistance, virulence and pathogenicity than comparable single-species biofilms. The presence of such complex biofilms in the lungs of CF patients is considered to be largely responsible for the chronic, persistent nature of these pulmonary infections, which are not only responsible for chronic, ongoing and progressive morbidity, but are also ultimately responsible for mortality in this population.

In addition to *P. aeruginosa*, other pathogens commonly found in CF patients' lungs include, but are not limited to, *Haemophilus influenzae, Staphylococcus aureus, Staphylococcus warneri, Staphylococcus lugdunensis, Staphylococcus epidermidis, Streptococcus milleri/anginous, Streptococcus pyogenes*, non-tuberculosis *mycobacterium, Mycobacterium tuberculosis, Burkholderia* spp., *Achromobacter xylosoxidans, Pandoraea sputorum, Stenotrophomonas maltophilia, Alcaligenes xylosoxidans, Haemophilus pittmaniae, Serratia marcescens, Candida albicans*, drug resistant *Candida albicans, Candida glabrata, Candida krusei, Candida guilliermondii, Candida auris, Candida tropicalis, Aspergillus niger, Aspergillus terreus, Aspergillus fumigatus, Aspergillus flavus, Morganella morganii, Inquilinus limosus, Ralstonia mannitolilytica, Pandoraea apista, Pandoraea pnomenusa, Pandoraea sputorum, Bdellovibrio bacteriovorus, Bordetella bronchiseptica, Vampirovibrio chlorellavorus, Actinobacter baumanni, Cupriadidus metallidurans, Cupriavidus pauculus, Cupriavidus respiraculi, Delftia acidivordans, Exophilia dermatitidis, Herbaspirillum frisingense, Herbaspirillum seropedicae, Klebsiella pneumoniae, Pandoraea norimbergensis, Pandoraea pulmonicola, Pseudomonas mendocina, Pseudomonas pseudoalcaligenes, Pseudomonas putida, Pseudomonas stutzeri, Ralstonia insidiosa, Ralstonia pickettii, Neisseria gonorrhoeae*, NDM-1 positive *E. coli, Enterobacter cloaca*, Vancomycin-resistant *E. faecium*, Vancomycin-resistant *E. faecalis, E. faecium, E. faecalis*, Clindamycin-resistant *S. agalactiae, S. agalactiae, Bacteroides fragilis, Clostridium difficile, Streptococcus pneumonia, Moraxella catarrhalis, Haemophilus haemolyticus, Haemophilus parainfluenzae, Chlamydophilia pneumoniae, Mycoplasma pneumoniae, Atopobium* spp., *Sphingomonas* spp., *Saccharibacteria* spp., *Leptotrichia* spp., *Capnocytophaga, Oribacterium* spp., *Aquabacterium* spp., *Lachnoanaerobaculum* spp., *Campylobacter* spp., *Acinetobacter* spp., *Agrobacterium* spp., *Bordetella* spp., *Brevundimonas* spp., *Chryseobacterium* spp., *Delftia* spp., *Enterobacter* spp., *Klebsiella* spp., *Pandoraea* spp., *Pseudomonas* spp., *Ralstonia* spp., and *Prevotella* spp.

Exemplary non-tuberculosis *mycobacterium* include, but are not limited to, *Mycobacterium abscessus, Mycobacterium avium, Mycobacterium intracellulare, Mycobacterium fortuitum, Mycobacterium gordonae, Mycobacterium kansasii, Mycobacterium avium* complex (MAC), *Mycobacterium abscessus* complex (MABSC) *Mycobacterium marinum, Mycobacterium terrae* and *Mycobacterium cheloni*.

Exemplary species of *Burkholderia* include, but are not limited to, *Burkholderia cepacia, Burkholderia multivorans, Burkholderia cenocepacia, Burkholderia stabilis, Burkholderia vietnamiensis, Burkholderia dolosa, Burkholderia ambifaria, Burkholderia anthina, Burkholderia pyrrocinia, Burkholderia gladioli, Burkholderia ubonensis, Burkholderia arboris, Burkholderia latens, Burkholderia lata, Burkholderia metallica, Burkholderia seminalis, Burkholderia contaminans,* and *Burkholderia diffusa*.

In some embodiments, the bacterial pathogen is selected from *Pseudomonas aeruginosa*, multi drug-resistant *Pseudomonas aeruginosa, Staphylococcus aureus*, multi drug-resistant *Staphylococcus aureus*, methicillin resistant *Staphylococcus aureus, Mycobacterium abscessus, Mycobacterium avium, Burkholderia cepacia, Burkholderia multivorans, Burkholderia cenocepacia, Burkholderia dolosa, Achromobacter xylosoxidans, Stenotrophomonas maltophilia Staphylococcus epidermidis*, and *Burkholderia vietnamiensis*. In certain embodiments, the bacterial pathogen is selected from *Haemophilus influenzae, Pseudomonas aeruginosa*, and *Staphylococcus aureus*. In certain embodiments, the bacterial pathogen is selected from biofilms of *Pseudomonas aeruginosa, Burkholderia cenocepacia, Burkholderia cepacia* complex, *Mycobacterium abscessus, Mycobacterium avium, Achromobacter* spp., *Staphylococcus epidermidis, Stenotrophomonas maltophilia,* and *Staphylococcus aureus*.

In some embodiments, the bacterial pathogen exhibits resistance to one or more antibiotics. Methicillin-resistant *S. aureus* (MRSA) is an example of a singly resistant strain that is difficult to treat in CF patients and the population at large, while even more challenging multi-drug resistant (MDR) strains can occur in bacteria such as *P. aeruginosa* and *S. aureus*. For example, a bacterial pathogen can become resistant to known standards of antibiotic care, including, but not limited to, amikacin, aztreonam, methicillin, vancomycin, nafcillin, gentamicin, ampicillin, chloramphenicol, doxycycline and tobramycin. In some embodiments, the resistant antibiotic is amikacin, aztreonam, or tobramycin.

Long-term, repeated treatment with antibiotics to treat CF-associated infections typically results in development of antibiotic-resistance, characterized by the presence of microbial biofilms. Recent research has repeatedly demonstrated a correlation between multi-drug resistant (MDR) bacteria, and stronger, more prolific biofilm-forming capabilities. Biofilm involvement in the lung is considered highly immunogenic, accelerating structural lung damage. Further, bacteria within biofilms are protected from antibiotics, which increases the minimal inhibitory concentration of such antibiotics. Biofilms tend to reduce the antimicrobial activity of aminoglycosides and beta-lactam antibiotics by both changing the pH of the respiratory mucosa and through the production of beta-lactamase enzymes. The involvement of biofilm-forming bacteria in CF is correlated with decreased lung function and reduced Quality of Life, decreased response to antibiotic therapy, increased exacerbations, and, over time, reduced survival.

In some embodiments, the BT composition is administered by inhalation, either orally or nasally, using an aerosol device, such as a nebulizer. A nebulizer can administer the BT composition topically to the lung tissue, which can include the lung mucosa, the alveoli (e.g. deep lung alveoli), the bronchi and/or the bronchioles. Thus, in some embodiments, the present disclosure provides for administration of the BT composition to the deep lung region of the lung (e.g. the deep lung alveoli). Local topical administration of the BT composition provides several key advantages over systemic antibiotic therapies. The term "systemic" refers to administration of a medication into the circulatory system of the subject such that the majority of the entire body can be exposed. Systemic administration of a medication can occur enterally (absorption through the gastrointestinal tract, e.g. oral administration) or parenterally (absorption through injection or infusion, e.g. intravenously).

Systemic anti-infective products have several disadvantages relating to the treatment of localized infections, including: (a) difficulty in achieving a therapeutically effective concentration at the site of local infection, particularly in the case of infections associated with topical locations, such as pulmonary airways, (b) frequent unintended toxic effects on organ systems exposed through systemic circulation, and (c) increased generation of antibiotic-resistant bacteria as a result of the widespread exposure of the body's normal flora to the anti-infective agent, (d) resulting in greater likelihood of transmission of such antibiotic-resistant bacteria to others as a result of long term sustained/repeated exposure of the entire body's complement of normal flora and (e) reduced preservation of the beneficial influence of the healthy normal flora throughout the body due to extensive systemic exposure.

In FIG. 11, plasma concentration is depicted for an orally and pulmonary dosed drug. Oral dosing (A) can result in high plasma concentrations that may lead to toxicity and varied inter-patient exposure (variable absorption and variable first-pass, hepatic clearance) or drug-drug interactions. High plasma exposure is necessary to achieve therapeutic exposure in the lungs. In contrast, inhaled dosing for topical lung indications requires a lower total dose to achieve an efficacious MIC, which results in significantly less systemic exposure. Inhaled dosing (B) achieves higher local concentrations in the lung that significantly exceed the MIC of the drug over a long period of time. Due to the delivery of high concentrations of drug directly to the lung, the achieved pulmonary concentrations following inhalation may greatly exceed those achieved by oral dosing. From previous experience with inhaled antibiotics, the lung concentration of drug upon inhalation is >100× greater than upon systemic/oral administration of the same dose.

In some embodiments, one or more of the following symptoms (e.g. cystic fibrosis-related symptoms) is lessened in severity in the subject: cough, wheezing, breathlessness, bronchiectasis, nasal polyps, hemoptysis, respiratory failure, and pulmonary exacerbation. Additional non-cystic fibrosis related infections may also be lessened in severity. FIG. 11 demonstrates the differences in side effect severity and efficacy of an inhaled antibiotic vs. one delivered systemically. Thus, inhaled formulations of the BT compositions disclosed herein provide a more targeted and effective antibiotic treatment than a corresponding formulation administered systemically.

BT compounds are known broad-spectrum antimicrobial (and anti-biofilm) small molecule drug product for the treatment of chronic, ultimately life-threatening pulmonary infections secondary to CF. Its efficacy extends to Gram-positive, antibiotic-resistant pathogens including methicillin-resistant *Staphylococcus aureus* (MRSA, including community-associated [CA]-MRSA), methicillin-resistant

*Staphylococcus epidermidis* (MRSE), and vancomycin-resistant *Enterococcus* (VRE). BT compounds are also potent against Multi-drug-resistant (MDR) Gram-negative pathogens including *Pseudomonas aeruginosa, Escherichia coli, Klebsiella pneumoniae* (including, in all of the afore-mentioned bacteria, carbapenem-resistant strains), and *Acinetobacter baumannii*.

BT compounds have the dual ability to overcome a) a very diversified spectrum of antibiotic resistance profiles (due to evolution/diversification driven by persistence, time and isolation in many different anatomical regions throughout the pulmonary airways), and b) antibiotic-resistant and MDR biofilms.

Disclosed herein are methods of treating, managing or lessening the severity of cystic fibrosis (CF) symptoms and infections in a subject, the method comprising administering to the subject a bismuth-thiol (BT) composition that comprises at least one BT compound. Also disclosed herein are methods of treating, managing or lessening the severity of symptoms and infections associated with one or more pulmonary diseases or infections in a subject, including non-CF associated diseases, the method comprising administering to the subject a bismuth-thiol (BT) composition that comprises at least one BT compound. In some embodiments, the subject has at least one pulmonary infection, such as a CF-related pulmonary infection. In other embodiments, the subject has at least two pulmonary infections and the infections are either concurrent or successive in order. The pulmonary infections could be cause by the same microbial pathogen and be located in two different lungs, or lobes of the lung. In other embodiments, the pulmonary infections could be caused by different microbial pathogens and be located in the same lung, or lobe of the lung. In some embodiments, the pulmonary infection is in one lung, while in others it is present in both lungs. In certain embodiments, the pulmonary infection is in one or more of the three lobes of the right lung. In other embodiments, the pulmonary infection is in one or both of the two lobes of the left lung. Any combination of one or more microbial pathogens, microbial pathogen quantity, and infection location in the lung is contemplated within the term "pulmonary infection". In some embodiments, the pulmonary infection is a bronchiectasis infection, pneumonia, valley fever, allergic bronchopulmonary aspergillosis (ABPA), ventilator acquired pneumonia, hospital acquired pneumonia, community acquired pneumonia, ventilator associated tracheobronchitis, lower respiratory tract infection, non-tuberculous Mycobacteria, anthrax, legionellosis, pertussis, bronchitis, Bronchiolitis, COPD-associated infection, and post-lung transplantation. In some embodiments, the pulmonary infection is a bronchiectasis infection.

In some embodiments, the pulmonary infection contains one or more bacterial or fungal pathogens. In some embodiments, the disclosed methods comprise treating the CF-related pulmonary infection. In some embodiments, the disclosed methods comprise managing the CF-related pulmonary infection. In some embodiments, the disclosed methods comprise lessening the severity of the CF-related pulmonary infection.

In some embodiments, the methods of the present invention may include treating, managing or lessening the severity of symptoms and infections associated with one or more pulmonary diseases or infections in a subject by administering to the subject a bismuth-thiol (BT) composition that comprises at least one BT compound. In a specific embodiment, the compound is bismuth-1,2-ethanedithiol (BisEDT).

In certain embodiments, the pulmonary infection is located in or on the lung mucosa, the bronchi and/or the bronchioles. In other embodiments, the pulmonary infection is located on the surface of or within a bacterial biofilm, aggregated bacteria, a fungal biofilm, or aggregated fungi. In some embodiments, the pulmonary infection is located in the sputum wherein the pulmonary infection involves and is, at least in part, present in the mucous/sputum layers associated with the lungs. In certain embodiments, the bacterial pathogen comprises one or more of gram-positive bacteria and gram-negative bacteria. The bacterial pathogen can comprise one or more of a bacterial biofilm and planktonic bacteria. In some embodiments, the fungal pathogen comprises one or more of a fungal biofilm and planktonic fungi. In certain embodiments, the fungal pathogen is *Candida albicans*, drug resistant *Candida albicans, Candida glabrata, Candida krusei, Candida guilliermondii, Candida auris, Candida tropicalis, Aspergillus niger, Aspergillus terreus, Aspergillus fumigatus*, and/or *Aspergillus flavus*.

In some embodiments, the method comprises at least one of: (i) reducing the microbial (e.g. bacterial or fungal) biofilm, (ii) impairing growth of the microbial (e.g. bacterial or fungal) biofilm, and (iii) preventing reformation of the microbial (e.g. bacterial or fungal) biofilm. In other embodiments, the BT composition treats, manages or lessens the severity of the pulmonary infection by one or more of:

prevention of the infection by the bacterial or fungal pathogen; —prevention of elaboration or secretion of exotoxins from the bacterial or fungal pathogen;

reduction of the bacterial or fungal pathogen (e.g. as measure by amount or titer);

inhibition of cell viability or cell growth of planktonic cells (e.g. substantially all of the cells) of the bacterial or fungal pathogen;

inhibition of biofilm formation by the bacterial or fungal pathogen;

inhibition of biofilm viability or biofilm growth of biofilm-form cells (e.g. substantially all of the cells) of the bacterial or fungal pathogen; and reducing the viscosity of the sputum.

In some embodiments, the bismuth-thiol composition comprises a plurality of microparticles that comprise a bismuth-thiol (BT) compound, substantially all of said microparticles having a volumetric mean diameter of from about 0.4 µm to about 5 µm, and wherein the BT compound comprises bismuth or a bismuth salt and a thiol-containing compound. In some embodiments, the bismuth salt is bismuth nitrate, bismuth subnitrate, or bismuth chloride. In some embodiments, the thiol-containing compound comprises one or more agents selected from 1,2-ethane dithiol, 2,3-dimercaptopropanol, pyrithione, dithioerythritol, 3,4 dimercaptotoluene, 2,3-butanedithiol, 1,3-propanedithiol, 2-hydroxypropanethiol, 1-mercapto-2-propanol, dithioerythritol, dithiothreitol, cysteamine, and alpha-lipoic acid. In some embodiments, at least 60%, 65%, 70, 75%, 80%, 90%, or 95% of the microparticles have a volumetric mean diameter of from about 0.4 µm to about 3 µm, or from about 0.5 µm to about 2 µm, or from about 0.7 µm to about 2 µm, or from about 0.8 µm to about 1.8 µm, or from about 0.8 µm to about 1.6 µm, or from about 0.9 µm to about 1.4 µm, or from about 1.0 µm to about 2.0 µm, or from about 1.0 µm to about 1.8 µm, or any narrow ranges between the specific ranges described above.

In some embodiments of the presently disclosed methods, at least 60%, 65%, 70, 75%, 80%, 90%, or 95% of the microparticles have a volumetric mean diameter of from about 0.6 µm to about 2.5 µm. In some embodiments, substantially all of the microparticles have a VMD of from about 0.6 µm to about 2.5 µm. In some embodiments, at least 70% of the aerosolized particles have a MMAD of about 0.9 µm to about 3 µm. In some embodiments, the composition is a suspension of microparticles having a volumetric mean diameter (VMD) from about 0.6 µm to about 2.5 µm and/or a mass median aerodynamic diameter (MMAD) from about 0.9 µm to about 3 µm. In some embodiments, the bismuth-thiol composition comprises a plurality of microparticles that comprise a bismuth-thiol (BT) compound, substantially all of said microparticles having a volumetric mean diameter of from about 0.4 µm to about 5 µm, and wherein the BT compound comprises bismuth or a bismuth salt and a thiol-containing compound.

In some embodiments, the BT composition comprises one or more BT compounds selected from $C_6H_{12}Bi_2S_6$
MW: 694.48

Combination Treatments

In certain embodiments, compounds disclosed herein can be used alone or conjointly administered with another type of therapeutic agent. As used herein, the phrase "conjoint administration" refers to any form of administration of two or more different therapeutic compounds such that the bismuth-2,3-dimercaptopropanol (2:3 molar ratio, BisBAL)
bismuth-dithioerythritol (2:3 molar ratio, BisERY)
bismuth-4-methyl-1,2-benzenedithiol (2:3 molar ratio, BisTOL)
bismuth-2,3-butanedithiol (BisBDT)
bismuth-2,3-butanedithiol, 2-mercaptopyridine N-oxide (2:1:2 molar ratio, BisBDT/PYR)
bismuth-2,3-dimercaptopropanol, 2-mercaptopyridine N-oxide (2:1:2 molar ratio, BisBAL/PYR)
bismuth-1,2-ethanedithiol, 2-mercaptopyridine N-oxide (2:1:2 molar ratio, BisEDT/PYR)
bismuth-4-methyl-1,2-benzenedithiol, 2-mercaptopyridine N-oxide (2:1:2 molar ratio, BisTOL/PYR)
bismuth-1,3-propanedithiol, 2-mercaptopyridine N-oxide (2:1:2 molar ratio, BisPDT/PYR)
bismuth-dithioerythritol, 2-mercaptopyridine N-oxide (2:1:2 molar ratio, BisERY/PYR)
bismuth-1-mercapto-2-propanol, 1,2-ethanedithiol (1:1:1 molar ratio, BisHPT/EDT)
bismuth with ethanedithiol and 2-mercaptobenzoimidazole (BisEDT/2MBI (1:1))
bismuth with ethanedithiol and 2-mercaptopyrimidine (BisEDT/SPN (2MPMD) (1:1))
bismuth with ethanedithiol and 3-mercapto-1,2,4-triazole (BisEDT/3MTZ (1:1))
bismuth with ethanedithiol and 1-propane thiol (BisEDT/PT (1:1))
bismuth with ethanedithiol and cysteamine (BisEDT/CSTMN (1:1))
bismuth with ethanedithiol and 3-mercaptopropionic acid (BisEDT/3MPA (1:1))
bismuth with lipoic acid (reduced) (BisALA (BisLipo) (1:1.5))
bismuth with 2-mercaptolpyridine N-oxide and 2-mercaptobenzoimidazole (BisPYR/2MBI (1:1))
bismuth with 2-mercaptolpyridine N-oxide and cysteamine (BisPYR/CSTMN (1:1))
bismuth with 2,3-dimercapto-1-propanol and 2-mercaptobenzoimidazole (BisBAL/2MBI (1:1))
bismuth with 2,3-dimercapto-1-propanol and cysteamine (BisBAL/CSTMN (1:1))
bismuth with 3,4 dimercapto toluene and 2-mercaptobenzoimidazole (BisTOL/2MBI (1:1))
bismuth with 3,4 dimercapto toluene and cysteamine (BisTOL/CSTMN (1:1))
bismuth with 2-mercapto pyridine (BisEDT/MPYR)

In some embodiments, the BT composition comprises one or more BT compounds selected from Bis-BAL, BisEDT, Bis-dimercaprol, Bis-DTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, Bi-sPyr/EDT, Bis-Pyr/PDT, Bis-Pyr/Tol, Bis-Pyr/Ery, bismuth-1-mercapto-2-propanol, and BisEDT/2-hydroxy-1-propanethiol. In other embodiments, the BT compound is selected from one or more of BisEDT, Bis-Bal, Bis-Pyr, Bis-Ery, Bis-Tol, Bis-BDT, or BisEDT/2-hydroxy-1-propane thiol. As used herein, MB-1B3 (or MB-1-B3) refers to BisEDT; MB-6 refers to BisBDT; MB-8-2 refers to BisBDT/PYR; and MB-11 refers to BisEDT/PYR.

In some embodiments, the bismuth thiol compound is BisEDT, which has the following structure:

second compound is administered while the previously administered therapeutic compound is still effective in the body (e.g., the two compounds are simultaneously effective in the subject). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds of the disclosure with one or more additional therapeutic agent(s) provides improved efficacy relative to each individual administration of the compound of the disclosure or the one or more additional therapeutic agent(s). In certain such embodiments, the conjoint administration provides an additive effect or synergistic effect, wherein an additive effect refers to the sum of each of the effects of individual administration of the compound of the disclosure and the one or more additional therapeutic agent(s). In some embodiments, the subject receives conjoint administration of a therapy for another disease, disorder, or condition. In some embodiments, the other therapy is a CFTR modulator or bronchodilator.

In some embodiments, the methods of the present disclosure comprise coadministering or conjointly administering to the subject an antibiotic selected from amikacin, tobramycin, gentamicin, piperacillin, mezlocillin, ticarcillin, imipenum, ciprofloxacin, ceftazidime, aztreonam, ticaricillin-clavulanate, dicloxacillin, amoxicillin, ticarcillin-clavulanate, trimethoprim-sulfamethoxazole, cephalexin, piperacillin-tazobactam, linezolid, daptomycin, vancomycin, metronidazole, clindamycin, colistin, tetracycline, levofloxacin, amoxicillin and clavulanic acid (Augmentin®), cloxacillin, dicloxacillin, cefdinir, cefprozil, cefaclor, cefuroxime, erythromycin/sulfisoxazole, erythromycin, clarithromycin, azithromycin, doxycycline, minocycline, tigecycline, imipenem, meripenem, colistimethate/Colistin®, methicillin, oxacillin, nafcillin, cabenicillin, azlocillin, piperacillin and tazobactam (Zosyn®), cefepime, ethambutol, rifampin, and meropenem. In some embodiments, the antibiotic is selected from meropenem, ceftazidime, tobramycin, amikacin, aztreonam, ciprofloxacin, colistin, and levofloxacin.

In certain embodiments of the present disclosure, the therapeutic agents that can be conjointly administered with compounds of the disclosure, such as a bismuth-thiol compound, include known antibiotics. In some embodiments, the antibiotic is selected from methicillin, vancomycin, nafcillin, gentamicin, ampicillin, chloramphenicol, doxycycline, colistin amikacin, aztreonam, and tobramycin. In some embodiments, the antibiotic is selected from tobramycin, imipenem, tetracycline, and minocycline. In some embodiments, the antibiotic is administered systemically after revision surgery. In some embodiments, the antibiotic is administered prior to revision surgery. The conjointly administered therapeutic agent, such as an antibiotic, can be administered with any suitable frequency and at any suitable dosage. Such dosage amount and frequency can be determined by those of ordinary skill in the art.

In certain embodiments, BT compounds of the disclosure can be conjointly administered with one or more other BT compounds of the disclosure. Moreover, such combinations can be conjointly administered with other therapeutic agents.

Pharmaceutical Compositions

The compositions and methods of the present disclosure can be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the disclosure and a pharmaceutically acceptable carrier. Pharmaceutically acceptable carriers are well known in the art and include, for example, aqueous solutions such as water, physiologically buffered saline, physiologically buffered phosphate, or other solvents or vehicles such as glycols, glycerol, oils such as olive oil, or injectable organic esters. In some embodiments, when such pharmaceutical compositions are for human administration, the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as lyophile for reconstitution, powder, solution, syrup, injection or the like. The composition can also be present in a solution suitable for topical administration.

A pharmaceutically acceptable carrier can contain physiologically acceptable agents that act, for example, to stabilize, increase solubility or to increase the absorption of a compound such as a compound of the disclosure. Such physiologically acceptable agents include, for example, carbohydrates, such as glucose, sucrose, or dextrans; antioxidants, such as ascorbic acid or glutathione; chelating agents; low molecular weight proteins; salts; or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, methyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols and sugar alcohols, such as glycerin, sorbitol, mannitol, xylitol, erythritol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances, including salts such as sodium chloride, employed in pharmaceutical formulations.

The formulations can conveniently be presented in unit dosage form and can be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect.

In some embodiments, the BT composition is a powder, spray, ointment, paste, cream, lotion, solution, patch, suspension or gel. In some embodiments, the BT composition is a solution. The BT composition can comprise any suitable concentration of bismuth-thiol compound. In some embodiments, the BT composition is administered as a dosage from about 0.25 mg/mL to about 15 mg/mL, from about 0.4 mg/mL to about 15 mg/mL, from about 0.6 mg/mL to about 15 mg/mL, from about 0.6 mg/mL to about 100 mg/mL, from about 5 mg/mL to about 100 mg/mL, from about 10 mg/mL to about 100 mg/mL, from about 25 mg/mL to about 100 mg/mL, from about 50 mg/mL to about 100 mg/mL, from about 0.8 mg/mL to about 15 mg/mL, from about 1 mg/mL to about 10 mg/mL, from 2.5 mg/mL to about 10 mg/mL, from about 4 mg/mL to about 10 mg/mL, from about 5 mg/mL to about 10 mg/mL, from about 6 mg/mL to about 10 mg/mL, 0.6 mg/mL to about 6 mg/mL, from about 4 mg/mL to about 15 mg/mL, from about 6 mg/mL to about 15 mg/mL, from about 50 µg/mL to about 750 µg/mL, from about 75 µg/mL to about 500 µg/mL, from about 100 µg/mL to about 250 µg/mL, from about 100 µg/mL to about 150 µg/mL, or from about 75 µg/mL to about 150 µg/mL; and/or the total amount of the BT composition administered to the lungs is from about 0.25 mg to about 15 mg, from about 0.4 mg to about 15 mg, from about 0.6 mg to about 15 mg, from about 0.8 mg to about 15 mg, from about 1 mg to about 10 mg, from 2.5 mg to about 10 mg, from about 4 mg to about 10 mg, from about 5 mg to about 10 mg, from about 6 mg to about 10 mg, 0.6 mg to about 6 mg, from about 4 mg to about 15 mg, from about 6 mg to about 15 mg, from about 50 µg to about 750 µg, from about 75 µg to about 500 µg, from about 100 µg to about 250 µg, from about 100 µg to about 150 µg, or from about 75 µg to about 150 µg. In certain embodiments, the BT composition is administered as a dosage from about 0.6 mg/mL to about 6 mg/mL.

In some embodiments, the BT composition is administered three times per day, two times per day, once daily, every other day, once every three days, once every week, once every other week, once monthly, to once every other month. In certain embodiments, the BT composition is administered once daily. In certain embodiments, the BT composition is administered once weekly. In certain embodiments, the BT composition is administered once every other week. In some embodiments, the BT composition is administered chronically in a 4 week on/4 week off dosing schedule. In some embodiments, the BT composition is administered chronically, for example as part of a background therapy. As will be appreciated by a person having ordinary skill in the art, the administration frequency may depend on a number of factors including dose and administration route. For example, if the BT composition is administered via an aerosol administration, a low dose such as 100-1000 µg/mL may be administered once or twice daily; however, a high dose such as 2.5-10 mg/mL may be administered e.g. once or twice a week.

In some embodiments, the BT composition further comprises one or more carriers selected from animal and vegetable fats, oils, waxes, paraffins, starch, tragacanth, cellulose derivatives, polyethylene glycols, silicones, bentonites, silicic acid, polymers, talc, and zinc oxide. In some embodiments, the carrier is methylcellulose. In some embodiments, the carrier is poly(methyl methacrylate).

Compositions can also be formulated so as to provide slow or controlled release of the active ingredient therein using, for example, hydroxypropylmethyl cellulose in varying proportions to provide the desired release profile, other polymer matrices, liposomes and/or microspheres. They can be sterilized by, for example, filtration through a bacteria-retaining filter, by ionizing radiation (gamma photons for example), autoclaving, or by incorporating sterilizing agents in the form of sterile solid compositions that can be dissolved in sterile water, or some other sterile injectable medium immediately before use.

Liquid dosage forms useful for topical administration include pharmaceutically acceptable emulsions, lyophiles for reconstitution, microemulsions, solutions, suspensions, gels, syrups and elixirs. In addition to the active ingredient, the liquid dosage forms can contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (such as cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the topical compositions can also include adjuvants such as wetting agents, emulsifying and suspending agents, and preservative agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound can be mixed under sterile conditions with a pharmaceutically acceptable carrier, and with any preservatives or buffers that can be required.

The ointments, pastes, creams and gels can contain, in addition to an active compound, one or more excipients or carriers, such as animal and vegetable fats, oils, waxes, paraffins, starch, tragacanth, cellulose derivatives, polyethylene glycols, silicones, bentonites, silicic acid, talc, polymers, salts, and zinc oxide, or mixtures thereof. In some embodiments, the BT composition is in the form of an aqueous solution. In some embodiments, the excipient comprises a salt selected from sodium chloride or potassium chloride. In some embodiments, the excipient comprises sodium chloride.

In certain embodiments, the BT composition is a suspension of one or more BT compounds in TWEEN® (e.g. TWEEN 80®) and/or in a buffer (e.g. sodium phosphate buffer). For example, in some embodiments, the BT composition is a suspension of one or more BT compounds in from about 0.1% TWEEN 80® to about 1.0% TWEEN 80®, including all ranges therebetween. For example, the BT composition is a suspension of one or more BT compounds in about 0.1% TWEEN 80®, about 0.2% TWEEN 80®, about 0.3% TWEEN 80®, about 0.4% TWEEN 80®, about 0.5% TWEEN 80®, about 0.6% TWEEN 80®, about 0.7% TWEEN 80®, about 0.8% TWEEN 80®, about 0.9% TWEEN 80®, or about 1% TWEEN 80®. In some embodiments, the BT composition is a suspension of one or more BT compounds in about 0.5% TWEEN 80®.

In a specific embodiment, the present invention may be a pharmaceutical composition comprising bismuth-thiol (BT) composition that comprises BisEDT suspended therein, wherein the BT composition comprises a plurality of microparticles. In a specific embodiment, the D90 of said microparticles is less than or equal to 4.5 µm, or 4.0 µm, or 3.5 µm, or 3.0 µm, or 2.5 µm, or 2.0 µm, or 1.9 µm, or 1.8 µm, or µm 1.7 µm, or 1.6 µm, or 1.5 µm or any ranges in between. In a specific embodiment, the D90 of said microparticles is less than or equal to 1.9 µm. In another specific embodiment, the D90 of said microparticles is less than or equal to 1.6 µm. In another specific embodiment, the D50 of said microparticles is less than or equal to 2.5 µm, or 2.0 µm, or 1.5 µm, or 1.3 µm, or 1.2 µm, or 1.1 µm, or 1.0 µm, or 0.9 µm, or 0.87 µm, or 0.72 µm or any ranges in between. In another specific embodiment, the D10 of said microparticles is less than or equal to 0.9 µm, or 0.8 µm, or 0.7 µm, or 0.6 µm, or 0.50 µm, or 0.40 µm, or 0.39 µm, or 0.38 µm, or 0.37 µm, or 0.36 µm, or 0.35 µm, or 0.34 µm, or 0.33 µm, or any ranges in between. In a specific embodiment, the pharmaceutical composition comprising bismuth-thiol (BT) composition comprises BisEDT suspended therein, wherein the BT composition comprises a plurality of microparticles, wherein the D90 of said microparticles is less than or equal to about 1.6 µm. In a specific embodiment, the BT composition comprises BisEDT at a concentration greater than about 0.1 mg/mL, about 0.05% to about 1.0% TWEEN 80®, about 0.05 to 40 mM sodium chloride, and optionally about 2 to 20 mM sodium phosphate at about pH. 7.4. In another specific embodiment, the compositions described above can be administered to a subject for treating, managing and/or lessening the severity of cystic fibrosis (CF) symptoms and infections in said subject, or any specific method of treating, managing and/or lessening the severity of cystic fibrosis (CF) symptoms described herein. In another specific embodiment, the compositions described above can be administered to a subject for treating, managing and/or lessening the severity of symptoms and infections associated with one or more pulmonary diseases or infections in a subject or any specific method of treating, managing and/or lessening the severity of symptoms and infections associated with one or more pulmonary diseases described herein.

A variety of buffers may be used in the context of the present disclosure and will be readily apparent to a person having ordinary skill in the art. For example, in some embodiments, suitable buffers include sodium or potassium citrate, citric acid, phosphate buffers such as sodium phosphate, boric acid, sodium bicarbonate and various mixed phosphate buffers including combinations of $Na_2HPO_4$, $NaH_2PO_4$ and $KH_2PO_4$. In some embodiments, sodium phosphate buffer is used. In some embodiments, sodium citrate buffer is used. Without being bound by any particular theory, changes in airway surface liquid pH may contribute to the host defense defect in cystic fibrosis soon after birth. Changes in lung pH may impact the airway surface liquid environment, improve airway defenses, and alter the disease course. Accordingly, the formulation pH may vary from about 5 to about 10. In some embodiments, the formulation pH is about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or about 10. In some embodiments, the formulation pH is about 7.4.

In some embodiments, the BT composition is a suspension of one or more BT compounds in about 0.5% TWEEN 80® in sodium phosphate buffer at a pH of about 7.4. In some embodiments, the one or more BT compounds are present in the composition at a concentration ranging from about 100 μg/mL to about 1000 mg/mL including all integers and ranges therebetween. For example, in some embodiments, the one or more BT compounds are present in the composition at a concentration ranging from about 100 μg/mL, 200 μg/mL, 300 μg/mL, 400 μg/mL, 500 μg/mL, 600 μg/mL, 700 μg/mL, 800 μg/mL, 900 μg/mL, 1000 μg/mL, 10 mg/mL, 25 mg/mL, 50 mg/mL, 100 mg/mL, 125 mg/mL, 150 mg/mL, 175 mg/mL, 200 mg/mL, 225 mg/mL, 250 mg/mL, 275 mg/mL, 300 mg/mL, 325 mg/mL, 350 mg/mL, 375 mg/mL, 400 mg/mL, 425 mg/mL, 450 mg/mL, 475 mg/mL, 500 mg/mL, 525 mg/mL, 550 mg/mL, 575 mg/mL, 600 mg/mL, 625 mg/mL, 650 mg/mL, 675 mg/mL, 700 mg/mL, 725 mg/mL, 750 mg/mL, 775 mg/mL, 800 mg/mL, 825 mg/mL, 850 mg/mL, 875 mg/mL, 900 mg/mL, 925 mg/mL, 950 mg/mL, 975 mg/mL, to about 1000 mg/mL. In some embodiments, the one or more BT compounds are present in the composition at a concentration ranging from about 100 μg/mL to about 1000 μg/mL.

In some embodiments, the composition osmolality may need to be further adjusted with an additive such as NaCl or TDAPS to achieve a desired osmolality. For example, in some embodiments, the osmolality of the composition is adjusted with sodium chloride to an osmolality ranging from about 100 mOsmol/kg to about 500 mOsmol/kg, including all integers and ranges therebetween. In some embodiments, the osmolality of the composition is from about 290 mOsmol/kg to about 310 mOsmol/kg. For example, in some embodiments, the osmolality of the composition is about 290 mOsmol/kg, 291 mOsmol/kg, 292 mOsmol/kg, 293 mOsmol/kg, 294 mOsmol/kg, 295 mOsmol/kg, 296 mOsmol/kg, 297 mOsmol/kg, 298 mOsmol/kg, 299 mOsmol/kg, 300 mOsmol/kg, 301 mOsmol/kg, 302 mOsmol/kg, 303 mOsmol/kg, 304 mOsmol/kg, 305 mOsmol/kg, 306 mOsmol/kg, 307 mOsmol/kg, 308 mOsmol/kg, 309 mOsmol/kg, to about 310 mOsmol/kg. In some embodiments, the osmolality is about 300 mOsmol/kg.

In some embodiments, the BT composition is a suspension of BisEDT in TWEEN® (e.g. TWEEN 80®) in a buffer (e.g. sodium phosphate buffer). In some embodiments, the BT composition is a suspension of BisEDT in about 0.5% TWEEN 80® in a sodium phosphate buffer at a pH of about 7.4. In some embodiments, the BT composition is a suspension of BisEDT in about 0.5% TWEEN 80® in a sodium phosphate buffer at a pH of about 7.4, wherein the composition has an osmolality of about 300 mOsmol/kg (e.g. adjusted to 300 mOsmol/kg with sodium chloride). In some embodiments, the BisEDT is present at a concentration of about 100 μg/mL, 250 μg/mL, 500 μg/mL, 750 μg/mL, 1000 μg/mL, 2.5 mg/mL, 10 mg/mL, 25 mg/mL, 50 mg/mL, 75 mg/mL, or about 100 mg/mL.

In some embodiments, the BT composition is a suspension formulation which is intended for pulmonary delivery. For example, the BT composition is a suspension formulation which is ultimately administered by inhalation either orally and/or nasally. Accordingly, in some embodiments, the BT composition is aerosolized by a device such as a nebulized.

Powders and sprays can contain, in addition to an active compound, excipients such as methylcellulose, sodium chloride, PMMA, lactose, talc, silicic acid, aluminum hydroxide, calcium silicates and polyamide powder, dipalmitoylphosphatidylcholine (DPPC), leucine, polyethyleneglycol, or mixtures of these substances. Sprays can additionally contain customary propellants, such as chlorofluorohydrocarbons and volatile unsubstituted hydrocarbons, such as butane and propane.

In some embodiments, the BT composition is administered by inhalation, orally or nasally, using an aerosol device, such as a nebulizer. Known nebulizers, such as PARI LC PLUS®, can administer the disclosed compositions as an aqueous solution, optionally in buffered saline. The solution can be provided to the subject in the form of an ampule for use in the nebulizer. The nebulizer can be reusable and includes a compressor that provides the formulation over a period of time, such as about 10-15 minutes or longer. Known compressors, such as APRI Vios Air and DeVilbiss Pulmo-aide, are suitable for administration. The nebulizer administers the formulation topically to the lung tissues, such as mucosa, the bronchi and/or the bronchioles, alveoli, deep lung alveoli. The formulation can penetrate lung mucosa and biofilms to reduce the microbial (e.g. bacterial or fungal) biofilm, impair the growth of the microbial (e.g. bacterial or fungal) biofilm, prevent reformation of the microbial (e.g. bacterial or fungal) biofilm, reduce planktonic growth, and/or inhibit planktonic growth.

In other embodiments, a nose-only aerosol device can be used for administration of the formulation.

An exemplary BT composition formulation is a neutral pH, isotonic, buffered aqueous solution of BT compound microparticles with a nonionic surfactant. In certain embodiments, the buffer is a phosphate buffer with added NaCl. In some embodiments, the microparticle size is a $D_{50}$ of about 1-5 µm. The formulation can be delivered using commercially available compressed air jet nebulizer. In some embodiments, the formulation concentration is about 0.1 µg/mL to about 100 mg/mL.

In some embodiments, the present disclosure provides an aerosol comprising a plurality of dispersed liquid droplets in a gas, said liquid droplets comprising a BT composition comprising at least one BT compound suspended therein, wherein the BT compound comprises bismuth and/or a bismuth salt and a thiol-containing compound; and wherein at least 60%, 65%, 70, 75%, 80%, 90%, or 95% of the liquid droplets have a mass median aerodynamic diameter (MMAD) from about 0.4 µm to about 5 µm when measured by laser time of flight and/or cascade impactor. In some embodiments, at least 60%, 65%, 70, 75%, 80%, 90%, or 95% of the liquid droplets have a MMAD of from about 0.4 µm to about 7 µm, or from about 0.5 µm to about 5 µm, or from about 0.7 µm to about 4 µm, or from about 0.7 µm to about 3.5 µm, or from about 0.8 µm to about 3.5 µm, or from about 0.9 µm to about 3.5 µm, or from about 0.9 µm to about 3 µm, or from about 0.8 µm to about 1.8 µm, or from about 0.8 µm to about 1.6 µm, or from about 0.9 µm to about 1.4 µm, or from about 1.0 µm to about 2.0 µm, or from about 1.0 µm to about 1.8 µm, including all ranges therebetween. In some embodiments, at least 60%, 65%, 70, 75%, 80%, 90%, or 95% of the liquid droplets have a MMAD of from about 0.8 µm to about 1.6 µm, or from about 0.9 µm to about 3.5 µm, or from about 0.9 µm to about 3 µm, or from about 0.9 µm to about 1.4 µm, or from about 1.0 µm to about 2.0 µm, or from about 1.0 µm to about 1.8 µm, and all ranges therebetween.

In some embodiments, the plurality of liquid droplets have a D90 of less than about 10 µm. For example, in some embodiments, the plurality of liquid droplets have a D90 of less than about 10 µm, 9 µm, 8 µm, 7 µm, 6 µm, 5 µm, 4 µm, 3 µm, 2 µm, or about 1 µm. In some embodiments, the plurality of liquid droplets have a D90 of less than about 3 µm. In some embodiments, the plurality of liquid droplets have a D90 ranging from about 1 µm to about 5 µm, or about 2 µm to about 6 µm, or about 2 µm to about 4 µm, or about 2 µm to about 3 µm, or about 1 µm to about 4 µm, or about 1 µm to about 3 µm.

In some embodiments, the plurality of liquid droplets are dispersed in a continuous gas phase.

In some embodiments, the BT compound of the aerosol comprises bismuth and/or a bismuth salt associated covalently and/or in a coordination complex with one or more thiol-containing compounds. For example, the bismuth salt is bismuth nitrate, bismuth subnitrate, or bismuth chloride. In some embodiments, the thiol-containing compound comprises one or more agents selected from 1,2-ethane dithiol, 2,3-dimercaptopropanol, pyrithione, dithioerythritol, 3,4 dimercaptotoluene, 2,3-butanedithiol, 1,3-propanedithiol, 2-hydroxypropanethiol, 1-mercapto-2-propanol, dithioerythritol, dithiothreitol and alpha-lipoic acid. In some embodiments, the BT composition comprises one or more BT compounds selected from BisBAL, BisEDT, Bis-dimercaprol, BisDTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, BisPyr/EDT, Bis-Pyr/PDT, Bis-Pyr/Tol, Bis-Pyr/Ery, bismuth-1-mercapto-2-propanol, BisEDT/CSTMN (1:1), BisPYR/CSTMN (1:1), BisBAL/CSTMN (1:1), Bis-TOL/CSTMN (1:1), and BisEDT/2-hydroxy-1-propanethiol. In some embodiments, the BT compound is selected from one or more of BisEDT, Bis-Bal, Bis-Pyr, Bis-Ery, Bis-Tol, Bis-BDT, or BisEDT/2-hydroxy-1-propane thiol. In some embodiments, the BT compound on the aerosol is BisEDT. In some embodiments, the BT compound of the aerosol is BisBDT or BisBAL.

In some embodiments, the BT compound (e.g. BisEDT) is suspended in the liquid droplet. The BT compounds of the present disclosure have little to no solubility in conventional solvents and aerosol carriers and therefore exist substantially as a suspension of BT particles in the aerosol droplet. For example, in some embodiments, the BT compound (such as BisEDT) is less than 1% soluble in the aerosol carrier and therefore exists primarily (>99%) as a solid.

In some embodiments, the droplets further comprise TWEEN 80™ (e.g. from about 0.05% to about 1%) and optionally a buffer (e.g. sodium phosphate or sodium citrate) at a pH of about 7.4; and/or sodium chloride.

The aerosols of the present disclosure have a very narrow MMAD distribution which is beneficial because of the need to concentrate the particle mass in the target size range, and minimize or eliminate the fraction of the product that is outside of the respirable range or 'fines', i.e. particles of typically less than 0.4 µm diameter. The ability to create a narrow droplet size distribution in the appropriate size range provides control of the initial evaporation rate and allows for high deposition efficiency. The limiting factor in terms of the lower limit of particle aerosol droplet size is the BT microparticle size (e.g. the BisEDT microparticle size). An aerosolized droplet cannot be smaller than the BisEDT microparticulate size. As such, the BT microparticle size distribution, as well as the uniformity and consistent reproducibility of the BT microparticulate size distribution, are important beneficial characteristics to support the generation of a safe, effective, and efficient aerosolized BisEDT drug product for inhalation purposes. Accordingly, in some embodiments, the aerosols of the present disclosure effectuate a deposition efficiency of greater than 3%, greater than 5%, greater than 10%, greater than 15%, greater than 20%, greater than 25%, greater than 30%, greater than 35% m greater than 40%, greater than 45%, greater than 50%, greater than 55%, greater than 60%, greater than 65%, greater than 70%, greater than 75%, and greater than 80%. In some embodiments, the deposition efficiency refers to deposition to the deep lung region of lung, for example, to the deep lung alveoli. In some embodiments, the aerosols of the present disclosure effectuate a deposition efficiency upon aerosolization via a nebulizer. For example, the nebulizer is a jet nebulizer. In some embodiments, the jet nebulizer is a PARI LC PLUS® jet nebulizer or PARI LC SPRINT® jet nebulizer. In some embodiments, the nebulizer has an inlet pressure from about 10 to about 40 psig (e.g. 20-25 psig). In some embodiments, the inlet flow is from about 3 L/min to about 8 L/min (e.g. 5.2 L/min). In some embodiments, the exhaust air flow is from about 3 L/min to about 8 L/min (e.g. 5 L/min).

The alveolar region of the lung has a minimal thickness (0.5 µm-2.5 µm) separating the blood flow from the lumen so conventional pulmonary agents that deposit on the alveolar epithelium have extremely short lung residence time due to systemic absorption. Accordingly, conventional pulmonary treatments typically require frequent dosing in order to maintain adequate levels of drug at the tissue level. However, the aerosolized particles of the present disclosure were surprisingly discovered to possess an exceptionally long residence time in the lungs (measured as half-life) and have reduced mucociliary clearance and macrophage uptake relative to conventional pulmonary treatments. Furthermore, the long residence time of the aerosols of the present minimizes systemic activity and associated systemic side effects. Without being bound by any particular theory, it is believed that the aerosolized microparticles dissolve slowly on the lung lumen and the systemic exposure is thus dissolution rate limited. Further, the increased lung residence time results in significant reductions in microbial colony due to the continuous presence of the BT microparticles.

Accordingly, in some embodiments, when the aerosol is deposited to the lung (e.g. to the deep lung alveoli), the BT compounds have an average half-life of at least 2 days. For example, the BT compounds have an average half-life of about 2, 3, 4, or 5 days. In some embodiments, the BT compound is BisEDT. In a specific embodiment, the lung tissue half-life of BisEDT is 30 hrs or more, 40 hrs or more, 50 hrs or more, 60 hrs or more, 70, hrs or more, 80 hrs or more, 90 hrs or more, 100 hrs or more, 110 hrs or more, 125 hrs or more, or 150 hrs or more. In a specific embodiment, the lung tissue half-life is after a single dose via inhalation. In another specific embodiment, lung tissue is from a rat. In another specific embodiment, lung tissue half-life of BisEDT is determined by the ue of protocol as in Example 8 herein.

In another embodiment, the lung tissue half-life of BisEDT is 80 hrs or more when the rat is given a single dose of 100 µg/kg lung using a PARI LC PLUS® jet nebulizer to administer to the rats with the formulations described herein. In another embodiment, the lung tissue half-life of BisEDT is 90 hrs or more. In another embodiment, the lung tissue half-life of BisEDT is 100 hrs or more.

In another embodiment, after delivering the aerosolized composition to a subject, at least 60%, 65%, 70, 75%, 80%, 90%, or 95% of the dose is deposited on the lung, as opposed to the orpharanygeal region and the conducting airways. In a specific embodiment, at least 80% of the dose is deposited on the lung, as opposed to the orpharanygeal region and the conducting airways. In another specific embodiment, at least 90% of the dose is deposited on the lung, as opposed to the orpharanygeal region and the conducting airways.

It was previously unheard of for an aerosolized pulmonary treatment to have aerosol particles with a narrow distribution that effectuate a high deposition efficiency coupled with an exceptionally long lung residence time for continuous treatment and little to no systemic absorption.

In some embodiments, the present disclosure provides a method of treating, managing or lessening the severity of cystic fibrosis (CF) symptoms and infections in a subject, the method comprising administering to the subject a bismuth-thiol (BT) composition that comprises at least one BT compound, wherein the composition is a suspension of microparticles having a volumetric mean diameter (VMD) from about 0.4 µm to about 5 µm and/or a mass median aerodynamic diameter (MMAD) from about 0.4 µm to about 5 µm. In some embodiments, the BT compound is BisEDT. In some embodiments, the BT composition comprises BisEDT at a concentration greater than about 0.1 mg/mL, about 0.05% to about 1.0% TWEEN 80®, about 0.05 to 40 mM sodium chloride, and optionally about 2 to 20 mM sodium phosphate at about pH. 7.4. For example, in some embodiments, the BT composition comprises BisEDT at a concentration greater than about 0.25 mg/mL, about 0.5% TWEEN 80®, about 10 mM sodium chloride, and about 10 mM sodium phosphate at about pH 7.4. In another embodiment of the methods herein, the BT composition is administered by aerosolization. In some embodiments, when the aerosol is deposited to the lung (e.g. to the deep lung alveoli), the BT compounds have an average half-life of at least 2 days. For example, the BT compounds have an average half-life of about 2, 3, 4, or 5 days. In some embodiments, the BT compound is BisEDT. In a specific embodiment, the lung tissue half-life of BisEDT is 30 hrs or more, 40 hrs or more, 50 hrs or more, 60 hrs or more, 70, hrs or more, 80 hrs or more, 90 hrs or more, 100 hrs or more, 110 hrs or more, 125 hrs or more, or 150 hrs or more. In a specific embodiment, the lung tissue half-life is after a single dose via inhalation. In another specific embodiment, lung tissue is from a rat. In another specific embodiment, lung tissue half-life of BisEDT is determined by the ue of protocol as in Example 8 herein.

In another embodiment, after delivering the aerosolized composition to a subject, at least 60%, 65%, 70%, 75%, 80%, 90%, or 95% of the dose is deposited on the lung, as opposed to the orpharanygeal region and the conducting airways. In a specific embodiment, at least 80% of the dose is deposited on the lung, as opposed to the orpharanygeal region and the conducting airways. In another specific embodiment, at least 90% of the dose is deposited on the lung, as opposed to the orpharanygeal region and the conducting airways. In a specific embodiment, the subject is a rat. In another specific embodiment, the percent deposition is determined using a PARI LC PLUS® jet nebulizer to administer to the rats with the formulations described herein.

In another embodiment, the lung tissue half-life of BisEDT is 80 hrs or more when the rat is given a single dose of 100 µg/kg lung using a PARI LC PLUS® jet nebulizer to administer to the rats with the formulations described herein. In another embodiment, the lung tissue half-life of BisEDT is 90 hrs or more. In another embodiment, the lung tissue half-life of BisEDT is 100 hrs or more.

In another embodiment, the methods of the present invention may include treating, managing or lessening the severity of cystic fibrosis (CF) symptoms and infections in a subject, by administering to the subject a bismuth-thiol (BT) composition that comprises at least one BT compound, wherein the composition is a suspension of microparticles having a volumetric mean diameter (VMD) from about 0.4 µm to about 5 µm and/or a mass median aerodynamic diameter (MMAD) from about 0.4 µm to about 5 µm.

In some embodiments, the composition is a suspension of microparticles having a volumetric mean diameter (VMD) from about 0.4 µm to about 5 µm. In some embodiments, at least 60%, 65%, 70%, 75%, 80%, 90%, or 95% of the microparticles have a VMD of from about 0.4 µm to about 5 µm, or from about 0.6 µm to about 2.5 µm, or from about 0.7 µm to about 4 µm, or from about 0.7 µm to about 3.5 µm, or from about 0.7 µm to about 3.0 µm, or from about 0.9 µm to about 3.5 µm, or from about 0.9 µm to about 3 µm, or from about 0.8 µm to about 1.8 µm, or from about 0.8 µm to about 1.6 µm, or from about 0.9 µm to about 1.4 µm, or from about 1.0 µm to about 2.0 µm, or from about 1.0 µm to about 1.8 µm and all ranges therebetween. In some embodiments, at least 60%, 65%, 70%, 75%, 80%, 90%, or 95% of the microparticles have a VMD of from about 0.6 µm to about 2.5 µm, or from about 0.8 µm to about 1.6 µm, or from about 0.9 µm to about 3.5 µm, or from about 0.9 µm to about 3 µm, or from about 0.9 µm to about 1.4 µm, or from about 1.0 µm to about 2.0 µm, or from about 1.0 µm to about 1.8 µm and all ranges therebetween. In some embodiments, the microparticles have a D90 of less than about 10 µm. For example, in some embodiments, the microparticles have a D90 of less than about 10 µm, 9 µm, 8 µm, 7 µm, 6 µm, 5 µm, 4 µm, 3 µm, 2 µm, or about 1 µm. In some embodiments, the microparticles have a D90 of less than about 3 µm. In some embodiments, the microparticles have a D90 ranging from about 1 µm to about 5 µm, or about 2 µm to about 6 µm, or about 2 µm to about 4 µm, or about 2 µm to about 3 µm, or about 1 µm to about 4 µm, or about 1 µm to about 3 µm.

In some embodiments, the BT composition is aerosolized, wherein the aerosolized liquid droplets have a MMAD from about of from about 0.4 μm to about 5 μm. In some embodiments, at least 60%, 65%, 70%, 75%, 80%, 90%, or 95% of the liquid droplets have a MMAD of from about 0.4 μm to about 7 μm, or from about 0.5 μm to about 5 μm, or from about 0.7 μm to about 4 μm, or from about 0.7 μm to about 3.5 μm, or from about 0.8 μm to about 3.5 μm, or from about 0.9 μm to about 3.5 μm, or from about 0.9 μm to about 3 μm, or from about 0.8 μm to about 1.8 μm, or from about 0.8 μm to about 1.6 μm, or from about 0.9 μm to about 1.4 μm, or from about 1.0 μm to about 2.0 μm, or from about 1.0 μm to about 1.8 μm and all ranges therebetween. In some embodiments, at least 60%, 65%, 70%, 75%, 80%, 90%, or 95% of the liquid droplets have a MMAD of from about 0.8 μm to about 1.6 μm, or from about 0.9 μm to about 3.5 μm, or from about 0.9 μm to about 3 μm, or from about 0.9 μm to about 1.4 μm, or from about 1.0 μm to about 2.0 μm, or from about 1.0 μm to about 1.8 μm and all ranges therebetween. In some embodiments, the plurality of liquid droplets have a D90 of less than about 10 μm. For example, in some embodiments, the plurality of liquid droplets have a D90 of less than about 10 μm, 9 μm, 8 μm, 7 μm, 6 μm, 5 μm, 4 μm, 3 μm, 2 μm, or about 1 μm. In some embodiments, the plurality of liquid droplets have a D90 of less than about 3 μm. In some embodiments, the plurality of liquid droplets have a D90 ranging from about 1 μm to about 5 μm, or about 2 μm to about 6 μm, or about 2 μm to about 4 μm, or about 2 μm to about 3 μm, or about 1 μm to about 4 μm, or about 1 μm to about 3 μm.

In some embodiments, the plurality of liquid droplets are dispersed in a continuous gas phase.

In some embodiments, the BT compound of the aerosol comprises bismuth and/or a bismuth salt associated covalently and/or in a coordination complex with one or more thiol-containing compounds. For example, the bismuth salt is bismuth nitrate, bismuth subnitrate, or bismuth chloride. In some embodiments, the thiol-containing compound comprises one or more agents selected from 1,2-ethane dithiol, 2,3-dimercaptopropanol, pyrithione, dithioerythritol, 3,4 dimercaptotoluene, 2,3-butanedithiol, 1,3-propanedithiol, 2-hydroxypropanethiol, 1-mercapto-2-propanol, dithioerythritol, dithiothreitol, cysteamine, and alpha-lipoic acid. In some embodiments, the BT composition comprises one or more BT compounds selected from BisBAL, BisEDT, Bis-dimercaprol, BisDTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, BisPyr/EDT, Bis-Pyr/PDT, Bis-Pyr/Tol, Bis-Pyr/Ery, BisEDT/CSTMN (1:1), BisPYR/CSTMN (1:1), BisBAL/CSTMN (1:1), BisTOL/CSTMN (1:1), bismuth-1-mercapto-2-propanol, and BisEDT/2-hydroxy-1-propanethiol. In some embodiments, the BT compound is selected from one or more of BisEDT, Bis-Bal, Bis-Pyr, Bis-Ery, Bis-Tol, Bis-BDT, or BisEDT/2-hydroxy-1-propane thiol. In some embodiments, the BT compound on the aerosol is BisEDT. In some embodiments, the BT compound of the aerosol is BisBDT or BisBAL.

In some embodiments of the presently disclosed compositions, at least 60%, 65%, 70%, 75%, 80%, 90%, or 95% of the microparticles have a volumetric mean diameter of from about 0.6 μm to about 2.5 μm. In some embodiments, substantially all of the microparticles have a VMD of from about 0.6 μm to about 2.5 μm. In some embodiments, at least 70% of the aerosolized particles have a MMAD of about 0.9 μm to about 3 μm. In some embodiments, the composition is a suspension of microparticles having a volumetric mean diameter (VMD) from about 0.6 μm to about 2.5 μm and/or a mass median aerodynamic diameter (MMAD) from about 0.9 μm to about 3 μm. In some embodiments, the bismuth-thiol composition comprises a plurality of microparticles that comprise a bismuth-thiol (BT) compound, substantially all of said microparticles having a volumetric mean diameter of from about 0.4 μm to about 5 μm, and wherein the BT compound comprises bismuth or a bismuth salt and a thiol-containing compound.

In some embodiments, the composition is aerosolized via a nebulizer. For example, the nebulizer is a jet nebulizer or vibrating mesh nebulizer. In some embodiments, the jet nebulizer is a PARI LC PLUS® jet nebulizer or PARI LC SPRINT® jet nebulizer. In some embodiments, the nebulizer has an inlet pressure from about 10 to about 40 psig (e.g. 20-25 psig). In some embodiments, the inlet flow is from about 3 L/min to about 8 L/min (e.g. 5.2 L/min). In some embodiments, the exhaust air flow is from about 3 L/min to about 8 L/min (e.g. 5 L/min).

Examples of suitable aqueous and nonaqueous carriers that can be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agentscan also be desirable to include isotonic agents, such as sugars, sodium chloride, and the like into the compositions. In addition, prolonged absorption of the injectable pharmaceutical form can be brought about by the inclusion of agents that delay absorption such as aluminum monostearate and gelatin.

In some cases, in order to prolong the effect of a drug, it is desirable to slow the absorption of the drug from subcutaneous or intramuscular injection. This can be accomplished by the use of a liquid suspension of crystalline or amorphous material having poor water solubility. The rate of absorption of the drug then depends upon its rate of dissolution, which, in turn, can depend upon crystal size and crystalline form. Alternatively, delayed absorption of a parenterally administered drug form is accomplished by dissolving or suspending the drug in an oil vehicle.

Actual dosage levels of the active ingredients in the pharmaceutical compositions can be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount can include, but are not limited to, the severity of the subject's condition, the disorder being treated, the stability of the compound, and, if desired, another type of therapeutic agent being administered with the compound of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable dose of an active compound used in the compositions and methods of the disclosure will be that amount of the compound that is the lowest dose effective to produce a therapeutic effect. Such an effective dose will generally depend upon the factors described above.

This disclosure includes the use of pharmaceutically acceptable salts of compounds of the disclosure in the compositions and methods of the present disclosure. In certain embodiments, contemplated salts of the disclosure include, but are not limited to, alkyl, dialkyl, trialkyl or tetra-alkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the disclosure include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

EMBODIMENTS

1. A method of treating, managing or lessening the severity of cystic fibrosis (CF) symptoms and infections in a subject, the method comprising administering to the subject a bismuth-thiol (BT) composition that comprises at least one BT compound.
2. The method of embodiment 1, wherein the subject has at least one pulmonary infection.
3. The method of embodiment 2, wherein the subject has at least two pulmonary infections and the infections are either concurrent or successive in order.
4. The method of embodiment 2 or 3, wherein the pulmonary infection is in one lung.
5. The method of any one of embodiments 2-4, wherein the pulmonary infection is in both lungs.
6. The method of any one of embodiments 2-5, wherein the pulmonary infection is in one or more of the three lobes of the right lung.
7. The method of any one of embodiments 2-6, wherein the pulmonary infection is in one or both of the two lobes of the left lung.
8. The method of any one of embodiments 2-7, wherein the pulmonary infection is bronchiectasis infection, pneumonia, valley fever, allergic bronchopulmonary aspergillosis (ABPA), ventilator acquired pneumonia, hospital acquired pneumonia, community acquired pneumonia, ventilator associated tracheobronchitis, lower respiratory tract infection, non-tuberculous Mycobacteria, anthrax, legionellosis, pertussis, bronchitis, Bronchiolitis, COPD-associated infection, and post-lung transplantation.
9. The method of any one of embodiments 2-8, wherein the pulmonary infection contains one or more bacterial and/or fungal pathogens.
10. The method of any one of embodiments 2-9, wherein the pulmonary infection is a CF-related pulmonary infection.
11. The method of embodiment 10, comprising treating the CF-related pulmonary infection.
12. The method of embodiment 10, comprising managing the CF-related pulmonary infection.
13. The method of embodiment 10, comprising lessening the severity of the CF-related pulmonary infection.
14. The method of any one of embodiments 2-13, wherein the pulmonary infection is located in or on the lung mucosa, the bronchi, the alveoli, the macrophages, and/or the bronchioles.
15. The method of any one of embodiments 2-13, wherein the pulmonary infection is located on the surface of or within a bacterial biofilm, aggregated bacteria, a fungal biofilm, a combined multispecies or multiphylum biofilm comprised of both bacteria and fungi, or aggregated fungi.

16. The method of any one of embodiments 2-13, wherein the pulmonary infection is located in the sputum.
17. The method of any one of embodiments 9-16, wherein the bacterial pathogen comprises one or more of gram-positive bacteria and/or gram-negative bacteria.
18. The method of any one of embodiments 9-17, wherein the bacterial pathogen comprises one or more of a bacterial biofilm and/or planktonic bacteria.
19. The method of embodiment 18, wherein the method comprises at least one of: (i) reducing the bacterial biofilm, (ii) impairing growth of the bacterial biofilm, (iii) preventing initial formation of the bacterial biofilm, and/or (iv) preventing reformation of the bacterial biofilm.
20. The method of any one of embodiments 9-16, wherein the fungal pathogen comprises planktonic fungi and/or biofilm fungi.
21. The method of any one of embodiments 9-20, wherein the BT composition treats, manages or lessens the severity of the pulmonary infection by one or both of:
    prevention of the infection by the bacterial or fungal pathogen; and
    reduction of the bacterial or fungal pathogen; and/or reducing the viscosity of the sputum.
22. The method of any one of embodiments 9-20, wherein the BT composition treats, manages or lessens the severity of the pulmonary infection by one or more of:
    prevention of elaboration or secretion of exotoxins from the bacterial or fungal pathogen;
    inhibition of cell viability or cell growth of planktonic cells of the bacterial or fungal pathogen;
    inhibition of biofilm formation by the bacterial or fungal pathogen;
    inhibition of biofilm invasiveness to pulmonary tissues;
    inhibition of biofilm pathogenicity to pulmonary tissues; and
    inhibition of biofilm viability or biofilm growth of biofilm-forming cells of the bacterial or fungal pathogen.
23. The method of any one of embodiments 9-22, wherein the one or more pathogens are selected from *Haemophilus influenzae*, *Pseudomonas aeruginosa*, *Staphylococcus aureus*, *Staphylococcus warneri Staphylococcus lugdunensis*, *Staphylococcus epidermidis*, *Streptococcus milleri/anginous*, *Streptococcus pyogenes*, non-tuberculosis *mycobacterium*, *Mycobacterium tuberculosis*, *Burkholderia* spp., *Achromobacter xylosoxidans*, *Pandoraea sputorum*, *Stenotrophomonas maltophilia*, *Alcaligenes xylosoxidans*, *Haemophilus pittmaniae*, *Serratia marcescens*, *Candida albicans*, drug resistant *Candida albicans*, *Candida glabrata*, *Candida krusei*, *Candida guilliermondii*, *Candida auris*, *Candida tropicalis*, *Aspergillus niger*, *Aspergillus terreus*, *Aspergillus fumigatus*, *Aspergillus flavus*, *Morganella morganii*, *Inquilinus limosus*, *Ralstonia mannitolilytica*, *Pandoraea apista*, *Pandoraea pnomenusa*, *Pandoraea sputorum*, *Bdellovibrio bacteriovorus*, *Bordetella bronchiseptica*, *Vampirovibrio chlorellavorus*, *Actinobacter baumanni*, *Cupriadidus metallidurans*, *Cupriavidus pauculus*, *Cupriavidus respiraculi*, *Delftia acidivordans*, *Exophilia dermatitidis*, *Herbaspirillum frisingense*, *Herbaspirillum seropedicae*, *Klebsiella pneumoniae*, *Pandoraea norimbergensis*, *Pandoraea pulmonicola*, *Pseudomonas mendocina*, *Pseudomonas pseudoalcaligenes*, *Pseudomonas putida*, *Pseudomonas stutzeri*, *Ralstonia insidiosa*, *Ralstonia pickettii*, *Neisseria gonorrhoeae*, NDM-1 positive *E. coli*, *Enterobacter cloaca*, Vancomycin-resistant *E. faecium*, Vancomycin-resistant *E. faecalis*, *E. faecium*, *E. faecalis*, Clindamycin-resistant *S. agalactiae*, *S. agalactiae*, *Bacteroides fragilis*, *Clostridium difficile*, *Streptococcus pneumonia*, *Moraxella catarrhalis*, *Haemophilus haemolyticus*, *Haemophilus parainfluenzae*, *Chlamydophilia pneumoniae*, *Mycoplasma pneumoniae*, *Atopobium*, *Sphingomonas*, *Saccharibacteria*, *Leptotrichia*, *Capnocytophaga*, *Oribacterium*, *Aquabacterium*, *Lachnoanaerobaculum*, *Campylobacter*, *Acinetobacter*; *Agrobacterium*; *Bordetella*; *Brevundimonas*; *Chryseobacterium*; *Delftia*; *Enterobacter*; *Klebsiella*; *Pandoraea*; *Pseudomonas*; *Ralstonia*, and *Prevotella*.
24. The method of embodiment 23, wherein the non-tuberculosis *mycobacterium* is selected from *Mycobacterium abscessus*, *Mycobacterium avium*, *Mycobacterium intracellulare*, *Mycobacterium fortuitum*, *Mycobacterium gordonae*, *Mycobacterium kansasii*, *Mycobacterium avium* complex, *Mycobacterium marinum*, *Mycobacterium terrae* and *Mycobacterium cheloni*.
25. The method of embodiment 23, wherein the *Burkholderia* spp. is selected from *Burkholderia cepacia*, *Burkholderia cepacia* complex, *Burkholderia multivorans*, *Burkholderia cenocepacia*, *Burkholderia stabilis*, *Burkholderia vietnamiensis*, *Burkholderia dolosa*, *Burkholderia ambifaria*, *Burkholderia anthina*, *Burkholderia pyrrocinia*, *Burkholderia gladioli*, *Burkholderia ubonensis*, *Burkholderia arboris*, *Burkholderia latens*, *Burkholderia lata*, *Burkholderia metallica*, *Burkholderia seminalis*, *Burkholderia contaminans*, and *Burkholderia diffusa*.
26. The method of embodiment 23, wherein the one or more pathogens are selected from *Pseudomonas aeruginosa*, single drug-resistant *Pseudomonas aeruginosa*, multi drug-resistant *Pseudomonas aeruginosa*, *Staphylococcus aureus*, single drug-resistant *Staphylococcus aureus*, multi drug-resistant *Staphylococcus aureus*, methicillin resistant *Staphylococcus aureus*, *Mycobacterium abscessus*, *Mycobacterium avium*, *Haemophilus influenzae*, *Burkholderia cepacia*, *Burkholderia multivorans*, *Burkholderia cenocepacia*, *Burkholderia dolosa*, *Achromobacter xylosoxidans*, *Stenotrophomonas maltophilia*, *Staphylococcus epidermidis*, and *Burkholderia vietnamiensis*.
27. The method of embodiment 23, wherein the one or more pathogens are selected from *Haemophilus influenzae*, *Pseudomonas aeruginosa*, and *Staphylococcus aureus*.
28. The method of any one of embodiments 18, 19 and 22, wherein the one or more pathogens are selected from biofilms of *Pseudomonas aeruginosa*, *Burkholderia cenocepacia*, *Burkholderia cepacia* complex, *Mycobacterium abscessus*, *Mycobacterium avium*, *Achromobacter* spp., *Staphylococcus epidermidis*, *Stenotrophomonas maltophilia*, and *Staphylococcus aureus*.
29. The method of embodiment 27, wherein the *Pseudomonas aeruginosa* and/or *Staphylococcus aureus* is multi-drug resistant.
30. The method of any one of embodiments 9-29, wherein the one or more pathogens exhibit resistance or is refractory to an antibiotic selected from amikacin, aztreonam, methicillin, vancomycin, nafcillin, gentamicin, ampicillin, chloramphenicol, doxycycline, colistin, delamanid, pretomanid, clofazimine, bedaquiline, and tobramycin.
31. The method of embodiment 30, wherein the antibiotic is amikacin or tobramycin.
32. The method of embodiment 30, wherein the bacterial pathogen is methicillin resistant *Staphylococcus aureus*.
33. The method of any one of embodiments 1-32, further comprising co-administering to the subject an antibiotic selected from amikacin, tobramycin, gentamicin, piperacillin, mezlocillin, ticarcillin, imipenem, ciprofloxacin, ceftazidime, aztreonam, ticarcillin-clavulanate, dicloxacillin, amoxicillin, trimethoprim-sulfamethoxazole, cephalexin, piperacillin-tazobactam, linezolid, daptomycin, vancomycin, metronidazole, clindamycin, colistin, tetracycline, levofloxacin, amoxicillin and clavulanic acid (Augmentin®), cloxacillin, dicloxacillin, cefdinir, cefprozil, cefaclor, cefuroxime, erythromycin/sulfisoxazole, erythromycin, clarithromycin, azithromycin, doxycycline, minocycline, tigecycline, imipenem, meropenem, colistimethate/Colistin®, methicillin, oxacillin, nafcillin, carbenicillin, azlocillin, piperacillin and tazobactam (Zosyn®), cefepime, ethambutol, rifampin, and meropenem.

34. The method of embodiment 33, wherein the antibiotic is selected from meropenem, ceftazidime, tobramycin, amikacin, aztreonam, ciprofloxacin, colistin, and levofloxacin.

35. The method of any one of embodiments 9-22, wherein the fungal pathogen is *Candida albicans*, drug resistant *Candida albicans, Candida glabrata, Candida krusei, Candida guilliermondii, Candida auris, Candida tropicalis, Aspergillus niger, Aspergillus terreus, Aspergillus fumigatus*, and/or *Aspergillus flavus*.

36. The method of any one of embodiments 1-35, comprising administering the BT composition via inhalation, orally or nasally, using an aerosol device.

37. The method of embodiment 36, wherein the aerosol device is a nebulizer.

38. The method of embodiment 36 or 37, wherein the BT composition is in the form of an aqueous solution, aqueous suspension, or dry powder.

39. The method of any one of embodiments 1-38, wherein the BT composition is administered topically to lung tissue.

40. The method of any one of embodiments 1-39, wherein the BT composition is administered as a dosage from about 0.25 mg/mL to about 15 mg/mL, from about 0.4 mg/mL to about 15 mg/mL, from about 0.6 mg/mL to about 15 mg/mL, from about 0.6 mg/mL to about 100 mg/mL, from about 5 mg/mL to about 100 mg/mL, from about 10 mg/mL to about 100 mg/mL, from about 25 mg/mL to about 100 mg/mL, from about 50 mg/mL to about 100 mg/mL, from about 0.8 mg/mL to about 15 mg/mL, from about 1 mg/mL to about 10 mg/mL, from 2.5 mg/mL to about 10 mg/mL, from about 4 mg/mL to about 10 mg/mL, from about 5 mg/mL to about 10 mg/mL, from about 6 mg/mL to about 10 mg/mL, 0.6 mg/mL to about 6 mg/mL, from about 4 mg/mL to about 15 mg/mL, from about 6 mg/mL to about 15 mg/mL, from about 50 μg/mL to about 750 μg/mL, from about 75 μg/mL to about 500 μg/mL, from about 100 μg/mL to about 250 μg/mL, from about 100 μg/mL to about 150 μg/mL, or from about 75 μg/mL to about 150 μg/mL; and/or the total amount of the BT composition administered to the lungs is from about 0.25 mg to about 15 mg, from about 0.4 mg to about 15 mg, from about 0.6 mg to about 15 mg, from about 0.8 mg to about 15 mg, from about 1 mg to about 10 mg, from 2.5 mg to about 10 mg, from about 4 mg to about 10 mg, from about 5 mg to about 10 mg, from about 6 mg to about 10 mg, 0.6 mg to about 6 mg, from about 4 mg to about 15 mg, from about 6 mg to about 15 mg, from about 50 μg to about 750 μg, from about 75 μg to about 500 μg, from about 100 μg to about 250 μg, from about 100 μg to about 150 μg, or from about 75 μg to about 150 μg.

41. The method of any one of embodiments 1-40, wherein the BT composition is administered as a dosage from about 0.6 mg/mL to about 6 mg/mL.

42. The method of any one of embodiments 1-41, wherein the BT composition is administered three times per day, two times per day, once daily, every other day, once every three days, once every week, once every other week, once every month, or once every other month.

43. The method of embodiment 42, wherein the BT composition is administered once every week.

44. The method of any one of embodiments 1-43, wherein one or more of the following cystic fibrosis symptoms is lessened in severity in the subject: cough, wheezing, breathlessness, bronchiectasis, nasal polyps, hemoptysis, respiratory failure, and pulmonary exacerbation.

45. The method of any one of embodiments 1-44, wherein the bismuth-thiol composition comprises a plurality of microparticles that comprise a bismuth-thiol (BT) compound, substantially all of said microparticles having a volumetric mean diameter of from about 0.4 μm to about 5 μm, and wherein the BT compound comprises bismuth or a bismuth salt and a thiol-containing compound.

46. The method of embodiment 45, wherein at least 60%, 65%, 70, 75%, 80%, 90%, or 95% of the microparticles have a volumetric mean diameter of from about 0.4 μm to about 3 μm, or from about 0.5 μm to about 2 μm, or from about 0.7 μm to about 2 μm, or from about 0.8 μm to about 1.8 μm, or from about 0.8 μm to about 1.6 μm, or from about 0.9 μm to about 1.4 μm, or from about 1.0 μm to about 2.0 μm, or from about 1.0 μm to about 1.8 μm.

47. The method of embodiments 45-46, wherein the bismuth salt is bismuth nitrate, bismuth subnitrate, or bismuth chloride.

48. The method of embodiments 45-46, wherein the thiol-containing compound comprises one or more agents selected from 1,2-ethane dithiol, 2,3-dimercaptopropanol, pyrithione, dithioerythritol, 3,4 dimercaptotoluene, 2,3-butanedithiol, 1,3-propanedithiol, 2-hydroxypropanethiol, 1-mercapto-2-propanol, dithioerythritol, dithiothreitol, cysteamine, and alpha-lipoic acid.

49. The method of any one of embodiments 45-48, wherein the BT composition comprises one or more BT compounds selected from BisBAL, BisEDT, Bis-dimercaprol, BisDTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, BisPyr/EDT, Bis-Pyr/PDT, Bis-Pyr/Tol, Bis-Pyr/Ery, bismuth-1-mercapto-2-propanol, BisEDT/CSTMN (1:1), BisPYR/CSTMN (1:1), BisBAL/CSTMN (1:1), BisTOL/CSTMN (1:1), and BisEDT/2-hydroxy-1-propanethiol.

50. The method of embodiment 49, wherein the BT compound is selected from one or more of BisEDT, Bis-Bal, Bis-Pyr, Bis-Ery, Bis-Tol, Bis-BDT, or BisEDT/2-hydroxy-1-propane thiol.

51. The method of embodiment 50, wherein the BT compound is BisEDT.

52. The method of embodiment 50, wherein the BT compound is BisBDT or BisBAL.

53. The method of any one of embodiments 1-52, wherein the total amount of the BT composition administered to the deep lung region is from about 0.25 mg to about 15 mg, from about 0.4 mg to about 15 mg, from about 0.6 mg to about 15 mg, from about 0.8 mg to about 15 mg, from about 1 mg to about 10 mg, from 2.5 mg to about 10 mg, from about 4 mg to about 10 mg, from about 5 mg to about 10 mg, from about 6 mg to about 10 mg, 0.6 mg to about 6 mg, from about 4 mg to about 15 mg, from about 6 mg to about 15 mg, from about 50 μg to about 750 μg, from about 75 μg to about 500 μg, from about 100 μg to about 250 μg, from about 100 μg to about 150 μg, or from about 75 μg to about 150 μg.

54. The method of embodiment 53, wherein the deep lung region is the deep lung alveoli.

55. An aerosol comprising a plurality of dispersed liquid droplets in a gas, said liquid droplets comprising a BT composition comprising at least one BT compound suspended therein, wherein the BT compound comprises bismuth and/or a bismuth salt and a thiol-containing compound; and wherein at least 60%, 65%, 70, 75%, 80%, 90%, or 95% of the liquid droplets have a mass median aerodynamic diameter (MMAD) from about of from about 0.4 μm to about 5 μm.

56. The aerosol of embodiment 55, wherein the liquid droplets have a MMAD of from about 0.4 μm to about 7 μm, or from about 0.5 μm to about 5 μm, or from about 0.7 μm to about 4 μm, or from about 0.7 μm to about 3.5 μm, or from about 0.8 μm to about 3.5 μm, or from about 0.9 μm to about 3.5 μm, or from about 0.9 μm to about 3 μm, or from about 0.8 μm to about 1.8 μm, or from about 0.8 μm to about 1.6 μm, or from about 0.9 μm to about 1.4 μm, or from about 1.0 μm to about 2.0 μm, or from about 1.0 μm to about 1.8 μm.

57. The aerosol of embodiment 56, wherein the liquid droplets have a MMAD of from about 0.8 μm to about 1.6 μm, or from about 0.9 μm to about 3.5 μm, or from about 0.9 μm to about 3 μm, or from about 0.9 μm to about 1.4 μm, or from about 1.0 μm to about 2.0 μm, or from about 1.0 μm to about 1.8 μm.

58. The aerosol of any one of embodiments 55-57, wherein the plurality of liquid droplets have a D90 of less than about 5 μm.

59. The aerosol of embodiment 58, wherein the plurality of liquid droplets have a D90 of less than about 3 μm.

60. The aerosol of any one of embodiments 55-59, wherein the plurality of liquid droplets are dispersed in a continuous gas phase.

61. The aerosol of any one of embodiments 55-60, wherein the BT compound comprises bismuth and/or a bismuth salt associated covalently and/or in a coordination complex with one or more thiol-containing compounds.

62. The aerosol of any one of embodiments 55-61, wherein the bismuth salt is bismuth nitrate, bismuth subnitrate, or bismuth chloride.

63. The aerosol of any one of embodiments 55-62, wherein the thiol-containing compound comprises one or more agents selected from 1,2-ethane dithiol, 2,3-dimercaptopropanol, pyrithione, dithioerythritol, 3,4 dimercaptotoluene, 2,3-butanedithiol, 1,3-propanedithiol, 2-hydroxypropanethiol, 1-mercapto-2-propanol, dithioerythritol, dithiothreitol, cysteamine, and alpha-lipoic acid.

64. The aerosol of any one of embodiments 55-63, wherein the BT composition comprises one or more BT compounds selected from BisBAL, BisEDT, Bis-dimercaprol, BisDTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, BisPyr/EDT, Bis-Pyr/PDT, Bis-Pyr/Tol, Bis-Pyr/Ery, bismuth-1-mercapto-2-propanol, BisEDT/CSTMN (1:1), BisPYR/CSTMN (1:1), BisBAL/CSTMN (1:1), BisTOL/CSTMN (1:1), and BisEDT/2-hydroxy-1-propanethiol.

65. The aerosol of embodiment 64, wherein the BT compound is selected from one or more of BisEDT, Bis-Bal, Bis-Pyr, Bis-Ery, Bis-Tol, Bis-BDT, or BisEDT/2-hydroxy-1-propane thiol.

66. The aerosol of embodiment 65, wherein the BT compound is BisEDT.

67. The aerosol of embodiment 55, wherein the mass median aerodynamic diameter (MMAD) is determined by laser time of flight and/or cascade impactor.

68. The aerosol of any one of embodiments 55-67, wherein the BT compound is suspended in the liquid droplet.

69. The aerosol of embodiment 68, wherein the BT compound is BisEDT.

70. The aerosol of any one of embodiments 55-69, wherein the droplets further comprise TWEEN 80® (e.g. from about 0.05% to about 1%) and optionally
   a buffer (e.g. sodium phosphate or sodium citrate) at a pH of about 7.4; and/or sodium chloride.

71. The aerosol of any one of embodiments 55-70, wherein if deposited to the deep lung region, the BT compounds have an average half-life of at least 2 days.

72. The aerosol of any one of embodiment 71, wherein if deposited to the deep lung region, the BT compounds have an average half-life of at least 4 days.

73. A method of treating, managing or lessening the severity of cystic fibrosis (CF) symptoms and infections in a subject, the method comprising administering to the subject a bismuth-thiol (BT) composition that comprises at least one BT compound, wherein the composition is a suspension of microparticles having a volumetric mean diameter (VMD) from about 0.4 μm to about 5 μm and/or a mass median aerodynamic diameter (MMAD) from about 0.4 μm to about 5 μm.

74. The method of embodiment 73, wherein the BT compound is BisEDT.

75. The method of embodiment 74, wherein the BT composition comprises BisEDT at a concentration greater than about 0.1 mg/mL, about 0.05% to about 1.0% TWEEN 80®, about 0.05 to 40 mM sodium chloride, and optionally about 2 to 20 mM sodium phosphate at about pH. 7.4.

76. The method of embodiment 75, wherein the BT composition comprises BisEDT at a concentration greater than about 0.25 mg/mL, about 0.5% TWEEN 80®, about 10 mM sodium chloride, and about 10 mM sodium phosphate at about pH 7.4.

77. The method of any one of embodiments 73-76, wherein when the BT composition is aerosolized, wherein the aerosolized liquid droplets have a MMAD from about of from about 0.4 μm to about 5 μm.

78. The method of embodiment 77, wherein at least 60%, 65%, 70, 75%, 80%, 90%, or 95% of the liquid droplets have a MMAD of from about 0.4 μm to about 7 μm, or from about 0.5 μm to about 5 μm, or from about 0.7 μm to about 4 μm, or from about 0.7 μm to about 3.5 μm, or from about 0.8 μm to about 3.5 μm, or from about 0.9 μm to about 3.5 μm, or from about 0.9 μm to about 3 μm, or from about 0.8 μm to about 1.8 μm, or from about 0.8 μm to about 1.6 μm, or from about 0.9 μm to about 1.4 μm, or from about 1.0 μm to about 2.0 μm, or from about 1.0 μm to about 1.8 μm.

79. The method of embodiment 78, wherein the liquid droplets have a MMAD of from about 0.8 μm to about 1.6 μm, or from about 0.9 μm to about 3.5 μm, or from about 0.9 μm to about 3 μm, or from about 0.9 μm to about 1.4 μm, or from about 1.0 μm to about 2.0 μm, or from about 1.0 μm to about 1.8 μm.

80. The method of any one of embodiments 77-79, wherein the plurality of liquid droplets have a D90 of less than about 3 μm.

81. The method of embodiment 80, wherein the plurality of liquid droplets have a D90 of less than about 2 μm.

82. The method of any one of embodiments 77-81, wherein the plurality of liquid droplets are dispersed in a continuous gas phase.

83. The method of any one of embodiments 77-82, wherein the BT compound comprises bismuth and/or a bismuth salt associated covalently and/or in a coordination complex with one or more thiol-containing compounds.

84. The method of any one of embodiments 77-83, wherein the bismuth salt is bismuth nitrate, bismuth subnitrate, or bismuth chloride.

85. The method of any one of embodiments 77-84, wherein the thiol-containing compound comprises one or more agents selected from 1,2-ethane dithiol, 2,3-dimercaptopropanol, pyrithione, dithioerythritol, 3,4 dimercaptotoluene, 2,3-butanedithiol, 1,3-propanedithiol, 2-hydroxypropanethiol, 1-mercapto-2-propanol, dithioerythritol, dithiothreitol, cysteamine, and alpha-lipoic acid.

86. The method of any one of embodiments 77-85, wherein the BT composition comprises one or more BT compounds selected from BisBAL, BisEDT, Bis-dimercaprol, BisDTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, BisPyr/EDT, Bis-Pyr/PDT, Bis-Pyr/Tol, Bis-Pyr/Ery, bismuth-1-mercapto-2-propanol, BisEDT/CSTMN (1:1), BisPYR/CSTMN (1:1), BisBAL/CSTMN (1:1), BisTOL/CSTMN (1:1), and BisEDT/2-hydroxy-1-propanethiol.

87. The method of embodiment 86, wherein the BT compound is selected from one or more of BisEDT, Bis-Bal, Bis-Pyr, Bis-Ery, Bis-Tol, Bis-BDT, or BisEDT/2-hydroxy-1-propane thiol.

88. The method of embodiment 87, wherein the BT compound is BisEDT.

89. The method of embodiment 87, wherein the BT compound is BisBDT or BisBAL.

90. The method of any one of embodiments 77-89, wherein the total amount of the BT composition administered to the deep lung region is from about 0.25 mg to about 15 mg, from about 0.4 mg to about 15 mg, from about 0.6 mg to about 15 mg, from about 0.8 mg to about 15 mg, from about 1 mg to about 10 mg, from 2.5 mg to about 10 mg, from about 4 mg to about 10 mg, from about 5 mg to about 10 mg, from about 6 mg to about 10 mg, 0.6 mg to about 6 mg, from about 4 mg to about 15 mg, from about 6 mg to about 15 mg, from about 50 µg to about 750 µg, from about 75 µg to about 500 µg, from about 100 µg to about 250 µg, from about 100 µg to about 150 µg, or from about 75 µg to about 150 µg.

91. The method of embodiment 90, wherein the deep lung region is the deep lung alveoli.

92. The method of any one of embodiments 77-91, wherein the total amount of the BT composition comprising BisEDT administered to the deep lung alveoli is from about 0.6 mg to about 6 mg.

93. The method of any one of embodiments 77-92, wherein the composition is aerosolized via a nebulizer.

94. The method of embodiment 93, wherein the nebulizer is a jet nebulizer.

95. The method of embodiment 94, wherein the jet nebulizer is a PARI LC PLUS® jet nebulizer or PARI LC SPRINT® jet nebulizer.

96. The method of any one of embodiments 93-95, wherein the nebulizer has an inlet pressure from about 10 to about 40 psig.

97. The method of any one of embodiments 93-96, wherein the inlet flow is from about 3 L/min to about 8 L/min.

98. The method of any one of embodiments 93-97, wherein the exhaust air flow is from about 3 L/min to about 8 L/min.

99. A method of treating, managing or lessening the severity of symptoms and infections associated with one or more pulmonary diseases or infections in a subject, the method comprising administering to the subject a bismuth-thiol (BT) composition that comprises at least one BT compound.

100. The method of embodiment 99, wherein the one or more pulmonary diseases or infections are not the result of or associated with cystic fibrosis.

101. The method of embodiment 99 or 100, wherein the subject has at least one pulmonary infection and if there are two or more pulmonary infections, the infections are either concurrent or successive in order.

102. The method of embodiment 100 or 101, wherein the pulmonary infection is in one lung.

103. The method of any one of embodiments 100-102, wherein the pulmonary infection is in both lungs.

104. The method of any one of embodiments 100-103, wherein the pulmonary infection is in one or more of the three lobes of the right lung.

105. The method of any one of embodiments 100-104, wherein the pulmonary infection is in one or both of the two lobes of the left lung.

106. The method of any one of embodiments 100-105, wherein the pulmonary infection is bronchiectasis infection, pneumonia, valley fever, allergic bronchopulmonary aspergillosis (ABPA), ventilator acquired pneumonia, hospital acquired pneumonia, community acquired pneumonia, ventilator associated tracheobronchitis, lower respiratory tract infection, non-tuberculous Mycobacteria, anthrax, legionellosis, pertussis, bronchitis, Bronchiolitis, COPD-associated infection, and post-lung transplantation.

107. The method of any one of embodiments 100-106, wherein the pulmonary infection contains one or more bacterial or fungal pathogens.

108. The method of any one of embodiments 101-107, wherein the pulmonary infection is a CF-related pulmonary infection.

109. The method of embodiment 108, comprising treating the CF-related pulmonary infection.

110. The method of embodiment 108, comprising managing the CF-related pulmonary infection.

111. The method of embodiment 108, comprising lessening the severity of the CF-related pulmonary infection.

112. The method of any one of embodiments 100-111, wherein the pulmonary infection is located in or on the lung mucosa, the bronchi and/or the bronchioles.

113. The method of any one of embodiments 100-111, wherein the pulmonary infection is located on the surface of or within a bacterial biofilm, aggregated bacteria, a fungal biofilm, or aggregated fungi.

114. The method of any one of embodiments 100-111, wherein the pulmonary infection is located in the sputum.

115. The method of any one of embodiments 107-114, wherein the bacterial pathogen comprises one or more of gram-positive bacteria and gram-negative bacteria.

116. The method of any one of embodiments 107-115, wherein the bacterial pathogen comprises one or more of a bacterial biofilm and planktonic bacteria.

117. The method of embodiment 116, wherein the method comprises at least one of: (i) reducing the bacterial biofilm, (ii) impairing growth of the bacterial biofilm, and (iii) preventing reformation of the bacterial biofilm.

118. The method of any one of embodiments 107-114, wherein the fungal pathogen comprises planktonic fungi and/or biofilm fungi.

119. The method of any one of embodiments 107-118, wherein the BT composition treats, manages or lessens the severity of the pulmonary infection by one or both of:
   prevention of the infection by the bacterial or fungal pathogen; and
   reduction of the bacterial or fungal pathogen; and/or reducing the viscosity of the sputum.

120. The method of any one of embodiments 107-118, wherein the BT composition treats, manages or lessens the severity of the pulmonary infection by one or more of:
   prevention of elaboration or secretion of exotoxins from the bacterial or fungal pathogen;
   inhibition of cell viability or cell growth of planktonic cells of the bacterial or fungal pathogen;
   inhibition of biofilm formation by the bacterial or fungal pathogen; and
   inhibition of biofilm viability or biofilm growth of biofilm-forming cells of the bacterial or fungal pathogen.

121. The method of any one of embodiments 107-120, wherein the one or more pathogens are selected from *Haemophilus influenzae*, *Pseudomonas aeruginosa*, *Staphylococcus aureus*, *Staphylococcus* warneri *Staphylococcus lugdunensis*, *Staphylococcus epidermidis*, *Streptococcus milleri anginous*, *Streptococcus pyogenes*, non-tuberculosis *mycobacterium*, *Mycobacterium tuberculosis*, *Burkholderia* spp., *Achromobacter xylosoxidans*, *Pandoraea sputorum*, *Stenotrophomonas maltophilia*, *Alcaligenes xylosoxidans*, *Haemophilus pittmaniae*, *Serratia marcescens*, *Candidia albacans*, *Candida parapsilosis*, *Candida guilliermondii*, *Morganella morganii*, *Inquilinus limosus*, *Ralstonia mannitolilytica*, *Pandoraea apista*, *Pandoraea pnomenusa*, *Pandoraea sputorum*, *Bdellovibrio bacteriovorus*, *Bordetella bronchiseptica*, *Vampirovibrio chlorellavorus*, *Actinobacter baumanni*, *Cupriadidus metallidurans*, *Cupriavidus pauculus*, *Cupriavidus respiraculi*, *Delftia acidivordans*, *Exophilia dermatitidis*, *Herbaspirillum frisingense*, *Herbaspirillum seropedicae*, *Klebsiella pneumoniae*, *Pandoraea norimbergensis*, *Pandoraea pulmonicola*, *Pseudomonas mendocina*, *Pseudomonas pseudoalcaligenes*, *Pseudomonas putida*, *Pseudomonas stutzeri*, *Ralstonia insidiosa*, *Ralstonia pickettii*, *Neisseria gonorrhoeae*, NDM-1 positive *E. coli*, *Enterobacter cloaca*, Vancomycin-resistant *E. faecium*, Vancomycin-resistant *E. faecalis*, *E. faecium*, *E. faecalis*, Clindamycin-resistant *S. agalactiae*, *S. agalactiae*, *Bacteroides fragilis*, *Clostridium difficile*, *Streptococcus pneumonia*, *Moraxella catarrhalis*, *Haemophilus haemolyticus*, *Haemophilus parainfluenzae*, *Chlamydophilia pneumoniae*, *Mycoplasma pneumoniae*, *Atopobium*, *Sphingomonas*, *Saccharibacteria*, *Leptotrichia*, *Capnocytophaga*, *Oribacterium*, *Aquabacterium*, *Lachnoanaerobaculum*, *Campylobacter*, *Acinetobacter*; *Agrobacterium*; *Bordetella*; *Brevundimonas*; *Chryseobacterium*; *Delftia*; *Enterobacter*; *Klebsiella*; *Pandoraea*; *Pseudomonas*; *Ralstonia*, and *Prevotella*.

122. The method of embodiment 121, wherein the non-tuberculosis *mycobacterium* is selected from *Mycobacterium abscessus*, *Mycobacterium avium*, *Mycobacterium intracellulare*, *Mycobacterium fortuitum*, *Mycobacterium gordonae*, *Mycobacterium kansasii*, *Mycobacterium avium* complex, *Mycobacterium marinum*, *Mycobacterium terrae* and *Mycobacterium cheloni*.

123. The method of embodiment 121, wherein the *Burkholderia* spp. is selected from *Burkholderia cepacia*, *Burkholderia multivorans*, *Burkholderia cenocepacia*, *Burkholderia stabilis*, *Burkholderia vietnamiensis*, *Burkholderia dolosa*, *Burkholderia ambifaria*, *Burkholderia anthina*, *Burkholderia pyrrocinia*, *Burkholderia gladioli*, *Burkholderia ubonensis*, *Burkholderia arboris*, *Burkholderia latens*, *Burkholderia lata*, *Burkholderia metallica*, *Burkholderia seminalis*, *Burkholderia contaminans*, and *Burkholderia diffusa*.

124. The method of embodiment 121, wherein the one or more pathogens are selected from *Pseudomonas aeruginosa*, single drug-resistant *Pseudomonas aeruginosa*, multi drug-resistant *Pseudomonas aeruginosa*, *Staphylococcus aureus*, single drug-resistant *Staphylococcus aureus*, multi drug-resistant *Staphylococcus aureus*, methicillin resistant *Staphylococcus aureus*, *Mycobacterium abscessus*, *Mycobacterium avium*, *Haemophilus influenzae*, *Burkholderia cepacia*, *Burkholderia multivorans*, *Burkholderia cenocepacia*, *Burkholderia dolosa*, *Achromobacter xylosoxidans*, *Stenotrophomonas maltophilia*, *Staphylococcus epidermidis*, and *Burkholderia vietnamiensis*.

125. The method of embodiment 121, wherein the one or more pathogens are selected from *Haemophilus influenzae*, *Pseudomonas aeruginosa*, and *Staphylococcus aureus*.

126. The method of any one of embodiments 117, 118, or 120, wherein the one or more pathogens are selected from biofilms of *Pseudomonas aeruginosa*, *Burkholderia cenocepacia*, *Burkholderia cepacia* complex, *Mycobacterium abscessus*, *Mycobacterium avium*, *Achromobacter* spp., *Staphylococcus epidermidis*, *Stenotrophomonas maltophilia*, and *Staphylococcus aureus*.

127. The method of embodiment 125, wherein the *Pseudomonas aeruginosa* and/or *Staphylococcus aureus* is multi-drug resistant.

128. The method of any one of embodiments 107-127, wherein the one or more pathogens exhibit resistance or is refractory to an antibiotic selected from amikacin, aztreonam, methicillin, vancomycin, nafcillin, gentamicin, ampicillin, chloramphenicol, doxycycline and tobramycin.

129. The method of embodiment 128, wherein the antibiotic is amikacin or tobramycin.

130. The method of embodiment 128, wherein the bacterial pathogen is methicillin resistant *Staphylococcus aureus*.

131. The method of any one of embodiments 99-130, further comprising coadministering or conjointly administering to the subject an antibiotic selected from amikacin, tobramycin, gentamicin, piperacillin, mezlocillin, ticarcillin, imipenem, ciprofloxacin, ceftazidime, aztreonam, ticarcillin-clavulanate, dicloxacillin, amoxicillin, trimethoprim-sulfamethoxazole, cephalexin, piperacillin-tazobactam, linezolid, daptomycin, vancomycin, metronidazole, clindamycin, colistin, tetracycline, levofloxacin, amoxicillin and clavulanic acid (Augmentin®), cloxacillin, dicloxacillin, cefdinir, cefprozil, cefaclor, cefuroxime, erythromycin/sulfisoxazole, erythromycin, clarithromycin, azithromycin, doxycycline, minocycline, tigecycline, imipenem, meropenem, colistimethate/Colistin®, methicillin, oxacillin, nafcillin, carbenicillin, azlocillin, piperacillin and tazobactam (Zosyn®), cefepime, ethambutol, rifampin, and meropenem.

132. The method of embodiment 131, wherein the antibiotic is selected from meropenem, ceftazidime, tobramycin, amikacin, aztreonam, ciprofloxacin, colistin, and levofloxacin.

133. The method of any one of embodiments 107-120, wherein the fungal pathogen is *Candida albicans*, drug resistant *Candida albicans*, *Candida glabrata*, *Candida krusei*, *Candida guilliermondii*, *Candida auris*, *Candida tropicalis*, *Aspergillus niger*, *Aspergillus terreus*, *Aspergillus fumigatus*, and/or *Aspergillus flavus*.

134. The method of any one of embodiments 99-133, comprising administering the BT composition by inhalation, orally or nasally, using an aerosol device.

135. The method of embodiment 134, wherein the aerosol device is a nebulizer.

136. The method of embodiment 134 or 135, wherein the BT composition is in the form of an aqueous solution or suspension.

137. The method of any one of embodiments 99-136, wherein the BT composition is administered topically to lung tissue.

138. The method of any one of embodiments 99-137, wherein
the BT composition is administered as a dosage from about 0.25 mg/mL to about 15 mg/mL, from about 0.4 mg/mL to about 15 mg/mL, from about 0.6 mg/mL to about 15 mg/mL, from about 0.6 mg/mL to about 100 mg/mL, from about 5 mg/mL to about 100 mg/mL, from about 10 mg/mL to about 100 mg/mL, from about 25 mg/mL to about 100 mg/mL, from about 50 mg/mL to about 100 mg/mL, from about 0.8 mg/mL to about 15 mg/mL, from about 1 mg/mL to about 10 mg/mL, from about 2.5 mg/mL to about 10 mg/mL, from about 4 mg/mL to about 10 mg/mL, from about 5 mg/mL to about 10 mg/mL, from about 6 mg/mL to about 10 mg/mL, 0.6 mg/mL to about 6 mg/mL, from about 4 mg/mL to about 15 mg/mL, from about 6 mg/mL to about 15 mg/mL, from about 50 µg/mL to about 750 µg/mL, from about 75 µg/mL to about 500 µg/mL, from about 100 µg/mL to about 250 µg/mL, from about 100 µg/mL to about 150 µg/mL, or from about 75 µg/mL to about 150 µg/mL; and/or the total amount of the BT composition administered to the lungs is from about 0.25 mg to about 15 mg, from about 0.4 mg to about 15 mg, from about 0.6 mg to about 15 mg, from about 0.8 mg to about 15 mg, from about 1 mg to about 10 mg, from 2.5 mg to about 10 mg, from about 4 mg to about 10 mg, from about 5 mg to about 10 mg, from about 6 mg to about 10 mg, 0.6 mg to about 6 mg, from about 4 mg to about 15 mg, from about 6 mg to about 15 mg, from about 50 µg to about 750 µg, from about 75 µg to about 500 µg, from about 100 µg to about 250 µg, from about 100 µg to about 150 µg, or from about 75 µg to about 150 µg.

139. The method of any one of embodiments 99-138, wherein the BT composition is administered as a dosage from about 0.6 mg/mL to about 6 mg/mL.

140. The method of any one of embodiments 99-139, wherein the BT composition is administered three times per day, two times per day, once daily, every other day, once every three days, once every week, once every other week, once every month, to once every other month.

141. The method of embodiment 140, wherein the BT composition is administered once every week.

142. The method of any one of embodiments 99-141, wherein one or more of the following symptoms is lessened in severity in the subject: cough, wheezing, breathlessness, bronchiectasis, nasal polyps, hemoptysis, respiratory failure, and pulmonary exacerbation.

143. The method of any one of embodiments 99-142, wherein the bismuth-thiol composition comprises a plurality of microparticles that comprise a bismuth-thiol (BT) compound, substantially all of said microparticles having a volumetric mean diameter of from about 0.4 µm to about 5 µm, and wherein the BT compound comprises bismuth or a bismuth salt and a thiol-containing compound.

144. The method of embodiment 143, wherein at least 60%, 65%, 70, 75%, 80%, 90%, or 95% of the microparticles have a volumetric mean diameter of from about 0.4 µm to about 3 µm, or from about 0.5 µm to about 2 µm, or from about 0.7 µm to about 2 µm, or from about 0.8 µm to about 1.8 µm, or from about 0.8 µm to about 1.6 µm, or from about 0.9 µm to about 1.4 µm, or from about 1.0 µm to about 2.0 µm, or from about 1.0 µm to about 1.8 µm.

145. The method of embodiments 142-143, wherein the bismuth salt is bismuth nitrate, bismuth subnitrate, or bismuth chloride.

146. The method of embodiments 142-143, wherein the thiol-containing compound comprises one or more agents selected from 1,2-ethane dithiol, 2,3-dimercaptopropanol, pyrithione, dithioerythritol, 3,4 dimercaptotoluene, 2,3-butanedithiol, 1,3-propanedithiol, 2-hydroxypropanethiol, 1-mercapto-2-propanol, dithioerythritol, dithiothreitol, cysteamine, and alpha-lipoic acid.

147. The method of any one of embodiments 143-146, wherein the BT composition comprises one or more BT compounds selected from BisBAL, BisEDT, Bis-dimercaprol, BisDTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, BisPyr/EDT, Bis-Pyr/PDT, Bis-Pyr/Tol, Bis-Pyr/Ery, bismuth-1-mercapto-2-propanol, BisEDT/CSTMN (1:1), BisPYR/CSTMN (1:1), BisBAL/CSTMN (1:1), Bis-TOL/CSTMN (1:1), and BisEDT/2-hydroxy-1-propanethiol.

148. The method of embodiment 147, wherein the BT compound is selected from one or more of BisEDT, Bis-Bal, Bis-Pyr, Bis-Ery, Bis-Tol, Bis-BDT, or BisEDT/2-hydroxy-1-propane thiol.

149. The method of embodiment 148, wherein the BT compound is BisEDT.

150. The method of embodiment 148, wherein the BT compound is BisBDT or BisBAL.

151. The method of any one of embodiments 99-150, wherein the total amount of the BT composition administered to the deep lung region is from about 0.25 mg to about 15 mg, from about 0.4 mg to about 15 mg, from about 0.6 mg to about 15 mg, from about 0.8 mg to about 15 mg, from about 1 mg to about 10 mg, from 2.5 mg to about 10 mg, from about 4 mg to about 10 mg, from about 5 mg to about 10 mg, from about 6 mg to about 10 mg, 0.6 mg to about 6 mg, from about 4 mg to about 15 mg, from about 6 mg to about 15 mg, from about 50 µg to about 750 µg, from about 75 µg to about 500 µg, from about 100 µg to about 250 µg, from about 100 µg to about 150 µg, or from about 75 µg to about 150 µg.

152. The method of embodiment 151, wherein the deep lung region is the deep lung alveoli.

153. The aerosol of any one of embodiments 55-72, wherein at least 60%, 65%, 70, 75%, 80%, 90%, or 95% of the microparticles have a volumetric mean diameter of from about 0.6 µm to about 2.5 µm.

154. The aerosol of embodiment 153, where substantially all of the microparticles have a VMD of from about 0.6 µm to about 2.5 µm.

155. The aerosol of any one of embodiments 55-72 or 153-154, wherein at least 70% of the aerosolized particles have a MMAD of about 0.9 µm to about 3 µm.

156. The aerosol of any one of embodiments 55-72 or 153-155, wherein the composition is a suspension of microparticles having a volumetric mean diameter (VMD) from about 0.6 µm to about 2.5 µm and/or a mass median aerodynamic diameter (MMAD) from about 0.9 µm to about 3 µm.

157. The aerosol of any one of embodiments 55-72 or 153-156, wherein the bismuth-thiol composition comprises a plurality of microparticles that comprise a bismuth-thiol (BT) compound, substantially all of said microparticles having a volumetric mean diameter of from about 0.4 µm to about 5 µm, and wherein the BT compound comprises bismuth or a bismuth salt and a thiol-containing compound.

158. The aerosol of any one of embodiments 55-72 or 153-157, wherein after delivering the aerosolized composition to a subject, at least 60%, 65%, 70, 75%, 80%, 90%, or 95% of the BT compound dose is deposited on the lung.

159. The aerosol of embodiment 158, wherein at least 80% of the BT compound dose is deposited on the lung.

160. The aerosol of embodiment 158, wherein at least 90% of the BT compound dose is deposited on the lung.

161. The method of any one of embodiments 1-54 or 73-152, wherein at least 60%, 65%, 70, 75%, 80%, 90%, or 95% of the microparticles have a volumetric mean diameter of from about 0.6 µm to about 2.5 µm.

162. The method of embodiment 161, where substantially all of the microparticles have a VMD of from about 0.6 µm to about 2.5 µm.

163. The method of any one of embodiments 1-54, 73-152, or 161-162, wherein at least 70% of the aerosolized particles have a MMAD of about 0.9 µm to about 3 µm.

164. The method of any one of embodiments 1-54, 73-152, or 161-163, wherein the composition is a suspension of microparticles having a volumetric mean diameter (VMD) from about 0.6 µm to about 2.5 µm and/or a mass median aerodynamic diameter (MMAD) from about 0.9 µm to about 3 µm.

165. The method of any one of embodiments 1-54, 73-152, or 161-164, wherein the bismuth-thiol composition comprises a plurality of microparticles that comprise a bismuth-thiol (BT) compound, substantially all of said microparticles having a volumetric mean diameter of from about 0.4 µm to about 5 µm, and wherein the BT compound comprises bismuth or a bismuth salt and a thiol-containing compound.

166. The method of any one of embodiments 1-54, 73-152, or 161-165, wherein if deposited to the lung (e.g. the deep lung region), the BT compounds have an average half-life of at least 2 days.

167. The method of any one of embodiment 166, wherein if deposited to the deep lung region, the BT compounds have an average half-life of at least 4 days.

168. The method of any one of embodiments 1-54, 73-152, or 161-167, wherein after delivering the aerosolized composition to a subject, at least 60%, 65%, 70, 75%, 80%, 90%, or 95% of the BT compound dose is deposited on the lung.

169. The aerosol of embodiment 168, wherein at least 80% of the BT compound dose is deposited on the lung.

170. The aerosol of embodiment 168, wherein at least 90% of the BT compound dose is deposited on the lung.

171. A method of treating, managing or lessening the severity of cystic fibrosis (CF) symptoms and infections in a subject, the method comprising administering to the subject a bismuth-thiol (BT) composition that comprises BisEDT suspended therein, wherein administering the BT composition is via inhalation, orally or nasally, using an aerosol device.

172. The method of embodiment 171, wherein the BT composition comprises a plurality of microparticles wherein at least 70% of said microparticles having a volumetric mean diameter (VMD) of from about 0.6 µm to about 2.5 µm.

173. The method of embodiment 172, wherein at least 80% of said microparticles having a VMD of from about 0.6 µm to about 2.5 µm.

174. The method of embodiment 172, wherein at least 90% of said microparticles having a VMD of from about 0.6 µm to about 2.5 µm.

175. The method of embodiment 172, wherein when the BT composition is aerosolized, at least 70% of the aerosolized liquid droplets have a mass median aerodynamic diameter (MMAD) from about of from about 0.9 µm to about 3 µm.

176. The method of embodiment 173, wherein when the BT composition is aerosolized, at least 80% of the aerosolized liquid droplets have a MMAD from about of from about 0.9 µm to about 3 µm.

177. The method of embodiment 174, wherein when the BT composition is aerosolized, at least 90% of the aerosolized liquid droplets have a MMAD from about of from about 0.9 µm to about 3 µm.

178. The method of embodiment 171, wherein the BT composition comprises BisEDT at a concentration greater than about 0.1 mg/mL, about 0.05% to about 1.0% TWEEN 80®, about 0.05 to 40 mM sodium chloride, and optionally about 2 to 20 mM sodium phosphate at about pH. 7.4.

179. The method of embodiment 171, wherein if deposited to the deep lung region, the BisEDT compounds have an average half-life of about 4 days.

180. The method of embodiment 171, wherein the subject has at least one pulmonary infection containing one or more bacterial pathogens and/or fungal pathogens.

181. The method of embodiment 180, wherein the method comprises at least one of: (i) reducing a bacterial biofilm, (ii) impairing growth of a bacterial biofilm, (iii) preventing initial formation of the bacterial biofilm, and/or (iv) preventing reformation of the bacterial biofilm.

182. The method of embodiment 180, wherein the one or more pathogens are selected from *Haemophilus influenzae, Pseudomonas aeruginosa, Staphylococcus aureus, Staphylococcus warneri Staphylococcus lugdunensis, Staphylococcus epidermidis, Streptococcus milleri anginous, Streptococcus pyogenes*, non-tuberculosis mycobacterium, *Mycobacterium tuberculosis, Burkholderia* spp., *Achromobacter xylosoxidans, Pandoraea sputorum, Stenotrophomonas maltophilia, Alcaligenes xylosoxidans, Haemophilus pittmaniae, Serratia marcescens, Candida albicans*, drug resistant *Candida albicans, Candida glabrata, Candida krusei, Candida guilliermondii, Candida auris, Candida tropicalis, Aspergillus niger, Aspergillus terreus, Aspergillus fumigatus, Aspergillus flavus, Morganella morganii, Inquilinus limosus, Ralstonia mannitolilytica, Pandoraea apista, Pandoraea pnomenusa, Pandoraea sputorum, Bdellovibrio bacteriovorus, Bordetella bronchiseptica, Vampirovibrio chlorellavorus, Actinobacter baumanni, Cupriadidus metallidurans, Cupriavidus pauculus, Cupriavidus respiraculi, Delftia acidivordans, Exophilia dermatitidis, Herbaspirillum frisingense, Herbaspirillum seropedicae, Klebsiella pneumoniae, Pandoraea norimbergensis, Pandoraea pulmonicola, Pseudomonas mendocina, Pseudomonas pseudoalcaligenes, Pseudomonas putida, Pseudomonas stutzeri, Ralstonia insidiosa, Ralstonia pickettii, Neisseria gonorrhoeae*, NDM-1 positive *E. coli, Enterobacter* cloaca, Vancomycin-resistant *E. faecium*, Vancomycin-resistant *E. faecalis, E. faecium, E. faecalis*, Clindamycin-resistant *S. agalactiae, S. agalactiae, Bacteroides fragilis, Clostridium difficile, Streptococcus pneumonia, Moraxella catarrhalis, Haemophilus haemolyticus, Haemophilus parainfluenzae, Chlamydophilia pneumoniae, Mycoplasma pneumoniae, Atopobium, Sphingomonas, Saccharibacteria, Leptotrichia, Capnocytophaga, Oribacterium, Aquabacterium, Lachnoanaerobaculum, Campylobacter, Acinetobacter; Agrobacterium; Bordetella; Brevundimonas; Chryseobacterium; Delftia; Enterobacter; Klebsiella; Pandoraea; Pseudomonas; Ralstonia,* and *Prevotella*.

183. An aerosol comprising a plurality of dispersed liquid droplets in a gas, said liquid droplets comprising a BT composition comprising BisEDT compound suspended therein; and
wherein at least 70% of the liquid droplets have a MMAD from about of from about 0.9 µm to about 3 µm.

184. The aerosol of embodiment 183, wherein prior to aerosolization, the BT composition comprises a plurality of microparticles wherein at least 70% of said microparticles have a VMD of from about 0.6 µm to about 2.5 µm.

185. The aerosol of embodiment 183, wherein least 80% of the liquid droplets have a MMAD from about of from about 0.9 µm to about 3 µm.

186. The aerosol of embodiment 183, wherein least 90% of the liquid droplets have a MMAD from about of from about 0.9 µm to about 3 µm.

187. The aerosol of embodiment 185, wherein prior to aerosolization, the BT composition comprises a plurality of microparticles wherein at least 80% of said microparticles have a VMD of from about 0.6 µm to about 2.5 µm.

188. The aerosol of embodiment 186, wherein prior to aerosolization, the BT composition comprises a plurality of microparticles wherein at least 90% of said microparticles have a VMD of from about 0.6 μm to about 2.5 μm.

189. The aerosol of embodiment 183, wherein the droplets further comprise TWEEN 80® (e.g. from about 0.05% to about 1%) and optionally a buffer (e.g. sodium phosphate or sodium citrate) at a pH of about 7.4; and/or sodium chloride.

190. The aerosol of embodiment 183, wherein if deposited to the deep lung region, the BisEDT compounds have an average half-life of more than 2 days.

191. The aerosol of embodiment 183, wherein if deposited to the deep lung region, the BisEDT compounds have an average half-life of about 4 days.

193. A pharmaceutical composition comprising bismuth-thiol (BT) composition that comprises BisEDT suspended therein, wherein the BT composition comprises a plurality of microparticles, wherein the D90 of said microparticles is less than or equal to 1.9 μm.

194. A pharmaceutical composition comprising bismuth-thiol (BT) composition comprises BisEDT suspended therein, wherein the BT composition comprises a plurality of microparticles, wherein the D90 of said microparticles is less than or equal to about 1.6 μm.

195. The pharmaceutical composition of embodiment 193, wherein at least 70% of said microparticles having a volumetric mean diameter of from about 0.6 μm to about 2.5 μm.

196. The pharmaceutical composition of embodiment 193, wherein at least 90% of said microparticles having a volumetric mean diameter of from about 0.6 μm to about 2.5 μm.

197. A method of treating, managing or lessening the severity of symptoms and infections associated with one or more pulmonary diseases or infections in a subject, the method comprising administering to the subject a bismuth-thiol (BT) composition that comprises BisEDT, wherein the BT composition comprises a plurality of microparticles wherein at least 70% of said microparticles having a volumetric mean diameter of from about 0.6 μm to about 2.5 μm, and wherein when the BT composition is aerosolized, at least 70% of the aerosolized liquid droplets have a MMAD from about of from about 0.9 μm to about 3 μm.

198. The method of embodiment 197, wherein the one or more pulmonary diseases or infections are not the result of or associated with cystic fibrosis.

199. The method of embodiment 198, wherein the pulmonary infection is bronchiectasis infection, pneumonia, valley fever, allergic bronchopulmonary aspergillosis (ABPA), ventilator acquired pneumonia, hospital acquired pneumonia, community acquired pneumonia, ventilator associated tracheobronchitis, lower respiratory tract infection, non-tuberculous Mycobacteria, anthrax, legionellosis, pertussis, bronchitis, Bronchiolitis, COPD-associated infection, and post-lung transplantation.

EXAMPLES

The following examples are provided to illustrate the present disclosure, and should not be construed as limiting thereof. Additional experimental procedures and details can be found in International Patent Application Nos. PCT/US2010/023108, PCT/US2011/023549, and PCT/US2011/047490, which are hereby incorporated by reference in their entireties for all purposes.

Example 1: General Synthesis of BisEDT

The starting materials and reagents used in preparing these compounds are either available from commercial supplier such as Aldrich Chemical Co., Bachem, etc., or can be made by methods well known in the art. The starting materials and the intermediates and the final products of the reaction can be isolated and purified if desired using conventional techniques, including but not limited to filtration, distillation, crystallization, chromatography, and the like and can be characterized using conventional means, including physical constants and spectral data. Unless specified otherwise, the reactions described herein take place at atmospheric pressure over a temperature range from about −78° C. to about 150° C.

$Bi_5O(OH)_9(NO_3)_4$ + HS–CH$_2$CH$_2$–SH →
$Bi_5H_9N_4O_{22}$
MW: 1461.98
$C_2H_6S_2$
MW: 94.20

[structure of BisEDT dimer]
$C_6H_{12}Bi_2S_6$
MW: 694.48

Microparticulate bismuth-1,2-ethanedithiol (BisEDT, soluble bismuth preparation) was prepared as follows: To an excess (11.4 L) of 5% aqueous HNO$_3$ at room temperature in a 15 L polypropylene carboy was slowly added by dropwise addition 0.331 L (~0.575 moles) of an aqueous Bi(NO$_3$)$_3$ solution (43% Bi(NO$_3$)$_3$ (w/w), 5% nitric acid (w/w), 52% water (w/w), Shepherd Chemical Co., Cincinnati, Ohio, product no. 2362; δ~1.6 g/mL) with stirring, followed by slow addition of absolute ethanol (4 L). Some white precipitate formed but was dissolved by continued stirring. An ethanolic solution (~1.56 L, ~0.55 M) of 1,2-ethanedithiol (CAS 540-63-6) was separately prepared by adding, to 1.5 L of absolute ethanol, 72.19 mL (0.863 moles) of 1,2-ethanedithiol using a 60 mL syringe, and then stirring for five minutes. The 1,2-ethanedithiol/EtOH reagent was then slowly added by dropwise addition over the course of five hours to the aqueous Bi(NO$_3$)$_3$/HNO$_3$ solution, with continued stirring overnight. The formed product was allowed to settle as a precipitate for approximately 15 minutes, after which the filtrate was removed at 300 mL/min using a peristaltic pump. The product was then collected by filtration on fine filter paper in a 15-cm diameter Buchner funnel, and washed sequentially with three, 500-mL volumes each of ethanol, USP water, and acetone to obtain BisEDT (694.51 gm/mole) as a yellow amorphous powdered solid. The product was placed in a 500 mL amber glass bottle and dried over CaCl$_2$) under high vacuum for 48 hours. Recovered material (yield ~200 g) gave off a thiol-characteristic odor. The crude product was redissolved in 750 mL of absolute ethanol, stirred for 30 min, then filtered and washed sequentially with 3×50 mL ethanol, 2×50 mL acetone, and washed again with 500 mL of acetone. The rewashed powder was triturated in 1M NaOH (500 mL), filtered and washed with 3×220 mL water, 2×50 mL ethanol, and 1×400 mL acetone to afford 156.74 gm of purified BisEDT. Subsequent batches prepared in essentially the same manner resulted in yields of about 78-91%.

The product was characterized as having the structure shown above by analysis of data from $^1$H and $^{13}$C nuclear magnetic resonance (NMR), infrared spectroscopy (IR), ultraviolet spectroscopy (UV), mass spectrometry (MS) and elemental analysis. An HPLC method was developed to determine chemical purity of BisEDT whereby the sample was prepared in DMSO (0.5 mg/mL). The $\lambda_{max}$ was determined by scanning a solution of BisEDT in DMSO between 190 and 600 nm. Isocratic HPLC elution at 1 mL/min was performed at ambient temperature in a mobile phase of 0.1% formic acid in acetonitrile:water (9:1) on a Waters (Millipore Corp., Milford, Mass.) model 2695 chromatograph with UV detector monitoring at 265 nm ($\lambda_{max}$), 2 µL injection volume, equipped with a YMC Pack PVC Sil NP, 5 µm, 250×4.6 mm inner diameter analytical column (Waters) and a single peak was detected, reflecting chemical purity of 100±0.1%. Elemental analysis was consistent with the structure of BisEDT as shown above.

The dried particulate matter was characterized to assess the particle size properties. Briefly, microparticles were resuspended in 2% Pluronic® F-68 (BASF, Mt. Olive, N.J.) and the suspension was sonicated for 10 minutes in a water bath sonicator at standard setting prior to analysis using a Nanosizer/Zetasizer Nano-S particle analyzer (model ZEN1600 (without zeta-potential measuring capacity), Malvern Instruments, Worcestershire, UK) according to the manufacturer's recommendations. From compiled data of two measurements, microparticles exhibited a unimodal distribution with all detectable events between about 0.6 microns and 4 microns in volumetric mean diameter (VMD) and having a peak VMD at about 1.3 microns.

Example 2: Preparation of Microparticulate bismuth-1-2-ethanedithiol (BisEDT)

Microparticulate bismuth-1,2-ethanedithiol (BisEDT) was prepared as follows: Water (25.5 L) and 70% nitric acid (1800 mL) were mixed together in a Nalgene reactor. Then, water (2300 mL) was added to an Erlenmeyer flask, followed by bismuth subnitrate (532 g), and the mixture was stirred. To the mixture was added 70% nitric acid (750 mL) to obtain a clear solution. This solution was transferred into the Nalgene reactor and the resulting mixture was stirred for 20 min. Then, 9.5 L of 95% EtOH was added to the reactor in three portions.

Separately, 1,2-ethanedithiol, 98%, (229 mL) was added to a bottle followed by two 250 mL EtOH portions with stirring. A further 5 L EtOH was added to the bottle with stirring. The 1,2-ethanedithiol solution was then added to the reactor over about 4 hours while stirring. After stirring for 18 hours, the solids were allowed to settle for 2 hours. EtOH (20 L) was added and the mixture stirred for 24 hours. The solids were allowed to settle for 1.5 hours, then separated by filtration of the mixture, followed by rinsing with EtOH.

To the empty reactor was added 9 L EtOH and the filtered solids, which was stirred for 18 hours. The solids were allowed to settle for 1 hour, then separated by filtration of the mixture, followed by rinsing with EtOH. Next, the empty reactor was charged with 9 L acetone, 99.5%, and the filtered solids, which was stirred for 15 hours. The solids were allowed to settle for 1.5 hours, then separated by filtration of the mixture, followed by rinsing with acetone. Again, the empty reactor was charged with 9 L acetone, 99.5%, and the filtered solids, which was stirred for 1.4 hours. The solids were filtered and air-dried for 69 hours, then vacuum-dried for 4 hours. After mixing the solid, it was sieved through a 10 mesh (2 mm) and then 18 mesh (1 mm) sieve to give BisEDT.

Example 3: Synthesis of Additional Bismuth Thiol Compounds

The following bismuth thiol compounds can also be prepared according to the methods of Examples 1 and 2:

bismuth-2,3-dimercaptopropanol (2:3 molar ratio, BisBAL)
bismuth-4-methyl-1,2-benzenedithiol (2:3 molar ratio, BisTOL)
bismuth-2,3-butanedithiol (BisBDT)

Example 4: Formulation(s) for CF Inhalant

Objective: The objective of this study was to develop methods for the nose-only inhalation exposures of BisEDT for rodents. The aerosols were generated from suspension formulations of BisEDT in aqueous media (0.5% TWEEN 80® in Sodium Phosphate Buffer, pH 7.4). Aerosols were generated with a commercial compressed air jet nebulizer into a rodent nose only inhalation exposure system. Suspension formulations were created by sonication with neat API with 0.5% TWEEN 80® in Sodium Phosphate Buffer, pH 7.4. This was further refined by adjusting the vehicle to an osmolality of 300 mOsmol/kg. Aerosols were characterized for particle size distribution and aerosol concentration. Aerosol concentration was determined by differential mass and chemical analysis of the aerosol filter samples.

Suspension concentrations between 2.5 and 100 mg/mL were evaluated for one formulation of BisEDT and ranged from 18.5 to 719 µg/L respectively. Further tests were performed with a new formulation of BisEDT and the suspension concentrations of 2.5 mg/mL, 10 mg/mL, 50 mg/mL and 100 mg/mL yielded aerosol concentrations of 18.4, 97.7, 159, and 1300 µg/L, respectively. The particle size increased with suspension concentration from ~1 µm to 3.5 µm MMAD, which is respirable for rodent inhalation exposures.

To support potential dose range finding studies in rat nose only inhalation exposures are typically recommended for between 30 and 180 minutes. Therefore the pulmonary deposited dose range from these suspension formulations are between 42 µg/kg and 17.5 mg/kg. As appropriate the suspension concentration and/or exposure time can be modulated to adjust pulmonary deposited dose.

Materials and Methods: BisEDT—Two separate lots of Bismuth Ethane Dithiol, BisEDT, were used as received. The initial stages of method development were performed with Lot #ED268-1-11-01 and the final stages were performed with Lot #XL-47-125, which had been shipped in preparation for exposures. The two materials behaved slightly differently, requiring a change in the final determination of exposure times.

Aerosol Methods: Formulation—Suspension formulations of BisEDT were prepared in 0.5% TWEEN 80® in Sodium Phosphate Buffer, pH 7.4. Suspensions of 2.5, 10, 25, 50, 75 and 100 mg/mL were prepared by sonication with a Covaris sonicator. In later tests, the vehicle was adjusted with sodium chloride to achieve an Osmolality of 300 mOsmol/kg. Suspensions were prepared at 2.5, 50, and 100 mg/mL.

Aerosol Delivery System: FIG. 1 shows a schematic of the aerosol generation and exposure system used during these tests. Aerosol was generated by using a PARI LC PLUS® compressed air jet nebulizer (Pari Respiratory Equipment Inc., Midlothian, Va.) with an inlet pressure of 20 psi. The aerosols transitioned into a rodent nose-only inhalation exposure system operated with an inlet air flow of ~8.5 L/min and an exhaust air flow of ~7.1 L/min. Aerosol generated by the nebulizer was delivered to a one-tier nose-only flow-past inhalation exposure system.

Aerosol concentration was measured at the breathing zone of the exposure system by collection of the aerosol onto 47-mm filters (Whatman GF/A membrane filters). Filter samples were collected at a nominal flowrate of 0.3 L/min. Aerosol mass concentration was determined by differential weight analysis of the filter samples. Filters were then transferred to the analytical chemistry laboratory for analysis using HPLC. Details of the analytical chemistry methods are included in analytical method ACM-1046-0 (Determination of BisEDT in Formulations and Filter Extracts by HPLC-UV).

Particle Size Distribution Measurement: Particle size distribution for exposure was measured by using an In-Tox Mercer 2.0 L/min cascade impactor (In-Tox, LLC, Moriarty, N. Mex.).

Calculation of Deposited Dose: The first two equations were used to calculate the presented aerosol dose and the theoretical deposited dose, respectively. In these calculations the average aerosol concentration (chemistry) along with projected body weights for rats are used.

$$D_P[\text{mg kg}^{-1}] = \frac{AC[\text{mg L}^{-1}]RMV[\text{L min}^{-1}]T[\text{min}]}{BW[\text{kg}]}$$

$$D_D[\text{mg kg}^{-1}] = \frac{AC[\text{mg L}^{-1}]RMV[\text{L min}^{-1}]T[\text{min}]DF}{BW[\text{kg}]}$$

$$RMV = 0.608 \, BW^{0.852}$$

Where: Dp: Presented dose; DD: Deposited Dose; AC: Aerosol Exposure Concentration; RMV: Respiratory Minute Volume (Alexander. D J, et al., 2008. Inhal Toxicol.; 20(13): 1179-89); T: Exposure time; BW: Body Weight; DF: Pulmonary deposition fraction (assumed 10%, Tepper et al., 2016 Int J Toxicol; 35(4):376-392); Time varied between 30 and 180 minutes.

Results

Aerosol Concentration and Particle Size: The average total aerosol concentration, BisEDT aerosol concentration and particle size for the formulations are shown for the first BisEDT formulation (Lot #ED268-1-11-01) in Table 1. An analogous table is shown for the second BisEDT formulation (Lot #XL-47-125) in Table 2. An example histogram of the particle size distribution for the 2.5 mg/mL concentration taken via cascade impactor is shown in FIG. 2. Example histograms of the particle size distributions for the 25, 50, 75, and 100 mg/mL concentrations taken via APS are shown in FIGS. 3, 4, 5, and 6; respectively. Repeated tests for size distributions for the second BisEDT formulation are depicted in FIGS. 7, 8, 9, and 10 for 100 mg/mL, 50 mg/mL, 10 mg/mL, and 2.5 mg/mL respectively.

TABLE 1

Summary of suspension aerosol testing for BisEDT (Lot # ED268-1-11-01)

| Formulation (mg/mL) | Total Aerosol Conc. (mg/L) | BisEDT Aerosol Conc. (µg/L) | Particle Size (GSD)* |
|---|---|---|---|
| 1 | | 9.9 | 1.65 (1.6) µm |
| 2.5 | 0.116 | 18.5 | 0.97 (3.0) µm |
| 10 | 0.184 | 80.7 | N/A |
| 25 | 0.441 | 87.9 (64.4)[+] | 2.98 (1.8) µm |
| 50 | 0.599 | 156 | 2.83 (1.9) µm |
| 75 | 0.618 | 530 | 3.16 (1.70) µm |
| 100 | 0.816 | 719 | 3.53 (1.71) µm |
| 100* | 0.731 | 568 | 3.60 (1.71) µm |

*All Particle size data collected with an APS except the 2.5 mg/mL formulation
[+]for one of the filters of the 25 mg/mL solution, chemical extraction yielded a less than expected concentration of BisEDT. 64.4 µg/L is the average value of all extracted concentrations, while 87.9 µg/L is the average excluding this outlier.

TABLE 2

Summary of suspension aerosol testing for BisEDT (Lot # XL-47-125) using a 300 mOsmol/kg vehicle

| Formulation (mg/mL) | Total Aerosol Conc. (mg/L) | BisEDT Aerosol Conc. (µg/L) | Particle Size (GSD) |
|---|---|---|---|
| 100 | 1.535 | 1300 | 2.90 (1.67) µm |
| 100 | 1.404 | N/A | 2.60 (1.65) µm |
| 50 | 0.711 | 159 | 2.79 (1.69) µm |
| 10 | 0.332 | 97.7 | 1.61 (1.65) µm |
| 2.5 | 0.175 | 18.4 | 1.44 (1.71) µm |

The aerosols in Tables 1 and 2 were generated with a PARI LC PLUS PERFORMANCE® nebulizer. The nebulizer was tested with a 1.2 bar compressor; measured with Malvern MasterSizer X at 50% relative humidity, 0.9 NaCl solution, inspiratory flow of 20 L/min, continuous nebulization at 23° C. with a fill volume of 2.5 mL.

Pulmonary Deposited Dose: Pulmonary deposited doses can be modulated via the aerosol concentration and/or the exposure duration. For a rodent nose-only inhalation exposure, the exposure duration is typically targeted between 30 and 180 minutes. Using the performance of the aerosol and the pulmonary dose equation above, the pulmonary deposited dose range for the first BisEDT formulation would be between 42 µg/kg and 9.6 mg/kg. The second formulation was more efficient in depositing BisEDT and is capable of giving a dose up to 17.5 mg/kg.

Methods for formulation and aerosol generation of BisEDT were developed. They support a pulmonary deposited dose between 42 µg/kg and 17.5 mg/kg. These exposure conditions are appropriate for rodent inhalation exposures.

Example 5: In Vitro Studies

This Example describes a series of experiments evaluating the suitability and feasibility of the development of bismuth-thiols, particularly BisEDT, as an inhaled drug product for the treatment of CF-related pulmonary infections. A CF-relevant range of infectious bacterial pathogens, including highly resistant strains and biofilm forming strains of such pathogens, were tested for susceptibility to bismuth-thiols. In addition, in vitro evaluations of toxicity against lung airway epithelial cells were conducted.

Standardized microbiological susceptibility testing was carried out with two bismuth-thiol compounds against a range of the most clinically-challenging, highly resistant CF isolates. MIC testing was standardized using ATCC strains of E. coli (25922) and S. aureus (29213).

The results of this testing demonstrated BisEDT was consistently potent against all CF isolates tested, including aminoglycoside-resistant and MDR P. aeruginosa, B. cenocepacia, Achromobacter spp., and S. maltophilia, with all test organisms demonstrating MICs of less than 1 µg/mL (see FIG. 12).

To expand upon this, the tested bacteria was expanded to include more *Burkholderia* spp., as well as to test a wider range of CF isolates and antibiotic-resistant strains.

Figure 13:
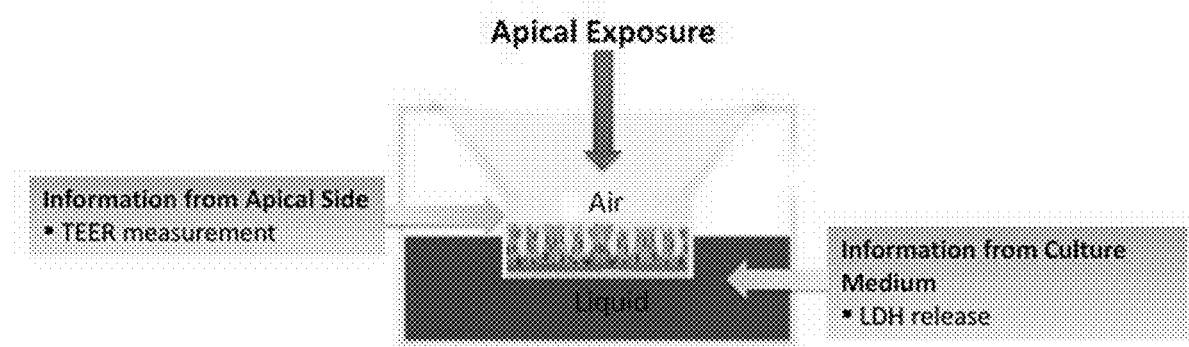
FIG. 13 is a diagram showing the evaluation of cytotoxicity through both LDH release (from the culture medium side) and trans-epithelial electrical resistance (TEER) from the apical/air-exposed side.

A range of CF-isolated strains of *Mycobacterium avium* and *Mycobacterium abscessus* were included; which allows for understanding of the activity against non-tubercular Mycobacteria (NTM). The results of this study are shown below. Two distinct bismuth-thiol compounds were evaluated, including BisEDT and BisBDT. *Mycobacterium avium* isolates were found to have the highest MICs, though BisEDT demonstrated lower MICs against these NTM bacteria than did BisBDT. The CF-isolates of greater clinical relevance, including both M *abscessus* spp. and *Burkholderia* spp., were both consistently found to be much more susceptible to BisEDT and BisBDT. This study demonstrated very compelling MIC data against CF-isolates of both NTM and *Burkholderia* spp., as few commercial antibiotics have this level and spectrum of activity.

through both LDH release (from the culture medium side) and trans-epithelial electrical resistance (TEER) from the apical/air-exposed side as well as pre- and post-exposure microscopic examination for morphological changes (FIG. 13).

With respect to evaluation of six concentrations of solubilized BisEDT, no changes in cellular morphology were noted at four different time points (up to 48 hours), nor were changes noted in LDH release and TEER, indicating that no toxic effects were observed, at all time points even at the highest tested concentration of 30 uM (20.83 ug/mL, which is approximately 20-347 fold higher than the MICs recently derived, against most tested CF bacterial isolates, including *M. abscessus* (including amikacin- and clarithromycin/macrolide-resistant strains), *Burkholderia* spp. (including beta-lactam, fluoroquinolone-, and sulfamethoxazole-resistant strains), *P. aeruginosa* (including multidrug-resistant (MDR) strains), *Achromobacter* spp., *Stenotrophomonas*

TABLE 3A

BisEDT and BisBDT MIC against bacterial strains

| Strain Designation | Species | Strain characteristics | BisEDT MIC (µg/mL) | BisBDT MIC (µg/mL) |
|---|---|---|---|---|
| MAC101 | *M. avium* | MAC reference strain, blood isolate from HIV patient | 2 | 1 |
| AMT 0193-13 | *M. avium* | MAC CF isolate, macrolide-S | 8 | >16 |
| AMT 0119-8 | *M. avium* | MAC CF isolate, macrolide-S | 8 | >16 |
| BC 5 | *B. multivorans* (cepacia complex) | CF isolate, beta lactam-S, TMP/SMX-S, FQ-I | 1 | 2 |
| PC 213 | *B. cepcacia* complex (not further speciated) | CF isolate, beta lactam-S, TMP/SMX-S, FQ-S | 0.25 | 1 |
| BC 9 | *B. cepcacia* complex (not further speciated) | CF isolate, beta lactam-S, TMP/SMX-S, FQ-R | 0.5 | 0.5 |
| BC 17 | *B. cepacia* (cepacia complex) | CF isolate, beta lactam-R, TMP/SMX-R, FQ-R | 8 | 4 |
| BC 11 | *B. dolosa* (cepacia complex) | CF isolate, beta lactam-R, TMP/SMX-S, FQ-R | 0.125 | 0.5 |
| ATCC 19977 | *M. abscessus abscessus* | ATCC type strain | 0.5 | 0.25 |
| AMT 0136-10 | *M. abscessus* complex | MABSC CF isolate, macrolide-R, amikacin-R | 0.125 | 0.0625 |
| AMT 0089-5 | *M. abscessus* complex | MABSC CF isolate, macrolide-R, amikacin-R | 0.25 | 0.125 |
| AMT 0166-29 | *M. abscessus* complex | MABSC CF isolate, macrolide-R, amikacin-R | 0.125 | 0.125 |
| AMT 0157-14 | *M. abscessus* complex | MABSC CF isolate, macrolide-R, amikacin-I | 0.125 | 0.125 |
| AMT 0130-8 | *M. abscessus* complex | MABSC CF isolate, macrolide-S, amikacin-I | 0.125 | 0.0625 |
| AMT 0153-9 | *M. abscessus* complex | MABSC CF isolate, macrolide-S, amikacin-I | 0.25 | 0.125 |
| AMT 0068-40 | *M. abscessus* complex | MABSC CF isolate, macrolide-S, amikacin-I | 0.25 | 0.125 |
| AMT 0119-7 | *M. abscessus* complex | MABSC CF isolate, macrolide-S, amikacin-I | 0.125 | 0.125 |
| AMT 0493-2 | *M. abscessus* complex | MABSC CF isolate, macrolide-S, amikacin-R | 0.5 | 0.5 |

TABLE 3B

BisEDT and BisBDT MIC against control bacterial strains

| ATCC strains used to control for drug activity (see detailed data for measured MICs with each assay set-up) | | Expected results: goal (acceptable range) mcg/mL | |
|---|---|---|---|
| | | BisEDT MIC | BisBDT MIC |
| ATCC 27853 | *P. aeruginosa* | 1-2 (0.5-4) | NA |
| ATCC 25922 | *E. coli* | 1 (0.5-2) | NA |
| ATCC 29213 | *S. aureus* | 0.25-0.5 (0.125-1) | 0.25 (0.125- |

Controlled in vitro evaluation of BisEDT, with respect to potential cytotoxicity on fully differentiated human airway epithelium was carried out. Both solubilized and solid (powder/particulate) forms of BisEDT were evaluated for cytotoxicity by Epithelix, a contract research organization (CRO) specializing in this form of cytotoxicity evaluation utilizing a proprietary, in vitro fully differentiated human airway epithelium test system (MUCILAIR™) The MUCI-LAIR™ system facilitated evaluation of cytotoxicity

*maltophilia*, and *S. aureus* (including MRSA)). The highest tested concentration of 20.83 µg/mL is also approximately 2.5-10 fold higher than the MIC for *M. avium*, which comparatively, had the highest MICs relative to BisEDT of any tested CF isolates. Additionally, since no hint of toxicity has been demonstrated with even the highest concentration of solubilized BisEDT, it is possible that higher concentrations may also be determined to be non-toxic/safe/well-tolerated.

With respect to evaluation of five concentrations of particulate BisEDT diluted in dextran as a carrier (weight/area), the lower two concentrations did not produce changes in cellular morphology at the four different time points (up to 48 hours), nor were changes noted in LDH release and TEER, indicating that no toxic effects were observed at any of the four time points.

With respect to morphology, the top three concentrations demonstrated changes that were more pronounced in the top two concentrations. With respect to the top three concentrations, no significant effect was noted with respect to TEER at any of these concentrations at the 1 hour time point, but at 8, 24, and 48 hours, TEER, loss of tissue integrity occurred with all three of the highest concentrations. Similarly, no effect on LDH release was noted at any time point with the lower two concentrations, nor at 1 hour for the top three concentrations; but beyond the 1 hour time point, there was a time and dose dependent increase in LDH release and decrease in TEER, indicating cytotoxicity under these conditions. It is notable that in Phase 1 human clinical studies, concentration of up to 2500 µg/cm$^2$ (~8-fold higher than the 333 µg/cm$^2$, the highest concentration tested in this in vitro study) was well-tolerated when administered topically humans for 6 hours, and a concentration of up to 75 µg/cm$^2$ (intermediate between 33.3 µg/cm$^2$ and 333 µg/cm$^2$) was tolerated when administered topically to humans for over 21 days continuous exposure to normal and abraded skin. This indicates that in vitro model conditions may be much more sensitive to the particulate form than in vivo physiologic conditions, thus over-representing the true risk of cytotoxicity of the particulate form. Nevertheless, the highest non-toxic concentrations of both forms of BisEDT tested in this in vitro cytotoxicity model, whether particulate or solubilized, provides 25-345 fold the MIC needed to be effective against a broad spectrum of antibiotic-resistant, difficult to treat CF bacterial pathogens.

The data from this study demonstrates that the solubilized version of BisEDT is safe at sufficient multiples of the anticipated clinical dose.

Activity of BT compounds against CF-isolate biofilms

Figure 14:
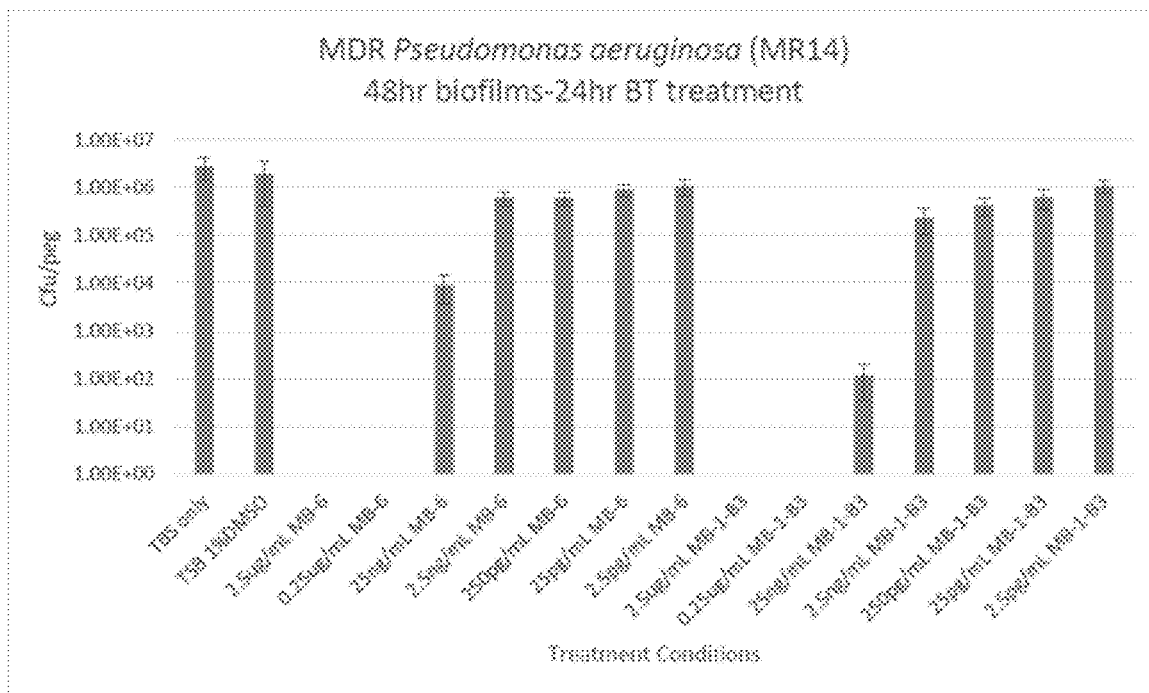
FIG. 14 shows the activity of BT compounds against biofilms grown from MR14, which is a multidrug-resistant CF-isolate of *Pseudomonas aeruginosa*.

The activity of BT compounds against biofilms grown from CF-isolates was tested. MR14 is a multidrug-resistant (MDR) CF-isolate of *Pseudomonas aeruginosa*. Reductions in biofilm cell viability of 2 logs (MB-6) to 4 logs (MB-1-B3) occurred at 25 ng/mL (FIG. 14). The bismuth-thiol compounds have previously been reported in the literature to have anti-biofilm effects at sub-inhibitory concentrations with 24 hour treatment with 0.25 µg/mL. There is nothing comparable in the scientific literature.

Figure 15:
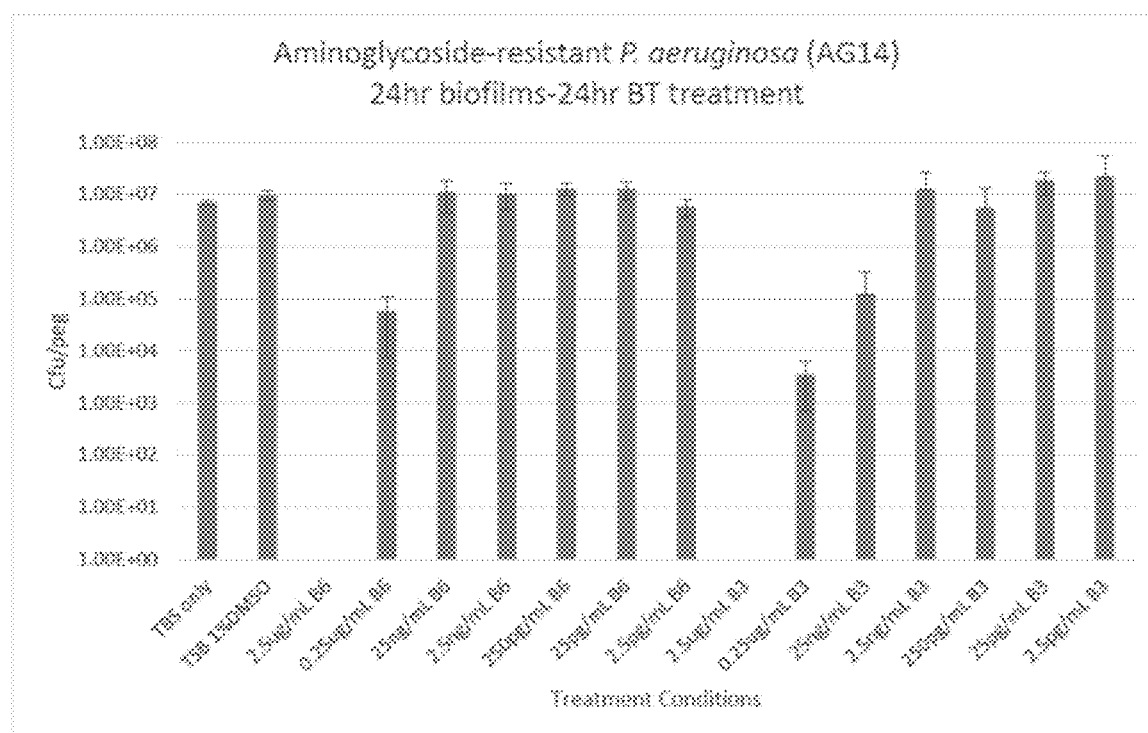
FIG. 15 shows the activity of BT compounds against biofilms grown from AG14, which is an aminoglycoside-resistant CF-isolate of *Pseudomonas aeruginosa*.

AG14 is an aminoglycoside-resistant CF-isolate of *Pseudomonas aeruginosa*. Reductions in biofilm cell viability of 2 logs (MB-6) to approximately 3.5 logs (MB-1-B3) occurred at 0.25 µg/mL. Once again, a very advanced level of anti-biofilm activity (a 6 log reduction) with 24 hour treatment occurred with 0.25 µg/mL; this potent level of activity is very likely to be unique to the bismuth-thiol compounds (FIG. 15).

Combined, the results of testing against Pseudomonal biofilms (MR14 and AG14) demonstrate an advanced, possibly unique level of anti-biofilm activity against antibiotic- and multidrug-resistant (MDR) *Pseudomonas aeruginosa*; this may represent an important new therapeutic activity and clinical strategy in the treatment of pulmonary infections associated with cystic fibrosis.

Figure 16:
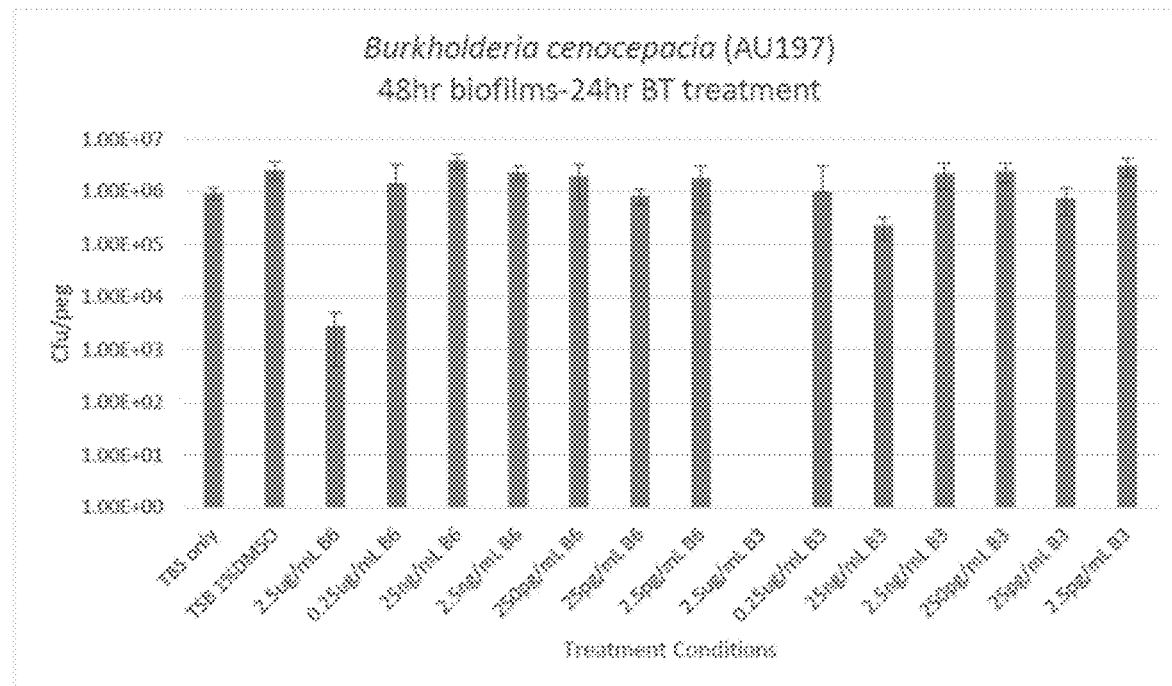
FIG. 16 shows the activity of BT compounds against biofilms grown from AU197, which is a CF-isolate of *Burkholderia. cenocepacia*.

AU197 is a CF-isolate of *B. cenocepacia*. While in this case, the anti-biofilm activity is not occurring at a subinhibitory level (as with the previous examples of *P. aeruginosa*), this level of anti-biofilm activity (a 6 log reduction at a concentration of 2.5 µg/mL of BisEDT) is nevertheless extremely potent, and is very likely to be therapeutically achievable (FIG. 16).

Figure 17:
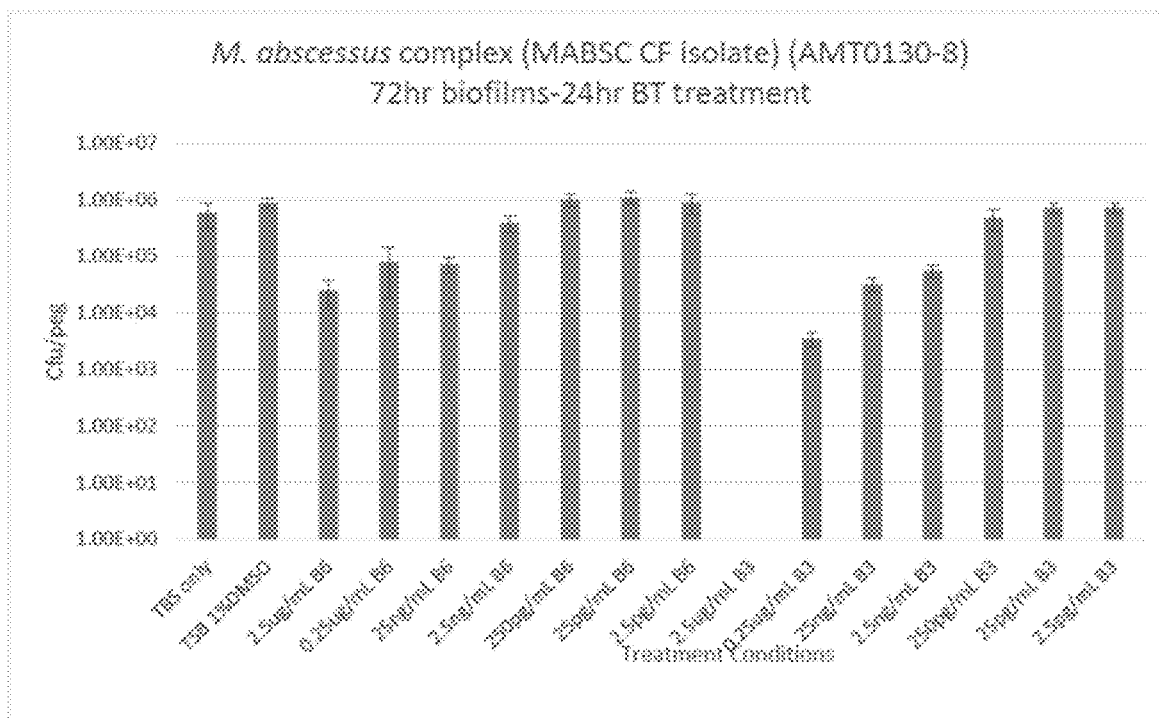
FIG. 17 shows the activity of BT compounds against biofilms grown from AMT0130-8, which represents a CF-isolate of the clinically relevant *Mycobacterium abscessus* complex (MABSC), which frequently complicates the treatment of CF pulmonary infections

AMT0130-8 represents a CF-isolate of the clinically relevant MABSC, which frequently complicates the treatment of CF pulmonary infections. In this case, while BisBDT demonstrated only very modest reductions in biofilm cell viability, once again, BisEDT demonstrated a 6 log reduction at 2.5 µg/mL, as well as a dose response from 2.5 ng/mL to 2.5 µg/mL. Interestingly, the MIC against this strain was demonstrated to be lower for BisBDT (0.0625 µg/mL) than for BisEDT (0.125 µg/mL), yet the anti-biofilm activity of BisEDT was apparently demonstrated to be much more potent—while it is not surprising to see such differences in activity between distinct bismuth-thiol compounds, this particular MABSC strain was apparently technically difficult to work with (see bullet point notes below figure), which may also have accounted for such (apparent) differences in activity (FIG. 17).

Figure 18:
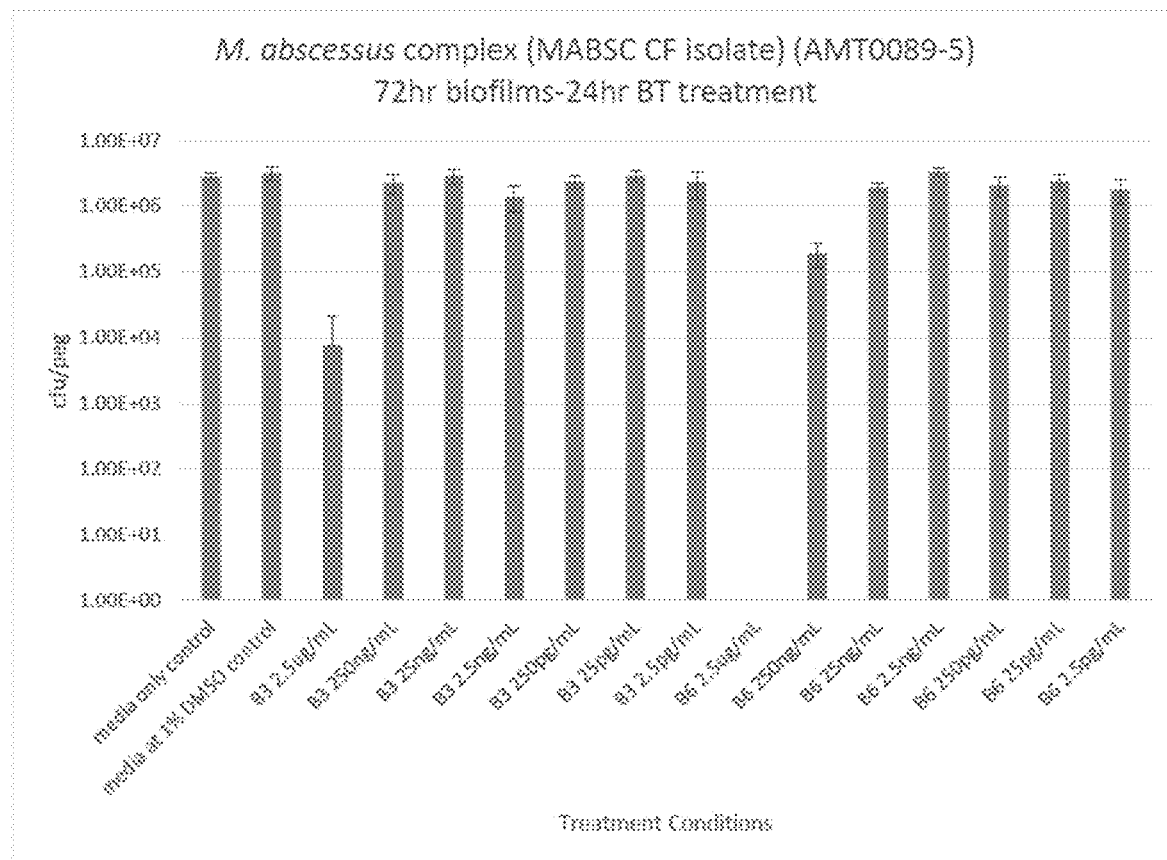
FIG. 18 shows the activity of BT compounds against biofilms grown from AMT0089-5, which is a macrolide-resistant, amikacin-resistant MABSC.

AMT0089-5 is a macrolide-resistant, amikacin-resistant MABSC. The involvement of such antibiotic-resistant strains of MABSC in the pulmonary infections of CF patients is extremely problematic. Here, while BisEDT showed a 2.5 log reduction in viable biofilm cells at a concentration of 2.5 µg/mL, BisBDT was demonstrated to have reduce viable biofilm cells by 6 logs at a concentration of 2.5 µg/mL (FIG. 18).

Figure 19:
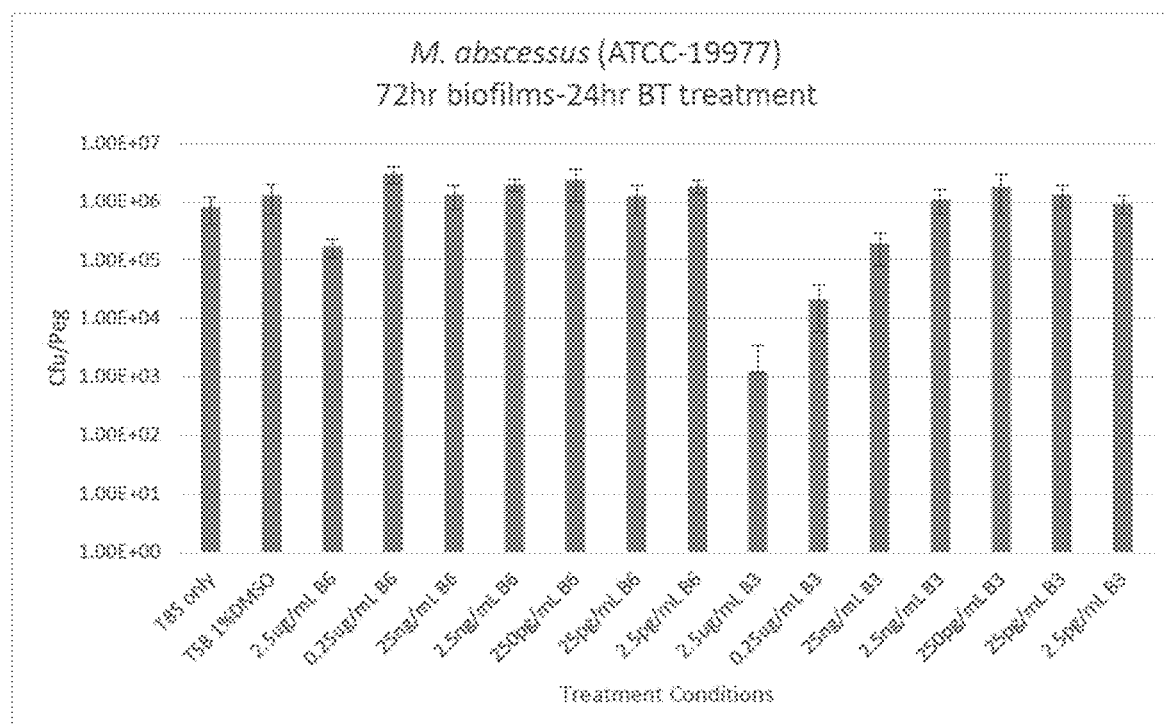
FIG. 19 shows the activity of BT compounds against biofilms grown from ATCC-19977, which is *M. abscessus* (macrolide-resistant; inducible).

ATCC-19977 is *M. abscessus* (macrolide-resistant; inducible). A dose response is demonstrated showing a 3 log reduction in viable biofilm cells at 2.5 µg/mL ATCC-19977 is *M. abscessus* (macrolide-resistant; inducible). A dose response is demonstrated below, with a 3 log reduction in viable biofilm cells at 2.5 µg/mL (FIG. 19).

Figure 20:
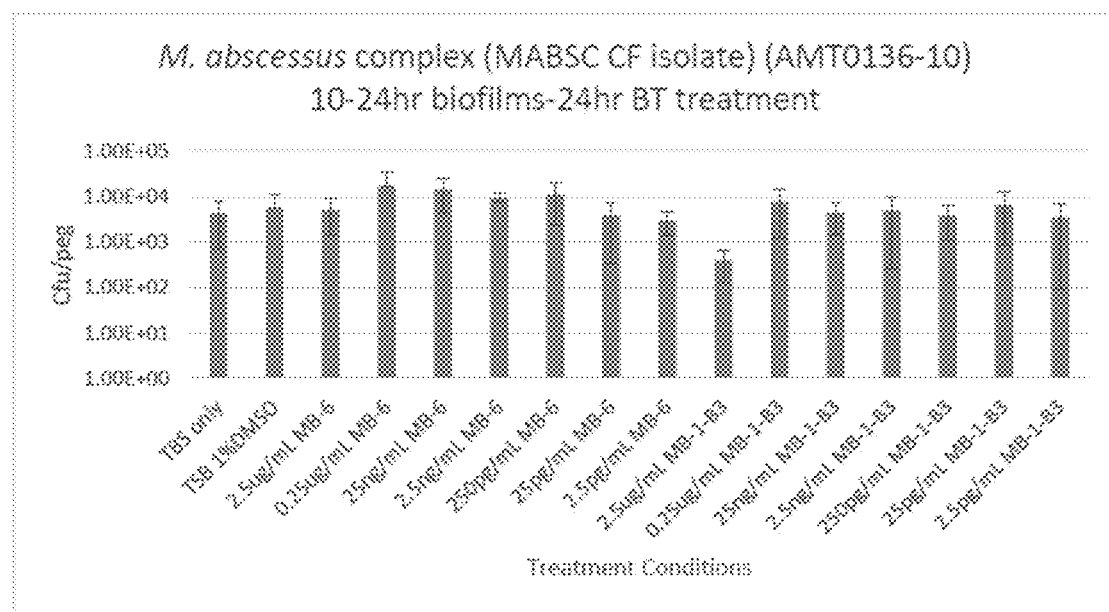
FIG. 20 shows the activity of BT compounds against biofilms grown from MABSC CF isolate.

The bismuth-thiols were not observed to be active against biofilm formed by a MABSC CF isolate, though this strain was so slow-growing, a longer exposure to the bismuth-thiol compounds may have been necessary to demonstrate activity (FIG. 20).

Figure 21:
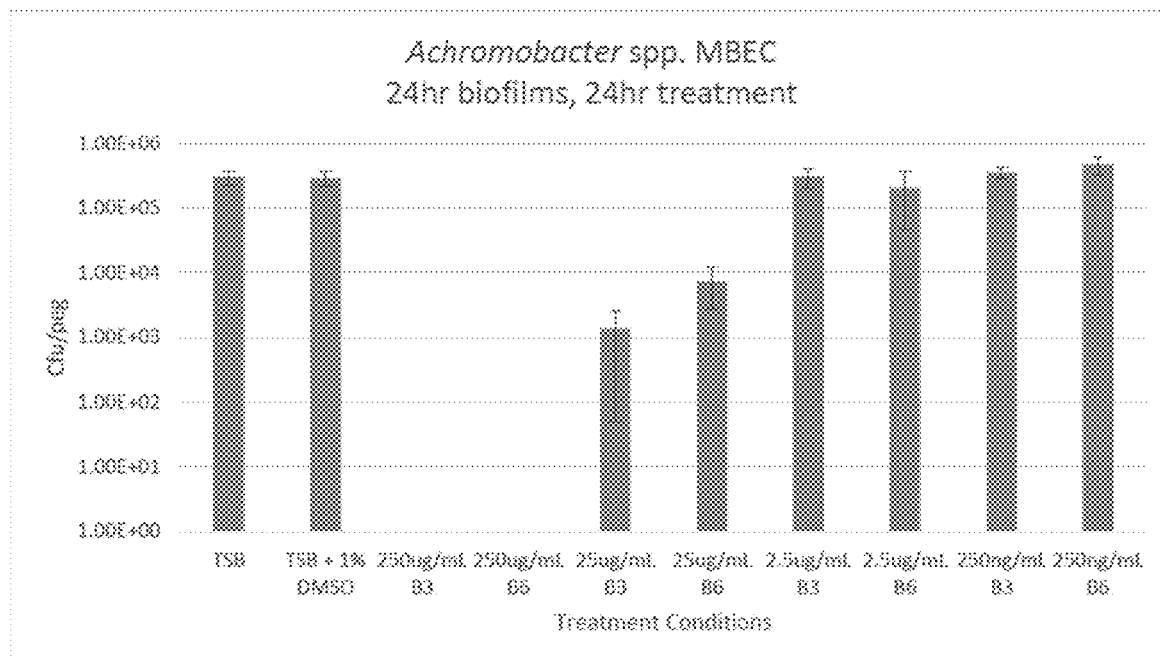
FIG. 21 shows the activity of BT compounds against biofilms grown from *Achromobacter* spp.

*Achromobacter* spp. were tested up to concentrations of 250 µg/mL of both BisEDT and BisBDT, which resulted in a 5 log reduction in viable biofilm cells. A dose response is also apparently associated with both compounds (FIG. 21).

Figure 22:
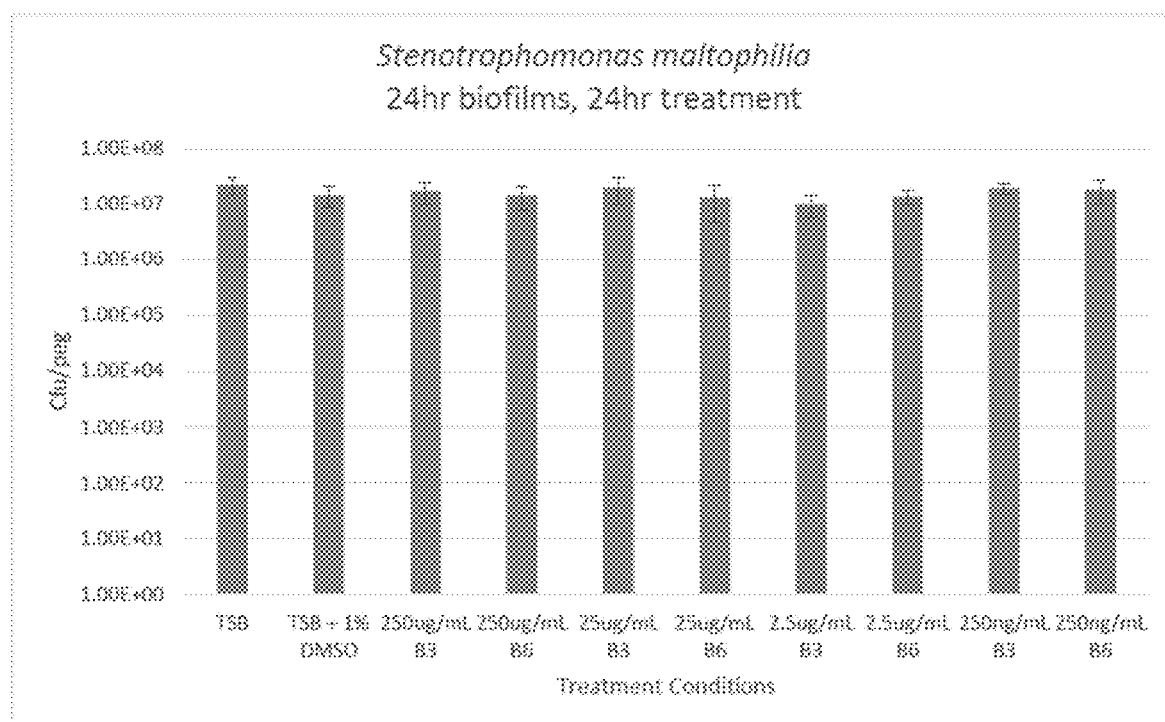
FIG. 22 shows the activity of BT compounds against biofilms grown from *Stenotrophomonas maltophilia*.

Unfortunately, no activity was apparent for either bismuth-thiol compound against *Stenotrophomonas maltophilia* (FIG. 22).

Figure 23:
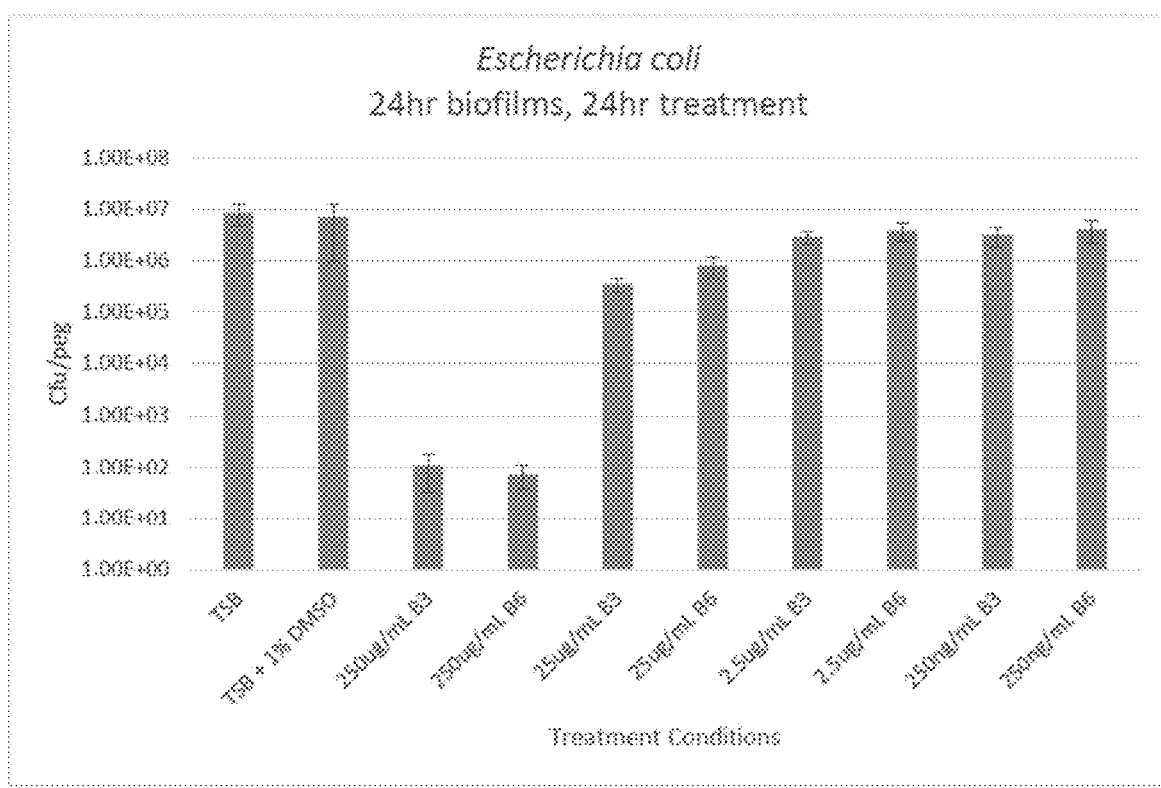
FIG. 23 shows the activity of BT compounds against biofilms grown from *E. coli*.

Finally, anti-biofilm activity was also demonstrated at the highest concentrations of both compounds (a 5 log reduction) when tested against *E. coli* (FIG. 23).

Both BisEDT and BisBDT are demonstrated to have very low MIC values against *M. abscessus*, MDR *P. aeruginosa*, *Achromobacter* spp., and *Burkholderia* spp. As before, ATCC control strains are utilized to standardize the data. However, in this evaluation, the bismuth-thiols were compared head to head with amikacin and clarithromycin (a clinically important macrolide antibiotic). As can be seen from this data below in Table 4, the bismuth-thiols are notably and consistently more potent than both amikacin and clarithromycin (most dramatically when considering the MABSC strain ATCC 19977, which was induced to be macrolide-resistant).

TABLE 4A

Comparison of conventional antibiotics vs BisEDT and BisBDT activity against bacterial strains
SUMMARY OF MIC RESULTS

| Strain Designation | Species | Special Strain characteristics (if any) | MIC (mcg/mL) Amikacin | MIC (mcg/mL) Clarithromycin | MIC (mcg/mL) Bis-EDT | MIC (mcg/mL) Bis-BDT |
|---|---|---|---|---|---|---|
| ATCC 19977 | M abscessus/massiliense complex | Macrolide resistant (inducible) | 8 [2] | >32 [2] | 0.06 [2] | <0.03 [2] |
| AMT0130-8 | M abscessus/massiliense complex | | 16 [2] | 1 | 0.06 [2] | <0.03 [2] |
| AMT153-9 | M abscessus/massiliense complex | | 32 [2] | 2 | 0.13 [2] | <0.03 [2] |
| AMT0068-40 | M abscessus/massiliense complex | | 32 [2] | 1 | 0.25 [2] | 0.06 [2] |
| AMT0119-7 | M abscessus/massiliense complex | | 32 [2] | 1 | 0.06 [2] | <0.03 [2] |
| AMT0493-2 | M abscessus/massiliense complex | Amikacin resistant | >64 [2] | 2 | 0.5 [2] | 0.125 [2] |
| AGR1 | P. aeruginosa | | 16 | na | 1 | 1 |
| AGR14 | P. aeruginosa | Multi-drug resistant | >64 | na | 0.5 | 1 |
| MR14 | P. aeruginosa | Multi-drug resistant | >64 | na | 1 | 1 |
| SM21 | S. maltophilia | | 64 | na | 0.25 | 0.13 |
| AX1 | Achromobacter spp. | | 64 | na | 1 | 1 |
| AX4 | A. xylosoxidans | | >64 | na | 0.25 | 0.5 |
| BC5b | B. multivorans (B cepacia complex) | | >64 | na | 0.25 | 1 |
| BC15 | B. cenocepacia (B cepacia complex) | | >64 | na | 2 | 4 |
| BC17 | B. cepacia (B cepacia complex) | | >64 | na | 8 | 8 |
| AU197 | B. cenocepacia (B cepacia complex) | | >64 | na | 0.5 | 4 |

TABLE 4B

BisEDT and BisBDT MIC against control bacterial strains

ATCC or other strains used to control for drug activity (see detailed data for measured MICs with each assay set-up)

Expected results (acceptable range) mcg/mL (per CLSI M100-S24 or provided by Microbion)

| Strain | Species | Amikacin | Clarithromycin | BisEDT | BisBDT |
|---|---|---|---|---|---|
| ATCC 29213 | S. aureus | 2 (1-4) | 0.25 (0.12-0.5) | 0.25-0.5 (0.13-1) | 0.25 (0.12-0.5) |
| ATCC 25922 | E. coli | 1-2 (0.5-4) | na | 1 (0.5-2) | na |

Evaluation of BT compound effect on cytotoxicity on a fully differentiated human airway epithelium (MUCILAIR™)

The aim of this study is to evaluate the potential local toxic effect of BisEDT on airway epithelium. The project is divided into 2 phases: Study 1: Acute Toxicity testing of BisEDT in solution; Study 2: Acute Toxicity testing of BisEDT as solid.

Figure 24:
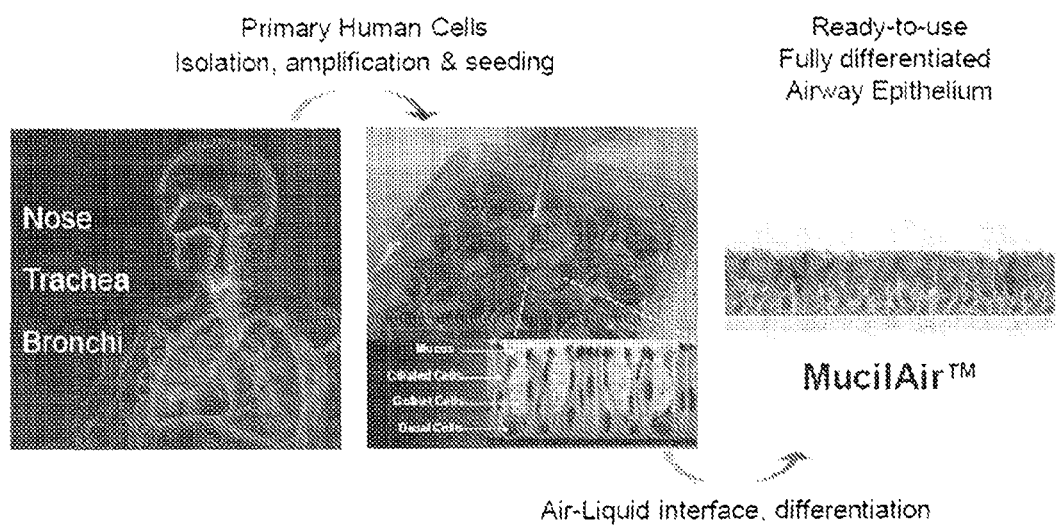
FIG. 24 shows an overview of MucilAir™ which is a fully differentiated model of the human airway epithelia. Epithelial cells were freshly isolated from the biopsies (nose and bronchi), then seeded onto a semi-porous membrane (Costar Transwell, pore size 0.4 μm). After about 45 days of culture at air-liquid interface, the epithelia were fully differentiated, both morphologically and functionally.

The assay system used in this study is Epithelix's proprietary technology MUCILAIR™ MUCILAIR™ is a fully differentiated and ready-to-use 3D model of human airway epithelium, constituted with primary human epithelial cells freshly isolated from nasal, tracheal or bronchial biopsies. MUCILAIR™ (FIG. 24), is not only morphologically and functionally differentiated, but can also be maintained in a homeostatic state for a long period of time (Huang et al., 2009).

MUCILAIR™ is composed of basal cells, ciliated cells and mucus cells. The proportion of these various cell types is preserved compared to what one observes in vivo (Huang et al., 2011). Moreover the epithelia are started from de-differentiated cells. The cells undergo a progressive differentiation with time. After 45 days of culture, the epithelia are fully ciliated, secret mucus and are electrically tight (TEER>200 $\Omega.cm^2$). The activity of the main epithelial ionic channels, such as CFTR, EnaC, Na/K ATPase, is preserved and the epithelia is shown to respond in a regulated and vectorial manner to the pro-inflammatory stimulus, TNF-α (Huang et al., 2011). A large panel of cytokines, chemokines and metalloproteinases has been detected in MUCILAIR™ (e.g. IL-8, IL-6, GM-CSF, MMP-9, GRO-α).

Acute Toxicity Testing of BisEDT in Solution

The aim of this phase is to evaluate the potential acute toxicity of BisEDT in solution once applied at the apical surface on a 3D model of fully differentiated human airway epithelium (MUCILAIR™) after 1, 8, 24 and 48 hours exposure.

TABLE 5 patient information

| Batch number | Age of the patient | Sex of the patients | Age of the culture | Special comments |
|---|---|---|---|---|
| MD014101 | 38 years | ND | 105 days | Normal donor |

TABLE 6

| | Test material | | |
|---|---|---|---|
| Identification Name | Concentrations | Vehicle | Solubility |
| BisEDT (MB-1-B3) | 0.001, 0.01, 0.1, 1, 10, 30 μM | 0.5% DMSO in Buffered Saline | OK |

BisEDT (MB-1-B3) was applied on the apical surface of MUCILAIR™ during 1, 8, 24 and 48 hours (FIG. 13). The effect of 6 concentrations was studied: 0.001, 0.01, 0.1, 1, 10 and 30 μM. The compound was diluted in a buffered saline solution (NaCl 0.9%-1.25 mM $CaCl_2$-10 mM HEPES) with 0.5% DMSO. 30 μl solution at the selected concentration was applied on the apical surface of MUCILAIR™. The negative control corresponds to the vehicle solution (0 μM) and untreated cultures. The positive control corresponds to 50 μl to 10% Triton X-100 diluted in a buffered saline solution. The study was run in triplicates.

During the study, inserts were maintained in a $CO_2$ incubator (37° C., 5% $CO_2$, 100% humidity). The following end-points were determined:
  Tissue integrity monitoring: Trans-Epithelial Electrical Resistance (TEER) measurement (quantitative) at D0, D1 and D2.
  Cytotoxicity monitoring: LDH test (quantitative) at D0, D1 and D2.
  Morphology: cellular and tissue integrity examined under contrast microscope at D0, D1 and D2.

Three days before the experiment, the following quality controls were performed on each epithelium:
  Washing: inserts were washed with 200 μl of MUCILAIR™ culture medium. Washing removes accumulated mucus on the tissue surface which may interfere with the test.
  Trans-Epithelial Electrical Resistance (TEER): TEER was measured to verify that all the selected inserts had tight epithelial barriers and the tissue itself was not disrupted prior to application of the test material.
  Tissue morphology: each insert was inspected under a conventional inverted microscope to ensure the quality of the epithelia and determine qualitatively that cilia motion was visible. The presence of mucus was detected by the refractive aspect of the apical surface.

Results

Error bars in the following graphs refer to standard error of the mean (SEM). All comparisons are versus the negative control (vehicle solution, 0 μM).

Before exposure: Each insert was inspected under a conventional inverted microscope to insure the quality of the epithelia. The movement of cilia was clearly visible for all the selected inserts. The presence of mucus was detected by the refractive aspect of the apical surface.

After exposure: No morphology changes were observed for the vehicle control and all tested concentrations and time points.

Figure 25:
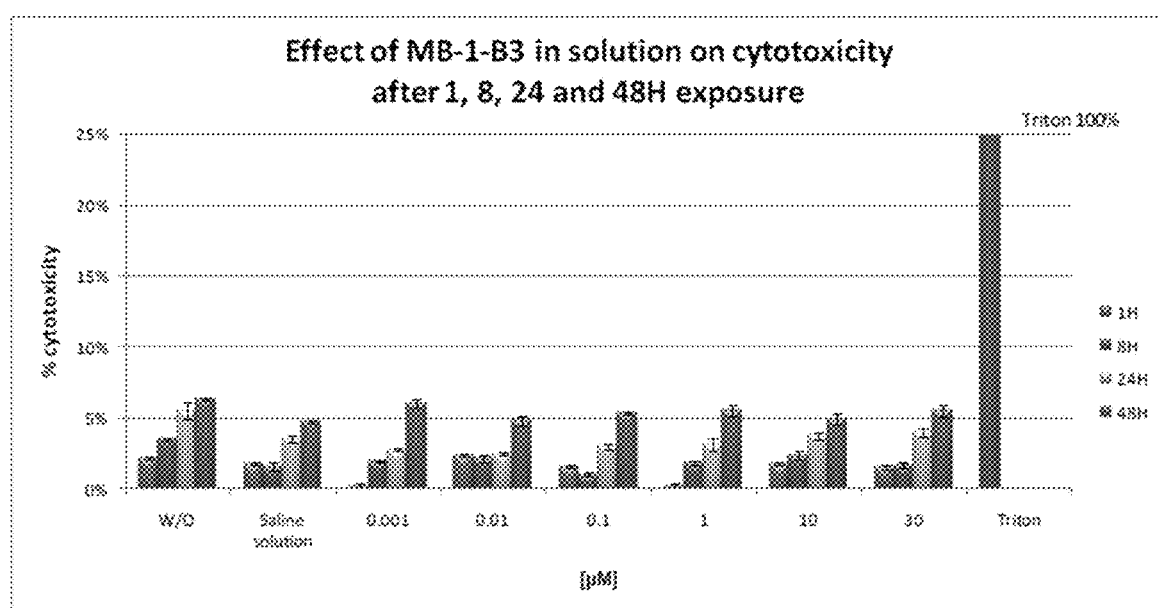
FIG. 25 shows the percentage of cytotoxicity (LDH measurement) of BisEDT in solution at 1, 8, 24 and 48 hours exposure. Bars representing 1, 8, 24 and 48 hours are shown from left to right for each concentration.

Cytotoxicity assessment: FIG. 25 shows the percentage of cytotoxicity (LDH measurement) at 1, 8, 24 and 48 hours exposure. The control (0 μM, vehicle solution) corresponds to a physiological release of LDH (<5%). LDH release was not altered after exposure to BisEDT at all tested concentrations and at all time-points. Therefore, no toxic effect was observed.

Figure 26:
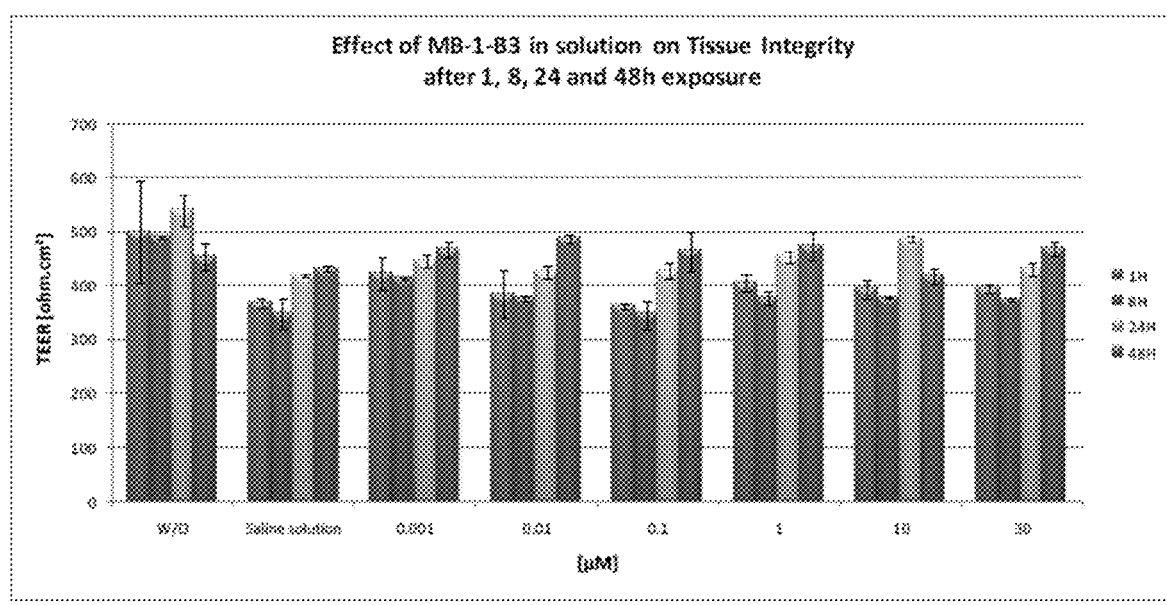
FIG. 26 shows the effect on tissue integrity of BisEDT in solution at 1, 8, 24 and 48 hours exposure. Bars representing 1, 8, 24 and 48 hours are shown from left to right for each concentration.

Tissue integrity assessment: FIG. 26 shows the monitoring of TEER at D1. It should be noted that TEER is a dynamic parameter that can be affected by several factors. A decrease of the ionic channel activity can lead to an increase of TEER, and an activation of the ion channels can decrease TEER values. When an epithelium is damaged, a decrease of TEER would be associated with an increase of LDH release. BisEDT didn't show significant effect on TEER at all tested concentrations and time points.

Acute Toxicity Testing of BisEDT as Solid: $1^{st}$ Set of Experiments

The aim of this study is to evaluate the potential acute toxicity of BisEDT as solid (at 0.033, 0.33, 3.33, 33.3, 333 μg/cm$^2$) once applied at the apical surface on a 3D model of fully differentiated human airway epithelium (MUCILAIR™) after 1, 8, 24 and 48 hours exposure.

TABLE 7

| Tissues (Patient information) | | | | |
|---|---|---|---|---|
| Batch number | Age of the patient | Sex of the patients | Age of the culture | Special comments |
| MD014101 | 38 years | ND | 119 days | Normal donor |

TABLE 8

| Test Material | | |
|---|---|---|
| Identification Name | Concentrations | Vehicle |
| MB-1-B3 | 0.033, 0.33, 3.33, 33.3, 333 μg/cm$^2$ | Dextran powder (C60) Ref: Pharmacosmos 5510 0060 1007 |

Compound BisEDT was applied on the apical surface of MUCILAIR™. The effect of 5 concentrations after 1, 8, 24 and 48 hours exposure was studied: 0.033, 0.33, 3.33, 33.3, 333 μg/cm$^2$. The compound was diluted in Dextran powder at the targeted concentration and compressed in order to obtain a tablet. The study was run in triplicates. During the study, inserts were maintained in a $CO_2$ incubator (37° C., 5% $CO_2$, 100% humidity). The mucociliary clearance analysis was performed after 1 hour and 24 hours exposure.

Quality control and washing of the apical surface: Three days before the experiment, the following quality controls were performed on each epithelium:
  Washing: inserts were washed with 200 μl of MUCILAIR™ culture medium. Washing removes accumulated mucus on the tissue surface which may interfere with the test.
  Trans-Epithelial Electrical Resistance (TEER): TEER was measured to verify that all the selected inserts had tight epithelial barriers and the tissue itself was not disrupted prior to application of the test material.
  Tissue morphology: each insert was inspected under a conventional inverted microscope to ensure the quality of the epithelia and determine qualitatively that cilia motion was visible. The presence of mucus was detected by the refractive aspect of the apical surface.

Results

Error bars in the following graphs refer to standard error of the mean (SEM). All comparisons are versus the negative control (Carrier, Dextran).

Before exposure: Each insert was inspected under a conventional inverted microscope to insure the quality of the epithelia. The movement of cilia was clearly visible for all the selected inserts. The presence of mucus was detected by the refractive aspect of the apical surface.

After exposure: No morphology changes were observed for the non-treated and the vehicle controls.

0.033 and 0.33 µg/cm²: No morphological modifications were observed.

3.33 µg/cm²: The tablets applied apically were poorly dissolved on the epithelia at 24 and 48 h after exposure. Cells were rounded and opaque at the periphery of inserts. Gradually the cells became detached from each other. The appearance of culture medium coming from the basal side on the apical surface was observed.

33.3 and 333 µg/cm²: The tablets applied apically was poorly dissolved on the epithelia at 8, 24 and 48 h after exposure. Cells were rounded and opaque on the inserts. Gradually the cells became detached from each other. The culture medium leaked to the apical side.

Figure 27:
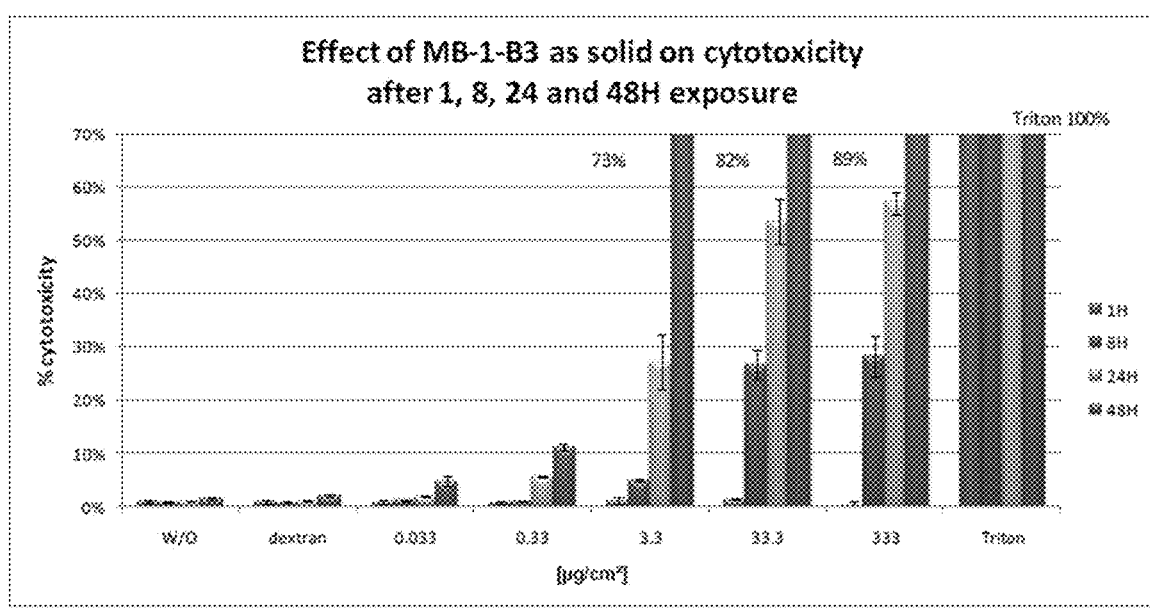
FIG. 27 shows the percentage of cytotoxicity (LDH measurement) of solid BisEDT at 1, 8, 24 and 48 hours exposure. Bars representing 1, 8, 24 and 48 hours are shown from left to right for each concentration.

Cytotoxicity assessment: FIG. 27 shows the percentage of cytotoxicity (LDH measurement) at D1. The control (Dextran) corresponds to a physiological release of LDH (<5%). No significant effect on LDH release at 0.033 and 0.33 µg/cm² at all tested time points. A time and dose dependent, cytotoxicity is observed at 3.3; 33.3 and 333 µg/cm².

Figure 28:
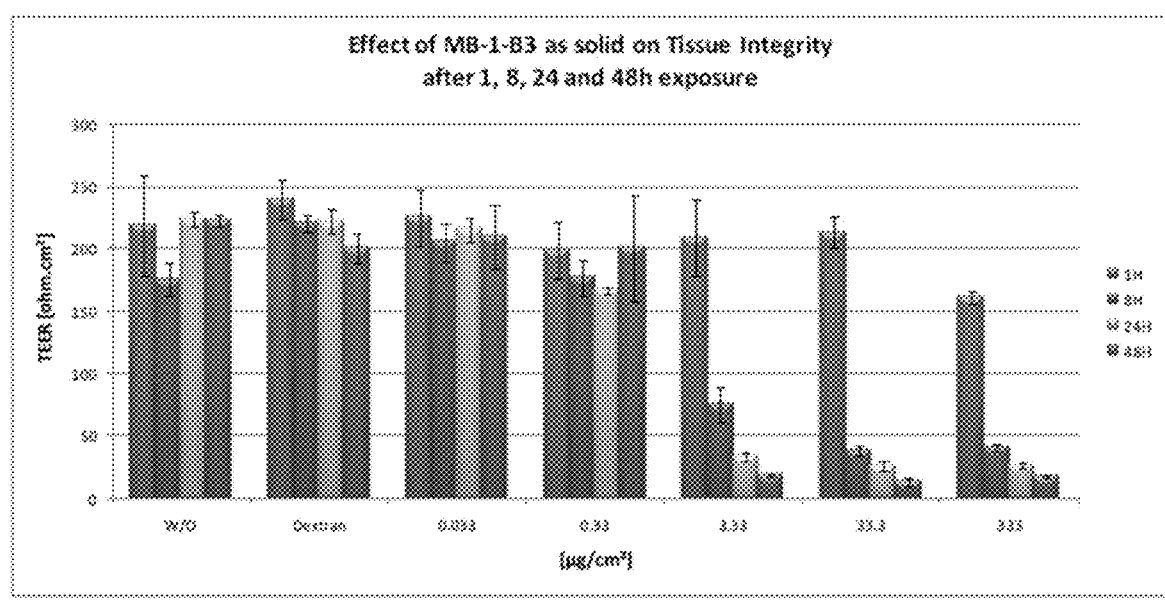
FIG. 28 shows the effect on tissue integrity of solid BisEDT at 1, 8, 24 and 48 hours exposure. Bars representing 1, 8, 24 and 48 hours are shown from left to right for each concentration.

Tissue integrity assessment: FIG. 28 shows the monitoring of TEER at D1. It should be noted that TEER is a dynamic parameter that can be affected by several factors. A decrease of the ionic channel activity can lead to an increase of TEER, and an activation of the ion channels can decrease TEER values. When an epithelium is damaged, a decrease of TEER would be associated with an increase of LDH release. No significant effect was observed on TEER at 0.033 and 0.33 µg/cm² at all tested time points. After 1 hour exposure, no significant effect on TEER is observed at all tested doses. Loss of tissue integrity is observed at 3.33, 33.3 and 333 µg/cm² after 8, 24 and 48H exposure.

Acute Toxicity Testing of BisEDT as Solid: $2^{nd}$ Set of Experiments

The aim of this phase is to evaluate the potential acute toxicity of BisEDT as solid (at 1 µg/cm²) once applied at the apical surface on a 3D model of fully differentiated human airway epithelium (MUCILAIR™) after 1, 8, 24 and 48 hours exposure.

TABLE 9

Patient Information

| Batch number | Age of the patient | Sex of the patients | Age of the culture | Special comments |
|---|---|---|---|---|
| MD014101 | 38 years | ND | 125 days | Normal donor |

TABLE 10

Compound Information

| Identification Name | Concentrations | Vehicle |
|---|---|---|
| MB-1-B3 | 1 µg/cm² | Dextran powder (C60) Ref: Pharmacosmos 5510 0060 1007 |

Testing Strategy and Protocol: Compound BisEDT was applied on the apical surface of MUCILAIR™. The effect of 1 µg/cm² concentrations after 1, 8, 24 and 48 hours exposure was studied. The compound was diluted in Dextran powder at the targeted concentration and compressed in order to obtain a tablet. The study was run in triplicates. During the study, inserts were maintained in a $CO^2$ incubator (37° C., 5% CO2, 100% humidity). The mucociliary clearance analysis was performed after 1 hour and 24 hours exposure.

Quality control and washing of the apical surface: Three days before the experiment, the following quality controls were performed on each epithelium:

Washing: inserts were washed with 200 µl of MUCILAIR™ culture medium. Washing removes accumulated mucus on the tissue surface which may interfere with the test.

Trans-Epithelial Electrical Resistance (TEER): TEER was measured to verify that all the selected inserts had tight epithelial barriers and the tissue itself was not disrupted prior to application of the test material.

Tissue morphology: each insert was inspected under a conventional inverted microscope to ensure the quality of the epithelia and determine qualitatively that cilia motion was visible. The presence of mucus was detected by the refractive aspect of the apical surface.

Results

Error bars in the following graphs refer to standard error of the mean (SEM). All comparisons are versus the negative control (Carrier Dextran).

Morphology

Morphology, Before exposure: Each insert was inspected under a conventional inverted microscope to insure the quality of the epithelia. The movement of cilia was clearly visible for all the selected inserts. The presence of mucus was detected by the refractive aspect of the apical surface.

Morphology, After exposure: No morphology changes were observed for the non-treated and the vehicle controls. 1 µg/cm²: after 1 hour and 8 hour exposure, no important morphological changes were observed. After 24 h exposure, the epithelial cells on 2 inserts out of 3 were dead. After 48 h the epithelial cells on all 3 inserts were dead.

Figure 29:
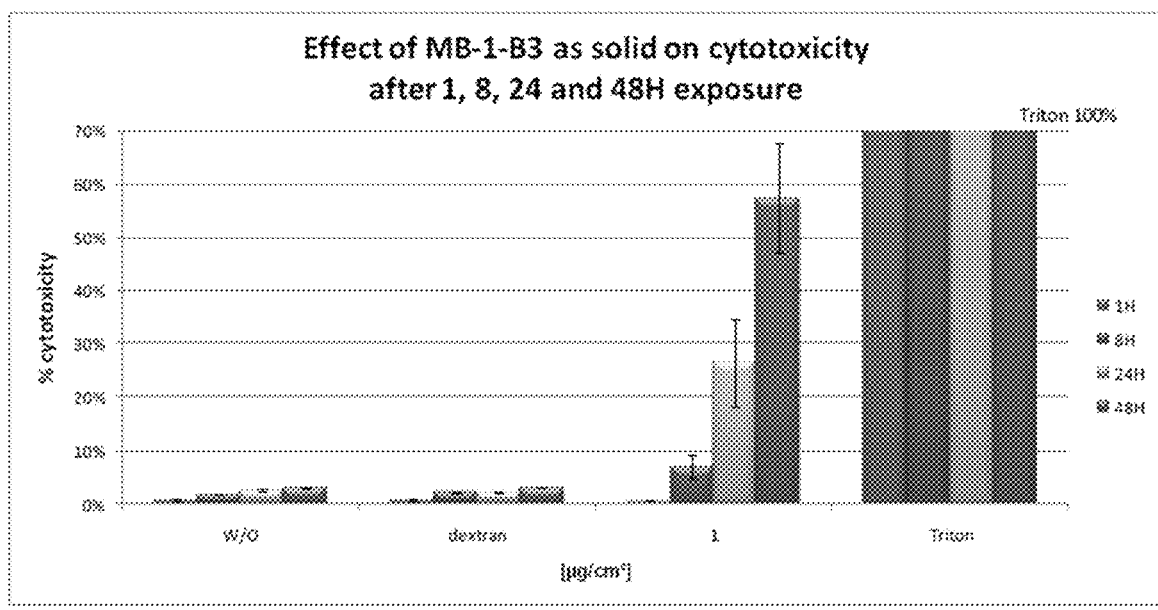
FIG. 29 shows the percentage of cytotoxicity (LDH measurement) of solid BisEDT at 1, 8, 24 and 48 hours exposure. Bars representing 1, 8, 24 and 48 hours are shown from left to right for each concentration.

Cytotoxicity assessment: FIG. 29 represents the percentage of cytotoxicity (LDH measurement) at D1. The control (Dextran) corresponds to a physiological release of LDH (<5%). No significant effect on LDH release at 1 µg/cm² after 1 hour exposure. A time- and dose-dependent cytotoxicity is observed at 8, 24 and 48 h after exposure.

Figure 30:
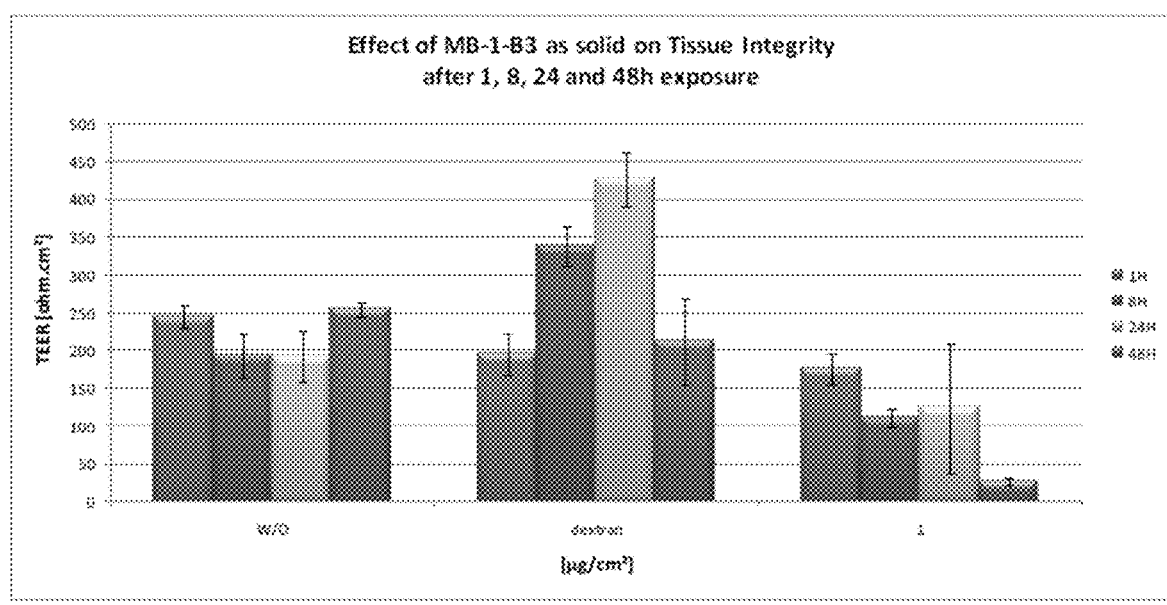
FIG. 30 shows the effect on tissue integrity of solid BisEDT at 1, 8, 24 and 48 hours exposure. Bars representing 1, 8, 24 and 48 hours are shown from left to right for each concentration.

Tissue Integrity Assessment: FIG. 30 represents the monitoring of TEER at D1. It should be noted that TEER is a dynamic parameter that can be affected by several factors. A decrease of the ionic channel activity can lead to an increase of TEER, and an activation of the ion channels can decrease TEER values. When an epithelium is damaged, a decrease of TEER would be associated with an increase of LDH release.

After 1 hour exposure, no significant effect on TEER was observed at 1 µg/cm². Loss of tissue integrity is observed at 1 µg/cm² after 8, 24 and 48H exposure. After 48H exposure, the epithelia were no more tight.

Conclusions

The aim of this study is to evaluate the potential local toxic effect of BisEDT on airway epithelium in liquid or solid solution. To evaluate potential effects of BisEDT exposure on fully differentiated human nasal epithelia cultured at the air-liquid interface, two sets of experiments were conducted namely BisEDT in liquid solutions or BisEDT as solid.

In general, within the presented study, BisEDT compound in liquid solution showed no local toxicity on the airway epithelium at different tested concentrations (0.001, 0.01, 0.1, 1, 10, 30 µM) and time exposure (1, 8, 24, and 48 hours). No effect on the morphology of the epithelia, on TEER and LDH release were observed.

Similar results were obtained when the compound was applied as solid at low doses (0.033 and 0.33 µg/cm² for 1, 8, 24, and 48 hour exposures). However, at 1 and 3.33 µg/cm², BisEDT induces cytotoxicity at 24 h and 48 h exposure, demonstrated by an increase of LDH release and a reduction of the TEER value. For higher concentrations (33.3, 333 µg/cm²), strong toxicity was observed with a high amount of LDH released, a very low TEER values and important morphological changes.

References

Huang, S; Caul-Futy, M; "A novel in vitro cell model of the human airway epithelium" 3R-Info-Bulletin No. 41, October 2009.

Huang, S., Wiszniewski, L, & Constant, S. (2011). The use of in vitro 3D cell models in drug development for respiratory diseases. Drug Discovery and Development—Present and Future Example 6: Sputum Studies Bacterial killing curves with BisEDT and BisBDT were performed in the presence of three cystic fibrosis patient sputum in order to determine whether the test compounds are potentially inactivated by sputum. The assay is described in King P, Lomovskaya O, Griffith D C, Burns J L, Dudley M N. In vitro pharmacodynamics of levofloxacin and other aerosolized antibiotics under multiple conditions relevant to chronic pulmonary infection in cystic fibrosis. *Antimicrob Agents Chemother*, 54:143-8, 2010.

Sputum was collected from cystic fibrosis (CF) patient volunteers without recent antibiotic exposure after appropriate IRB approval. Sputum was sterilized by UV irradiation and sterilization was confirmed by culture. An overnight culture of *Pseudomonas aeruginosa* strain PA01 was used to inoculate fresh cultures in cation-adjusted Mueller-Hinton broth or cation-adjusted Mueller-Hinton broth plus 10% CF patient sputum. Drugs were added to individual culture tubes with and without sputum at the following final concentrations:

BisEDT: 0.1 µg/mL, 2 µg/mL, and 20 µg/mL
BisBDT: 0.1 µg/mL, 4 µg/mL, and 20 µg/mL Tobramycin at 1 µg/mL was used as a comparator drug control known to be partially inactivated by patient sputum. Cultures were incubated with shaking at 37° C. and aliquots were removed every hour for quantitation of colony forming units per mL (CFU/mL) by serial dilution and plating on tryptic soy agar for a total of 6 hours. CFU were counted after incubation of the plates overnight at 37° C.

Figure 31:
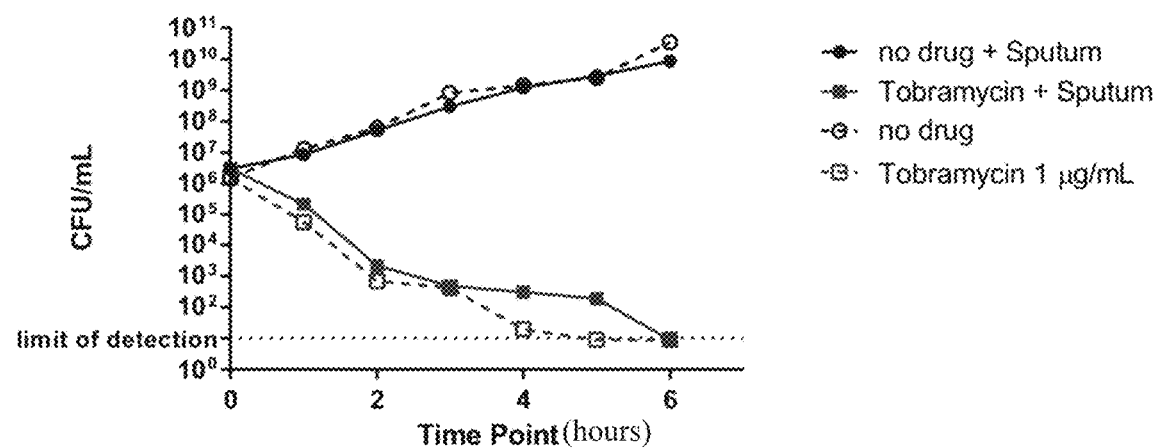
FIG. 31 shows the effect of sputum on the bacterial killing activity of tobramycin.

The controls for this assay performed as expected. The growth of PA01 was not obviously inhibited or enhanced by the addition of sterile patient sputum in the absence of additional drug to bacterial cultures (FIG. 31, closed and open circles). As shown, sputum partially inhibits the bacterial killing activity of tobramycin, with approximately 0.5-1 log CFU/mL higher at most time points in cultures with sputum compared to cultures without sputum.

Figure 32:
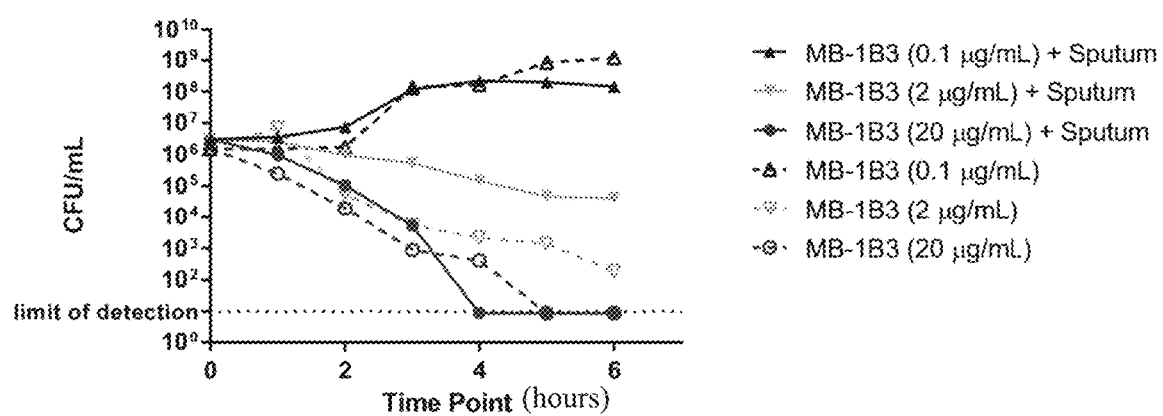
FIG. 32 shows that the bactericidal activity of BisEDT appears to be partially inhibited by CF patient sputum.

The bactericidal activity of BisEDT appears to be partially inhibited by CF patient sputum based on this assay (FIG. 32). BisEDT is not bactericidal against PA01 at 0.1 µg/mL. With BisEDT at 2 µg/mL, the addition of sputum reduces killing by approximately 1-2 log CFU/mL at 3 to 6 hours. When the concentration of BisEDT is further increased to 20 µg/mL the inhibition of bacterial killing by sputum is less pronounced, with killing in the presence of sputum lagging by only 0.5-1 log CFU/mL behind cultures without sputum at early time points (1-3 hours). Eventually, with this highest dose tested, bacteria in the culture with sputum is reduced below the limit of detection 1 hour earlier than the sample without sputum, suggesting that at higher drug concentrations inhibition of BisEDT by sputum is largely overcome.

Figure 33:
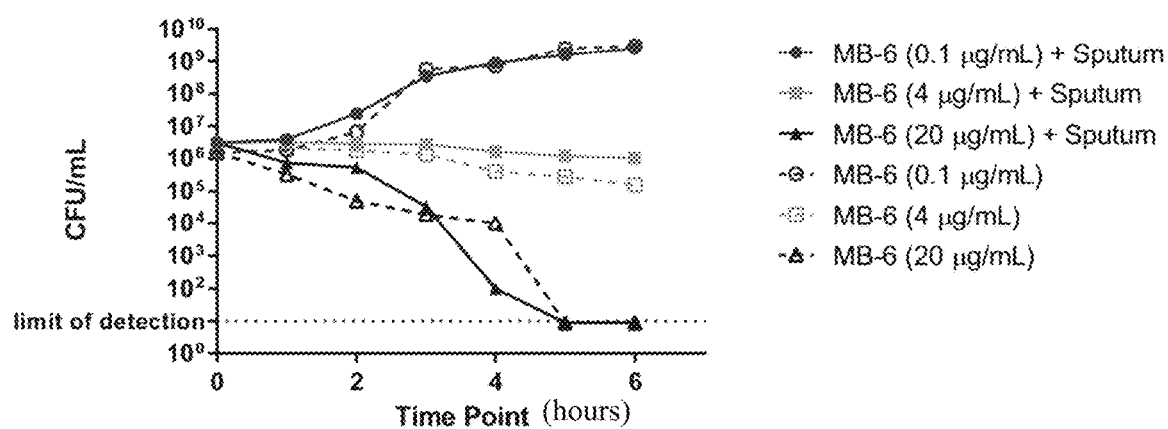
FIG. 33 shows that the bactericidal activity of BisBDT appears to be partially inhibited by CF patient sputum.

Similarly, the bactericidal activity of BisBDT appears to be partially inhibited by CF patient sputum (FIG. 33). BisBDT at 0.1 µg/mL is not bactericidal against PA01. In the absence of sputum, 4 µg/mL BisBDT demonstrated very slow bactericidal activity against PA01, with killing of only about 1 log over the 6 hour assay; cultures with sputum demonstrated approximately 0.5-0.8 log CFU/mL more surviving at 3-6 hours. At the highest concentration of BisBDT tested, 20 g/mL, there is an initial lag in killing in PA01 at 1-2 hours with the addition of sputum, but both samples with and without sputum are sterilized below the limit of detection by 5 hours.

Both compounds BisEDT and BisBDT are bactericidal against *Pseudomonas aeruginosa* strain PA01 in this assay, and this bactericidal activity is partially inhibited in the presence of CF patient sputum. This partial inhibition of bactericidal activity can be overcome by increased concentration of the test compounds. Thus, a higher concentration of bismuth-thiol compound maybe needed in areas where sputum is present compared to bodily compartments without sputum.

Example 7: In Vitro Activity of Bismuth Thiols and Comparators Against *Haemophilus influenza* Clinical Isolates In this Example, the activity of three Bismuth thiol compounds are evaluated against *Haemophilus influenzae*, a prevalent pathogen of respiratory disease including pneumonia, otitis media, conjunctivitis, and meningitis.

Test and Control Agents: The test compounds (BisEDT, and analogs BisBDT/PYR and BisEDT/PYR) were shipped from to Micromyx and stored at −20° C. until assayed. The solvent for all test compounds was 100% DMSO, the stock concentration was 2560 µg/mL, and the range tested was 64-0.06 µg/mL. All stock solutions were allowed to stand for at least one hour prior to use to auto-sterilize.

Comparator drugs were provided by Micromyx. Suppliers, lot numbers, diluent, stock concentrations, and test ranges were as follows:

| Test/Control Agents | Supplier | Lot No. | Diluent | Concentration of Stock Solution (µg/mL) | Test Range (µg/mL) |
|---|---|---|---|---|---|
| Azithromycin | USP | JOI240 | DMSO | 2560 | 64-0.06 |
| Ampicillin | Sigma | BCBF0407V | Sorenson Buffer pH 7.5 | 1280 | 32-0.03 |
| Cefuroxime | Sigma | 031M0823V | dH₂O | 2560 | 64-0.06 |
| Levofloxacin | Sigma | BCBC2112V | DMSO | 2560 | 64-0.06 |
| | | | | | 1-0.001 |

Test Organisms

The test organisms were maintained frozen at −80° C. The organisms were originally acquired from the American Type Culture Collection or from clinical laboratories. The isolates were sub-cultured on Chocolate Agar plates (Remel; Lenexa, Kans.) and incubated overnight at 35° C. with 5% $CO_2$. *H. influenzae* ATCC 49247 was tested for the purposes of quality control for the comparator compounds.

Minimal Inhibitory Concentration (MIC) Assay Media: The medium employed for the broth microdilution MIC assay was *Haemophilus* Test Medium (HTM; Remel; Lenexa, Kans.; Catalog No. R112380; Lot No. 056737) as recommended by the Clinical Laboratory Standards Institute (CLSI; 1).

Broth Dilution Minimal Inhibitory Concentration (MIC) Assay Procedure: MIC values were determined using a broth microdilution method as recommended by CLSI (1, 2). Automated liquid handlers (Multidrop 384, Labsystems, Helsinki, Finland; Biomek 2000 and Biomek F/X, Beckman Coulter, Fullerton Calif.) were used to conduct serial dilutions and make liquid transfers.

The wells of a standard 96-well microdilution plate (Costar 3795; Corning Inc.; Corning, N.Y.) were filled with 150 µL of the appropriate solvent in columns 2-12 on the Multidrop 384. This plate was used to prepare the drug "mother plate" which provided the serial drug dilutions for the replicate "daughter plates". The Biomek 2000 was used to transfer 150 µl of each stock solution from the wells in Column 1 of the mother plate to make ten subsequent 2-fold serial dilutions. The wells of Column 12 contained no drug and were the organism growth control wells. Each mother plate has the capacity to create a total of 15 daughter plates.

The daughter plates were loaded with 185 µL of HTM using the Multidrop 384. The wells of the daughter plates ultimately contained 185 µL of HTM, 5 µL of drug solution, and 10 µL of inoculum. The daughter plates were prepared on the Biomek F/X instrument which transferred 5 µL of drug solution from each well of the mother plate to each corresponding well of each daughter plate in a single step.

A standardized inoculum of each organism was prepared per CLSI methods (1). The inoculum for each organism was dispensed into sterile reservoirs divided by length (Beckman Coulter), and the Biomek 2000 was used to inoculate the plates. Daughter plates were placed on the Biomek 2000 work surface reversed so that inoculation takes place from low to high drug concentration. The Biomek 2000 delivered 10 µL of standardized inoculum into each well. These dilutions yielded a final cell concentration in the daughter plates of approximately $5.0 \times 10^5$ colony-forming-units/mL.

Plates were stacked three high, covered with a lid on the top plate, placed in plastic bags, and incubated at 35° C. for approximately 24 hr. Following incubation, the microplates were removed from the incubator and viewed from the bottom using a plate viewer. An un-inoculated solubility control plate was observed for evidence of drug precipitation. The MIC was read and recorded as the lowest concentration of drug that inhibited significant visible growth of the organism.

Results

Examination of the un-inoculated drug solubility plates revealed no precipitation of any of the evaluated agents over the tested concentration range. Against *H. influenzae* ATCC 49247, evaluated comparators had MICs within the acceptable range for quality control established by CLSI (2) where applicable.

All Bismuth Thiol test compounds were active against all evaluated *H. influenzae* strains regardless of resistance to other agents, including isolates which were beta-lactamase negative ampicillin-resistant (BLNAR). The MICs of BisEDT and analogs BisEDT/PYR and BisBDT/PYR were all at or below the lowest concentration evaluated in the study (<0.06 µg/mL). This activity was greater than azithromycin ($MIC_{50}$ and $MIC_{90}$ of 2 µg/mL), ampicillin ($MIC_{50}$ of 2 µg/mL and $MIC_{90}$ of 4 µg/mL), and cefuroxime ($MIC_{50}$ of 4 µg/mL and $MIC_{90}$ of 16 µg/mL). Levofloxacin, which was tested down as low as 0.001 µg/mL for purposes of quality control had an $MIC_{50}$ and $MIC_{90}$ of 0.015 µg/mL. As the Bismuth Thiol compounds were tested from 0.06-64 µg/mL in this study, and their MICs were <0.06 µg/mL, it is not known whether their activity exceeds that of levofloxacin which was generally had MICs of 0.015 µg/mL.

This study demonstrated a high degree of potency for the tested Bismuth Thiol compounds against *H. influenzae* at levels exceeding that of ampicillin, azithromycin, and cefuroxime. This activity illustrates that *H. influenzae* is included as part of the broad spectrum of activity shown in vitro for this class of novel therapeutic agents.

References

1.) Clinical and Laboratory Standards Institute. Methods for Dilution Antimicrobial Susceptibility Tests for Bacteria That Grow Aerobically; Approved Standard—Ninth Edition. Clinical and Laboratory Standards Institute document M07-A9 [ISBN 1-56238-784-7]. Clinical and Laboratory Standards Institute, 940 West Valley Road, Suite 1400, Wayne, Pa. 19087-1898 USA, 2012.

2.) Clinical and Laboratory Standards Institute. Performance Standards for Antimicrobial Susceptibility Testing; Twenty-Second Informational Supplement. CLSI document M100-S22 [ISBN 1-56238-786-3]. Clinical and Laboratory Standards Institute, 940 West Valley Road, Suite 1400, Wayne, Pa. 19087 USA, 2012.

Example 8: In Vivo Studies

Objectives: The primary objective of this study is to assess the tolerance of BisEDT (Dalton Pharma Services; Lot #ED268-1-11-01 stored at room temperature) following nose only inhalation exposure in F344 rats. Animals will be exposed to differing concentrations (low, middle, high) for up to 180 minutes. Blood will be collected at predetermined timepoints to analyze for systemic presence of BisEDT. At the conclusion of the study (24 hr post exposure) animals will be euthanized and undergo necropsy where lungs will be lavaged and collected for potential, future analysis. Additional respiratory tract related tissues such as the nasal cavity, larynx, pharynx, nasopharynx, trachea, bronchus, and carina will also be collected. Lavage fluid will be analyzed for clinical chemistry and hematology parameters including cell counts and differentials. Liver, kidney, esophagus, stomach, small intestine, and large intestine will also be collected for potential, future analysis.

Animals: Male and female F344 rats provided by Charles River Labs, Wilmington, Mass. were used in this study. The rats were approximately 7-9 weeks old at the time of arrival and 8-10 weeks at study initiation. Body weights of individual animals were ±20% of the group mean. Animals will be uniquely identified by numeric tail markings (made with indelible ink such as a Sharpie®) for body weights, randomization, and treatment administration. Color coded cage cards will also be placed on the cages. A total of forty (40) male and female F344 rats (20 M/20 F) (including spares) were ordered for the study. Thirty six (36) animals were randomized into 3 study groups each consisting of 12 animals per group (6 M/6F). The remaining 4 animals (2 M 12 F) were spares. Upon removal from quarantine, thirty six (36) rats will be randomized into 3 study groups each consisting of 12 animals (6 M/6 F) per group by body weight stratification. Unused spares will be either euthanized or conveyed to another approved study protocol. Prior to the start of exposures, animals will be conditioned to nose-only exposure tubes.

Animal Husbandry: Animals will be housed for a minimum of 7 days, up to 2 per cage in polycarbonate shoebox cages with Alpha Dri or hardwood chip bedding. Caging and bedding were autoclaved. Prior to injection, animals were introduced at least once to restraint tubes that will be used for tail vein dosing. Animal feed was 2016C Harlan Global Certified Rodent Chow, (Harlan Tekland, Madison, Wis.), unlimited access except during study procedures. Each batch of feed was analyzed for contaminants by the manufacturer and will be used within the manufacturer's designated shelf-life. Animals were provided municipal water (filtered at 5, 1, and 0.2 p.m.), unlimited access except during study procedures. Only healthy animals were used in this study. A laboratory animal veterinarian or designee visually examined the animals before release from quarantine.

Environmental Conditions: The targeted conditions for animal room environment and photoperiod will be as follows: Temperature: 18-26° C.; Humidity: 30-70%; Light Cycle: 12-h. Light, humidity, and temperature excursions are defined as a sustained reading that falls out of the specified range for more than 3 hours.

Experimental Design: The experimental design for this study was: Group 1: Low dose; inhalation; 6 males and 6 females; blood collection at 0.5, 2 hr and 8 hr post exposure and 24 hr (terminal); and necropsy at 24 hours-post inhalation. Group 2: Mid dose; inhalation; 6 males and 6 females; blood collection at 0.5, 2 hr and 8 hr post exposure and 24 hr (terminal); and necropsy at 24 hours-post inhalation. Group 3: high dose; inhalation; 6 males and 6 females; blood collection at 0.5, 2 hr and 8 hr post exposure and 24 hr (terminal); and necropsy at 24 hours-post inhalation. Animals were weighed and randomized into study groups following the quarantine period. Animals were broken into 3 groups each consisting of 6 M and 6 F per group. Groups were exposed to three different dose levels of BisEDT. The initial exposure was to a formulation concentration of 100 mg/mL for an exposure time of 60 minutes; based on method development this is expected to result in a dose of 3 mg/kg. The maximum duration for exposures was 180 minutes and the maximum formulation concentration was 100 mg/mL.

Following exposure, non-terminal blood collections were performed on 2 animals per sex at 0.5, 2, and 8 hours post exposure. At the conclusion of the study (24 hr post exposure) animals were euthanized and underwent necropsy. The right lung was lavaged, flash frozen, and collected for potential, future analysis. The left lung was flash frozen for potential, future analysis. Additional respiratory tract related tissues such as the nasal cavity, larynx, pharynx, nasopharynx, trachea, bronchus, and carina were collected. Lavage fluid was analyzed for clinical chemistry and hematology parameters including cell counts and differentials. Liver, kidney, esophagus, stomach, small intestine, and large intestine were collected for potential, future analysis. These organ tissue samples were flash frozen and stored pending study completion. The lavage fluid were analyzed for clinical pathology and hematology (including cell counts and differentials). A maximum whole blood collection was also collected at necropsy. Blood samples were analyzed for clinical chemistry and hematology as well as an aliquot snap frozen for potential analysis for BisEDT.

Inhalation Exposure: The initial exposure of BisEDT (Bismuth-1,2-ethanedithiol) was formulated as a solution at 100 mg/mL in suspension in 0.5% TWEEN 80®, 10 mM sodium phosphate, pH 7.4, in NaCl (adjusted to approximately 300 mOsm). Aerosols were generated with a commercial compressed air jet nebulizer, PAD LC PLUS®, operated with an inlet pressure of 20 psi. A schematic is shown in FIG. 1. The aerosols were transitioned into a rodent nose-only inhalation exposure system. The exposure system was operated with an inlet air flow of—5.2 L/min and an exhaust air flow of—5 L/min. This resulted in 0.31 L/min to each port which is slightly greater than 1.5× the respiratory minute volume of a rat.

Exposure Concentration and Particle Size Monitoring: Aerosol concentration was monitored at the breathing zone by collection onto a GF/a filter. The filters were analyzed via differential mass and other methods known in the art. Aerosol particle size was measured using a TSI Aerodynamic Particle Sizer (Model 3321, TSI, Inc., Shoreview, Minn.) or an In-Tox Mercer 2.0 L/min cascade impactor.

Observations and measurements: Observations were documented in Provantis database or the Animal Management System (AMS, LRRI, Albuquerque).

Clinical Observations and Mortality/Morbidity: Detailed clinical observations were recorded starting on dose day with observations recorded prior to exposure, during exposure, after exposure as the animals are returned to their home cages, and in the afternoon post-exposure. Observations will be recorded according to a standard lexicon (SOP TXP-1532-Pharmacologic and Toxicologic Observations of Experimental Animals). General observations include but are not limited to apnea, labored breathing, malaise, marked nasal discharge, etc. Special attention was paid to clinical signs associated with the respiratory tract. Animals showing severe signs of distress were euthanized immediately at the discretion of the Study Director in consultation with veterinary staff. Examinations were also oriented toward (1) identifying dead, weak, or moribund animals, and (2) documenting the onset and progression of any abnormal clinical signs. Moribund or dead animals were necropsied as soon as possible after being found but in no case later than 16 hours after being found.

Body Weights: All animals were weighed after release from quarantine and that weight will be the pre-study body weight used to randomize animals into dose groups. Body weights were collected in the morning prior to exposure and again at necropsy.

Blood Collection for Clinical Chemistry and Hematology: Blood samples for hematology and clinical chemistry were collected during necropsy. For Complete Blood Count (CBC) with absolute differentials, whole blood (target 0.5 mL) was collected and placed into tubes containing tripotassium ethylenediaminetetraacetate ($K_3$EDTA) as an anticoagulant. Hematology samples was analyzed by automated (ADVIA™ 120 Hematology System, Siemens Medical Solutions Diagnostics, Tarrytown, N.Y.) analyses. The parameters for hematology are: Red Blood Cell Count (RBC) $10^6/\mu L$; Hemoglobin (HGB) g/dL; Hematocrit (HCT) %; Mean Corpuscular Volume (MCV) fL; Concentration (MCHC) g/dL; Mean Corpuscular Hemoglobin (MCH) pg; Platelet Count (PLT) ($10^3/\mu L$); Percent Reticulocytes (RETIC) % RBC; White Blood Cell Count (WBC) $10^3/\mu L$; Neutrophils (PMN) $10^3/\mu L$; Lymphocytes (LYM) $10^3/\mu L$; Monocytes (MONO) $10^3/\mu L$; Eosinophils (EOS) $10^3/\mu L$; Basophils (BASO) $10^3/\mu L$; Large Unstained Cells (LUC) $10^3/\mu L$.

For clinical chemistry analyses, whole blood (≥0.5 mL) was placed into serum separator or clot tube for centrifugation and separation into cellular and serum fractions. Serum samples were analyzed on a Hitachi Modular Analytics Clinical Chemistry System (Roche Diagnostics, Indianapolis, Ind.). The clinical chemistry parameters measured or calculated are: Alanine Aminotransferase (Alanine Transaminase)-Serum (ALT) IU/L; Albumin (ALB) g/dL; Aspartate Aminotransferase (Aspartate Transaminase)-Serum (AST) IU/L; Bilirubin (Total) (BILI-T) mg/dL; Blood Urea Nitrogen (BUN) mg/dL; Calcium (CA) mg/dL; Chloride (Serum) (CL-S) mmol/L; Cholesterol (Total) (CHOL) mg/dL; Creatinine (Serum) (CRE-S) mg/dL; Glucose (GLU) mg/dL; Gamma Glutamyltransferase (GGT) IU/L; Alkaline Phosphatase (ALP) IU/L; Phosphate (PHOS) mg/dL; Potassium (Serum) (K—S) mmol/L; Protein (Total) (TP) g/dL; Sodium (Serum) (NA-S) mmol/L; Triglycerides (TRIG) mg/dL; Albumin/Globulin (A/G) no units; Blood Urea Nitrogen/Creatinine (BUN/CRE) no units; Globulin (GLOBN) g/dL.

Hematology and clinical chemistry evaluations were performed on all study animals for which adequate sample volumes are obtained and for which no analytical problems are encountered. If target collection volumes are not obtained or if evaluations are not performed, a reason and notation will be included in the raw data. The remaining blood samples or serum will be discarded after the analyses.

Blood Collection for Bioanalytical Analysis: Following exposure, non-terminal blood collections were performed on 2 animals per sex at 0.5, 2, and 8 hours post exposure. Approximately 1 mL of systemic whole blood was collected by jugular vein into tubes containing $K_3EDTA$ as an anticoagulant. The tubes were flash frozen with liquid nitrogen stored without processing at −70 to −90° C. until shipping for analysis using ICP-MS assay for quantitation of bismuth as a surrogate for BisEDT.

Euthanasia and necropsy: Animals were fasted overnight prior to scheduled necropsy (24 hr post exposure). At scheduled necropsy or in cases of morbidity, animals were euthanized by intraperitoneal injection of an overdose of a barbiturate-based sedative. Detailed gross necropsies were performed on all animals (found dead, moribund, or scheduled necropsy) and consisted of a complete external and internal examination including body orifices and cranial, thoracic, and abdominal organs and tissues. All gross findings will be recorded in descriptive terms. Whole blood was collected for bioanalytical analysis, hematology, and clinical chemistry at necropsy. Lungs collected and weighed. The left lobe were tied off and flash frozen for potential, future analysis. The right lobes were lavaged 3× using 4 mL/lavage of phosphate buffered saline (PBS). After lavage is complete the right lobes were flash frozen in liquid nitrogen for potential, future analysis.

Figure 34:
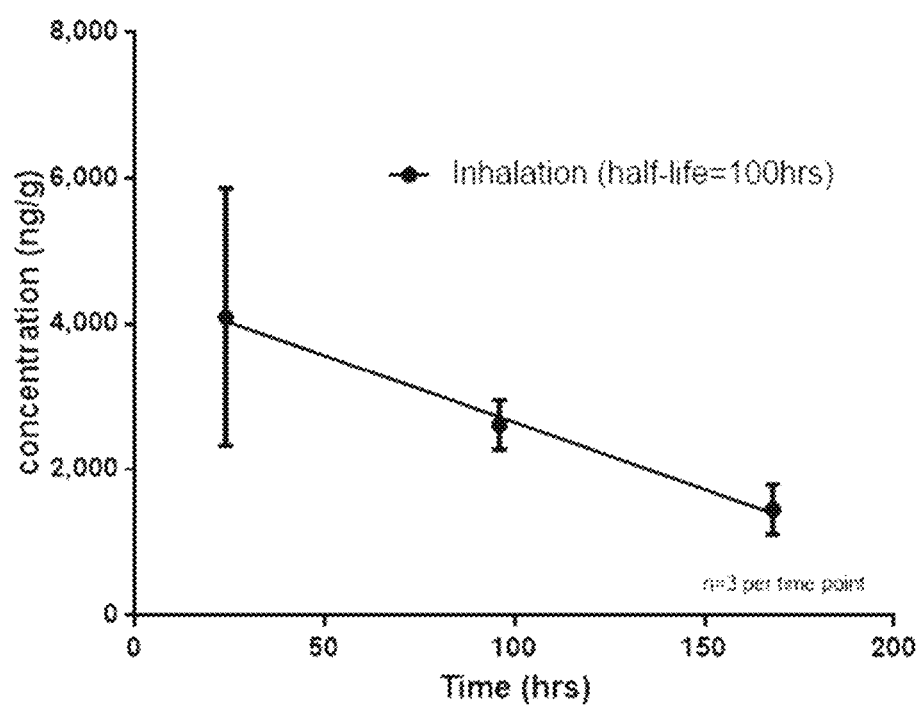
FIG. 34 shows a graph of lung tissue BisEDT concentration vs. time after a single 100 μg/kg lung deposited dose in rats.

This Example describes the results of BisEDT single-dose rat PK studies comparing inhalation, IV, and oral dosing. The primary takeaways are that (1) BisEDT remains in lung tissue after inhalation dosing with a half-life of about 4 days (FIG. 34); (2) there are very low, but sustained and measurable blood concentrations after oral dosing; (3) IV dosing appears to follow a biphasic pattern with initial distribution into tissues for 18 hours, followed by a slow systemic elimination phase; (4) BisEDT does not appreciably partition into lung tissue after IV or oral dosing—no lung levels after oral and low lung levels detected after IV dosing (<5% vs inhalation group) and levels dropped rapidly with about 24 hour half-life. This indicates that systemic BisEDT does not partition into lung tissue and that lung levels measured after inhalation dosing are due to deposited drug particles on the apical surface; (5) after inhalation dosing, there is sustained, moderate, blood exposure with relatively stable concentrations across time, indicating the drug in the lungs is acting as a depot; (6) BisEDT was tolerated at 100 μg/kg inhalation and IV and 250 μg/kg oral. Based on these data, low doses given daily or every other day are likely to provide very stable drug levels in tissue and blood (small differences between min and max). If the safety margin is demonstrated to be large enough during GLP toxicology and/or clinical studies, it is possible to lengthen the dosing interval and the increase the dose accordingly. Increasing the dose and interval leads to larger fluctuations in tissue and blood levels between peak (after dosing) and trough levels (prior to dosing).

Figure 35:
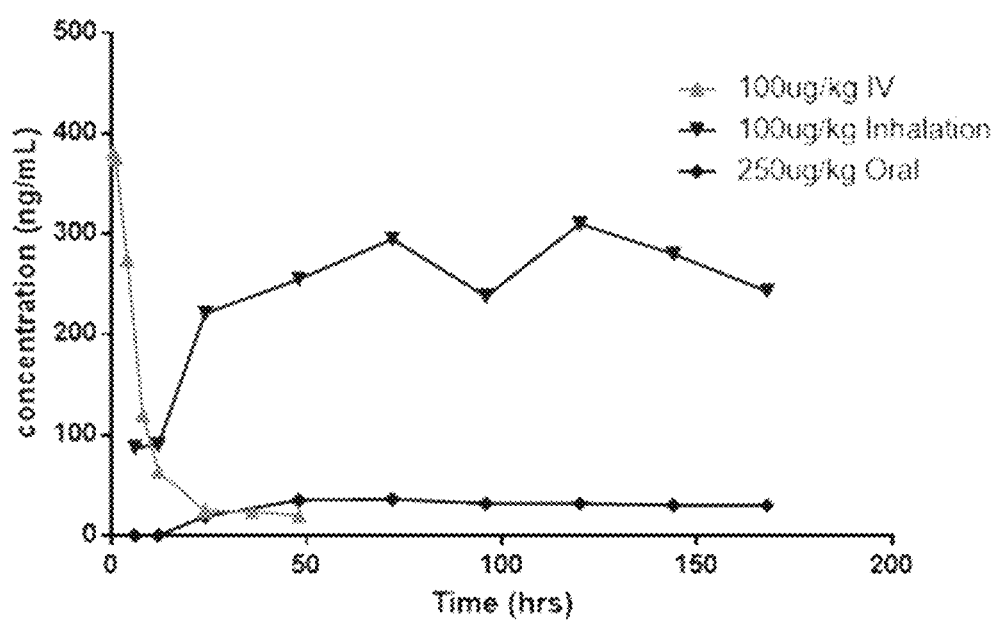
FIG. 35 shows whole blood BisEDT concentration vs. time (100 μg/kg IV or 100 μg/kg inhalation or 250 μg/kg oral dose).
Figure 36:
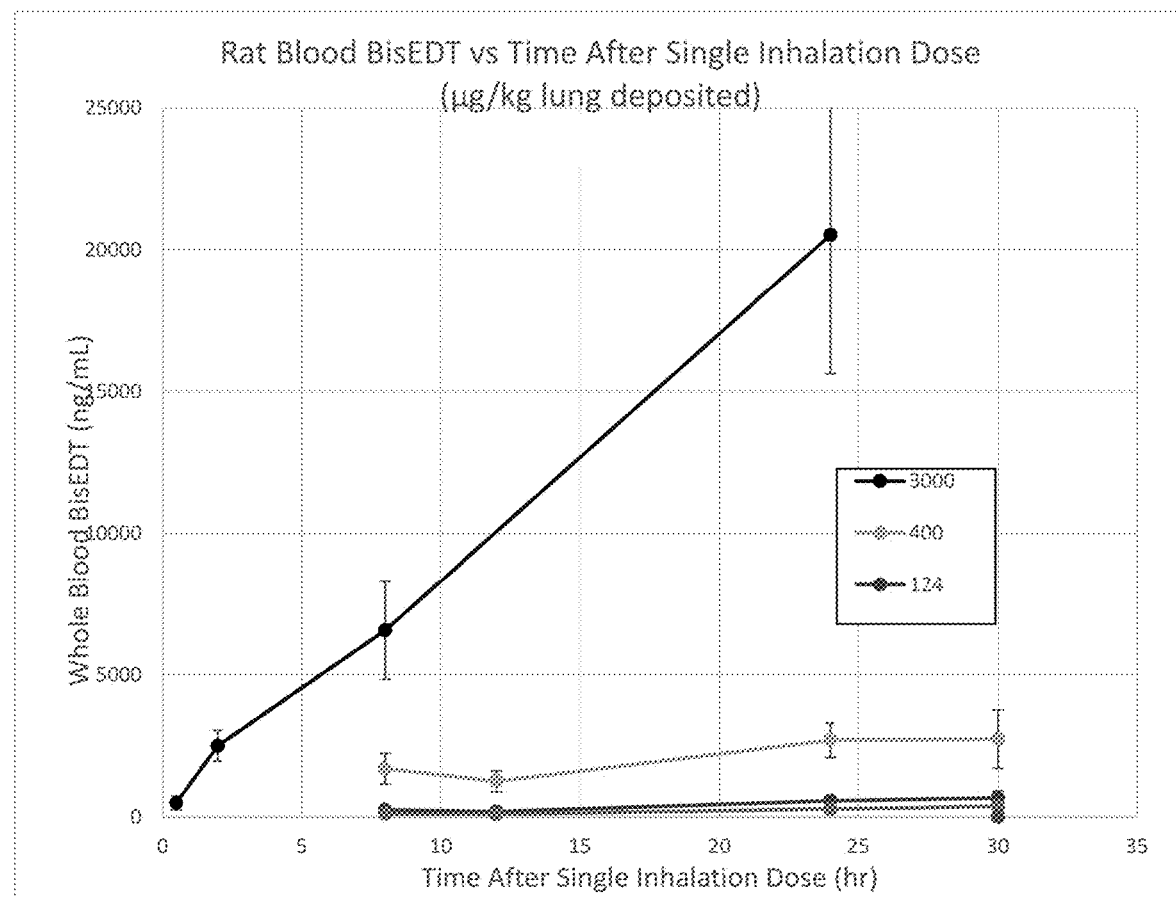
FIG. 36 shows rat blood BisEDT vs time after single inhalation dose (μg/kg lung deposited).

Based on existing in vivo and in vitro toxicology data as well as rat PK and in vitro MIC data, BisEDT suspension for inhalation can be reliably administered at doses providing efficacious lung levels that are tolerated, and it is therefore a viable clinical development candidate. As noted above, BisEDT remains in lung tissue long after inhalation dosing with a half-life of about 4 days (FIG. 35). 24 hours after single inhalation dose 4,093 ng/g was measured in the lung tissue (which equates to 123 μg/mL in lung fluid) and 4 days (96 hrs) after single dose 2,600 ng/g in lung tissue (which equates to 78 μg/mL in lung fluid). Without being bound by any particular theory, it is believed BisEDT's low solubility provides slow dissolution and long exposure on lung surface fluids with limited systemic exposure via diffusion through lung epithelium. The lung appears to act as a depot for slow systemic exposure with about 10× lower systemic levels than seen in the lung. The terminal phase of the IV data appears to show slow elimination after initial tissue distribution (FIG. 36).

Figure 37:
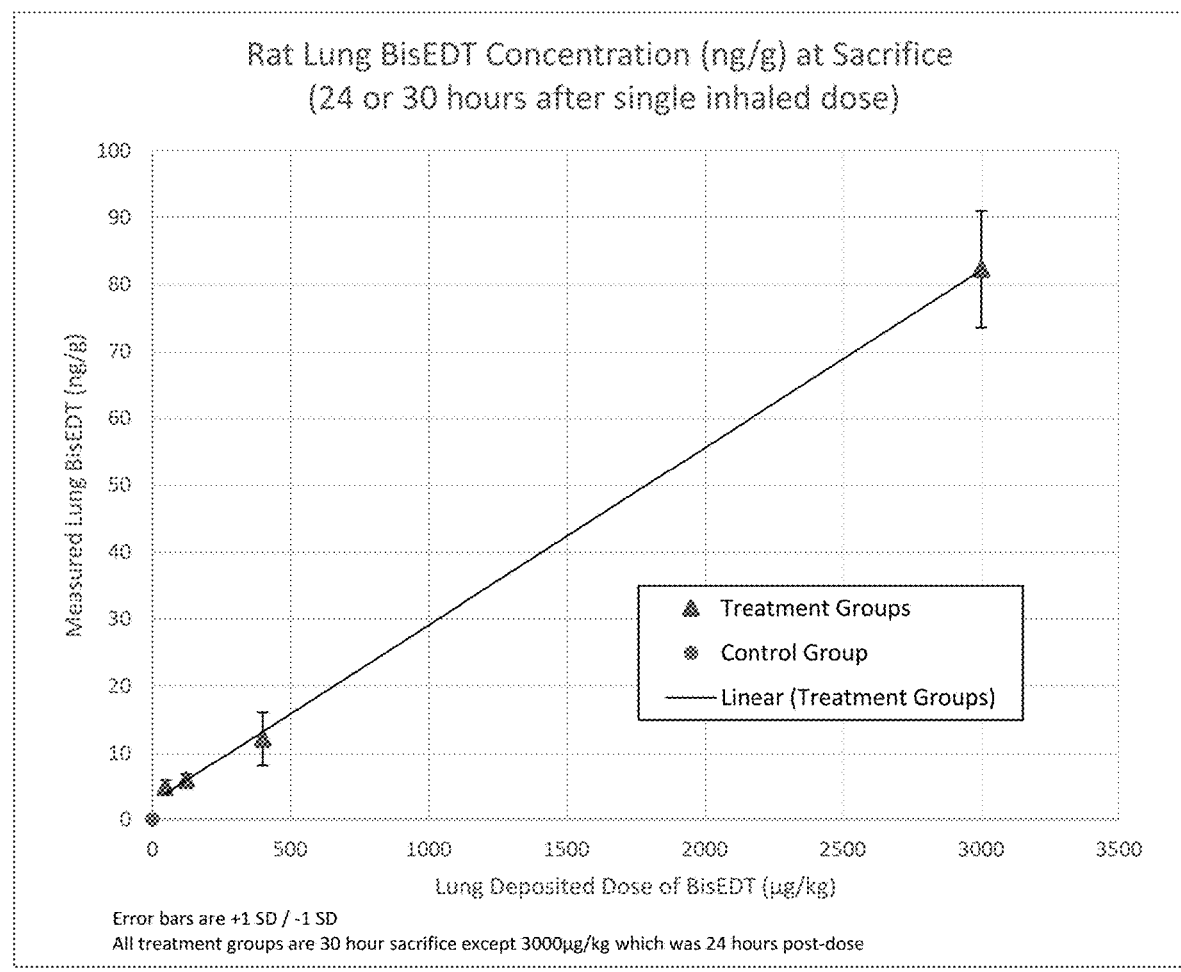
FIG. 37 shows rat lung BisEDT concentration (ng/g) at sacrifice (24 or 30 hours after single inhaled dose).
Figure 38:
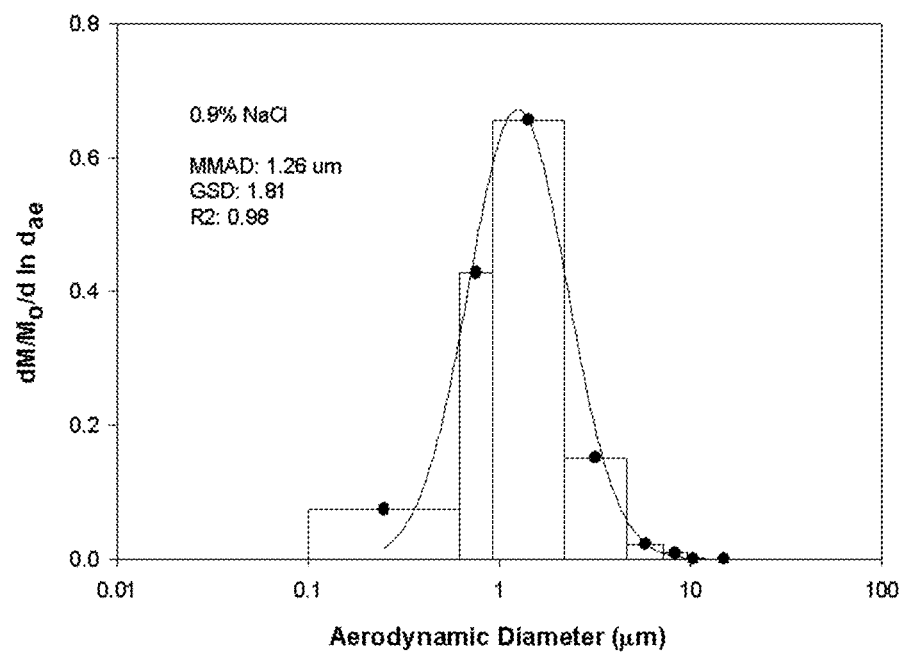
FIG. 38 shows Particle Size Distribution for vehicle.

Tables 11 and 12 below show whole blood BisEDT versus time data and lung BisEDT concentration at sacrifice time data respectively. These results are also shown graphically in FIGS. 37 and 38.

TABLE 11

Whole Blood BisEDT versus Time Data

| Dose (μg/kg) | Nominal Time (hr) | Mean BisEDT Conc (ng/mL) | STDEV |
| --- | --- | --- | --- |
| 3000 | 1 | 485 | 244 |
| 3000 | 2 | 2504 | 547 |
| 3000 | 8 | 6570 | 1729 |
| 3000 | 24 | 20525 | 4907 |
| 47 | 8 | 114 | 64 |
| 47 | 12 | 98 | 35 |
| 47 | 24 | 282 | 84 |
| 47 | 30 | 373 | 201 |
| 400 | 8 | 1701 | 542 |
| 400 | 12 | 1252 | 368 |
| 400 | 24 | 2700 | 607 |
| 400 | 30 | 2738 | 1028 |
| 124 | 8 | 247 | 3 |
| 124 | 12 | 187 | 78 |
| 124 | 24 | 571 | 93 |
| 124 | 30 | 668 | 239 |
| 0 | 30 | 0 | N/A |
| 0 | 30 | 0 | N/A |
| 0 | 30 | 0 | N/A |

TABLE 12

Lung BisEDT Conc. at Sacrifice

| Dose (μg/kg) | Sac time (hr) | Mean BisEDT Conc (ng/g) | STDEV |
|---|---|---|---|
| 3000 | 24 | 82.3 | 8.7 |
| 400 | 30 | 12.1 | 4 |
| 124 | 30 | 5.9 | 0.9 |
| 47 | 30 | 4.8 | 1.1 |
| 0 | 30 | 0 | N/A |

The efficacy of BisEDT in reducing pulmonary bacterial burden associated with pulmonary infection in a rat model of pulmonary *Pseudomonas aeruginosa* infection was evaluated. The results follow.

Aerosol concentration: The results of aerosol concentration (gravimetric and chemistry) are presented in Table 13. No BisEDT was detected by chemical analysis of the vehicle, as expected. Gravimetric analysis is listed. The positive control (Tobramycin) concentration was determined gravimetrically and all exposure atmospheres varied by less than 10% through both cohorts and all exposure days. The test article concentration, determined by chemical analysis, varied by less than 5.1% for all exposure cohorts and days and was 11.5 μg/L.

TABLE 13

Average concentration of exposure atmospheres

| Group | Analysis Method | Concentration Average | RSD |
|---|---|---|---|
| Vehicle | Gravimetric | 0.11 ± 0.02 mg/L | 14.8% |
| Tobramycin | Gravimetric | 1.26 ± 0.10 mg/L | 8.3% |
| BisEDT | Chemical | 11.5 ± 0.6 μg/L | 5.1% |

Dose Delivered: Tables 14 and 15 describe the calculated presented and theoretical deposited doses delivered to the animals in this study. The presented dose is defined as the total inhaled amount of material, comprising material deposited in the sinuses, throat, oropharyngeal region, lung, as well as exhaled material. The theoretical deposited dose, or amount of material that is actually deposited on the surface of the lung, is considered to be 10% of the presented dose in rats (Inhal Toxicol. 2008 October; 20(13):1179-89. doi: 10.1080/08958370802207318, which is hereby incorporated by reference in its entirety). Each animal's current body weight and exposure condition were factored into the equations above for dose determination. Group 3 and Group 4 exposures were 13 minutes and 30 minutes in duration, respectively. The vehicle filters were analyzed chemically for BisEDT and all filters were below detection limits. The positive control (tobramycin) filters were analyzed gravimetrically and the average presented dose for all cohorts and days was 29.0 mg/kg, higher than the 20 mg/kg value specified in the study protocol. The average presented doses for the low and high concentration groups of BisEDT were 0.114 mg/kg and 0.264 mg/kg, respectively. The study protocol called for doses of 0.1 mg/kg and 0.25 mg/kg for those groups. Details of doses received by exposure groups by day and cohort are listed in Tables 14 and 15 below.

TABLE 14

Presented Dose Summary

| Group | Day | Cohort 1 Dose (mg/kg) | Cohort 2 Dose (mg/kg) |
|---|---|---|---|
| Vehicle | 0 | BDL | BDL |
| Vehicle | 2 | BDL | BDL |
| Vehicle | 4 | BDL | BDL |
| Tobramycin | 1 | 31.0 ± 3.4 | 28.9 ± 1.8 |
| Tobramycin | 2 | 29.0 ± 1.9 | 27.9 ± 0.8 |
| Tobramycin | 3 | 27.9 ± 0.7 | 29.3 ± 1.8 |
| Tobramycin | 4 | 29.3 ± 1.7 | 28.5 ± 2.3 |
| BisEDT (0.1 mg/kg) | 0 | 0.121 ± 0.002 | 0.110 ± 0.002 |
| BisEDT (0.1 mg/kg) | 2 | 0.120 ± 0.002 | 0.120 ± 0.002 |
| BisEDT (0.1 mg/kg) | 4 | 0.101 ± 0.002 | 0.114 ± 0.002 |
| BisEDT 0.25 mg/kg | -1 | 0.263 ± 0.005 | 0.264 ± 0.003 |

TABLE 15

Theoretical Deposited Dose Summary

| Group | Day | Cohort 1 Dose | Cohort 2 Dose |
|---|---|---|---|
| Vehicle | 0 | BDL | BDL |
| Vehicle | 2 | BDL | BDL |
| Vehicle | 4 | BDL | BDL |
| Tobramycin | 1 | 3.1 mg/kg | 2.9 mg/kg |
| Tobramycin | 2 | 2.9 mg/kg | 2.8 mg/kg |
| Tobramycin | 3 | 2.8 mg/kg | 2.9 mg/kg |
| Tobramycin | 4 | 2.9 mg/kg | 2.9 mg/kg |
| BisEDT (0.1 mg/kg) | 0 | 12.1 μg/kg | 11.0 μg/kg |
| BisEDT (0.1 mg/kg) | 2 | 12.0 μg/kg | 12.0 μg/kg |
| BisEDT (0.1 mg/kg) | 4 | 10.1 μg/kg | 11.4 μg/kg |
| BisEDT 0.25 mg/kg | -1 | 26.5 μg/kg | 26.4 μg/kg |

Figure 40:
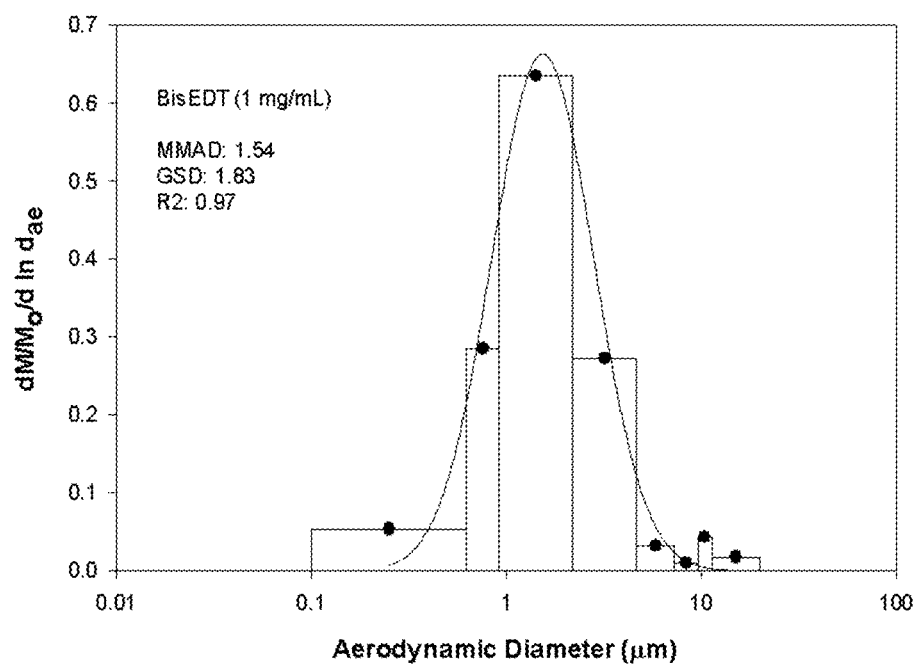
FIG. 40 shows Particle Size Distribution for BisEDT.

Particle Size Distribution: Particle size distributions (FIGS. 38-40) for each exposure condition was determined using an In-Tox Mercer Impactor. FIG. 39 shows the aerosol size distribution of BisEDT measured during the study. Table 16 provides summaries of particle size distributions (PSD) and geometric standard deviations (GSD) for each exposure type.

TABLE 16

Summary of size distributions for different exposure conditions

| Exposure Conditions | MMAD (μm) | GSD (μm) |
|---|---|---|
| Vehicle | 1.26 | 1.81 |
| Tobramycin | 2.81 | 1.87 |
| BisEDT | 1.54 | 1.83 |

FIG. 42 shows rat efficacy figures showing cumulative (total) administered dose (lung deposited) at days 3 and 5. As can be seen from this figure, the mass ratio of delivered drug is staggering compared to Tobi.

Conclusion: Animals were divided into four experiment inhalational treatment groups: 1) Group 1, a negative control group treated with saline on Days 0, 2, and 4; 2) Group 2, a positive control group treated with tobramycin (target of 20 mg/kg, BID, Days 1-4); 3) Group 3, BisEDT (target of 0.1 mg/kg, QD, Days 0, 2, 4); and Group 4, BisEDT (target of 0.25 mg/kg, once, Day -1). Animals were further divided into two cohorts, separated by one day, to accommodate the challenge and treatment of the number of animals. All animals were exposed per protocol except Group 1 and 3, cohort 2. These animals were exposed on Days 0, 1, and 4 instead of on Days 0, 2, 4.

BisEDT was not detected in animals receiving saline (negative control). Animals treated twice daily (8 doses) with tobramycin received an average dose of 29.0 mg/kg. This dose represents 145% of the targeted dose. As tobramycin is used as a positive control to ensure the model function rather than as a direct comparison, or as a competitor, for the activity of the test article, the increased dose does not impact the study. Animals treated with three targeted doses of 0.1 mg/kg BisEDT received an average of 0.114 mg/kg which represents 114% of the targeted dose. For Group 3 (targeted dose of 0.1 mg/kg), cohort 1 and 2 average doses for each day were, 0.114 and 0.115, respectively. An unpaired t-test (GraphPad Prism 5.0) comparing average dose over the three treatment days demonstrated the differences between cohorts to not be significant (p-value=0.93). Animals which received the single prophylactic targeted dose of 0.25 mg/kg received nearly identical doses of 0.263 mg/kg (cohort 1) and 0.264 mg/kg (cohort 2) of BisEDT, or 105% and 106%, respectively of the targeted dose.

The particles generated for exposure were considered respirable. The positive control (tobramycin) average MMAD of 2.81 µm with a GSD 1.87 µm. Aerosol particle MMAD of negative control (saline) treatment and test article (BisEDT) treatment were 1.26 µm and 1.54 µm with a GSD of 1.81 and 1.83, respectively.

Example 9: Study of BisEDT Following Face Mask Inhalation in Beagle Dogs

The objective of the study is to determine the maximum tolerated dose (MTD) or maximum feasible dose (MFD) of inhaled bismuth ethanedithiol (BisEDT) after face-mask inhalation exposure (up to 60 min of exposure) in male and female beagle dogs. Animals will be monitored for up to 14 days following the first day of exposure and blood will be collected at predetermined timepoints to analyze the pharmacokinetics of BisEDT. In addition, a coagulation panel will be conducted prior to necropsy. At the conclusion of the study animals will be euthanized and undergo necropsy during which the respiratory tract will be harvested for bioanalytical and histopathological analysis. Results obtained will inform a follow up repeated dose GLP study. This test article is currently being developed as a novel formulation of a broad spectrum antimicrobial/antibiofilm agent, indicated for the treatment of lung infections in patients with cystic fibrosis.

Materials: BisEDT was supplied by Dalton Pharma Services; Lot #ED268-I-II-O I and stored at room temperature. The vehicle used int his study was 0.5% TWEEN 80®, 10 mM sodium phosphate, pH 7.4, in NaCl (adjusted to approximately 300 mOsm) in water which was stored at room temperature.

Canines: Male and female canine, beagle dogs, aged 5-7 months were used int his study. Males weighed 6-10 kg and females weighed 5-9 kg. 6 male and 6 female were used.

Housing: Animals are housed in indoor or outdoor dog kennels.

Conditioning: Animals are conditioned to restraint and face masks.

Feed: 2025C Harlan Global 25% Protein Diet (Harlan Teklad, Madison, Wis.) once daily (except during conditioning and inhalation exposures). All dogs are fasted the evening prior to all blood samples collected for hematology, clinical chemistry, and coagulation analyses. Each batch of feed is analyzed for contaminants by the manufacturer and used within the manufacturer's designated shelf-life. No contaminants are expected to be present at levels that would interfere with the outcome of the study. Municipal water with unlimited access was used, except during conditioning and inhalation exposures.

Environmental Conditions: The targeted conditions for kennel temperature and photoperiod will be as follows: Temperature: 18-29° C.; Light Cycle: 12-h (on each day of exposure the light cycle may be extended to accommodate blood sample collections).

Morbidity and Mortality: Animals are observed twice daily for morbidity and mortality. If found moribund, animals will be euthanized by an overdose of an approved euthanasia solution. Only healthy animals are studied.

Once adequately conditioned to the restraint device and face-masks, the animals are individually exposed to the test article aerosols. The experimental design is shown in Table 17. Animals receive a single face-mask inhalation exposure in a ramp study design to test article aerosols for up to 60 min. Animal observations during and post exposure determine the tolerance of inhaled BisEDT aerosols.

Group 1 (vehicle) are exposed to a vehicle atmosphere for 30 minutes. Group 2 (50 µg/kg) are exposed to BisEDT for 30 minutes. Target concentrations and exposure durations for Groups 3-5 are based on the presence of any toxicity via clinical observations or gross necropsy findings. In each of Groups 3-5, if no adverse clinical signs of toxicity are observed, the next groups' exposure will be conducted at a higher target dose. If adverse clinical signs of toxicity are observed, the next groups' exposure will be conducted at a lower target dose. This approach is repeated for all BisEDT doses. The final documented exposure duration is the maximum tolerated dose or the maximum feasible dose.

Blood is collected for pharmacokinetic (PK) analysis, hematology, clinical chemistry, and coagulation analysis.

At each scheduled timepoint (or in cases of morbidity) animals will be euthanized.

TABLE 17

| | Experimental Design | | | |
|---|---|---|---|---|
| Group | Exposure[a] | Target Dose | Gender/Animal IDs | Blood Collection[d,e] |
| 1 | Day 0 and Day 7: TA Vehicle | n/a | Male: 1001 Female: 1002 | NA |
| 2 | Day 0 and Day 7: BisEDT | Low 50 µg/kg | Male: 2001 Female: 2002 | 4 hrs (±5 min), Day 1, Day 2, Day 7 |

TABLE 17-continued

Experimental Design

| Group | Exposure[a] | Target Dose | Gender/Animal IDs | Blood Collection[d,e] |
|---|---|---|---|---|
| 3 | Day 0 and Day 7: BisEDT | Low-Mid: TBD[c] | Male: 3001 Female: 3002 | (pre-exposure), Day 7 (post-exposure), Day 8, Day 9, Day 10, Day 11, Day 12, Day 13, Day 14 |
| 4 | Day 0 and Day 7: BisEDT | Mid-High: TBD[c] | Male: 4001, 4003 Female: 4002, 4004 | |
| 5[b] | Day 0 and Day 7: BisEDT | High: TBD[c] | Male: 5001 Female: 5002 | |

[a]All groups consist of 1 male and 1 female animal exposed on Day 0 and Day 7. All Groups are terminal on Day 14. Group 4 includes 2 additional animals (1 female and 1 male) with necropsy performed on Day 21.
[b]Group 5 will be included if Group 4 does not show signs of toxicity.
[c]TBD: Concentrations will be documented by memo and included in the final study report and will be based on the results of the previous exposure group.
[d]Blood collections for the additional animals (4003 and 4004) in Group 4 are: Day 15, Day 16, Day 17, Day 18, Day 19, Day 20, Day 21.
[e]Blood collection for PK analysis.

BisEDT formulation: The initial 5.0 mg/ml BisEDT formulation is prepared in 0.5% TWEEN 80®, 10 mM sodium phosphate, pH 7.4, in NaCl (adjusted to approximately 300 mOsm). On each exposure day the formulation is analyzed.

Figure 41:
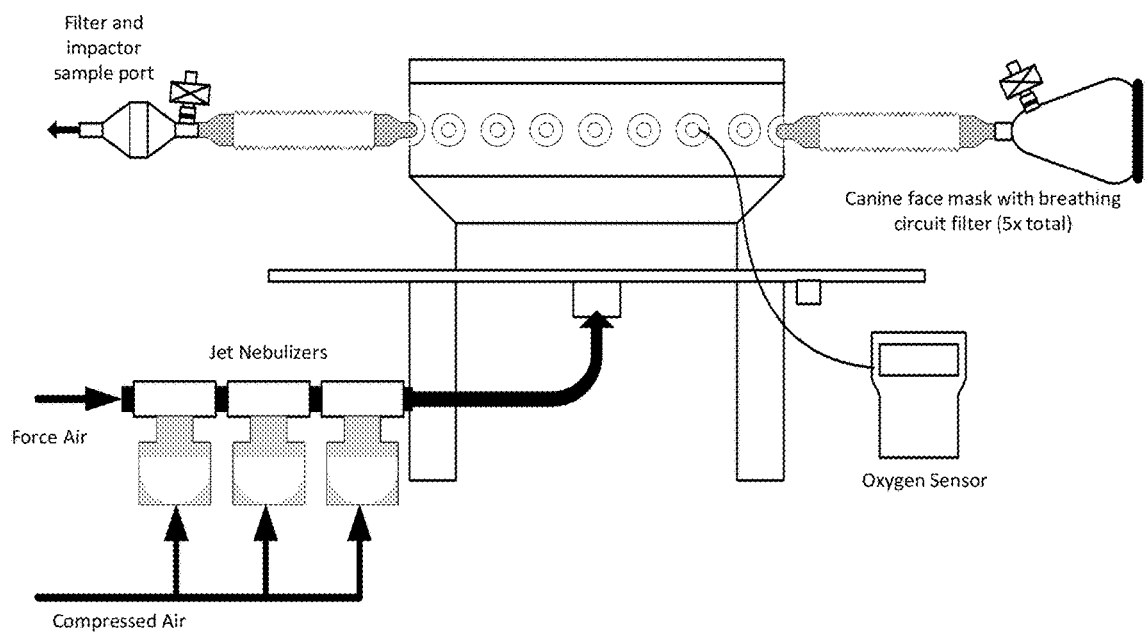
FIG. 41 shows an example schematic diagram of the dog exposure system.

Test Article Administration: A representative schematic is presented in FIG. 41. The aerosol generation system couples a commercially available compressed air jet nebulizer to a chamber that allows the aerosols to transition to the animals. Exposure is by face-mask inhalation per the study design above. Exposure durations do not exceed 60 min. Formulation concentration and exposure duration are modulated to achieve target doses if necessary.

Animals will be transported to the exposure room and placed onto exposure tables with restraint harnesses. Facemasks connected to the chamber will be placed on the animal immediately prior to the beginning of the exposure period. Temperature and exposure chamber oxygen (%) will be monitored throughout the exposure.

Concentration Monitoring: Aerosol concentration monitoring is conducted by collecting aerosols onto pre-weighed GF/A 47-mm filters. The filters are sampled from the exposure chamber throughout the exposure. The aerosol sampling flow rate through GF/A filters is maintained at 0.5±0.1 L/min. After sample collection, filters are weighed to determine the total aerosol concentration in the exposure system. The filters are extracted and analyzed. Based on BisEDT average exposure aerosol concentration the deposited dose is calculated.

Particle Size Determination: Particle size distribution of aerosols are measured from the breathing zone of the exposure chamber by a Mercer-style, seven-stage cascade impactor (Intox Products, Inc., Albuquerque, N. Mex.). The particle size distribution is determined in terms of mass median aerodynamic diameter (MMAD) and geometric standard deviation (GSD). Cascade impactor sample is collected at a flow rate of 2.0±0.1 L/min.

Determination of Pulmonary Dose: Deposited dose is calculated using the equation below. In this calculation, the average aerosol concentration measured from the exposure along with the individual animals' body weight for each specific exposure day will be used. In this manner, the Estimated amount of BisEDT that is deposited in the lungs will be calculated using the measured BisEDT aerosol concentration.

$$DD(\mu g/kg) = \frac{AC(\mu g/L) \times RMV(L/min.) \times DF \times T(min.)}{BW(kg)}$$

Where:
Deposited Dose=(DD) µg/kg
Respiratory minute volume (RMV)=$0.608 \times BW^{0.852}$ (Alexander D J et al., 2008)
Aerosol exposure concentration (AC)=BisEDT aerosol concentration (µg/L)
Deposition Fraction (DF)=assumed deposition fraction of 25%
BW=body weight of the individual animal on study (kg)

Observations and Measurements

Clinical Observations and Mortality/Morbidity: Detailed clinical observations are recorded starting on dose day with observations recorded twice per day (morning and afternoon) from arrival to the day of exposure. General observations include but are not limited to apnea, labored breathing, malaise, marked nasal discharge, etc. Special attention are paid to clinical signs associated with the respiratory tract. Animals showing severe signs of distress are euthanized at the discretion of the Study Director and in consultation with veterinary staff. Examinations are oriented toward (1) identifying dead, weak, or moribund animals, and (2) documenting the onset and progression of any abnormal clinical signs. Moribund or dead animals are necropsied as soon as possible after being found but in no case later than 16 hrs after being found.

Body Weights: All animals are weighed after release from quarantine and that weight will be the pre-study body weight used to randomize animals into dose groups. Body weights are collected in the morning prior to exposure and at necropsy.

Blood Collections and Bioanalytical Analysis: Blood are collected for pharmacokinetic (PK) analysis prior to exposure, then at 4 hr (±5 min) post exposure, and again on Day 1, Day 2, Day 7 (pre- and 4 hr (±5 min)-post exposure), Day 8, Day 9, Day 10, Day 11, Day 12, Day 13, and Day 14. A total of 0.25 mL is collected at each timepoint. No PK blood is collected from the vehicle control (Group 1) animals; only animals exposed to BisEDT have blood collected for PK analysis. Collected samples are flash frozen without processing for shipment to Medpace for bioanalytical analysis. Additional blood is collected from all animals in all groups for hematology (1 mL) and clinical chemistry (1 mL) at baseline, Day 7 (pre-exposure), and again at euthanasia. Blood (2-2 mL) is collected from all animals at necropsy for coagulation analysis (d-Dimer, fibrinogen, PT, and PTT).

Blood samples are collected from either the jugular vein or another peripheral vein (cephalic or saphenous).

Blood for pharmacokinetic analysis (0.25 mL) is collected into tubes containing $K_3$EDTA as an anticoagulant. The tubes are flash frozen with liquid nitrogen and stored without processing at −70 to −90° C. until shipping for analysis using ICP-MS assay for quantitation of bismuth as a surrogate for BisEDT.

For hematology analyses, whole blood (1 ml) will be collected with vacutainers containing $K_3$EDTA as an anticoagulant.

For clinical chemistry analyses, whole blood (1 mL) is placed into serum separator or clot tube and processed to plasma by centrifugation at a minimum of 1300 g at 2 to 8° C. for 10 (±1) min. Plasma samples are stored at −70 to −90° C. until analysis.

For coagulation analyses, blood (2-2 mL samples) are collected into tubes containing sodium citrate anticoagulant, processed, and the citrated plasma frozen and held for analysis. Prothrombin Time (PT), activated Partial Thromboplastin Time (aPTT), d-Dimer, and fibrinogen are analyzed on each animal. Samples will be centrifuged (1500 rpm, 15 minutes), plasma aliquoted into cryogenic vials, and stored frozen (−70 to −90° C.) until analysis.

Hematology and Clinical Chemistry: All dogs are fasted the evening prior to all blood samples collected for hematology, clinical chemistry, and coagulation analyses.

Hematology samples are analyzed by automated (ADVIA™ 120 Hematology System, Siemens Medical Solutions Diagnostics, Tarrytown, N.Y.) analyses. Disposition will be recorded on the sample processing form. Parameters for hematology are shown in Table 18.

Clinical chemistry samples are analyzed on a Hitachi Modular Analytics Clinical Chemistry System (Roche Diagnostics, Indianapolis, Ind.). The clinical chemistry parameters are shown in Table 19.

If target collection volumes needed for hematology or clinical chemistry analysis are not obtained, no analyses will be performed for that animal. In addition, if evaluations cannot be performed, a reason and notation will be included in the study file.

TABLE 18

Hematology Parameters

| Parameter | Abbreviation[a] | Units |
|---|---|---|
| Red Blood Cell Count | RBC | $10^6/\mu L$ |
| Hemoglobin | HGB | g/dL |
| Hematocrit | HCT | % |
| Mean Corpuscular Volume | MCV | fL |
| Mean Corpuscular Hemoglobin Concentration | MCHC | g/dL |
| Mean Corpuscular Hemoglobin | MCH | pg |
| Platelet Count | PLT | $10^3/\mu L$ |
| Percent Reticulocytes | RETIC | % RBC |
| White Blood Cell Count and Absolute Differential | | |
| White Blood Cell Count | WBC | $10^3/\mu L$ |
| Neutrophils | PMN | $10^3/\mu L$ |
| Lymphocytes | LYM | $10^3/\mu L$ |
| Monocytes | MONO | $10^3/\mu L$ |
| Eosinophils | EOS | $10^3/\mu L$ |
| Basophils | BASO | $10^3/\mu L$ |
| Large Unstained Cells | LUC | $10^3/\mu L$ |

[a]Abbreviations from the hematology system differ from those listed above, however the final results will be reported as described above

TABLE 19

Clinical Chemistry Parameters

| Analyte | Abbreviation[a] | Units |
|---|---|---|
| Alanine Aminotransferase (Alanine Transaminase)-Serum | ALT | IU/L |
| Albumin | ALB | g/dL |
| Aspartate Aminotransferase (Aspartate Transaminase)-Serum | AST | IU/L |
| Bilirubin (Total) | BILI-T | mg/dL |
| Blood Urea Nitrogen | BUN | mg/dl |
| Calcium | CA | mg/dL |
| Chloride (Serum) | CL-S | mmol/L |
| Cholesterol (Total) | CHOL | mg/dL |
| Creatinine (Serum) | CRE-S | mg/dL |
| Glucose | GLU | mg/dL |
| Gamma Glutamyltransferase | GGT | IU/L |
| Alkaline Phosphatase | ALP | IU/L |
| Phosphate | PHOS | mg/dL |
| Potassium (Serum) | K-S | mmol/L |
| Protein (Total) | TP | g/dL |
| Sodium (Serum) | NA-S | mmol/L |
| Triglycerides | TRIG | mg/dL |
| Calculated Parameters and Ratios | | |
| Albumin/Globulin | A/G | None |
| Blood Urea Nitrogen/Creatinine | BUN/CRE | None |
| Globulin | GLOBN | g/dL |

[a]Abbreviations from the chemistry system differ from those listed above, however the final results will be reported as described above Euthanasia, Necropsy, and Histology Euthanasia: At scheduled necropsies (Day 14 or Day 21, respectively) or in cases of moribundity, animals are tranquilized and euthanized by a veterinarian or their. Animals are tranquilized by administration of acepromazine (0.02-0.2 mg/kg, IM) and butorphanol (≥0.33 mg/kg, IM). After sedation, an intravenous catheter is placed to accommodate administration of a ketamine/diazepam cocktail and flushed with a saline solution. The cocktail is a proportional mixture of 1 mL of ketamine (100 mg/mL) and 1 mL of diazepam (5 mg/mL). The cocktail is then be administered at a dose of ≥1 mL/9 kg body weight. Note: If a dog is sufficiently sedated after use of acepromazine and butorphanol, administration of ketamine/diazepam cocktail may not be required or administered and will be documented. The animal is then euthanized by an overdose of a barbiturate-based sedative (EUTHASOL®, ≥1 mL/4.5 kg, IV) and flushed with a saline solution. If needed, exsanguination may be performed.

Necropsy: Detailed gross necropsies are performed on all animals and will consist of a complete external and internal examination including body orifices (ears, nostrils, mouth, anus, etc.) and cranial, thoracic, and abdominal organs and tissues. All gross findings are recorded in descriptive terms, typically including location(s), size (in mm), shape, color, consistency, and number. Animals found dead will be refrigerated until necropsy can be performed. A cause of death is determined if possible.

The left lobe of the lung is used for histopathology and will be fixed in 10% NBF. The right middle lobe has three approximately 1 gram sections collected and flash frozen with liquid nitrogen for bioanalytical analysis; samples will be stored at −70 to −90° C. until shipping for analysis using ICP-MS assay for quantitation of bismuth as a surrogate for BisEDT. Liver, spleen, kidney, brain, heart, and respiratory tract are collected and fixed for potential, future analysis.

Histology and Pathology: Lungs are, prepared, and embedded, cut and mounted on slides, stained with hematoxylin and eosin, and evaluated by a Pathologist. In addition, representative lesions observed and collected during necropsy may be evaluated. Histology is conducted on Group 1 and Group 4; additional analyses may be conducted by Amendment to the Approved Study Protocol.

Results

Table 20 shows the actual deposited dose of BisEDT in the lung for dogs tested. Table 21 shows hematology results and Table 22 shows clinical chemistry results for the dogs tested.

TABLE 20

Actual lung deposited doses per group/animal #:

| Animal # | Group | Lung deposited dose, ug/kg |
|---|---|---|
| 1001 | 1 | 0 |
| 1002 | 1 | 0 |
| 2001 | 2 | 55 |
| 2002 | 2 | 56 |
| 3001 | 3 | 112 |
| 3002 | 3 | 111 |
| 4001 | 4 | 176 |
| 4002 | 4 | 180 |
| 4003 | 4 | 195 |
| 4004 | 4 | 197 |

TABLE 21

Hematology Summary

| Subject/QC Lot | Sex/QC Identifier | WBC ^3/uL | RBC ^6/uL | HGB g/dL | HCT % | MCV fL | MCH pg | MCHC g/dL | PLT ^3/uL | NEUT ^3/uL | LYMP ^3/uL | MONO ^3/uL | EOS ^3/uL | BASO ^3/uL | LUC ^3/uL | RET % |
|---|---|---|---|---|---|---|---|---|---|---|---|---|---|---|---|---|
| 1001 | Male | 13.48 | 6.75 | 15.9 | 46.6 | 69.1 | 23.5 | 34.0 | 250 | 8.56 | 3.73 | 0.82 | 0.15 | 0.20 | 0.03 | 0.72 |
| 1001 | Male | 7.98 | 5.89 | 13.8 | 39.8 | 67.7 | 23.4 | 34.7 | 241 | 5.00 | 2.26 | 0.54 | 0.08 | 0.07 | 0.02 | 0.34 |
| 1001 | Male | 9.32 | 6.15 | 14.3 | 42.8 | 69.6 | 23.2 | 33.4 | 106 | 6.37 | 2.22 | 0.57 | 0.05 | 0.08 | 0.01 | 0.39 |
| 1002 | Female | 9.18 | 7.54 | 17.0 | 51.2 | 67.9 | 22.6 | 33.2 | 297 | 3.97 | 3.89 | 0.39 | 0.73 | 0.17 | 0.02 | 0.51 |
| 1002 | Female | 8.67 | 6.75 | 16.0 | 44.6 | 66.1 | 23.6 | 35.8 | 168 | 5.92 | 1.83 | 0.68 | 0.10 | 0.13 | 0.01 | 0.23 |
| 1002 | Female | 7.98 | 6.47 | 15.0 | 45.2 | 69.9 | 23.3 | 33.3 | 193 | 5.38 | 1.75 | 0.72 | 0.07 | 0.06 | 0.02 | 0.44 |
| Grp 1 | Avg | 11.33 | 7.15 | 16.5 | 48.9 | 68.5 | 23.1 | 33.6 | 273.5 | 6.27 | 3.81 | 0.61 | 0.44 | 0.19 | 0.03 | 0.62 |
| Grp 1 | Avg | 8.33 | 6.32 | 14.9 | 42.2 | 66.9 | 23.5 | 35.3 | 204.5 | 5.46 | 2.05 | 0.61 | 0.09 | 0.10 | 0.02 | 0.29 |
| Grp 1 | Avg | 8.65 | 6.31 | 14.7 | 44.0 | 69.8 | 23.3 | 33.4 | 149.5 | 5.88 | 1.99 | 0.65 | 0.06 | 0.07 | 0.02 | 0.42 |
| 2001 | Male | 9.18 | 6.83 | 15.6 | 45.8 | 67.0 | 22.8 | 34.1 | 197 | 5.31 | 2.81 | 0.63 | 0.30 | 0.12 | 0.01 | 0.34 |
| 2001 | Male | 9.13 | 6.49 | 15.0 | 43.1 | 66.4 | 23.2 | 34.9 | 166 | 5.11 | 2.73 | 0.67 | 0.45 | 0.15 | 0.01 | 0.55 |
| 2001 | Male | 5.99 | 6.28 | 14.2 | 41.8 | 66.5 | 22.7 | 34.1 | 161 | 2.88 | 2.09 | 0.53 | 0.39 | 0.08 | 0.02 | 0.60 |
| 2002 | Female | 6.99 | 7.05 | 16.4 | 49.0 | 69.5 | 23.2 | 33.4 | 206 | 3.96 | 2.27 | 0.50 | 0.14 | 0.11 | 0.02 | 0.65 |
| 2002 | Female | 7.77 | 6.74 | 15.0 | 43.7 | 64.8 | 22.3 | 34.4 | 294 | 4.26 | 2.82 | 0.51 | 0.09 | 0.10 | 0.01 | 0.25 |
| 2002 | Female | 8.10 | 6.50 | 14.3 | 42.9 | 66.0 | 21.9 | 33.2 | 304 | 4.83 | 2.61 | 0.51 | 0.06 | 0.07 | 0.01 | 0.31 |
| Grp 2 | Avg | 8.09 | 6.94 | 16.0 | 47.4 | 68.3 | 23.0 | 33.8 | 201.5 | 4.64 | 2.54 | 0.57 | 0.22 | 0.12 | 0.02 | 0.50 |
| Grp 2 | Avg | 8.45 | 6.62 | 15.0 | 43.4 | 65.6 | 22.8 | 34.7 | 230.0 | 4.69 | 2.78 | 0.59 | 0.27 | 0.13 | 0.01 | 0.40 |
| Grp 2 | Avg | 7.05 | 6.39 | 14.3 | 42.4 | 66.3 | 22.3 | 33.7 | 232.5 | 3.86 | 2.35 | 0.52 | 0.23 | 0.08 | 0.02 | 0.46 |
| 3001 | Male | 8.74 | 6.11 | 13.6 | 40.2 | 65.8 | 22.3 | 33.9 | 310 | 4.36 | 3.29 | 0.44 | 0.57 | 0.07 | 0.02 | 0.61 |
| 3001 | Male | 7.25 | 6.35 | 14.2 | 41.0 | 64.6 | 22.3 | 34.5 | 321 | 3.52 | 2.93 | 0.45 | 0.27 | 0.07 | 0.02 | 0.79 |
| 3001 | Male | 12.97 | 6.98 | 15.8 | 48.2 | 69.1 | 22.7 | 32.8 | 255 | 7.28 | 4.35 | 0.83 | 0.38 | 0.11 | 0.02 | 1.02 |
| 3002 | Female | 11.50 | 7.17 | 16.2 | 47.3 | 65.9 | 22.6 | 34.3 | 325 | 6.77 | 3.67 | 0.67 | 0.17 | 0.20 | 0.03 | 0.91 |
| 3002 | Female | 9.18 | 6.12 | 14.6 | 43.1 | 70.4 | 23.9 | 34.0 | 247 | 5.29 | 2.86 | 0.79 | 0.12 | 0.10 | 0.02 | 0.94 |
| 3002 | Female | 14.08 | 7.36 | 16.7 | 49.8 | 67.6 | 22.7 | 33.5 | 319 | 9.25 | 3.80 | 0.76 | 0.15 | 0.10 | 0.02 | 0.72 |
| Grp 3 | Avg | 10.12 | 6.64 | 14.9 | 43.8 | 65.9 | 22.5 | 34.1 | 317.5 | 5.57 | 3.48 | 0.56 | 0.37 | 0.14 | 0.03 | 0.76 |
| Grp 3 | Avg | 8.22 | 6.24 | 14.4 | 42.1 | 67.5 | 23.1 | 34.3 | 284.0 | 4.41 | 2.90 | 0.62 | 0.20 | 0.09 | 0.02 | 0.87 |
| Grp 3 | Avg | 13.53 | 7.17 | 16.3 | 49.0 | 68.4 | 22.7 | 33.2 | 287.0 | 8.27 | 4.08 | 0.80 | 0.27 | 0.11 | 0.02 | 0.87 |
| 4001 | Male | 8.23 | 6.44 | 14.8 | 42.7 | 66.3 | 23.0 | 34.7 | 208 | 4.61 | 2.68 | 0.39 | 0.48 | 0.07 | 0.01 | 0.41 |
| 4001 | Male | 10.09 | 6.81 | 16.0 | 47.5 | 69.7 | 23.4 | 33.6 | 214 | 5.96 | 3.18 | 0.37 | 0.50 | 0.07 | 0.02 | 0.33 |
| 4001 | Male | 9.86 | 6.37 | 14.6 | 45.4 | 71.3 | 22.9 | 32.2 | 213 | 6.30 | 2.78 | 0.37 | 0.35 | 0.04 | 0.01 | 0.58 |
| 4004 | Female | 10.41 | 6.46 | 14.7 | 41.9 | 64.8 | 22.8 | 35.2 | 246 | 5.98 | 2.88 | 0.49 | 0.95 | 0.09 | 0.02 | 0.27 |
| 4004 | Female | 10.37 | 7.19 | 16.6 | 50.6 | 70.4 | 23.1 | 32.8 | 238 | 5.95 | 3.04 | 0.50 | 0.77 | 0.09 | 0.01 | 0.62 |
| 4004 | Female | 10.50 | 6.71 | 15.4 | 47.6 | 70.9 | 22.9 | 32.4 | 251 | 6.74 | 2.82 | 0.39 | 0.47 | 0.06 | 0.01 | 0.43 |
| Grp 4 | Avg | 9.32 | 6.45 | 14.75 | 42.30 | 65.55 | 22.90 | 34.95 | 227.00 | 5.30 | 2.78 | 0.44 | 0.72 | 0.08 | 0.02 | 0.34 |
| Grp 4 | Avg | 10.23 | 7.00 | 16.30 | 49.05 | 70.05 | 23.25 | 33.20 | 226.00 | 5.96 | 3.11 | 0.44 | 0.64 | 0.08 | 0.02 | 0.48 |
| Grp 4 | Avg | 10.18 | 6.54 | 15.00 | 46.50 | 71.10 | 22.90 | 32.30 | 232.00 | 6.52 | 2.80 | 0.38 | 0.41 | 0.05 | 0.01 | 0.51 |
| 4002 | Female | 10.21 | 5.68 | 13.7 | 39.8 | 70.1 | 24.1 | 34.4 | 257 | 6.73 | 2.46 | 0.73 | 0.18 | 0.09 | 0.01 | 1.07 |
| 4002 | Female | 7.45 | 6.61 | 13.8 | 40.7 | 61.6 | 20.9 | 34.0 | 308 | 4.11 | 2.59 | 0.50 | 0.13 | 0.10 | 0.02 | 0.88 |
| 4003 | Male | 6.63 | 6.11 | 12.8 | 37.1 | 60.8 | 21.0 | 34.6 | 313 | 3.60 | 2.32 | 0.45 | 0.19 | 0.04 | 0.02 | 0.51 |
| 4003 | Male | 11.18 | 5.92 | 14.3 | 44.2 | 74.7 | 24.2 | 32.4 | 248 | 7.39 | 2.87 | 0.61 | 0.21 | 0.10 | 0.01 | 0.83 |
| Grp 4 | Avg | 8.42 | 5.90 | 13.25 | 38.45 | 65.45 | 22.55 | 34.50 | 285.00 | 5.17 | 2.39 | 0.59 | 0.19 | 0.07 | 0.02 | 0.79 |
| Grp 4 | Avg | 9.32 | 6.27 | 14.05 | 42.45 | 68.15 | 22.55 | 33.20 | 278.00 | 5.75 | 2.73 | 0.56 | 0.17 | 0.10 | 0.02 | 0.86 |

TABLE 22

Clinical Summary

| Subject/QC Lot | Sex/QC Identifier | Na mmo/L | K mmo/L | Cl mmo/L | GLUC mg/dL | BUN mg/dL | CREA mg/dL | P mg/dL | TBIL mg/dL | ALPK IU/L | ALT IU/L | AST IU/L | GGT IU/L | TP g/dL | ALB g/dL | CA2 mg/dL | TRIG mg/dL | CHOL mg/dL | GLOB g/dL | AGR |
|---|---|---|---|---|---|---|---|---|---|---|---|---|---|---|---|---|---|---|---|---|
| 1001 | Male | 149 | 4.7 | 109 | 90 | 14 | 0.7 | 7.6 | 0.15 | 248 | 25 | 29 | 3 | 5.0 | 3.3 | 11.0 | 53 | 132 | 1.7 | 1.9 |
| 1001 | Male | 146 | 4.7 | 111 | 78 | 15 | 0.5 | 6.4 | 0.15 | 243 | 29 | 29 | 3 | 5.0 | 3.3 | 10.6 | 39 | 133 | 1.7 | 1.9 |
| 1001 | Male | 150 | 4.2 | 113 | 92 | 17 | 0.5 | 6.6 | 0.15 | 235 | 21 | 33 | 3 | 5.5 | 3.7 | 10.9 | 38 | 130 | 1.8 | 2.1 |
| 1002 | Female | 148 | 5.1 | 109 | 92 | 13 | 0.7 | 6.4 | 0.15 | 91 | 24 | 27 | 3 | 4.9 | 3.3 | 10.3 | 37 | 107 | 1.6 | 2.1 |
| 1002 | Female | 147 | 4.9 | 113 | 88 | 15 | 0.7 | 6.4 | 0.15 | 125 | 26 | 33 | 3 | 5.0 | 3.6 | 10.7 | 32 | 129 | 1.4 | 2.6 |
| 1002 | Female | 148 | 4.5 | 113 | 89 | 13 | 0.7 | 6.2 | 0.15 | 120 | 27 | 34 | 3 | 5.0 | 3.5 | 10.4 | 29 | 116 | 1.5 | 2.3 |
| Grp 1 | Avg | 149 | 4.9 | 109 | 91 | 14 | 0.7 | 7.0 | 0.15 | 170 | 25 | 28 | 3 | 5.0 | 3.3 | 10.7 | 45 | 120 | 1.7 | 2.0 |
| Grp 1 | Avg | 147 | 4.8 | 112 | 83 | 15 | 0.6 | 6.4 | 0.15 | 184 | 28 | 31 | 3 | 5.0 | 3.5 | 10.7 | 36 | 131 | 1.6 | 2.3 |
| Grp 1 | Avg | 149 | 4.4 | 113 | 91 | 15 | 0.6 | 6.4 | 0.15 | 178 | 24 | 34 | 3 | 5.3 | 3.6 | 10.7 | 34 | 123 | 1.7 | 2.2 |
| 2001 | Male | 149 | 4.5 | 109 | 91 | 12 | 0.7 | 6.8 | 0.15 | 130 | 22 | 48 | 3 | 5.0 | 3.3 | 10.9 | 66 | 168 | 1.7 | 1.9 |
| 2001 | Male | 147 | 4.9 | 113 | 97 | 16 | 0.6 | 5.9 | 0.15 | 140 | 22 | 36 | 3 | 5.1 | 3.4 | 10.8 | 80 | 167 | 1.7 | 2.0 |
| 2001 | Male | 147 | 4.7 | 108 | 102 | 15 | 0.6 | 5.5 | 0.15 | 128 | 22 | 36 | 3 | 5.5 | 3.5 | 11.0 | 63 | 152 | 2.0 | 1.8 |
| 2002 | Female | 149 | 5.0 | 110 | 95 | 13 | 0.6 | 7.4 | 0.15 | 241 | 18 | 35 | 3 | 5.2 | 3.3 | 10.9 | 38 | 138 | 1.9 | 1.7 |
| 2002 | Female | 147 | 5.2 | 114 | 98 | 14 | 0.6 | 6.4 | 0.15 | 111 | 29 | 41 | 3 | 5.2 | 3.6 | 10.8 | 39 | 123 | 1.6 | 2.3 |
| 2002 | Female | 148 | 4.6 | 113 | 89 | 14 | 0.6 | 5.7 | 0.15 | 103 | 27 | 38 | 3 | 5.3 | 3.7 | 10.6 | 31 | 114 | 1.6 | 2.3 |
| Grp 2 | Avg | 149 | 4.8 | 110 | 93 | 13 | 0.7 | 7.1 | 0.15 | 186 | 20 | 42 | 3 | 5.1 | 3.3 | 10.9 | 52 | 153 | 1.8 | 1.8 |
| Grp 2 | Avg | 147 | 5.1 | 114 | 98 | 15 | 0.6 | 6.2 | 0.15 | 126 | 26 | 39 | 3 | 5.2 | 3.5 | 10.8 | 60 | 145 | 1.7 | 2.2 |
| Grp 2 | Avg | 148 | 4.7 | 111 | 96 | 15 | 0.6 | 5.6 | 0.15 | 116 | 25 | 37 | 3 | 5.4 | 3.6 | 10.8 | 47 | 133 | 1.8 | 2.1 |
| 3001 | Male | 146 | 4.7 | 111 | 100 | 13 | 0.6 | 6.5 | 0.15 | 142 | 26 | 30 | 3 | 4.8 | 3.2 | 10.7 | 26 | 100 | 1.6 | 2.0 |
| 3001 | Male | 148 | 5.1 | 110 | 88 | 17 | 0.7 | 6.8 | 0.15 | 135 | 24 | 32 | 3 | 5.1 | 3.4 | 10.5 | 34 | 111 | 1.7 | 2.0 |
| 3001 | Male | 146 | 5.8 | 109 | 51 | 33 | 1.0 | 7.2 | 0.15 | 121 | 22 | 33 | 3 | 5.0 | 3.4 | 10.0 | 52 | 111 | 1.6 | 2.1 |
| 3002 | Female | 149 | 5.5 | 112 | 112 | 11 | 0.6 | 6.6 | 0.15 | 164 | 28 | 30 | 3 | 5.0 | 3.5 | 11.2 | 34 | 126 | 1.5 | 2.3 |
| 3002 | Female | 145 | 5.3 | 109 | 90 | 12 | 0.5 | 6.6 | 0.15 | 90 | 20 | 28 | 3 | 5.5 | 3.5 | 10.8 | 43 | 175 | 2.0 | 1.8 |
| 3002 | Female | 149 | 5.9 | 110 | 65 | 25 | 0.9 | 7.5 | 0.15 | 176 | 20 | 30 | 3 | 5.1 | 3.7 | 10.4 | 58 | 141 | 1.4 | 2.6 |
| Grp 3 | Avg | 148 | 5.1 | 110 | 106 | 12 | 0.6 | 6.6 | 0.15 | 153 | 27 | 30 | 3 | 4.9 | 3.4 | 11.0 | 30 | 113 | 1.6 | 2.2 |
| Grp 3 | Avg | 146 | 5.2 | 112 | 89 | 15 | 0.6 | 6.7 | 0.15 | 113 | 22 | 30 | 3 | 5.3 | 3.5 | 10.7 | 39 | 143 | 1.9 | 1.9 |
| Grp 3 | Avg | 149 | 5.9 | 110 | 58 | 29 | 1.0 | 7.4 | 0.15 | 149 | 21 | 32 | 3 | 5.1 | 3.6 | 10.2 | 55 | 126 | 1.5 | 2.4 |
| 4001 | Male | 152 | 4.7 | 120 | 102 | 11 | 0.7 | 6.5 | 0.15 | 103 | 27 | 33 | 3 | 5.2 | 3.6 | 10.8 | 49 | 153 | 1.6 | 2.3 |
| 4001 | Male | 147 | 4.8 | 116 | 82 | 12 | 0.7 | 6.6 | 0.15 | 114 | 27 | 39 | 3 | 5.3 | 3.4 | 10.6 | 46 | 147 | 1.8 | 1.8 |
| 4001 | Male | 145 | 4.7 | 113 | 86 | 11 | 0.6 | 6.0 | 0.15 | 119 | 28 | 34 | 3 | 4.9 | 3.2 | 10.4 | 40 | 111 | 1.7 | 1.9 |
| 4004 | Female | 153 | 4.6 | 119 | 102 | 13 | 0.6 | 5.9 | 0.15 | 103 | 28 | 33 | 3 | 5.1 | 3.4 | 10.8 | 53 | 125 | 2.0 | 1.7 |
| 4004 | Female | 148 | 5.1 | 115 | 70 | 13 | 0.6 | 6.3 | 0.15 | 93 | 25 | 38 | 3 | 5.2 | 3.3 | 10.8 | 49 | 124 | 1.6 | 1.9 |
| 4004 | Female | 146 | 4.3 | 114 | 96 | 13 | 0.6 | 5.6 | 0.15 | 95 | 24 | 31 | 3 | 5.0 | 3.3 | 10.6 | 44 | 112 | 1.4 | 2.2 |
| Grp 4 | Avg | 153 | 4.7 | 120 | 102 | 12 | 0.7 | 6.2 | 0.15 | 103 | 28 | 33 | 3 | 5.2 | 3.5 | 10.8 | 51 | 139 | 1.7 | 2.2 |
| Grp 4 | Avg | 148 | 5.0 | 116 | 76 | 12 | 0.7 | 6.5 | 0.15 | 104 | 26 | 39 | 3 | 5.2 | 3.4 | 10.7 | 48 | 136 | 1.9 | 1.8 |
| Grp 4 | Avg | 146 | 4.5 | 114 | 91 | 12 | 0.6 | 5.8 | 0.15 | 107 | 26 | 33 | 3 | 4.9 | 3.2 | 10.5 | 42 | 111 | 1.7 | 1.9 |
| 4002 | Female | 153 | 5.3 | 116 | 106 | 13 | 0.6 | 6.4 | 0.15 | 147 | 20 | 32 | 3 | 5.6 | 3.5 | 11.1 | 34 | 182 | 2.1 | 1.7 |
| 4002 | Female | 149 | 5.3 | 112 | 79 | 12 | 0.5 | 6.9 | 0.15 | 103 | 21 | 35 | 3 | 5.5 | 3.5 | 11.2 | 41 | 169 | 2.0 | 1.8 |
| 4003 | Male | 149 | 4.9 | 117 | 109 | 16 | 0.6 | 7.2 | 0.15 | 146 | 40 | 30 | 3 | 5.4 | 3.5 | 11.2 | 55 | 152 | 1.9 | 1.8 |
| 4003 | Male | 147 | 4.9 | 112 | 81 | 15 | 0.7 | 7.1 | 0.15 | 129 | 23 | 33 | 3 | 5.4 | 3.3 | 11.0 | 53 | 176 | 2.1 | 1.6 |

References

Alexander D J, Collins C J, Coombs D W, Gilkison, I S, Hardy, C J, Healey, G, Karantabias, G, Johnson, N, Karlsson, A, Kilgour, J D, and McDonald, P. Association of Inhalation Toxicologists (AIT) working party recommendation for standard delivered dose calculation and expression in non-clinical aerosol inhalation toxicology studies with pharmaceuticals. *Inhalation Toxicology;* 20(13): 1179-89, 2008.

National Research Council, 2011. *Guide for the Care and Use of Laboratory Animals.* National Academy Press, Washington, D.C.

Tepper, J S, Kuehl, P K, Cracknell, S, Nikula, K J, Pei, L, and Blanchard, J D. 2016. Symposium Summary: "Breath In, Breath Out, Its Easy: What You Need to Know About Developing Inhaled Drugs." *Int. J Toxicol.* 35(4) 376-392.

Example 10: Antimicrobial Interaction of BisEDT with Agents Used to Treat Cystic Fibrosis Infections Caused by *Pseudomonas aeruginosa* and *Burkholderia cepacia* Complex Introduction: The interaction between BisEDT and a variety of agents used in the treatment of patients with cystic fibrosis (CF) was evaluated against *P. aeruginosa* and *Burkholderia* spp. The antimicrobial interaction was determined by measuring fractional inhibitory concentrations (FIC) in a checkerboard assay.

Materials and Methods

Test articles: BisEDT was provided as a dry powder and was stored at room temperature in the dark prior to testing. The comparator compounds were handled in accordance with guidelines from the Clinical and Laboratory Standards Institute (CLSI; 1, 2). Specific information on the individual drug lots and concentration ranges tested is shown in the Table 23 below:

TABLE 23 drug lots and concentration ranges tested

| Test Articles | Supplier | Lot Number | Solvent | Concentration Ranges tested (µg/ml) (MIC) | Concentration Ranges tested (µg/ml) (FIC) |
|---|---|---|---|---|---|
| BisEDT | Microbion | ED268-1-11-01 | DMSO | 64-0.06 | 16-0.25; 4-0.06 |
| Tobramycin | Sigma | 109K1184 | Sterile dH$_2$O | 256-0.25; 2-0.002 | 256-0.25 |
| Amikacin | Sigma | 058K0803 | Sterile dH$_2$O | 256-0.25; 2-0.002 | 256-0.25 |
| Aztreonam | USP | R041F0 | Saturated NaHCO$_3$ | 256-0.25; 2-0.002 | 256-0.25 |
| Meropenem | USP | J0K434 | Sterile dH$_2$O | 256-0.25; 2-0.002 | 64-0.06 |
| Ciprofloxacin | USP | R05170 | Sterile dH$_2$O | 256-0.25; 2-0.002 | 256-0.25 |
| Colistin | Sigma | SLBV1747 | Sterile dH$_2$O | 256-0.25; 2-0.002 | 256-0.25 |

Appropriate solvents were added to the drugs which were prepared at 40-fold the top testing concentration. The stock solutions were allowed to stand for approximately 1 hr at room temperature in the dark to auto-sterilize before being used for testing. Drug stocks of the comparators were frozen and stored at −80° C.

Organisms: The test organisms were clinical isolates previously acquired by Micromyx or from the American Type Culture Collection (ATCC). Upon receipt at Micromyx, the isolates were streaked under suitable conditions onto agar medium appropriate to each organism. The organisms were incubated for 18-24 hr at 35° C. Colonies harvested from these growth plates were resuspended in the appropriate medium containing a cryoprotectant. Aliquots of each suspension were then frozen at −80° C. Prior to the assay, the organisms were streaked onto trypticase soy agar plus 5% sheep blood (BD; Sparks, Md.; Lot No. 8179506) and were incubated as described above.

Test Media: The medium employed for the assay was cation-adjusted Mueller Hinton broth (MHB II; Becton-Dickinson, Sparks, Md.; Lot No 8096574). The medium was prepared according to CLSI guidelines (2).

MIC Assay Methodology: MIC assay plates were prepared using the CLSI broth microdilution procedure (1, 2). Automated liquid handlers (Multidrop 384, Biomek 2000 and Biomek FX) were used to conduct serial dilutions and liquid transfers. All wells in columns 2 through 12 of a standard 96-well microdilution plate (Costar 3795) were filled with 150 µL of the proper diluent. Three hundred µL of each test drug (at 40x) were added to each well in Column 1 of the plates. This plate was used to prepare the drug "mother plate" which provided the serial drug dilutions for the replicate "daughter plates". The Biomek 2000 was used to complete the serial transfers through Column 11 in the mother plates. The wells of Column 12 contained no drug and were the organism growth control wells.

The daughter plates were loaded with 185 µL per well of the CAMHB described using the Multidrop 384. The daughter plates were completed on the Biomek FX instrument which transferred 5 µL of drug solution from each well of a mother plate to each corresponding well of each daughter plate in a single step.

A standardized inoculum of each organism was prepared per CLSI methods (2). Suspensions were prepared to equal a 0.5 McFarland standard, followed by dilution in test media 1:20. The inocula were dispensed into sterile reservoirs divided by length (Beckman Coulter) and the Biomek 2000 was used to inoculate the plates. Daughter plates were placed on the Biomek 2000 work surface in reverse orientation so that inoculation took place from low to high drug concentration. The Biomek 2000 delivered 10 µL of the diluted suspension into each well resulting in a final concentration of approximately 5×10$^5$ CFU/mL. Plates were stacked 3-4 high, covered with a sterile lid on the top plate, placed in plastic bags, and incubated at 35° C. for approximately 18 hr.

The microplates were viewed from the bottom using a plate viewer and the MIC was read. The MIC was recorded as the lowest concentration of drug that inhibited visible growth of the organism. Uninoculated solubility control plates were also observed for evidence of drug precipitation.

FIC Assay Procedure: FIC test ranges were set based on broth microdilution MIC test data. FIC assay plates were prepared using the CLSI broth microdilution procedure (1, 2) and automated liquid handlers (Multidrop 384, Biomek 2000 and Biomek FX) to conduct serial dilutions and liquid transfers.

The wells of a standard 96-well microdilution plate (Costar) were filled with 150 μL of the appropriate diluent in columns 2 through 12. A 300 μL aliquot at 40× the highest final concentration to be tested was added to each well in Column 1 of the plate. The Biomek 2000 was used to make eleven 2-fold serial dilutions in the "combination agent mother" plate from columns 2 through 11.

The wells of the "test agent mother" plate were filled with 150 μL of diluent in rows B-H. Row A of this plate was filled with 300 μL of the test agent stock solutions at 40× the highest final concentration to be tested. Serial 2-fold dilutions were then prepared from row B-G by hand using a multichannel pipette.

The "daughter plates" were loaded with 180 μL of cation-adjusted Mueller-Hinton broth (CAMHB) using the Multidrop 384. The Biomek FX was used to transfer 5 μL of drug solution from each well of the combination agent mother plate to the corresponding well in all of the daughter plates in a single step. Then a 5 μL aliquot from each well of the test agent mother plate was transferred with the Biomek FX into the corresponding well of the daughter plate. Row H and Column 12 each contained serial dilutions of combination agent and the test agent alone, respectively, for determination of the MIC. This procedure was repeated for test agents and combination agents evaluated.

A standardized inoculum of each organism was prepared per CLSI methods (2). Colonies were picked from the primary plate and a suspension was prepared to equal a 0.5 McFarland turbidity standard. The suspensions were additionally diluted 1:20. A 10 μL standardized inoculum was delivered into each well using the Biomek 2000 from low to high concentration. These inoculations yielded a final cell concentration in the daughter plates of approximately $5 \times 10^5$ CFU/mL in each well.

The test format resulted in the creation of an 8×12 checkerboard where each compound was tested alone (Column 12 and Row H) and in combination at varying ratios of drug concentration (see FIG. 43).

Plates were stacked 3-4 high, covered with a sterile lid on the top plate, placed in plastic bags, and incubated at 35° C. for approximately 18 hr (with the exception of *P. aeruginosa* isolate 8798 which was incubated for 42 hr due to poor growth at 18 hr). Plates were viewed from the bottom using a plate viewer. Prepared reading sheets were marked for the MIC of the combination agent (row H), the MIC of test agent (column 12), and the wells of the growth-no growth interface for wells containing test agent and combination agent at varying ratios. The FIC was read and recorded as the lowest concentration of drug that exhibited no growth of the organism by row where agents were tested in combination (rows B through G). Pinpoint trailing was not interpreted as growth.

FIC/FICI Calculations: FICs were calculated essentially as described by Eliopoulos, et al. (3), as applicable.

For each relevant row of the panel, the FIC index (FICI) was calculated as below:

$$FIC_{drug\ A}/MIC_{drug\ A} + FIC_{drug\ B}/MIC_{drug\ B} = FIC\ index\ (FICI)$$

Mean FICI were determined for the combination.

In the instance where an MIC for one of the test agents was off-scale (greater than the highest test concentration evaluated, e.g. >32 pg/mL), the MIC was set to the next highest 2-fold concentration for determination of the FIC (e.g. if the MIC was >32 μg/mL, the FIC was calculated based on an MIC of 64 μg/mL).

Using the criteria described by Odds (4), the mean FICI for the combination was interpreted as follows: ≤0.5=synergy, >0.5-4=additive/indifferent, and >4=antagonism.

An interpretation of "synergy" is consistent with inhibition of organism growth by combinations at concentrations significantly below (>4-fold) the MIC of either compound alone, resulting in a low FICI value (≤0.50). An interpretation of "indifference" is consistent with growth inhibition at concentrations at or slightly below/above the MIC values of the individual compounds alone, resulting in an FICI value of >0.50 but less than or equal to 4.0. An interpretation of "antagonism" results when the concentrations of the compounds in combination that are required to inhibit organism growth are substantially greater (>4-fold) than those for the compounds individually, resulting in an FICI value of >4.0.

Results and Discussion

Broth microdilution MIC values for the evaluated agents against the test organisms as observed during initial MIC testing are summarized in Table 24. MIC values for BisEDT and the other test agents against *P. aeruginosa* ATCC 27853 were within CLSI QC ranges (1). BisEDT maintained activity across the evaluated isolates despite the high degree of resistance to other agents. Based on the resulting phenotypes, isolates shaded in grey were selected for subsequent evaluation in checkerboard assays with BisEDT in combination with the other test agents.

The MIC values observed during FIC testing are summarized in Table 25. As expected, these results were consistent (typically identical or within 2-fold) with those observed during initial MIC testing (Table 24). The rare instances where MIC values differed 4-fold with those observed during initial MIC testing are shaded in grey. As during initial MIC testing, BisEDT and the other test agents had MIC values within the QC ranges for *P. aeruginosa* ATCC 27853. The median MIC value of BisEDT as observed across 6 checkerboard panels is reported in Table 25 alongside the MIC range. The MIC values observed with BisEDT were consistent across checkerboard panels during FIC testing as expected.

All test data from FIC panels are shown by organism in Tables 28-87. The mean FICI values observed for BisEDT in combination with all evaluated agents across the selected isolates are summarized in Table 26. Instances where individual FICI values on checkerboard panels exhibited synergy/antagonism are also noted.

Excluding colistin and ciprofloxacin, the majority of the interactions observed between BisEDT and other agents by FICI were additive/indifferent with mean FICI values and individual FICI values across checkerboard panels generally between 0.5 to 4. For a subset of isolates, synergy between BisEDT and colistin was observed based on mean FICI values ≤0.50; for the lone colistin-R *P. aeruginosa* (isolate 8798), for both isolates of *B. cepacia*, and for one isolate of *B. cenocepacia* (isolate 0548). For one of the *P. aeruginosa* (isolate 9108), antagonism between BisEDT and ciprofloxacin was observed based on a mean FICI value >4. For BisEDT in combination with ciprofloxacin, there were 3 additional isolates where there was at least one row on the FIC panel that had an FICI value indicative of antagonism. There was also one isolate of *B. cepacia* (isolate 1793) where there was one row with an FICI value indicative of antagonism for BisEDT in combination with meropenem.

In summary, the overall interaction between BisEDT and other agents used to treat CF was additive/indifferent against the CF pathogens *P. aeruginosa* and *B. cepacia* complex with the exception of select instances where synergy was apparent for BisEDT in combination with colistin and select instances where antagonism was apparent for BisEDT in combination with ciprofloxacin. Whether these instances indicate true synergy or antagonism for these combinations requires further investigation by time-kill kinetic analysis.

TABLE 24

Summary of activity as observed during initial MIC testing

| Organism | Isolate ID | Phenotype[1] | MIC (μg/mL) | | | | | | |
|---|---|---|---|---|---|---|---|---|---|
| | | | BisEDT | MEM | TOB | AMK | CIP | AZT | COL |
| *P. aeruginosa* | 103 (ATCC 25922) | — | 1 (0.5-4)[2] | 1 (0.12-1) | 1 (0.25-1) | 2 (1-4) | 0.5 (0.12-1) | 8 (2-8) | 0.5 (0.5-4) |
| | 1497 | TOB-R, AMK-R, CIP-I, AZT-R, COL-R | 0.5 | 0.06 | 16 | 64 | 2 | 32 | 4 |
| | 1530 | TOB-R, AMK-R, CIP-R | 1 | 0.5 | 32 | 64 | 8 | 4 | 0.5 |
| | 1553 | TOB-R, AMK-R, CIP-R | 2 | 0.5 | >256 | 64 | 4 | 8 | 0.5 |
| | 6322 | MEM-R, TOB-R, AMK-R, CIP-R, AZT-R | 2 | 16 | 128 | 64 | 64 | 64 | 0.5 |
| | 6977 | MEM-I, TOB-R, CIP-R, AZT-I | 1 | 4 | 128 | 16 | 128 | 16 | 1 |
| | 7745 | MEM-R, CIP-R, AZT-R | 2 | 16 | 0.5 | 4 | 4 | 32 | 0.5 |
| | 7754 | MEM-R, TOB-R, CIP-R, AZT-I | 1 | 32 | 32 | 8 | 8 | 16 | 0.5 |
| | 7762 | MEM-I, CIP-I | 2 | 4 | 1 | 8 | 2 | 8 | 1 |
| | 7871 | MEM-R, AZT-I | 1 | 8 | 0.5 | 2 | 0.25 | 16 | 0.5 |
| | 7886 | MEM-R, CIP-R, AZT-R | 2 | 32 | 1 | 8 | 8 | 64 | 0.5 |
| | 7874 | — | 1 | 1 | 0.5 | 2 | 0.12 | 4 | 1 |
| | 8797 | MEM-R, TOB-R, AMK-R, CIP-R, AZT-R, COL-R | 0.25 | 32 | >256 | >256 | 8 | >256 | >256 |
| | 8798 | MEM-R, TOB-R, AMK-R, CIP-R, AZT-R, COL-R | 2 | 64 | 32 | 128 | 4 | 256 | >256 |
| | 9108 | CIP-R, AZT-I | 2 | 0.5 | 0.5 | 4 | 32 | 16 | 0.5 |

TABLE 25

Summary of activity as observed during initial MIC testing

| Organism | Isolate ID | Phenotype[1] | MIC (μg/mL) | | | | | | |
|---|---|---|---|---|---|---|---|---|---|
| | | | BisEDT | MEM | TOB | AMK | CIP | AZT | COL |
| *B. cepacia* | 0546 | — | 2 | 4 | 64 | 64 | 2 | 16 | >256 |
| | 0547 | — | 1 | 2 | 128 | 128 | 1 | 16 | >256 |
| | 9040 | — | 1 | 4 | 8 | 8 | 1 | 32 | >256 |
| | 1793 | — | 0.5 | 4 | 64 | 64 | 0.5 | 128 | >256 |
| | 1794 | — | 2 | 4 | 64 | 128 | 1 | 32 | >256 |
| *B. cenocepacia* | 0548 | CIP-R | 8 | 4 | 64 | 256 | 8 | 64 | >256 |
| | 0813 | CPI-I | 2 | 2 | 256 | >256 | 4 | 8 | >256 |
| | 1631 | — | 2 | 4 | 128 | 256 | 2 | 32 | >256 |
| | 1783 | — | 2 | 4 | 128 | 256 | 2 | 32 | >256 |
| | 8555 | — | 2 | 4 | 128 | 256 | 2 | 256 | >256 |
| *B. multivorans* | 1580 | CIP-R | 2 | 2 | 128 | 128 | 8 | 64 | >256 |
| | 1791 | — | 1 | 4 | 64 | 128 | 1 | 4 | >256 |
| | 1795 | MEM-I, CIP-R | 2 | 8 | >256 | >256 | 32 | 4 | >256 |
| | 5665 | CIP-I | 1 | 2 | 64 | 256 | 4 | 4 | >256 |
| | 8952 | CIP-I | 4 | 2 | 16 | 64 | 4 | 8 | >256 |

MEM = meropenem,

TOB = tobramycin,

AMK = amikacin,

CIP = ciprofloxacin,

AZT = aztreonam,

COL = colistin,

-R = resistant,

-I = intermediate

[1] Phenotype is based off of MIC interpretation in accordance with CLSI breakpoints (1) or in the case of colistin and *P. aeruginosa* EUCAST breakpoints (v.8.1)

Note that *B. cepacia* complex are intrinsically resistant to aminoglycosides, aztreonam, and colistin (1)

[2] CLSI QC range shown in parenthesis where applicable

Cells shaded grey were selected for FIC testing

TABLE 26

Summary of activity as observed during FIC testing

| Organism | Isolate ID | Phenotype[1] | BisEDT[3] | MEM | TOB | AMK | CIP | AZT | COL |
|---|---|---|---|---|---|---|---|---|---|
| *P. aeruginosa* | 103 (ATCC 25922)[2] | — | 1 (0.5-4) | 1 (0.12-1) | 1 (0.25-1) | 4 (1-4) | 1 (0.12-1) | 8 (2-8) | 0.5 (0.5-4) |
| | 6322 | MEM-R, TOB-R, AMK-R, CIP-R, AZT-R | 1-2 (2) | 16 | 128 | 64 | 128 | 32 | 0.5 |
| | 6977 | MEM-I, TOB-R, CIP-R, AZT-I | 1 (1) | 8 | 128 | 16 | 128 | 64 | 1 |
| | 7745 | MEM-R, CIP-R, AZT-R | 1-2 (2) | 16 | 0.5 | 4 | 2 | 16 | 0.5 |
| | 8798 | MEM-R, TOB-R, AMK-R, CIP-R, AZT-R, COL-R | 2 (2) | 32 | 16 | 128 | 8 | >256 | >256 |
| | 9108 | CIP-R, AZT-I | 2-4 (2) | 1 | 0.5 | 4 | 16 | 16 | 0.5 |
| *B. cepacia* | 0546 | — | 2-4 (2, 4) | 4 | 32 | 64 | 2 | 32 | >256 |
| | 1793 | — | 1-2 (1) | 4 | 16 | 32 | 0.5 | 128 | >256 |
| *B. cenocepacia* | 0548 | CIP-R | 4 (4) | 4 | 32 | 128 | 2 | 64 | >256 |
| | 0813 | CIP-I | 2-4 (2, 4) | 2 | 256 | >256 | 2 | 32 | >256 |
| *B. multivorans* | 1795 | MEM-I, CIP-R | 2 (2) | 4 | >256 | >256 | 32 | 16 | >256 |

MEM = meropenem,
TOB = tobramycin,
AMK = amikacin,
CIP = ciprofloxacin,
AZT = aztreonam,
COL = colistin,
-R = resistant,
-I = intermediate

[1]Phenotype determined based on initial MIC testing as shown in Table 1

Note that *B. cepacia* complex are intrinsically resistant to aminoglycosides, aztreonam, and colistin (1)

[2]CLSI QC range shown in parenthesis for ATCC 25922; ATCC 25922 was not tested on checkerboard panels with agents in combination, each agent was tested alone solely for the purpose of QC

[3]With the exception of ATCC 25922 where only one replicate was tested for the purpose of quality control (QC range shown in parenthesis), the MIC result for BisEDT represents the MIC range and mode as observed across six different FIC panels.

TABLE 27

Summary of mean FICI data for BisEDT in combination with evaluated agents

| Isolate ID | Phenotype[1] | Mean FICI | | | | | |
|---|---|---|---|---|---|---|---|
| | | MEM | TOB | AMK | CIP | AZT | COL |
| 6322 | MEM-R, TOB-R, AMK-R, CIP-R, AZT-R | 1.19 | 1.19 | 2.23 | 1.19 | 1.19 | 1.23 |
| 6977 | MEM-I, TOB-R, CIP-R, AZT-1 | 1.73 | 2.23 | 2.23 | 2.23 | 1.23 | 1.23 |
| 7745 | MEM-R, CIP-R, AZT-R | 0.64 | 1.19 | 1.23 | 2.59* | 0.99 | 1.19 |
| 8798 | MEM-R, TOB-R, AMK-R, CIP-R, AZT-R, COL-R | 1.19 | 0.91 | 1.09 | 0.99 | 0.89 | 0.22 |
| 9108 | CIP-R, AZT-I | 1.19 | 1.19 | 1.29 | 4.50 | 0.79 | 1.08 |
| 0546 | — | 1.99 | 0.69 | 0.64 | 1.35 | 1.16 | 0.25 |
| 1793 | — | 2.59* | 1.11 | 1.29 | 1.98 | 1.23 | 0.33 |
| 0548 | CIP-R | 1.11 | 0.67 | 0.67 | 3.23* | 1.23 | 0.41 |
| 0813 | CIP-I | 1.08 | 0.91 | 0.99 | 2.85* | 1.19 | 0.72 |
| 1795 | MEM-I, CIP-R | 1.33 | 1.33 | 1.33 | 1.19 | 1.39 | 1.33 |

MEM = meropenem,
TOB = tobramycin,
AMK = amikacin,
CIP = ciprofloxacin,
AZT = aztreonam,
COL = colistin,
-R = resistant,
-I = intermediate

[1]Phenotype determined based on initial MIC testing as shown in Table 1

** indicates that at least one row on the test panel had an individual FICI value ≤ 0.5 (indicative of synergy)

*indicates that at least one row on the test panel had an individual FICI value > 4 (indicative of antagonism)

TABLE 28

MIC (μg/mL), FIC, FICI, for BisEDT in combination with Meropenem

| Organism: | P. aeruginosa | 6322 | | FICI (N): | 5 |
| Drug A: | BisEDT | Drug A MIC: | 2 | SUM FICI: | 5.97 |
| Drug B: | Meropenem | Drug B MIC: | 16 | MEAN FICI: | 1.19 |

| Row | $MIC_A$ | $FIC_A$ | $MIC_B$ | $FIC_B$ | FICI |
| --- | --- | --- | --- | --- | --- |
| A | | | | | |
| B | | | | | |
| C | 1 | 0.5 | 16 | 1 | 1.5 |
| D | 0.5 | 0.25 | 16 | 1 | 1.25 |
| E | 0.25 | 0.125 | 16 | 1 | 1.125 |
| F | 0.12 | 0.06 | 16 | 1 | 1.06 |
| G | 0.06 | 0.03 | 16 | 1 | 1.03 |
| H | | | | | |

TABLE 29

MIC (μg/mL), FIC, FICI, for BisEDT in combination with Tobramycin

| Organism: | P. aeruginosa | 6322 | | FICI (N): | 5 |
| Drug A: | BisEDT | Drug A MIC: | 2 | SUM FICI: | 5.97 |
| Drug B: | Tobramycin | Drug B MIC: | 128 | MEAN FICI: | 1.19 |

| Row | $MIC_A$ | $FIC_A$ | $MIC_B$ | $FIC_B$ | FICI |
| --- | --- | --- | --- | --- | --- |
| A | | | | | |
| B | | | | | |
| C | 1 | 0.5 | 128 | 1 | 1.5 |
| D | 0.5 | 0.25 | 128 | 1 | 1.25 |
| E | 0.25 | 0.125 | 128 | 1 | 1.125 |
| F | 0.12 | 0.06 | 128 | 1 | 1.06 |
| G | 0.06 | 0.03 | 128 | 1 | 1.03 |
| H | | | | | |

TABLE 30

MIC (μg/mL), FIC, FICI, for BisEDT in combination with Amikacin

| Organism: | P. aeruginosa | 6322 | | FICI (N): | 4 |
| Drug A: | BisEDT | Drug A MIC: | 1 | SUM FICI: | 8.93 |
| Drug B: | Amikacin | Drug B MIC: | 64 | MEAN FICI: | 2.23 |

| Row | $MIC_A$ | $FIC_A$ | $MIC_B$ | $FIC_B$ | FICI |
| --- | --- | --- | --- | --- | --- |
| A | | | | | |
| B | | | | | |
| C | | | | | |
| D | 0.5 | 0.5 | 128 | 2 | 2.5 |
| E | 0.25 | 0.25 | 128 | 2 | 2.25 |
| F | 0.12 | 0.12 | 128 | 2 | 2.12 |
| G | 0.06 | 0.06 | 128 | 2 | 2.06 |
| H | | | | | |

TABLE 31

MIC (μg/mL), FIC, FICI, for BisEDT in combination with Ciprofloxacin

| Organism: | P. aeruginosa | 6322 | | FICI (N): | 5 |
| Drug A: | BisEDT | Drug A MIC: | 2 | SUM FICI: | 5.97 |
| Drug B: | Ciprofloxacin | Drug B MIC: | 128 | MEAN FICI: | 1.19 |

| Row | $MIC_A$ | $FIC_A$ | $MIC_B$ | $FIC_B$ | FICI |
| --- | --- | --- | --- | --- | --- |
| A | | | | | |
| B | | | | | |
| C | 1 | 0.5 | 128 | 1 | 1.5 |
| D | 0.5 | 0.25 | 128 | 1 | 1.25 |
| E | 0.25 | 0.125 | 128 | 1 | 1.125 |
| F | 0.12 | 0.06 | 128 | 1 | 1.06 |
| G | 0.06 | 0.03 | 128 | 1 | 1.03 |
| H | | | | | |

TABLE 32

MIC (µg/mL), FIC, FICI, for BisEDT
in combination with Aztreonam

| Organism: | *P. aeruginosa* | 6322 | | FICI (N): | 5 |
| Drug A: | BisEDT | Drug A MIC: | 2 | SUM FICI: | 5.97 |
| Drug B: | Aztreonam | Drug B MIC: | 32 | MEAN FICI: | 1.19 |

| Row | MIC$_A$ | FIC$_A$ | MIC$_B$ | FIC$_B$ | FICI |
|---|---|---|---|---|---|
| A | | | | | |
| B | | | | | |
| C | 1 | 0.5 | 16 | 0.5 | 1 |
| D | 0.5 | 0.25 | 16 | 0.5 | 0.75 |
| E | 0.25 | 0.125 | 32 | 1 | 1.125 |
| F | 0.12 | 0.06 | 32 | 1 | 1.06 |
| G | 0.06 | 0.03 | 64 | 2 | 2.03 |
| H | | | | | |

TABLE 33

MIC (µg/mL), FIC, FICI, for BisEDT in combination with Colistin

| Organism: | *P. aeruginosa* | 6322 | | FICI (N): | 4 |
| Drug A: | BisEDT | Drug A MIC: | 1 | SUM FICI: | 4.93 |
| Drug B: | Colistin | Drug B MIC: | 0.5 | MEAN FICI: | 1.23 |

| Row | MIC$_A$ | FIC$_A$ | MIC$_B$ | FIC$_B$ | FICI |
|---|---|---|---|---|---|
| A | | | | | |
| B | | | | | |
| C | | | | | |
| D | 0.5 | 0.5 | 0.5 | 1 | 1.5 |
| E | 0.25 | 0.25 | 0.5 | 1 | 1.25 |
| F | 0.12 | 0.12 | 0.5 | 1 | 1.12 |
| G | 0.06 | 0.06 | 0.5 | 1 | 1.06 |
| H | | | | | |

TABLE 34

MIC (µg/mL), FIC, FICI, for BisEDT
in combination with Meropenem

| Organism: | *P. aeruginosa* | 6977 | | FICI (N): | 4 |
| Drug A: | BisEDT | Drug A MIC: | 1 | SUM FICI: | 6.93 |
| Drug B: | Meropenem | Drug B MIC: | 8 | MEAN FICI: | 1.73 |

| Row | MIC$_A$ | FIC$_A$ | MIC$_B$ | FIC$_B$ | FICI |
|---|---|---|---|---|---|
| A | | | | | |
| B | | | | | |
| C | | | | | |
| D | 0.5 | 0.5 | 16 | 2 | 2.5 |
| E | 0.25 | 0.25 | 16 | 2 | 2.25 |
| F | 0.12 | 0.12 | 8 | 1 | 1.12 |
| G | 0.06 | 0.06 | 8 | 1 | 1.06 |
| H | | | | | |

TABLE 35

MIC (µg/mL), FIC, FICI, for BisEDT in combination with Tobramycin

| Organism: | *P. aeruginosa* | 6977 | | FICI (N): | 4 |
| Drug A: | BisEDT | Drug A MIC: | 1 | SUM FICI: | 8.93 |
| Drug B: | Tobramycin | Drug B MIC: | 128 | MEAN FICI: | 2.23 |

| Row | MIC$_A$ | FIC$_A$ | MIC$_B$ | FIC$_B$ | FICI |
|---|---|---|---|---|---|
| A | | | | | |
| B | | | | | |
| C | | | | | |
| D | 0.5 | 0.5 | 256 | 2 | 2.5 |
| E | 0.25 | 0.25 | 256 | 2 | 2.25 |
| F | 0.12 | 0.12 | 256 | 2 | 2.12 |
| G | 0.06 | 0.06 | 256 | 2 | 2.06 |
| H | | | | | |

TABLE 36

MIC (µg/mL), FIC, FICI, for
BisEDT in combination with Amikacin

| Organism: | *P. aeruginosa* | 6977 | | FICI (N): | 4 |
| Drug A: | BisEDT | Drug A MIC: | 1 | SUM FICI: | 8.93 |
| Drug B: | Amikacin | Drug B MIC: | 16 | MEAN FICI: | 2.23 |

| Row | MIC$_A$ | FIC$_A$ | MIC$_B$ | FIC$_B$ | FICI |
|---|---|---|---|---|---|
| A | | | | | |
| B | | | | | |
| C | | | | | |
| D | 0.5 | 0.5 | 32 | 2 | 2.5 |
| E | 0.25 | 0.25 | 32 | 2 | 2.25 |
| F | 0.12 | 0.12 | 32 | 2 | 2.12 |
| G | 0.06 | 0.06 | 32 | 2 | 2.06 |
| H | | | | | |

TABLE 37

MIC (µg/mL), FIC, FICI, for BisEDT in combination with Ciprofloxacin

| Organism: | P. aeruginosa | 6977 | FICI (N): | 4 |
|---|---|---|---|---|
| Drug A: | BisEDT | Drug A MIC: | 1 | SUM FICI: | 8.93 |
| Drug B: | Ciprofloxacin | Drug B MIC: | 128 | MEAN FICI: | 2.23 |

| Row | $MIC_A$ | $FIC_A$ | $MIC_B$ | $FIC_B$ | FICI |
|---|---|---|---|---|---|
| A | | | | | |
| B | | | | | |
| C | | | | | |
| D | 0.5 | 0.5 | 256 | 2 | 2.5 |
| E | 0.25 | 0.25 | 256 | 2 | 2.25 |
| F | 0.12 | 0.12 | 256 | 2 | 2.12 |
| G | 0.06 | 0.06 | 256 | 2 | 2.06 |
| H | | | | | |

TABLE 38

MIC (µg/mL), FIC, FICI, for BisEDT in combination with Aztreonam

| Organism: | P. aeruginosa | 6977 | FICI (N): | 4 |
|---|---|---|---|---|
| Drug A: | BisEDT | Drug A MIC: | 1 | SUM FICI: | 4.93 |
| Drug B: | Aztreonam | Drug B MIC: | 64 | MEAN FICI: | 1.23 |

| Row | $MIC_A$ | $FIC_A$ | $MIC_B$ | $FIC_B$ | FICI |
|---|---|---|---|---|---|
| A | | | | | |
| B | | | | | |
| C | | | | | |
| D | 0.5 | 0.5 | 64 | 1 | 1.5 |
| E | 0.25 | 0.25 | 64 | 1 | 1.25 |
| F | 0.12 | 0.12 | 64 | 1 | 1.12 |
| G | 0.06 | 0.06 | 64 | 1 | 1.06 |
| H | | | | | |

TABLE 39

MIC (µg/mL), FTC, FICI, for BisEDT in combination with Colistin

| Organism: | P. aeruginosa | 6977 | FICI (N): | 4 |
|---|---|---|---|---|
| Drug A: | BisEDT | Drug A MIC: | 1 | SUM FICI: | 4.93 |
| Drug B: | Colistin | Drug B MIC: | 1 | MEAN FICI: | 1.23 |

| Row | $MIC_A$ | $FIC_A$ | $MIC_B$ | $FIC_B$ | FICI |
|---|---|---|---|---|---|
| A | | | | | |
| B | | | | | |
| C | | | | | |
| D | 0.5 | 0.5 | 1 | 1 | 1.5 |
| E | 0.25 | 0.25 | 1 | 1 | 1.25 |
| F | 0.12 | 0.12 | 1 | 1 | 1.12 |
| G | 0.06 | 0.06 | 1 | 1 | 1.06 |
| H | | | | | |

TABLE 40

MIC (µg/mL), FIC, FICI, for BisEDT in combination with Meropenem

| Organism: | P. aeruginosa | 7745 | FICI (N): | 5 |
|---|---|---|---|---|
| Drug A: | BisEDT | Drug A MIC: | 2 | SUM FICI: | 3.22 |
| Drug B: | Meropenem | Drug B MIC: | 16 | MEAN FICI: | 0.64 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 4 | 0.25 | 0.75 |
| D | 0.5 | 0.25 | 8 | 0.5 | 0.75 |
| E | 0.25 | 0.125 | 8 | 0.5 | 0.625 |

TABLE 40-continued

MIC (µg/mL), FIC, FICI, for BisEDT in combination with Meropenem

| F | 0.12 | 0.06 | 8 | 0.5 | 0.56 |
|---|---|---|---|---|---|
| G | 0.06 | 0.03 | 8 | 0.5 | 0.53 |
| H | | | | | |

TABLE 41

MIC (µg/mL), FIC, FICI, for BisEDT in combination with Tobramycin

| Organism: | P. aeruginosa | 7745 | FICI (N): | 5 |
|---|---|---|---|---|
| Drug A: | BisEDT | Drug A MIC: | 2 | SUM FICI: | 5.97 |
| Drug B: | Tobramycin | Drug B MIC: | 0.5 | MEAN FICI: | 1.19 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 0.5 | 1 | 1.5 |
| D | 0.5 | 0.25 | 0.5 | 1 | 1.25 |
| E | 0.25 | 0.125 | 0.5 | 1 | 1.125 |
| F | 0.12 | 0.06 | 0.5 | 1 | 1.06 |
| G | 0.06 | 0.03 | 0.5 | 1 | 1.03 |
| H | | | | | |

TABLE 42

MIC (µg/mL), FIC, FICI, for BisEDT in combination with Amikacin

| Organism: | P. aeruginosa | 7745 | FICI (N): | 4 |
|---|---|---|---|---|
| Drug A: | BisEDT | Drug A MIC: | 1 | SUM FICI: | 4.93 |
| Drug B: | Amikacin | Drug B MIC: | 4 | MEAN FICI: | 1.23 |

| Row | $MIC_A$ | $FIC_A$ | $MIC_B$ | $FIC_B$ | FICI |
|---|---|---|---|---|---|
| A | | | | | |
| B | | | | | |
| C | | | | | |
| D | 0.5 | 0.5 | 4 | 1 | 1.5 |
| E | 0.25 | 0.25 | 4 | 1 | 1.25 |
| F | 0.12 | 0.12 | 4 | 1 | 1.12 |
| G | 0.06 | 0.06 | 4 | 1 | 1.06 |
| H | | | | | |

TABLE 43

MIC (μg/mL), FIC, FICI, for BisEDT in combination with Ciprofloxacin

| Organism: | P. aeruginosa | 7745 | | FICI (N): | 5 |
|---|---|---|---|---|---|
| Drug A: | BisEDT | Drug A MIC: | 2 | SUM FICI: | 12.97 |
| Drug B: | Ciprofloxacin | Drug B MIC: | 2 | MEAN FICI: | 2.59 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 4 | 2 | 2.5 |
| D | 0.5 | 0.25 | 8 | 4 | 4.25 |
| E | 0.25 | 0.125 | 4 | 2 | 2.125 |
| F | 0.12 | 0.06 | 4 | 2 | 2.06 |
| G | 0.06 | 0.03 | 4 | 2 | 2.03 |
| H | | | | | |

TABLE 44

MIC (μg/mL), FIC, FICI, for BisEDT in combination with Aztreonam

| Organism: | P. aeruginosa | 7745 | | FICI (N): | 5 |
|---|---|---|---|---|---|
| Drug A: | BisEDT | Drug A MIC: | 2 | SUM FICI: | 4.97 |
| Drug B: | Aztreonam | Drug B MIC: | 16 | MEAN FICI: | 0.99 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 8 | 0.5 | 1 |
| D | 0.5 | 0.25 | 8 | 0.5 | 0.75 |
| E | 0.25 | 0.125 | 16 | 1 | 1.125 |
| F | 0.12 | 0.06 | 16 | 1 | 1.06 |
| G | 0.06 | 0.03 | 16 | 1 | 1.03 |
| H | | | | | |

TABLE 45

MIC (μg/mL), FICI, for BisEDT in combination with Colistin

| Organism: | P. aeruginosa | 7745 | | FICI (N): | 5 |
|---|---|---|---|---|---|
| Drug A: | BisEDT | Drug A MIC: | 2 | SUM FICI: | 5.97 |
| Drug B: | Colistin | Drug B MIC: | 0.5 | MEAN FICI: | 1.19 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 0.5 | 1 | 1.5 |
| D | 0.5 | 0.25 | 0.5 | 1 | 1.25 |
| E | 0.25 | 0.125 | 0.5 | 1 | 1.125 |
| F | 0.12 | 0.06 | 0.5 | 1 | 1.06 |
| G | 0.06 | 0.03 | 0.5 | 1 | 1.03 |
| H | | | | | |

TABLE 46

MIC (μg/mL), FIC, FICI, for BisEDT in combination with Meropenem

| Organism: | P. aeruginosa | 8798 | | FICI (N): | 5 |
|---|---|---|---|---|---|
| Drug A: | BisEDT | Drug A MIC: | 2 | SUM FICI: | 5.97 |
| Drug B: | Meropenem | Drug B MIC: | 32 | MEAN FICI: | 1.19 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 32 | 1 | 1.5 |
| D | 0.5 | 0.25 | 32 | 1 | 1.25 |
| E | 0.25 | 0.125 | 32 | 1 | 1.125 |
| F | 0.12 | 0.06 | 32 | 1 | 1.06 |
| G | 0.06 | 0.03 | 32 | 1 | 1.03 |
| H | | | | | |

TABLE 47

MIC (μg/L), FIC, FICI, for BisEDT in combination with Tobramycin

| Organism: | P. aeruginosa | 8798 | | FICI (N): | 6 |
|---|---|---|---|---|---|
| Drug A: | BisEDT | Drug A MIC: | 2 | SUM FICI: | 5.47 |
| Drug B: | Tobramycin | Drug B MIC: | 16 | MEAN FICI: | 0.91 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 8 | 0.5 | 1 |
| D | 0.5 | 0.25 | 16 | 1 | 1.25 |
| E | 0.25 | 0.125 | 16 | 1 | 1.125 |
| F | 0.12 | 0.06 | 16 | 1 | 1.06 |
| G | 0.06 | 0.03 | 16 | 1 | 1.03 |
| H | | | | | |

TABLE 48

MIC (μg/mL), FIC, FICI, for BisEDT in combination with Amikacin

| Organism: | P. aeruginosa | 8798 | | FICI (N): | 5 |
|---|---|---|---|---|---|
| Drug A: | BisEDT | Drug A MIC: | 2 | SUM FICI: | 5.47 |
| Drug B: | Amikacin | Drug B MIC: | 128 | MEAN FICI: | 1.09 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 64 | 0.5 | 1 |
| D | 0.5 | 0.25 | 128 | 1 | 1.25 |
| E | 0.25 | 0.125 | 128 | 1 | 1.125 |
| F | 0.12 | 0.06 | 128 | 1 | 1.06 |
| G | 0.06 | 0.03 | 128 | 1 | 1.03 |
| H | | | | | |

TABLE 49

MIC (μg/mL), FIC, FICI, for BisEDT in combination with Ciprofloxacin

| Organism: | P. aeruginosa | 8798 | | FICI (N): | 5 |
|---|---|---|---|---|---|
| Drug A: | BisEDT | Drug A MIC: | 2 | SUM FICI: | 4.97 |
| Drug B: | Ciprofloxacin | Drug B MIC: | 8 | MEAN FICI: | 0.99 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 4 | 0.5 | 1 |
| D | 0.5 | 0.25 | 4 | 0.5 | 0.75 |
| E | 0.25 | 0.125 | 8 | 1 | 1.125 |
| F | 0.12 | 0.06 | 8 | 1 | 1.06 |
| G | 0.06 | 0.03 | 8 | 1 | 1.03 |
| H | | | | | |

TABLE 50

MIC (µg/mL), FIC, FICI, for BisEDT in combination with Aztreonam

| Organism: | *P. aeruginosa* | 8798 | | FICI (N): | 5 |
|---|---|---|---|---|---|
| Drug A: | BisEDT | Drug A MIC: | 2 | SUM FICI: | 4.47 |
| Drug B: | Aztreonam | Drug B MIC: | >256 | MEAN FICI: | 0.89 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 256 | 0.5 | 1 |
| D | 0.5 | 0.25 | 256 | 0.5 | 0.75 |
| E | 0.25 | 0.125 | 256 | 0.5 | 1.625 |
| F | 0.12 | 0.06 | >256 | 1 | 1.06 |
| G | 0.06 | 0.03 | >256 | 1 | 1.03 |
| H | | | | | |

TABLE 51

MIC (µg/mL), FIC, FICI, for BisEDT in combination with Colistin

| Organism: | *P. aeruginosa* | 8798 | | FICI (N): | 5 |
|---|---|---|---|---|---|
| Drug A: | BisEDT | Drug A MIC: | 2 | SUM FICI: | 1.12 |
| Drug B: | Colistin | Drug B MIC: | >256 | MEAN FICI: | 0.22 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 8 | 0.016 | 0.516 |
| D | 0.5 | 0.25 | 8 | 0.016 | 0.266 |
| E | 0.25 | 0.125 | 16 | 0.031 | 0.156 |
| F | 0.12 | 0.06 | 16 | 0.031 | 0.091 |
| G | 0.06 | 0.03 | 32 | 0.063 | 0.093 |
| H | | | | | |

TABLE 52

MIC (µg/mL), FIC, FICI, for BisEDT in combination with Meropenem

| Organism: | *P. aeruginosa* | 9108 | | FICI (N): | 5 |
|---|---|---|---|---|---|
| Drug A: | BisEDT | Drug A MIC: | 1 | SUM FICI: | 5.97 |
| Drug B: | Meropenem | Drug B MIC: | 1 | MEAN FICI: | 1.19 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 1 | 1 | 1.5 |
| D | 0.5 | 0.25 | 1 | 1 | 1.25 |
| E | 0.25 | 0.125 | 1 | 1 | 1.125 |
| F | 0.12 | 0.06 | 1 | 1 | 1.06 |
| G | 0.06 | 0.03 | 1 | 1 | 1.03 |
| H | | | | | |

TABLE 53

MIC (µg/mL), FIC, FICI, for BisEDT in combination with Tobramycin

| Organism: | *P. aeruginosa* | 9108 | | FICI (N): | 5 |
|---|---|---|---|---|---|
| Drug A: | BisEDT | Drug A MIC: | 2 | SUM FICI: | 5.97 |
| Drug B: | Tobramycin | Drug B MIC: | 0.5 | MEAN FICI: | 1.19 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 0.5 | 1 | 1.5 |
| D | 0.5 | 0.25 | 0.5 | 1 | 1.25 |
| E | 0.25 | 0.125 | 0.5 | 1 | 1.125 |
| F | 0.12 | 0.06 | 0.5 | 1 | 1.06 |
| G | 0.06 | 0.03 | 0.5 | 1 | 1.03 |
| H | | | | | |

TABLE 54

MIC (µg/mL), FIC, FICI, for BisEDT in combination with Amikacin

| Organism: | *P. aeruginosa* | 9108 | | FICI (N): | 5 |
|---|---|---|---|---|---|
| Drug A: | BisEDT | Drug A MIC: | 2 | SUM FICI: | 4.47 |
| Drug B: | Amikacin | Drug B MIC: | 4 | MEAN FICI: | 1.29 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 2 | 0.5 | 1 |
| D | 0.5 | 0.25 | 8 | 2 | 2.25 |
| E | 0.25 | 0.125 | 4 | 1 | 1.125 |
| F | 0.12 | 0.06 | 4 | 1 | 1.06 |
| G | 0.06 | 0.03 | 4 | 1 | 1.03 |
| H | | | | | |

TABLE 55

MIC (µg/mL), FIC, FICI, for BisEDT in combination with Ciprofloxacin

| Organism: | *P. aeruginosa* | 9108 | | FICI (N): | 6 |
|---|---|---|---|---|---|
| Drug A: | BisEDT | Drug A MIC: | 4 | SUM FICI: | 27.00 |
| Drug B: | Ciprofloxacin | Drug B MIC: | 16 | MEAN FICI: | 4.50 |

| Row | $MIC_A$ | $FIC_A$ | $MIC_B$ | $FIC_B$ | FICI |
|---|---|---|---|---|---|
| A | | | | | |
| B | 2 | 0.5 | 0.25 | 0.01563 | 0.51563 |
| C | 1 | 0.25 | 128 | 8 | 8.25 |
| D | 0.5 | 0.125 | 128 | 8 | 8.125 |
| E | 0.25 | 0.063 | 64 | 4 | 4.063 |
| F | 0.12 | 0.03 | 64 | 4 | 4.03 |
| G | 0.06 | 0.015 | 32 | 2 | 2.015 |
| H | | | | | |

TABLE 56

MIC (µg/mL), FIC, FICI, for BisEDT in combination with Aztreonam

| Organism: | *P. aeruginosa* | 9108 | | FICI (N): | 5 |
|---|---|---|---|---|---|
| Drug A: | BisEDT | Drug A MIC: | 2 | SUM FICI: | 3.97 |
| Drug B: | Aztreonam | Drug B MIC: | 16 | MEAN FICI: | 0.79 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 8 | 0.5 | 1 |
| D | 0.5 | 0.25 | 8 | 0.5 | 0.75 |
| E | 0.25 | 0.125 | 8 | 0.5 | 0.625 |
| F | 0.12 | 0.06 | 8 | 0.5 | 0.56 |
| G | 0.06 | 0.03 | 16 | 1 | 1.03 |
| H | | | | | |

TABLE 57

MIC (μg/mL), FIC, FICI, for BisEDT in combination with Colistin

| Organism: | P. aeruginosa 9108 | | FICI (N): | 6 |
|---|---|---|---|---|
| Drug A: | BisEDT | Drug A MIC: 4 | SUM FICI: | 6.48 |
| Drug B: | Colistin | Drug B MIC: 0.5 | MEAN FICI: | 1.08 |

| Row | $MIC_A$ | $FIC_A$ | $MIC_B$ | $FIC_B$ | FICI |
|---|---|---|---|---|---|
| A | | | | | |
| B | 2 | 0.5 | 0.25 | 0.5 | 1 |
| C | 1 | 0.25 | 0.5 | 1 | 1.25 |
| D | 0.5 | 0.125 | 0.5 | 1 | 1.125 |
| E | 0.25 | 0.0625 | 0.5 | 1 | 1.0625 |
| F | 0.12 | 0.03 | 0.5 | 1 | 1.03 |
| G | 0.06 | 0.015 | 0.5 | 1 | 1.015 |
| H | | | | | |

TABLE 58

MIC (μg/mL), FIC, FICI, for BisEDT in combination with Meropenem

| Organism: | B. cepacia 546 | | FICI (N): | 5 |
|---|---|---|---|---|
| Drug A: | BisEDT | Drug A MIC: 2 | SUM FICI: | 9.97 |
| Drug B: | Meropenem | Drug B MIC: 4 | MEAN FICI: | 1.99 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 4 | 1 | 1.5 |
| D | 0.5 | 0.25 | 8 | 2 | 2.25 |
| E | 0.25 | 0.125 | 8 | 2 | 2.125 |
| F | 0.12 | 0.06 | 8 | 2 | 2.06 |
| G | 0.06 | 0.03 | 8 | 2 | 2.03 |
| H | | | | | |

TABLE 59

MIC (μg/mL), FIC, FICI, for BisEDT in combination with Tobramycin

| Organism: | B. cepacia 546 | | FICI (N): | 5 |
|---|---|---|---|---|
| Drug A: | BisEDT | Drug A MIC: 2 | SUM FICI: | 3.47 |
| Drug B: | Tobramycin | Drug B MIC: 32 | MEAN FICI: | 0.69 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 16 | 0.5 | 1 |
| D | 0.5 | 0.25 | 16 | 0.5 | 0.75 |
| E | 0.25 | 0.125 | 16 | 0.5 | 0.625 |
| F | 0.12 | 0.06 | 16 | 0.5 | 0.56 |
| G | 0.06 | 0.03 | 16 | 0.5 | 0.53 |
| H | | | | | |

TABLE 60

MIC (μg/mL), FIC, FICI, for BisEDT in combination with Amikacin

| Organism: | B. cepacia 546 | | FICI (N): | 5 |
|---|---|---|---|---|
| Drug A: | BisEDT | Drug A MIC: 2 | SUM FICI: | 3.22 |
| Drug B: | Amikacin | Drug B MIC: 64 | MEAN FICI: | 0.64 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 16 | 0.25 | 0.75 |
| D | 0.5 | 0.25 | 32 | 0.5 | 0.75 |
| E | 0.25 | 0.125 | 32 | 0.5 | 0.625 |
| F | 0.12 | 0.06 | 32 | 0.5 | 0.56 |
| G | 0.06 | 0.03 | 32 | 0.5 | 0.53 |
| H | | | | | |

TABLE 61

MIC (μg/mL), FIC, FICI, for BisEDT in combination with Ciprofloxacin

| Organism: | B. cepacia 546 | | FICI (N): | 6 |
|---|---|---|---|---|
| Drug A: | BisEDT | Drug A MIC: 4 | SUM FICI: | 8.11 |
| Drug B: | Ciprofloxacin | Drug B MIC: 2 | MEAN FICI: | 1.35 |

| Row | $MIC_A$ | $FIC_A$ | $MIC_B$ | $FIC_B$ | FICI |
|---|---|---|---|---|---|
| A | | | | | |
| B | 2 | 0.5 | 0.25 | 0.125 | 0.625 |
| C | 1 | 0.25 | 4 | 2 | 2.25 |
| D | 0.5 | 0.125 | 4 | 2 | 2.125 |
| E | 0.25 | 0.063 | 2 | 1 | 1.063 |
| F | 0.12 | 0.03 | 2 | 1 | 1.03 |
| G | 0.06 | 0.015 | 2 | 1 | 1.015 |
| H | | | | | |

TABLE 62

MIC (μg/mL), FIC, FICI, for BisEDT in combination with Aztreonam

| Organism: | B. cepacia 546 | | FICI (N): | 6 |
|---|---|---|---|---|
| Drug A: | BisEDT | Drug A MIC: 4 | SUM FICI: | 6.98 |
| Drug B: | Aztreonam | Drug B MIC: 32 | MEAN FICI: | 1.16 |

| Row | $MIC_A$ | $FIC_A$ | $MIC_B$ | $FIC_B$ | FICI |
|---|---|---|---|---|---|
| A | | | | | |
| B | 2 | 0.5 | 32 | 1 | 1.5 |
| C | 1 | 0.25 | 32 | 1 | 1.25 |
| D | 0.5 | 0.125 | 32 | 1 | 1.125 |
| E | 0.25 | 0.063 | 32 | 1 | 1.063 |
| F | 0.12 | 0.03 | 32 | 1 | 1.03 |
| G | 0.06 | 0.015 | 32 | 1 | 1.015 |
| H | | | | | |

TABLE 63

MIC (μg/mL), FIC, FICI, for BisEDT in combination with Colistin

| Organism: | B. cepacia 546 | | FICI (N): | 6 |
|---|---|---|---|---|
| Drug A: | BisEDT | Drug A MIC: 4 | SUM FICI: | 1.44 |
| Drug B: | Colistin | Drug B MIC: >256 | MEAN FICI: | 0.24 |

| Row | $MIC_A$ | $FIC_A$ | $MIC_B$ | $FIC_B$ | FICI |
|---|---|---|---|---|---|
| A | | | | | |
| B | 2 | 0.5 | 0.25 | 0.0005 | 0.500 |
| C | 1 | 0.25 | 8 | 0.016 | 0.266 |
| D | 0.5 | 0.125 | 32 | 0.063 | 0.188 |
| E | 0.25 | 0.063 | 64 | 0.125 | 0.188 |
| F | 0.12 | 0.03 | 64 | 0.125 | 0.155 |
| G | 0.06 | 0.015 | 64 | 0.125 | 0.14 |
| H | | | | | |

TABLE 64

MIC (µg/mL), FIC, FICI, for BisEDT in combination with Meropenem

| Organism: | B. cepacia 1793 | | | FICI (N): | 5 |
|---|---|---|---|---|---|
| Drug A: | BisEDT | Drug A MIC: | 2 | SUM FICI: | 12.97 |
| Drug B: | Meropenem | Drug B MIC: | 4 | MEAN FICI: | 2.59 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 8 | 2 | 2.5 |
| D | 0.5 | 0.25 | 8 | 2 | 2.25 |
| E | 0.25 | 0.125 | 16 | 4 | 4.125 |
| F | 0.12 | 0.06 | 8 | 2 | 2.06 |
| G | 0.06 | 0.03 | 8 | 2 | 2.03 |
| H | | | | | |

TABLE 65

MIC (µg/mL), FIC, FICI, for BisEDT in combination with Tobramycin

| Organism: | B. cepacia 1793 | | | FICI (N): | 4 |
|---|---|---|---|---|---|
| Drug A: | BisEDT | Drug A MIC: | 1 | SUM FICI: | 4.43 |
| Drug B: | Tobramycin | Drug B MIC: | 16 | MEAN FICI: | 1.11 |

| Row | $MIC_A$ | $FIC_A$ | $MIC_B$ | $FIC_B$ | FICI |
|---|---|---|---|---|---|
| A | | | | | |
| B | | | | | |
| C | | | | | |
| D | 0.5 | 0.5 | 8 | 0.5 | 1 |
| E | 0.25 | 0.25 | 16 | 1 | 1.25 |
| F | 0.12 | 0.12 | 16 | 1 | 1.12 |
| G | 0.06 | 0.06 | 16 | 1 | 1.06 |
| H | | | | | |

TABLE 66

MIC (µg/mL), FIC, FICI, for BisEDT in combination with Amikacin

| Organism: | B. cepacia 1793 | | | FICI (N): | 5 |
|---|---|---|---|---|---|
| Drug A: | BisEDT | Drug A MIC: | 1 | SUM FICI: | 6.43 |
| Drug B: | Amikacin | Drug B MIC: | 32 | MEAN FICI: | 1.29 |

| Row | $MIC_A$ | $FIC_A$ | $MIC_B$ | $FIC_B$ | FICI |
|---|---|---|---|---|---|
| A | | | | | |
| B | | | | | |
| C | 1 | 1 | 16 | 0.5 | 1.5 |
| D | 0.5 | 0.5 | 32 | 1 | 1.5 |
| E | 0.25 | 0.25 | 32 | 1 | 1.25 |
| F | 0.12 | 0.12 | 32 | 1 | 1.12 |
| G | 0.06 | 0.06 | 32 | 1 | 1.06 |
| H | | | | | |

TABLE 67

MIC (µg/mL), FIC, FICI, for BisEDT in combination with Ciprofloxacin

| Organism: | B. cepacia 1793 | | | FICI (N): | 4 |
|---|---|---|---|---|---|
| Drug A: | BisEDT | Drug A MIC: | 1 | SUM FICI: | 7.93 |
| Drug B: | Ciprofloxacin | Drug B MIC: | 0.5 | MEAN FICI: | 1.98 |

| Row | $MIC_A$ | $FIC_A$ | $MIC_B$ | $FIC_B$ | FICI |
|---|---|---|---|---|---|
| A | | | | | |
| B | | | | | |
| C | | | | | |
| D | 0.5 | 0.5 | 1 | 2 | 2.5 |

TABLE 67-continued

MIC (µg/mL), FIC, FICI, for BisEDT in combination with Ciprofloxacin

| E | 0.25 | 0.25 | 1 | 2 | 2.25 |
|---|---|---|---|---|---|
| F | 0.12 | 0.12 | 1 | 2 | 2.12 |
| G | 0.06 | 0.06 | 0.5 | 1 | 1.06 |
| H | | | | | |

TABLE 68

MIC (µg/mL), FIC, FICI, for BisEDT in combination with Aztreonam

| Organism: | B. cepacia 1793 | | | FICI (N): | 4 |
|---|---|---|---|---|---|
| Drug A: | BisEDT | Drug A MIC: | 1 | SUM FICI: | 4.93 |
| Drug B: | Aztreonam | Drug B MIC: | 128 | MEAN FICI: | 1.23 |

| Row | $MIC_A$ | $FIC_A$ | $MIC_B$ | $FIC_B$ | FICI |
|---|---|---|---|---|---|
| A | | | | | |
| B | | | | | |
| C | | | | | |
| D | 0.5 | 0.5 | 128 | 1 | 1.5 |
| E | 0.25 | 0.25 | 128 | 1 | 1.25 |
| F | 0.12 | 0.12 | 128 | 1 | 1.12 |
| G | 0.06 | 0.06 | 128 | 1 | 1.06 |
| H | | | | | |

TABLE 69

MIC (µg/mL), FIC, FICI, for BisEDT in combination with Colistin

| Organism: | B. cepacia 1793 | | | FICI (N): | 4 |
|---|---|---|---|---|---|
| Drug A: | BisEDT | Drug A MIC: | 1 | SUM FICI: | 1.32 |
| Drug B: | Colistin | Drug B MIC: | >256 | MEAN FICI: | 0.33 |

| Row | $MIC_A$ | $FIC_A$ | $MIC_B$ | $FIC_B$ | FICI |
|---|---|---|---|---|---|
| A | | | | | |
| B | | | | | |
| C | | | | | |
| D | 0.5 | 0.5 | 8 | 0.016 | 0.516 |
| E | 0.25 | 0.25 | 64 | 0.125 | 0.375 |
| F | 0.12 | 0.12 | 64 | 0.125 | 0.245 |
| G | 0.06 | 0.06 | 128 | 0.125 | 0.185 |
| H | | | | | |

TABLE 70

MIC (µg/mL), FIC, FICI, for BisEDT in combination with Meropenem

| Organism: | B. cenocepacia 548 | | | FICI (N): | 4 |
|---|---|---|---|---|---|
| Drug A: | BisEDT | Drug A MIC: | 4 | SUM FICI: | 4.44 |
| Drug B: | Meropenem | Drug B MIC: | 4 | MEAN FICI: | 1.11 |

| Row | $MIC_A$ | $FIC_A$ | $MIC_B$ | $FIC_B$ | FICI |
|---|---|---|---|---|---|
| A | | | | | |
| B | | | | | |
| C | | | | | |
| D | 2 | 0.5 | 2 | 0.5 | 1 |
| E | 1 | 0.25 | 4 | 1 | 1.25 |
| F | 0.5 | 0.125 | 4 | 1 | 1.125 |
| G | 0.25 | 0.063 | 4 | 1 | 1.063 |
| H | | | | | |

TABLE 71

MIC (µg/mL), FIC, FICI, for BisEDT in combination with Tobramycin

| Organism: | B. cenocepacia 548 | | FICI (N): | 4 |
|---|---|---|---|---|
| Drug A: | BisEDT | Drug A MIC: | 4 SUM FICI: | 2.69 |
| Drug B: | Tobramycin | Drug B MIC: | 32 MEAN FICI: | 0.67 |

| Row | $MIC_A$ | $FIC_A$ | $MIC_B$ | $FIC_B$ | FICI |
|---|---|---|---|---|---|
| A | | | | | |
| B | | | | | |
| C | | | | | |
| D | 2 | 0.5 | 8 | 0.25 | 0.75 |
| E | 1 | 0.25 | 16 | 0.5 | 0.75 |
| F | 0.5 | 0.125 | 16 | 0.5 | 0.625 |
| G | 0.25 | 0.063 | 16 | 0.5 | 0.563 |
| H | | | | | |

TABLE 72

MIC (µg/mL), FIC, FICI, for BisEDT in combination with Amikacin

| Organism: | B. cenocepacia 548 | | FICI (N): | 4 |
|---|---|---|---|---|
| Drug A: | BisEDT | Drug A MIC: | 4 SUM FICI: | 2.69 |
| Drug B: | Amikacin | Drug B MIC: | 128 MEAN FICI: | 0.67 |

| Row | $MIC_A$ | $FIC_A$ | $MIC_B$ | $FIC_B$ | FICI |
|---|---|---|---|---|---|
| A | | | | | |
| B | | | | | |
| C | | | | | |
| D | 2 | 0.5 | 32 | 0.25 | 0.75 |
| E | 1 | 0.25 | 64 | 0.5 | 0.75 |
| F | 0.5 | 0.125 | 64 | 0.5 | 0.625 |
| G | 0.25 | 0.063 | 64 | 0.5 | 0.563 |
| H | | | | | |

TABLE 73

MIC (µg/mL), FIC, FICI, for BisEDT in combination with Ciprofloxacin

| Organism: | B. cenocepacia 548 | | FICI (N): | 4 |
|---|---|---|---|---|
| Drug A: | BisEDT | Drug A MIC: | 4 SUM FICI: | 12.94 |
| Drug B: | Ciprofloxacin | Drug B MIC: | 2 MEAN FICI: | 3.23 |

| Row | $MIC_A$ | $FIC_A$ | $MIC_B$ | $FIC_B$ | FICI |
|---|---|---|---|---|---|
| A | | | | | |
| B | | | | | |
| C | | | | | |
| D | 2 | 0.5 | 8 | 4 | 4.5 |
| E | 1 | 0.25 | 8 | 4 | 4.25 |
| F | 0.5 | 0.125 | 4 | 2 | 2.125 |
| G | 0.25 | 0.063 | 4 | 2 | 2.063 |
| H | | | | | |

TABLE 74

MIC (µg/mL), FIC, FICI, for BisEDT in combination with Aztreonam

| Organism: | B. cenocepacia 548 | | FICI (N): | 4 |
|---|---|---|---|---|
| Drug A: | BisEDT | Drug A MIC: | 4 SUM FICI: | 4.94 |
| Drug B: | Aztreonam | Drug B MIC: | 64 MEAN FICI: | 1.23 |

| Row | $MIC_A$ | $FIC_A$ | $MIC_B$ | $FIC_B$ | FICI |
|---|---|---|---|---|---|
| A | | | | | |
| B | | | | | |
| C | | | | | |
| D | 2 | 0.5 | 64 | 1 | 1.5 |

TABLE 74-continued

MIC (µg/mL), FIC, FICI, for BisEDT in combination with Aztreonam

| | | | | | |
|---|---|---|---|---|---|
| E | 1 | 0.25 | 64 | 1 | 1.25 |
| F | 0.5 | 0.125 | 64 | 1 | 1.125 |
| G | 0.25 | 0.063 | 64 | 1 | 1.063 |
| H | | | | | |

TABLE 75

MIC (µg/mL), FIC, FICI, for BisEDT in combination with Colistin

| Organism: | B. cenocepacia 548 | | FICI (N): | 4 |
|---|---|---|---|---|
| Drug A: | BisEDT | Drug A MIC: | 4 SUM FICI: | 1.63 |
| Drug B: | Colistin | Drug B MIC: | >256 MEAN FICI: | 0.41 |

| Row | $MIC_A$ | $FIC_A$ | $MIC_B$ | $FIC_B$ | FICI |
|---|---|---|---|---|---|
| A | | | | | |
| B | | | | | |
| C | | | | | |
| D | 2 | 0.5 | 32 | 0.063 | 0.563 |
| E | 1 | 0.25 | 64 | 0.125 | 0.375 |
| F | 0.5 | 0.125 | 128 | 0.25 | 0.375 |
| G | 0.25 | 0.063 | 128 | 0.25 | 0.313 |
| H | | | | | |

TABLE 76

MIC (µg/mL), FIC, FICI, for BisEDT in combination with Meropenem

| Organism: | B. cenocepacia 813 | | FICI (N): | 6 |
|---|---|---|---|---|
| Drug A: | BisEDT | Drug A MIC: | 4 SUM FICI: | 6.48 |
| Drug B: | Meropenem | Drug B MIC: | 2 MEAN FICI: | 1.08 |

| Row | $MIC_A$ | $FIC_A$ | $MIC_B$ | $FIC_B$ | FICI |
|---|---|---|---|---|---|
| A | | | | | |
| B | 2 | 0.5 | 1 | 0.5 | 1 |
| C | 1 | 0.25 | 2 | 1 | 1.25 |
| D | 0.5 | 0.125 | 2 | 1 | 1.125 |
| E | 0.25 | 0.063 | 2 | 1 | 1.063 |
| F | 0.12 | 0.03 | 2 | 1 | 1.03 |
| G | 0.06 | 0.015 | 2 | 1 | 1.015 |
| H | | | | | |

TABLE 77

MIC (µg/mL), FIC, FICI, for BisEDT in combination with Tobramycin

| Organism: | B. cenocepacia 813 | | FICI (N): | 6 |
|---|---|---|---|---|
| Drug A: | BisEDT | Drug A MIC: | 4 SUM FICI: | 5.48 |
| Drug B: | Tobramycin | Drug B MIC: | 256 MEAN FICI: | 0.91 |

| Row | $MIC_A$ | $FIC_A$ | $MIC_B$ | $FIC_B$ | FICI |
|---|---|---|---|---|---|
| A | | | | | |
| B | 2 | 0.5 | 128 | 0.5 | 1 |
| C | 1 | 0.25 | 128 | 0.5 | 0.75 |
| D | 0.5 | 0.125 | 128 | 0.5 | 0.625 |
| E | 0.25 | 0.063 | 256 | 1 | 1.063 |
| F | 0.12 | 0.03 | 256 | 1 | 1.03 |
| G | 0.06 | 0.015 | 256 | 1 | 1.015 |
| H | | | | | |

TABLE 78

MIC (µg/mL), FIC, FICI, for BisEDT in combination with Amikacin

| Organism: | *B. cenocepacia* 813 | | FICI (N): | 5 |
| Drug A: | BisEDT | Drug A MIC: | 2 SUM FICI: | 4.97 |
| Drug B: | Amikacin | Drug B MIC: | >256 MEAN FICI: | 0.99 |

| Row | MIC$_A$ | FIC$_A$ | MIC$_B$ | FIC$_B$ | FICI |
|---|---|---|---|---|---|
| A | | | | | |
| B | | | | | |
| C | 1 | 0.5 | 256 | 0.5 | 1 |
| D | 0.5 | 0.25 | 256 | 0.5 | 0.75 |
| E | 0.25 | 0.125 | >256 | 1 | 1.125 |
| F | 0.12 | 0.06 | >256 | 1 | 1.06 |
| G | 0.06 | 0.03 | >256 | 1 | 1.03 |
| H | | | | | |

TABLE 79

MIC (µg/mL), FIC, FICI, for BisEDT in combination with Ciprofloxacin

| Organism: | *B. cenocepacia* 813 | | FICI (N): | 6 |
| Drug A: | BisEDT | Drug A MIC: | 4 SUM FICI: | 17.11 |
| Drug B: | Ciprofloxacin | Drug B MIC: | 2 MEAN FICI: | 2.85 |

| Row | MIC$_A$ | FIC$_A$ | MIC$_B$ | FIC$_B$ | FICI |
|---|---|---|---|---|---|
| A | | | | | |
| B | 2 | 0.5 | 0.25 | 0.125 | 0.625 |
| C | 1 | 0.25 | 8 | 4 | 4.25 |
| D | 0.5 | 0.125 | 8 | 4 | 4.125 |
| E | 0.25 | 0.063 | 8 | 4 | 4.063 |
| F | 0.12 | 0.03 | 4 | 2 | 2.03 |
| G | 0.06 | 0.015 | 4 | 2 | 2.015 |
| H | | | | | |

TABLE 80

MIC (µg/mL), FIC, FICI, for BisEDT in combination with Aztreonam

| Organism: | *B. cenocepacia* 813 | | FICI (N): | 5 |
| Drug A: | BisEDT | Drug A MIC: | 2 SUM FICI: | 5.97 |
| Drug B: | Aztreonam | Drug B MIC: | 32 MEAN FICI: | 1.19 |

| Row | MIC$_A$ | FIC$_A$ | MIC$_B$ | FIC$_B$ | FICI |
|---|---|---|---|---|---|
| A | | | | | |
| B | | | | | |
| C | 1 | 0.5 | 32 | 1 | 1.5 |
| D | 0.5 | 0.25 | 32 | 1 | 1.25 |
| E | 0.25 | 0.125 | 32 | 1 | 1.125 |
| F | 0.12 | 0.06 | 32 | 1 | 1.06 |
| G | 0.06 | 0.03 | 32 | 1 | 1.03 |
| H | | | | | |

TABLE 81

MIC (µg/mL), FIC, FICI, for BisEDT in combination with Colistin

| Organism: | *B. cenocepacia* 813 | | FICI (N): | 5 |
| Drug A: | BisEDT | Drug A MIC: | 2 SUM FICI: | 3.59 |
| Drug B: | Colistin | Drug B MIC: | >256 MEAN FICI: | 0.72 |

| Row | MIC$_A$ | FIC$_A$ | MIC$_B$ | FIC$_B$ | FICI |
|---|---|---|---|---|---|
| A | | | | | |
| B | | | | | |
| C | 1 | 0.5 | 64 | 0.125 | 0.625 |
| D | 0.5 | 0.25 | 256 | 0.5 | 0.75 |
| E | 0.25 | 0.125 | 256 | 0.5 | 0.625 |
| F | 0.12 | 0.06 | 256 | 0.5 | 0.56 |
| G | 0.06 | 0.03 | >256 | 1 | 1.03 |
| H | | | | | |

TABLE 82

MIC (µg/mL), FIC, FICI, for BisEDT in combination with Meropenem

| Organism: | *B. multivorans* 1795 | | FICI (N): | 6 |
| Drug A: | BisEDT | Drug A MIC: | 2 SUM FICI: | 7.97 |
| Drug B: | Meropenem | Drug B MIC: | 4 MEAN FICI: | 1.33 |

| Row | MIC$_A$ | FIC$_A$ | MIC$_B$ | FIC$_B$ | FICI |
|---|---|---|---|---|---|
| A | | | | | |
| B | 2 | 1 | 4 | 1 | 2 |
| C | 1 | 0.5 | 4 | 1 | 1.5 |
| D | 0.5 | 0.25 | 4 | 1 | 1.25 |
| E | 0.25 | 0.125 | 4 | 1 | 1.125 |
| F | 0.12 | 0.06 | 4 | 1 | 1.06 |
| G | 0.06 | 0.03 | 4 | 1 | 1.03 |
| H | | | | | |

TABLE 83

MIC (µg/mL), FIC, FICI, for BisEDT in combination with Tobramycin

| Organism: | *B. multivorans* 1795 | | FICI (N): | 6 |
| Drug A: | BisEDT | Drug A MIC: | 2 SUM FICI: | 7.97 |
| Drug B: | Tobramycin | Drug B MIC: | >256 MEAN FICI: | 1.33 |

| Row | MIC$_A$ | FIC$_A$ | MIC$_B$ | FIC$_B$ | FICI |
|---|---|---|---|---|---|
| A | | | | | |
| B | 2 | 1 | >256 | 1 | 2 |
| C | 1 | 0.5 | >256 | 1 | 1.5 |
| D | 0.5 | 0.25 | >256 | 1 | 1.25 |
| E | 0.25 | 0.125 | >256 | 1 | 1.125 |
| F | 0.12 | 0.06 | >256 | 1 | 1.06 |
| G | 0.06 | 0.03 | >256 | 1 | 1.03 |
| H | | | | | |

TABLE 84

MIC (µg/mL), FIC, FICI, for BisEDT in combination with Amikacin

| Organism: | *B. multivorans* 1795 | | FICI (N): | 6 |
| Drug A: | BisEDT | Drug A MIC: | 2 SUM FICI: | 7.97 |
| Drug B: | Amikacin | Drug B MIC: | >256 MEAN FICI: | 1.33 |

| Row | MIC$_A$ | FIC$_A$ | MIC$_B$ | FIC$_B$ | FICI |
|---|---|---|---|---|---|
| A | | | | | |
| B | 2 | 1 | >256 | 1 | 2 |
| C | 1 | 0.5 | >256 | 1 | 1.5 |
| D | 0.5 | 0.25 | >256 | 1 | 1.25 |
| E | 0.25 | 0.125 | >256 | 1 | 1.125 |
| F | 0.12 | 0.06 | >256 | 1 | 1.06 |
| G | 0.06 | 0.03 | >256 | 1 | 1.03 |
| H | | | | | |

TABLE 85

MIC (µg/mL), FIC, FICI, for BisEDT in combination with Ciprofloxacin

| Organism: | B. multivorans 1795 | | FICI (N): | 5 |
|---|---|---|---|---|
| Drug A: | BisEDT | Drug A MIC: | 2 SUM FICI: | 5.97 |
| Drug B: | Ciprofloxacin | Drug B MIC: | 32 MEAN FICI: | 1.19 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 32 | 1 | 1.5 |
| D | 0.5 | 0.25 | 32 | 1 | 1.25 |
| E | 0.25 | 0.125 | 32 | 1 | 1.125 |
| F | 0.12 | 0.06 | 32 | 1 | 1.06 |
| G | 0.06 | 0.03 | 32 | 1 | 1.03 |
| H | | | | | |

TABLE 86

MIC (µg/mL), FIC, FICI, for BisEDT in combination with Aztreonam

| Organism: | B. multivorans 1795 | | FICI (N): | 5 |
|---|---|---|---|---|
| Drug A: | BisEDT | Drug A MIC: | 2 SUM FICI: | 6.97 |
| Drug B: | Aztreonam | Drug B MIC: | 16 MEAN FICI: | 1.39 |

| Row | $MIC_A$ | $FIC_A$ | $MIC_B$ | $FIC_B$ | FICI |
|---|---|---|---|---|---|
| A | | | | | |
| B | | | | | |
| C | 1 | 0.5 | 16 | 1 | 1.5 |
| D | 0.5 | 0.25 | 16 | 1 | 1.25 |
| E | 0.25 | 0.125 | 16 | 1 | 1.125 |
| F | 0.12 | 0.06 | 16 | 1 | 1.06 |
| G | 0.06 | 0.03 | 32 | 2 | 2.03 |
| H | | | | | |

TABLE 87

MIC (µg/mL), FIC, FICI, for BisEDT in combination with Colistin

| Organism: | B. multivorans 1795 | | FICI (N): | 6 |
|---|---|---|---|---|
| Drug A: | BisEDT | Drug A MIC: | 2 SUM FICI: | 7.97 |
| Drug B: | Colistin | Drug B MIC: | >256 MEAN FICI: | 1.33 |

| Row | $MIC_A$ | $FIC_A$ | $MIC_B$ | $FIC_B$ | FICI |
|---|---|---|---|---|---|
| A | | | | | |
| B | 2 | | >256 | 1 | 2 |
| C | 1 | 0.5 | >256 | 1 | 1.5 |
| D | 0.5 | 0.25 | >256 | 1 | 1.25 |
| E | 0.25 | 0.125 | >256 | 1 | 1.125 |
| F | 0.12 | 0.06 | >256 | 1 | 1.06 |
| G | 0.06 | 0.03 | >256 | 1 | 1.03 |
| H | | | | | |

References

1.) Clinical and Laboratory Standards Institute (CLSI). *Performance Standards for Antimicrobial Susceptibility Testing.* 28th ed. CLSI supplement M100. CLSI, 950 West Valley Road, Suite 2500, Wayne, Pa. 19087 USA, 2018.

2.) CLSI. Methods for Dilution Antimicrobial Susceptibility Tests for Bacteria That Grow Aerobically; Approved Standard—11th Edition. CLSI standard M07. CLSI, 950 West Valley Road, Suite 2500, Wayne, Pa. 19087 USA, 2018.

3.) Eliopoulos G and R Moellering. 1991. Antimicrobial combinations. In Antibiotics in Laboratory Medicine, Third Edition, edited by V Lorian. Williams and Wilkins, Baltimore, Md., pp. 432-492.

4.) Odds FC. 2003. Synergy, antagonism, and what the chequerboard puts between them. J Antimicrob Chemother 52(1):1.

Example 11: In Vitro Activity of Bismuth Thiols and Comparators Against Drug Resistant Gram-Positive and -Negative Bacteria and Yeast Introduction: The in vitro activity of three Bismuth Thiol compounds were evaluated against organisms currently identified by the Centers for Disease Control (CDC; 1) as top drug-resistant threats in the United States, including ESKAPE pathogens (2, 3), *C. difficile*, resistant gonococci, and azole-resistant *Candida* spp. The susceptibility of test isolates to the Bismuth Thiol compounds MB-1-B3, MB-2B, and MB-6 and relevant comparators was evaluated in accordance with guidelines from the Clinical and Laboratory Standards Institute (CLSI; 4-8).

Materials and Methods

Test and Comparator Agents: The test agents were stored at room temperature until assayed. All test agents were suspended and diluted in 100% dimethylsulfoxide (DMSO), and were ultimately tested at a final concentration of 0.06-64 µg/mL. The stock solutions were allowed to stand for at least 1 hr prior to use to auto-sterilize.

Comparator drugs were tested over a concentration range spanning established quality control ranges and breakpoints. Information on comparator compounds used during testing are described in Table 88 below:

TABLE 88

Comparator Comounds

| Drug | Manufacturer | Lot No. | Solvent | Diluent |
|---|---|---|---|---|
| Levofloxacin | Sigma | BCBC2112V | 0.1M NaOH | Water |
| Meropenem | USP | I0J244 | Water | Water |
| Ceftazidime | USP | L1K237 | Water | Water |
| Gentamicin | Sigma | SLBM9736V | Water | Water |
| Vancomycin | | | Water | Water |
| Penicillin | Sigma | 071M0740V | Water | Water |
| Oxacillin | Sigma | BCBF5635V | Water | Water |
| Clindamycin | Sigma | 021M1533V | Water | Water |
| Erythromycin | Sigma | 011M1510V | 95% ethanol | Water |
| Ciprofloxacin | USP | 1134335 | Water | Water |
| Metronidazole | Sigma | 095K0693 | DMSO | Water |
| Fidaxomicin | Merck | SE-B13-01-001885 | DMSO | Water |
| Fluconazole | USP | H1L308 | DMSO | DMSO |
| Amphotericin B | Sigma | 063M4043V | DMSO | DMSO |
| Trimethoprim | Sigma | 080M4044 | Water | Water |
| Sulfamethoxazole | Fluka | BCBC7096V | Water and 2.5M NaOH dropwise | Water |
| Ceftriaxone | USP | J1L040 | Water | Water |

Test Organisms: The test organisms consisted of reference strains from the American Type Culture Collection (ATCC; Manassas, Va.) or clinical isolates from the MMNX repository. The spectrum of organisms evaluated and their corresponding phenotypic information is shown in Tables 89-95. Relevant quality control organisms were included on each day of testing as specified by CLSI (4-8). The isolates were sub-cultured onto an appropriate agar medium prior to testing.

Test Media: Test media were prepared and stored in accordance with guidelines from CLSI (4, 6, 7). Broth microdilution susceptibility testing of aerobic bacteria was performed using cation adjusted Mueller-Hinton Broth (CAMHB; Becton Dickinson [BD], Sparks, Md.; Lot No. 6117994) with the exception of streptococci where CAMHB was supplemented with 5% (v/v) lysed horse blood (Cleveland Scientific, Bath, Ohio; Lot No. 322799). *Neisseria gonorrhoeae* were evaluated by agar dilution using agar consisting of GC medium base (BD; Lot No. 4274618) supplemented with 1% IsoVitaleX (BD; Lot No. 5246843).

The susceptibility of anaerobic bacteria was determined by agar dilution using *Brucella* Agar (BD/BBL; Lot No. 5237692) supplemented with 5 μg/mL hemin (Sigma, St. Louis, Mo.; Lot No. 108K1088), 1 μg/mL Vitamin K1 and 5% (v/v) laked sheep blood (Cleveland Scientific, Bath, Ohio; Lot No. 322799).

The susceptibility of yeast isolates was determined by broth microdilution in RPMI medium (HyClone Laboratories, Logan, Utah; Lot No. AZC184041B) buffered with 0.165 M MOPS (Calbiochem, Billerica, Mass.; Lot No. 2694962). The pH of the medium was adjusted to 7.0 with 1 N NaOH, sterile filtered using a 0.2 μm PES filter, and stored at 4° C. until used.

Broth Microdilution MIC Testing (Aerobic Bacteria and Yeast): The broth microdilution assay method employed for the susceptibility testing of aerobic bacteria (excluding *N. gonorrhoeae* which was evaluated by agar dilution) and yeast essentially followed the procedures described by CLSI (3, 4, 7, 8) and employed automated liquid handlers to conduct serial dilutions and liquid transfers. Automated liquid handlers included the Multidrop 384 (Labsystems, Helsinki, Finland) and Biomek 2000 (Beckman Coulter, Fullerton Calif.). The wells in columns 2-12 in standard 96-well microdilution plates (Costar 3795) were filled with 150 μl of the correct diluent. These would become the 'mother plates' from which 'daughter' or test plates would be prepared. The drugs (300 μL at 40× the desired top concentration in the test plates) were dispensed into the appropriate well in Column 1 of the mother plates. The Biomek 2000 was used to make serial two-fold dilutions through Column 11 in the "mother plate". The wells of Column 12 contained no drug and ultimately served as the organism growth control wells.

The daughter plates were loaded with 185 μL per well of the appropriate test media using the Multidrop 384. The daughter plates were prepared using the Biomek FX which transferred 5 μL of drug solution from each well of a mother plate to the corresponding well of the correct daughter plate in a single step.

A standardized inoculum of each organism was prepared per CLSI methods (3, 7). Isolated colonies of each test isolate were picked from the primary plate and a suspension was prepared to equal a 0.5 McFarland turbidity standard. Standardized suspensions were then diluted 1:100 in test media (1:100 for yeast, 1:20 for bacteria). After dilution, the inoculum suspensions were then transferred to compartments of sterile reservoirs divided by length (Beckman Coulter), and the Biomek 2000 was used to inoculate all plates. Daughter plates were placed on the Biomek 2000 in reverse orientation so that plates were inoculated from low to high drug concentration.

The Biomek 2000 delivered 10 μL of standardized inoculum into each well of the appropriate daughter plate for an additional 1:20 dilution. The wells of the daughter plates ultimately contained 185 μL of the appropriate media, 5 μL of drug solution, and 10 μL of inoculum which corresponded to a final inoculum concentration of 0.5-2.5×103 CFU/mL of yeast and approximately $5 \times 10^5$ CFU/mL of bacteria per test well. The final concentration of DMSO (if used as a solvent) in the test well was 2.5%.

Plates were stacked 4 high, covered with a lid on the top plate, placed into plastic bags, and incubated at 35° C. for approximately 24-48 hr for all yeast isolates and 16-24 hr for aerobic bacteria. Plates were viewed from the bottom using a plate viewer. An un-inoculated solubility control plate was observed for evidence of drug precipitation. MIC endpoints for the test agents and control compounds were read per CLSI criteria (3, 7).

Agar Dilution MIC Testing (Anaerobic Bacteria and Gonococci): MIC values for anaerobic bacteria were determined using a reference agar dilution method as described by CLSI (6). Organisms were grown at 35° C. in the Bactron II Anaerobic Chamber (Shel Lab, Cornelius, Oreg.) for approximately 48 hr prior to the assay. Drug dilutions and drug-supplemented agar plates were prepared manually per CLSI (6). The plates were allowed to stand at room temperature for 1 hr to allow the agar surface to dry and pre-reduced for approximately 1 hr in the anaerobe chamber prior to inoculation. Each isolate was suspended to the equivalent of a 0.5 McFarland standard in *Brucella* broth using a turbidity meter (Dade Behring MicroScan, West Sacramento, Calif.). Each bacterial cell suspension was then diluted 1:10 in *Brucella* broth and transferred to wells in a stainless steel replicator block which was used to inoculate the test plates. The prongs on the replicator deliver approximately 1-2 μl of inoculum to an agar surface. The resulting inoculum spots contained approximately $1 \times 10^5$ CFU/spot. After the inoculum dried, the inoculated drug-supplemented agar plates and no drug growth control plates were incubated at 35° C. for 42-48 hr in the anaerobe chamber. The MIC was read per CLSI guidelines (6).

MIC values for *N. gonorrhoeae* were determined using the reference agar dilution method as described by CLSI (4). This method followed the same agar dilution method described above for anaerobes with the exception that agar plates contained GC medium base supplemented with 1% IsoVitaleX and, after inoculation, plates were incubated aerobically at 35° C. in 5% CO2 for 20-24 hr.

Results and Discussion

The activity of the Bismuth Thiol test agents MB-1-B3, MB-2B, and MB-6 and comparators are shown below for Enterobacteriaceae (Table 89), *Pseudomonas aeruginosa* and *Acinetobacter baumannii* (Table 90), *Staphylococcus aureus* and *Enterococcus* spp. (Table 91), streptococci (Table 92), *N. gonorrhoeae* (Table 93), anaerobes (Table 94), and *Candida* spp. (Table 95). Across all evaluated organisms, MIC results for comparator agents were within the established CLSI QC ranges for the relevant ATCC QC isolate (5, 8).

The evaluated Enterobacteriaceae (Table 1) consisted of the *Escherichia coli* ATCC QC isolate, ESBL-positive *E. coli* and *Klebsiella pneumoniae*, KPC-positive *K. pneumoniae*, and NDM-1 positive *E. coli, K. pneumoniae*, and *Enterobacter cloacae*. Excluding the ATCC QC isolate of *E. coli* which was susceptible, the activity of the comparators illustrates the drug-resistant nature of these isolates. Regardless of the high degree of drug resistance, the evaluated Bismuth Thiol test agents had consistent activity across all isolates. MB-1-B3 (MIC values of 0.5-4 μg/mL) and MB-6 (MIC values of 0.5-2 μg/mL) had similar activity and this activity was typically 2- to 16-fold lower than that observed with MB-2B (MIC values of 2-32 μg/mL).

The evaluated *P. aeruginosa* and *A. baumannii* (Table 90) consisted of the susceptible *P. aeruginosa* ATCC QC isolate, and various isolates with either metallo-beta-lactamases or multi-drug resistance. Excluding the QC isolate, the activity of comparators illustrates the drug-resistant nature of these isolates. Regardless of the high degree of drug resistance, the evaluated Bismuth Thiol test agents had consistent activity across all isolates. MB-1-B3 and MB-6 (MIC values of 0.5-2 µg/mL) had similar activity and this activity was typically 2- to 32-fold lower than that observed with MB-2B (MIC values of 2-16 µg/mL).

Against *S. aureus* and *Enterococcus* spp. (Table 91), all 3 Bismuth Thiol test compounds had potent activity regardless of resistance phenotype (MRSA for *S. aureus* and VRE for *E. faecalis* and *E. faecium*). The evaluated MRSA were largely susceptible to vancomycin and gentamicin but resistant to the remaining comparators. Regardless of resistance, MB-1-B3 and MB-6 had MIC values of <0.06 µg/mL against MRSA and MB-2B also had MIC values of <0.06 µg/mL with the exception of the QC isolate and MRSA MMX 9203 (MIC values of 0.5 and 0.25 µg/mL, respectively). Against enterococci, there was little activity observed with the evaluated comparators. The Bismuth Thiol test agents were active though with slightly higher MIC values for vancomycin-resistant *E. faecium* relative to vancomycin-resistant *E. faecalis*. As with the Gram-negative aerobic isolates, for enterococci MB-1-B3 (MIC values of 0.25-2 µg/mL) and MB-6 (MIC values of 0.25-1 µg/mL) had similar activity and this activity was typically 4- to 8-fold lower than that observed with MB-2B (MIC values of 2-4 µg/mL).

The evaluated streptococci (Table 92) consisted of the susceptible *S. pneumoniae* QC isolate, multi-drug resistant pneumococci, macrolide-resistant *S. pyogenes*, and clindamycin-resistant *S. agalactiae*. Regardless of drug-resistance phenotype, the bismuth-thiol test agents maintained activity against streptococci. Among the 3 Bismuth Thiol test agents, there was trend towards slightly higher MIC values against pneumococci relative to beta-hemolytic streptococci for MB-1-B3 and MB-6. Against pneumococci, MB-1-B3 (MIC values of 0.5-1 µg/mL) and MB-6 (MIC values of 0.5-8 µg/mL) had similar activity and this activity was typically 8- to 16-fold lower than that observed with MB-2B (MIC values of 1-8 µg/mL). Against beta-hemolytic streptococci, MB-1-B3 (MIC values of 0.03-1 µg/mL) and MB-6 (MIC values of 0.03-2 µg/mL) had similar activity and this activity was typically 4- to 16-fold lower than that observed with MB-2B (MIC values of 0.25-8 µg/mL).

As shown in Table 93, the Bismuth Thiol test agents had potent activity against the susceptible QC isolate of *N. gonorrhoeae*, the 3 ciprofloxacin-resistant isolates, and the single ceftriaxone non-susceptible isolate. Similar activity was observed with MB-1-B3 (MIC values of 0.06-0.12 µg/mL) and MB-6 (MIC values of 0.06-0.25 µg/mL) and this activity was slightly greater than that observed for MB-2B (MIC values of 0.12-0.5 µg/mL).

Against the evaluated anaerobes (Table 94) which consisted of the susceptible *Bacteroides fragilis* and *Clostridium difficile* QC isolates and *C. difficile* with various clinically important ribotypes including 027 (hypervirulent strain), MB-1-B3 (MIC values of 0.25-2 µg/mL) and MB-6 (MIC values of 1-4 µg/mL) had similar activity and this activity was typically slightly greater than that observed with MB-2B (MIC values of 2-16 µg/mL). Resistance to comparators clindamycin, metronidazole, and fidaxomicin appeared to have no impact of the activity of the Bismuth Thiol test agents.

Finally, against azole-resistant isolates of clinically prevalent *Candida* spp. (Table 95) including *C. parapsilosis, C. albicans, C. glabrata,* and *C. tropicalis*, the Bismuth Thiol test agents were active. A trend towards higher MIC values for the test agents was observed with *C. albicans* and *C. tropicalis* relative to *C. parapsilosis* and *C. glabrata*. All 3 Bismuth Thiol test agents had similar activity against yeast, with MIC values of 0.25-0.5 µg/mL at 24 hr against *C. parapsilosis* and *C. glabrata*, 1-4 µg/mL against *C. albicans*, and 1-16 µg/mL against *C. tropicalis*.

In summary, the broad spectrum activity of the Bismuth Thiol test agents evaluated in this study was clear and the activity observed against susceptible QC isolates was maintained against drug resistant isolates regardless of the organism or resistance phenotype evaluated. The Bismuth Thiol test agents were the most active against MRSA, *N. gonorrhoeae*, and beta-hemolytic streptococci based on MIC values but were also highly active against Gram-negative aerobes, *S. pneumoniae, C. difficile,* and yeast. In general, test agents MB-1-B3 and MB-6 had similar activity by MIC and both were more potent than MB-2B, with the exception of yeast and to a lesser extent *N. gonorrhoeae* where all 3 compounds had similar activity profiles.

TABLE 89

Minimal Inhibitory Concentration (MIC) Values for Microbion Bismuth Thiol Test Agents and Comparators Against Enterobacteriaceae

| Isolate | Type | MIC (µg/mL) | | | | | | | |
| --- | --- | --- | --- | --- | --- | --- | --- | --- | --- |
| | | MB-1-B3 | MB-2B | MB-6 | Levofloxacin | Ciprofloxacin | Meropenem | Ceftazidime | Gentamicin |
| *E. coli* MMX 102 (ATCC 25922) | QC | 0.5 | 2 | 0.5 | 0.015 (0.008-0.06)[1] | 0.008 (0.004-0.015) | 0.03 (0.008-0.06) | 0.12 (0.06-0.5) | 1 (0.25-1) |
| *E. coli* MMX 8423 | ESBL Lev$^R$ CAZ$^R$ Gm$^R$ | 1 | 2 | 1 | 16 | 32 | 0.03 | 32 | 64 |
| *E. coli* MMX 8424 | ESBL CAZ$^R$ | 0.5 | 4 | 0.5 | 0.06 | 0.015 | 0.03 | 16 | 0.25 |
| *E. coli* MMX 8425 | ESBL Lev$^R$ CAZ$^R$ Gm$^R$ | 1 | 2 | 1 | 16 | >64 | 0.015 | 16 | >64 |

TABLE 89-continued

Minimal Inhibitory Concentration (MIC) Values for Microbion Bismuth
Thiol Test Agents and Comparators Against Enterobacteriaceae

| | | MIC (μg/mL) | | | | | | | |
|---|---|---|---|---|---|---|---|---|---|
| Isolate | Type | MB-1-B3 | MB-2B | MB-6 | Levofloxacin | Ciprofloxacin | Meropenem | Ceftazidime | Gentamicin |
| E. coli MMX 5980 (ATCC BAA-2469) | NDM-1 Lev$^R$ MEM$^R$ CAZ$^R$ Gm$^R$ | 1 | 2 | 1 | 16 | >64 | 32 | >32 | >64 |
| K. pneumoniae MMX 4683 | KPC-2 Lev$^R$ MEM$^R$ CAZ$^R$ | 1 | 8 | 1 | >64 | >64 | 32 | >32 | 1 |
| K. pneumoniae MMX 4622 | KPC-2 MEM$^R$ CAZ$^R$ | 2 | 16 | 1 | 1 | 0.03 | >64 | >32 | 0.25 |
| K. pneumoniae MMX 4623 | KPC-2 MEM$^R$ CAZ$^R$ GM$^R$ | 2 | 32 | 0.5 | 1 | 2 | >64 | >32 | 64 |
| K. pneumoniae MMX 4694 | KPC-3 Lev$^R$ MEM$^R$ CAZ$^R$ | 2 | 8 | 1 | 64 | >64 | 32 | >32 | 8 |
| K. pneumoniae MMX 4653 | KPC-3 Lev$^R$ MEM$^R$ CAZ$^R$ | 4 | 16 | 2 | 64 | >64 | >64 | >32 | 1 |
| K. pneumoniae MMX 4684 | ESBL MEM$^R$ | 4 | 32 | 2 | 0.03 | 0.5 | 8 | 8 | 0.25 |
| K. pneumoniae MMX 4685 | ESBL Lev$^R$ MEM$^R$ CAZ$^R$ | 2 | 8 | 1 | 32 | 64 | 4 | >32 | 1 |
| K. pneumoniae MMX 5979 | NDM-1 Lev$^R$ MEM$^R$ CAZ$^R$ Gm$^R$ | 2 | 16 | 1 | >64 | >64 | >64 | >32 | >64 |
| E. cloacae MMX 5981 (ATCC BAA-2468) | NDM-1 Lev$^R$ MEM$^R$ CAZ$^R$ Gm$^R$ | 4 | 32 | 2 | 64 | >64 | >64 | >32 | >64 |

QC = quality control;
ESBL = extended-spectrum beta-lactamase;
KPC = K. pneumoniae carbapenemase;
NDM = New Delhi Metallo-beta-lactamase;
Lev$^R$ = Levofloxacin-resistant;
MEM$^R$ = Meropenem-resistant;
CAZ$^R$ = ceftazidime-resistant;
Gm$^R$ = Gentamicin-resistant
[1]CLSI QC ranges shown in parenthesis where applicable

TABLE 90

Minimal Inhibitory Concentration (MIC) Values for Microbion Bismuth Thiol
Test Agents and Comparators Against P. aeruginosa and A. baumannii

| | | MI | | | | | | | |
|---|---|---|---|---|---|---|---|---|---|
| Isolate | Type | MB-1-B3 | MB-2B | MB-6 | Levofloxacin | Ciprofloxacin | Meropenem | Ceftazidime | Gentamicin |
| P. aeruginosa MMX 103 (ATCC 27853) | QC | 1 | 8 | 1 | 1 (0.5-4) | 0.5 (0.25-1) | 0.5 (0.25-1) | 2 (1-4) | 1 (0.5-2) |
| P. aeruginosa MMX 4697 | VIM-2 Lev$^R$ Cip$^R$ MEM$^R$ CAZ$^R$ | 1 | 16 | 2 | 32 | 32 | 8 | 32 | 4 |

TABLE 90-continued

Minimal Inhibitory Concentration (MIC) Values for Microbion Bismuth Thiol
Test Agents and Comparators Against *P. aeruginosa* and *A. baumannii*

| Isolate | Type | MB-1-B3 | MB-2B | MB-6 | Levofloxacin | Ciprofloxacin | Meropenem | Ceftazidime | Gentamicin |
|---|---|---|---|---|---|---|---|---|---|
| *P. aeruginosa* MMX 4654 | IMP-7 Lev$^R$ Cip$^R$ MEM$^R$ CAZ$^R$ | 2 | 8 | 2 | 64 | 32 | >64 | >32 | >64 |
| *P. aeruginosa* MMX 2562 | MDR Lev$^R$ Cip$^R$ MEM$^R$ CAZ$^R$ | 1 | 4 | 2 | 64 | 64 | 32 | >32 | 8 |
| *P. aeruginosa* MMX 1381 | MDR Lev$^R$ Cip$^R$ MEM$^R$ CAZ$^R$ | 1 | 2 | 1 | 64 | 32 | 16 | 32 | 8 |
| *P. aeruginosa* MMX 3991 | MDR Lev$^R$ Cip$^R$ MEM$^R$ CAZ$^R$ | 1 | 8 | 2 | 64 | 32 | 16 | 16 | 4 |
| *A. baumannii* MMX 4651 (NCTC 13304) | MDR; OXA-27 Lev$^R$ Cip$^R$ MEM$^R$ CAZ$^R$ Gm$^I$ | 0.5 | 16 | 0.5 | 8 | 32 | 64 | >32 | 8 |
| *A. baumannii* MMX 2592 | MDR Lev$^R$ Cip$^R$ MEM$^R$ CAZ$^R$ Gm$^R$ | 0.5 | 16 | 0.5 | 64 | >64 | 64 | 32 | >64 |
| *A. baumannii* MMX 2593 | MDR Lev$^R$ Cip$^R$ MEM$^R$ CAZ$^R$ Gm$^R$ | 1 | 16 | 0.5 | 32 | >64 | 64 | 32 | >64 |
| *A. baumannii* MMX 3372 | MDR Cip$^R$ MEM$^I$ CAZ$^I$ | 1 | 16 | 1 | 1 | 4 | 4 | 16 | 0.5 |
| *A. baumannii* MMX 3373 | Sensitive | 1 | 16 | 0.5 | 0.12 | 0.5 | 0.5 | 4 | 0.12 |

QC = quality control;

VIM/IMP = metallo-beta lactamase type;

OXA = type D extended-spectrum beta-lactamase;

MDR = multi-drug resistant (based on resistance to at least 3 different classes of antibiotic);

Lev$^R$ = levofloxacin-resistant;

CIP$^R$ = Ciprofloxacin-resistant;

MEM$^I$ = meropenem intermediate resistance;

MEM$^R$ = meropenem-resistant;

CAZ$^R$ = ceftazidime-resistant;

CAZ$^I$ = ceftazidime intermediate resistance;

Gm$^R$ = gentamicin-resistant;

Gm$^I$ = gentamicin intermediate resistance.

[1] CLSI QC ranges shown in parenthesis where applicable

TABLE 91

Minimal Inhibitory Concentration (MIC) Values for Microbion Bismuth Thiol
Test Agents and Comparators Against *S. aureus* and *Enterococcus* spp.

| | | MIC (µg/mL) | | | | | | | | | | | |
|---|---|---|---|---|---|---|---|---|---|---|---|---|---|
| Isolate | Type | MB-1-B3 | MB-2B | MB-6 | Levo-floxacin | Cipro-floxacin | Genta-micin | Vanco-mycin | Mero-penem | Ceftaz-idime | Clind-amycin | Eryth-romycin | Oxa-cillin |
| *S. aureus* MMX 101 (ATCC 29213) | QC; MSSA | ≤0.06 | 0.5 | ≤0.06 | 0.12 (0.06-0.5)[1] | 0.5 (0.12-0.5) | 0.12 (0.12-1) | 1 (0.5-2) | 0.06 (0.03-0.12) | 8 (4-16) | 0.12 (0.06-0.25) | 0.5 (0.25-1) | 0.25 (0.12-0.25) |
| *S. aureus* MMX 9203 | MRSA[2] Lev$^R$ Cip$^R$ Ery$^R$ Ox$^R$ | ≤0.06 | 0.25 | ≤0.06 | 4 | 16 | 0.12 | 2 | 4 | >32 | 0.12 | >64 | 64 |
| *S. aureus* MMX 9204 | MRSA Lev$^R$ Cip$^R$ Ery$^R$ Ox$^R$ | ≤0.06 | ≤0.06 | ≤0.06 | 4 | 16 | 0.25 | 1 | 4 | >32 | 0.12 | >64 | 64 |
| *S. aureus* MMX 9205 | MRSA Lev$^R$ Cip$^R$ CC$^R$ Ery$^R$ Ox$^R$ | ≤0.06 | ≤0.06 | ≤0.06 | >64 | >64 | 0.25 | 2 | 64 | >32 | >32 | >64 | >64 |
| *S. aureus* MMX 5373 | MRSA Lev$^R$ Cip$^R$ CC$^R$ Ery$^R$ Ox$^R$ | ≤0.06 | ≤0.06 | ≤0.06 | 32 | >64 | 0.25 | 2 | 32 | >32 | >32 | >64 | >64 |
| *S. aureus* MMX 6311 | MRSA Lev$^R$ Cip$^R$ CC$^R$ Ery$^R$ Ox$^R$ | ≤0.06 | ≤0.06 | ≤0.06 | 32 | >64 | 0.25 | 0.25 | 8 | >32 | >32 | >64 | 32 |
| *E. faecalis* MMX 8960 | VRE Lev$^R$ Cip$^R$ Ery$^R$ | 0.5 | 2 | 0.5 | 32 | 64 | >64 | >64 | 8 | >32 | >32 | >64 | >64 |
| *E. faecalis* MMX 8961 | VRE Lev$^R$ Cip$^R$ Ery$^R$ | 0.25 | 2 | 0.25 | 64 | 64 | 8 | >64 | 8 | >32 | >32 | >64 | 64 |
| *E. faecalis* MMX 8962 | VRE Lev$^R$ Cip$^R$ Ery$^R$ | 0.5 | 2 | 0.25 | 64 | 64 | >64 | >64 | 2 | >32 | >32 | >64 | 16 |
| *E. faecium* MMX 752 | VRE vanA Lev$^R$ Cip$^R$ Ery$^R$ | 2 | 4 | 1 | >64 | >64 | >64 | >64 | >64 | >32 | >32 | >64 | >64 |
| *E. faecium* MMX 485 | VRE vanA Lev$^R$ Cip$^R$ Ery$^R$ | 1 | 2 | 0.5 | >64 | >64 | >64 | >64 | >64 | >32 | >32 | >64 | >64 |

QC = quality control;
MSSA = methicillin-susceptible *S. aureus*;
MRSA = methicillin-resistant *S. aureus*;
VRE = vancomycin-resistant enterococci;
vanA = vanA-type VRE (based on vancomycin- and teicoplanin-resistant phenotype);
Lev$^R$ = levofloxacin-resistant;
CIP$^R$ = Ciprofloxacin-resistant;
CC$^R$ = Clindamycin-resistant;
Ery$^R$ = Erythromycin-resistant;
Ox$^R$ = oxacillin-resistant
[1] CLSI QC ranges shown in parenthesis where applicable
[2] MRSA do not have breakpoints for ceftazidime and meropenem - resistance is presumed.

TABLE 92

Minimal Inhibitory Concentration (MIC) Values for Microbion Bismuth Thiol Test Agents and Comparators Against *Streptococcus* spp.

| | | MIC (μg/mL) | | | | | | | | | | |
|---|---|---|---|---|---|---|---|---|---|---|---|---|
| Isolate | Type | MB-1-B3 | MB-2B | MB-6 | Levo-floxacin | Cipro-floxacin | Mero-penem | Vanco-mycin | Trimeth/Sulfa | Clinda-mycin | Eryth-romycin | Peni-cillin |
| *S. pneumoniae* MMX 6837 (ATCC 49619) | QC | 0.5 | 8 | 0.5 | 0.5 (0.5-2)[1] | 0.5 | 0.06 (0.06-0.25) | 0.25 (0.12-0.5) | 0.25/4.8 (0.12/2.4-1/19) | 0.06 (0.03-0.12) | 0.03 (0.03-0.12) | 0.25 (0.25-1) |
| *S. pneumoniae* MMX 880 | Lev[R] SXT[R] CC[R] Ery[R] Pen[R] | 1 | 8 | 0.5 | 8 | 32 | 0.5 | 0.5 | 4/76 | >8 | >8 | 2 |
| *S. pneumoniae* MMX 937 | Mem[R] SXT[R] CC[R] Ery[R] Pen[R] | 1 | 1 | 8 | 1 | 1 | 1 | 0.5 | 16/304 | >8 | >8 | 4 |
| *S. pneumoniae* MMX 3959 | CC[R] Ery[R] | 1 | 8 | 1 | 1 | 4 | 0.03 | 0.5 | 2/38 | >8 | >8 | 0.12 |
| *S. pneumoniae* MMX 5440 | Mem[R] SXT[R] CC[R] Ery[R] Pen[R] | 1 | 8 | 0.5 | 1 | 2 | 1 | 0.25 | 16/304 | >8 | >8 | 4 |
| *S. pneumoniae* MMX 5445 | Mem[R] SXT[R] CC[R] Ery[R] Pen[R] | 0.5 | 8 | 0.5 | 1 | 2 | 1 | 0.25 | 8/152 | >8 | >8 | 4 |
| *S. pneumoniae* MMX 8133 | Mem[R] SXT[R] CC[R] Ery[R] Pen[R] | 0.25 | 8 | 0.5 | 1 | 1 | 1 | 0.25 | 8/152 | >8 | >8 | 4 |
| *S. pyogenes* MMX 3068 | Ery[R] | 0.12 | 2 | 0.12 | 0.5 | 0.5 | ≤0.008 | 0.5 | 0.12/2.4 | 0.06 | >8 | ≤0.008 |
| *S. pyogenes* MMX 3820 | ERY[R] CLI[R] | 0.25 | 1 | 0.5 | 0.25 | 0.12 | ≤0.008 | 0.5 | 0.12/2.4 | 1 | >8 | ≤0.008 |
| *S. pyogenes* MMX 3919 | ERY[R] | 0.03 | 0.25 | 0.03 | 0.12 | 0.25 | ≤0.008 | 0.5 | 0.06/1.2 | 0.12 | >8 | ≤0.008 |
| *S. pyogenes* MMX 3929 | ERY[R] CC[R] | 0.25 | 1 | 0.5 | 0.5 | 0.5 | ≤0.008 | 0.5 | 0.25/4.8 | >8 | >8 | ≤0.008 |
| *S. pyogenes* MMX 5091 | ERY[R] CC[R] | 0.5 | 1 | 1 | 0.25 | 0.25 | ≤0.008 | 0.5 | 0.06/1.2 | >8 | >8 | ≤0.008 |
| *S. agalactiae* MMX 3741 | ERY[R] CC[R] | 0.5 | 4 | 0.25 | 0.5 | 0.5 | 0.03 | 0.5 | 0.12/2.4 | >8 | 8 | 0.03 |
| *S. agalactiae* MMX 3743 | ERY[R] CC[R] | 0.25 | 4 | 0.25 | 1 | 1 | 0.06 | 0.5 | 0.12/2.4 | >8 | >8 | 0.06 |
| *S. agalactiae* MMX 4077 | ERY[R] CC[R] | 0.5 | 4 | 0.25 | 0.5 | 1 | 0.06 | 0.5 | 0.12/2.4 | >8 | >8 | 0.06 |
| *S. agalactiae* MMX 4079 | ERY[R] CC[R] Pen[R] MEM[R] | 1 | 8 | 0.5 | 1 | 1 | 8 | 2 | 0.12/2.4 | >8 | >8 | 2 |
| *S. agalactiae* MMX 4086 | ERY[R] CC[R] | 0.25 | 2 | 0.25 | 0.5 | 0.5 | 0.06 | 1 | 0.12/2.4 | >8 | >8 | 0.06 |

QC = quality control;
Trimeth = trimethoprim;
Sulfa = sulfamethoxazole;
MDR = multi-drug resistant (based on resistance to at least 3 different classes of antibiotic);
Ery[R] = erythromycin-resistant;
CC[R] = clindamycin-resistant;
SXT[R] = Trimethoprim/Sulfamethoxazole-resistant;
MEM[R] = Meropenem-resistant;
Pen[R] = Penicillin-resistant
[1]CLSI QC ranges shown in parenthesis where applicable

TABLE 93

Minimal Inhibitory Concentration (MIC) Values for Microbion Bismuth Thiol Test Agents and Comparators Against *N. gonorrhoeae*

| | | MIC (µg/mL) | | | | |
|---|---|---|---|---|---|---|
| Isolate | Type | MB-1-B3 | MB-2B | MB-6 | Ciprofloxacin | Ceftriaxone |
| *N. gonorrhoeae* MMX 683 (ATCC 49226) | QC | 0.06 | 0.12 | 0.06 | 0.008 (0.001-0.008)[1] | 0.015 (0.004-0.015) |
| *N. gonorrhoeae* MMX 6791 | CIP$^R$ | 0.12 | 0.12 | 0.12 | >8 | 0.06 |
| *N. gonorrhoeae* MMX 6792 | CIP$^R$ | 0.12 | 0.12 | 0.12 | >8 | 0.06 |
| *N. gonorrhoeae* MMX 6793 | CIP$^R$ | 0.12 | 0.5 | 0.25 | >8 | 0.03 |
| *N. gonorrhoeae* MMX 6757 | CTX NS | 0.06 | 0.5 | 0.06 | 0.03 | 1 |

QC = quality control;
Cip$^R$ = ciprofloxacin-resistant;
CTX NS = ceftriaxone non-susceptible
[1]CLSI QC ranges shown in parenthesis where applicable

TABLE 94

Minimal Inhibitory Concentration (MIC) Values for Microbion Bismuth Thiol Test Agents and Comparators Against Anaerobes

| | | MIC (µg/mL) | | | | | |
|---|---|---|---|---|---|---|---|
| Isolate | Type | MB-1-B3 | MB-2B | MB-6 | Clindamycin | Metronidazole | Fidaxomicin |
| *B. fragilis* MMX 123 (ATCC 25285) | QC | 2 | 8 | 1 | 1 (0.5-2)[1] | 0.5 (0.25-1) | >64 |
| *C. difficile* MMX 4381 (ATCC 700057) | QC CC$^I$ | 4 | 8 | 4 | 4 (2-8) | 0.5 (0.12-0.5) | 0.25 (0.06-0.25) |
| *C. difficile* MMX 5681 (NCTC 13307) | ribotype 012 CC$^R$ | 4 | 8 | 2 | >64 | 0.5 | 0.5 |
| *C. difficile* MMX 5680 (NCTC 13336) | ribotype 027 CC$^I$ MET$^R$ | 1 | 2 | 2 | 4 | >64 | 4 |
| C. difficile MMX 8272 | ribotype 255 CC$^I$ | 4 | 8 | 2 | 4 | 0.5 | 0.5 |
| *C. difficile* MMX 8279 | ribotype 005 CC$^R$ | 4 | 16 | 2 | >64 | 0.5 | 0.5 |
| *C. difficile* MMX 8281 | ribotype 010 CC$^R$ | 2 | 8 | 2 | >64 | 8 | 0.5 |

QC = quality control;
CC$^I$ = Clindamycin intermediate resistance;
CC$^R$ = Clindamycin-resistant;
MET$^R$ = Metronidazole-resistant
[1]CLSI QC ranges shown in parenthesis where applicable

TABLE 95

Minimal Inhibitory Concentration (MIC) Values for Microbion Bismuth Thiol Test Agents and Comparators Against *Candida* species

| | | MIC[1] (µg/mL) | | | | |
|---|---|---|---|---|---|---|
| Isolate | Type | MB-1-B3 | MB-2B | MB-6 | Fluconazole | Amphotericin B |
| *C. parapsilosis* MMX 2323 (ATCC 22019) | QC | 0.5, 1 | 0.5, 1 | 0.5, 1 | 2, 2 (0.5-4, 1-4)[2] | 0.5, 1 (0.25-2, 0.5-4) |
| *C. parapsilosis* MMX 7370 | FLU$^R$ | 0.5, 0.5 | 0.5, 0.5 | 0.25, 0.5 | 32, 32 | 0.5, 1 |

TABLE 95-continued

Minimal Inhibitory Concentration (MIC) Values for Microbion Bismuth Thiol Test Agents and Comparators Against *Candida* species

| Isolate | Type | MIC[1] (μg/mL) | | | | |
|---|---|---|---|---|---|---|
| | | MB-1-B3 | MB-2B | MB-6 | Fluconazole | Amphotericin B |
| *C. parapsilosis* MMX 7555 | FLU[R] | 0.5, 1 | 0.25, 1 | 0.25, 0.5 | 32, 64 | 0.5, 0.5 |
| *C. albicans* MMX 7039 | Sensitive | 4, 16 | 2, 2 | 2, 2 | 0.5, 0.5 | 0.5, 0.5 |
| *C. albicans* MMX 7055 | Sensitive | 2, 16 | 1, 4 | 2, 2 | 0.25, 0.5 | 0.25, 0.5 |
| *C. glabrata* MMX 7086 | FLU[R] | 0.5, 1 | 0.5, 1 | 0.5, 1 | 32, 64 | 0.5, 1 |
| *C. glabrata* MMX 7318 | FLU[R] | 0.5, 1 | 0.25, 1 | 0.25, 0.5 | >64, >64 | 0.5, 1 |
| *C. tropicalis* MMX 7247 | FLU[R] | 4, 16 | 2, 4 | 4, 4 | 64, >64 | 0.5, 1 |
| *C. tropicalis* MMX 7248 | FLU[R] | 16, 32 | 4, 4 | 4, 8 | 32, >64 | 0.5, 1 |
| *C. tropicalis* MMX 7360 | FLU[R] | 2, 16 | 1, 2 | 2, 2 | 64, >64 | 0.5, 0.5 |

QC = quality control;
FLU[R] = fluconazole-resistant
[1]MIC reported after incubation at 24 and 48 hr
[2]CLSI QC ranges shown in parenthesis where applicable References 1.) Centers for Disease Control and Prevention. Antibiotic resistance threats in the United States, 2013. Available from http://www.cdc.gov/drugresistance/pdf/ar-threats-2013-508.pdf Accessed on Jun. 13, 2016.
2.) Boucher H W, Talbot G H, Bradley J S, Edwards J E, Gilbert D, Rice L B, Scheld M, Spellberg B, Bartlett J. Bad bugs, no drugs: no ESKAPE! An update from the Infectious Diseases Society of America. Clin Infect Dis 2009; 48: 1-12.
3.) Rice L B. Federal funding for the study of antimicrobial resistance in nosocomial pathogens: no ESKAPE. J Infect Dis 2008; 197: 1079-1081.
4.) Clinical and Laboratory Standards Institute (CLSI). Methods for Dilution Antimicrobial Susceptibility Tests for Bacteria That Grow Aerobically; Approved Standard—Tenth Edition. Clinical and Laboratory Standards Institute document M07-A10. CLSI, 940 West Valley Road, Suite 1400, Wayne, Pa. 19087-1898 USA, 2015.
5.) CLSI. Performance Standards for Antimicrobial Susceptibility Testing; Twenty-Sixth Informational Supplement. CLSI document M100-S26. CLSI, 940 West Valley Road, Suite 1400, Wayne, Pa. 19087 USA, 2016.
6.) CLSI. Methods for Antimicrobial Susceptibility Testing of Anaerobic Bacteria; Approved Standard—Eighth Edition. CLSI document M11-A8. CLSI, 940 West Valley Road, Suite 1400, Wayne, Pa. 19087-1898 USA, 2012.
7.) CLSI. Reference Method for Broth Dilution Antifungal Susceptibility Testing of Yeasts; Approved Standard—Third Edition. CLSI document M27-A3. CLSI, 940 West Valley Road, Suite 1400, Wayne, Pa. 19087-1898 USA, 2008.
8.) CLSI. Reference Method for Broth Dilution Antifungal Susceptibility Testing of Yeasts; Fourth Informational Supplement. CLSI document M27-S4. CLSI, 940 West Valley Road, Suite 1400, Wayne, Pa. 19087-1898 USA, 2012.

Example 12: Susceptibility Testing of Three Bismuth Thiols Against Vancomycin-Intermediate *S. aureus* and β-Lactamase Producing Gram-Negative Bacteria Introduction The in vitro activity of BisEDT and two additional bismuth-thiol investigational agents (MB-2B and MB-6) was determined for isolates of *Escherichia coli, Klebsiella pneumoniae, Pseudomonas aeruginosa* and *Acinetobacter baumannii* characterized for extended-spectrum β-lactamases (ESBL) and/or carbapenem resistance. In addition, vancomycin-intermediate *Staphylococcus aureus* (VISA) were evaluated. The majority of the isolates tested in the current study were multidrug-resistant (MDR) as defined by resistance to at least three different antibiotic classes. Susceptibility to the investigational compounds and relevant comparators was determined by broth microdilution conducted in accordance with guidelines from the Clinical and Laboratory Standards Institute (CLSI; 2,3).

Materials and Methods

Test Compounds: The test agents BisEDT (MB-1-B3; Lot No. ED268-1-11-01), MB-2B, and MB-6 were stored at room temperature, in the dark, until assayed. The solvent and diluent for the test agents was DMSO (Sigma; St. Louis, Mo.; Lot No. SHBB9319V) and the prepared stock concentration was 6,464 μg/mL (101× the final test concentration).

Comparator drugs were supplied and shown in Table 96 below:

TABLE 96

Comparator drugs

| Test Agents | Supplier | Catalog Number | Lot Number | Solvent/Diluent |
|---|---|---|---|---|
| BisEDT | Microbion | — | ED268-1-11-01 | DMSO/DMSO |
| MB-2B | Microbion | — | TA-8-167-01 | DMSO/DMSO |
| MB-6 | Microbion | — | 5-21-14 | DMSO/DMSO |
| Amikacin | Sigma | A2324-5G | 058K0803 | $H_2O/H_2O$ |
| Ceftazidime | Sigma | C3809-1G | 076M4770V | $H_2O/H_2O$ |
| Clavulanate | Sigma | 33454-100MG | STBH5214 | Phos. buff. pH 6.0 |
| Clindamycin | Sigma | C5269-100MG | 021M1533 | $H_2O/H_2O$ |
| Daptomycin | Cubist | — | MCB2009 | $H_2O/H_2O$ |
| Levofloxacin | Sigma | 28266-1G-F | BCBF7004V | $H_2O$ + $NaOH/H_2O$ |
| Linezolid | Selleck Chemicals | S1408 | S140802 | $H_2O/H_2O$ |
| Meropenem | USP | 1392454 | J0K434 | $H_2O/H_2O$ |
| Vancomycin | Sigma | V2002-1G | 080M1341V | $H_2O/H_2O$ |

Test compounds were evaluated at a concentration range of 0.06-64 µg/mL. For Gram-negative test isolates, amikacin and ceftazidime (alone and with clavulanate at a fixed concentration of 4 µg/mL) were evaluated over a concentration range of 0.06-64 µg/mL; meropenem and levofloxacin were evaluated over a concentration range of 0.008-8 µg/mL. For the testing of S. aureus, clindamycin, daptomycin, levofloxacin and vancomycin were evaluated at a concentration range of 0.008-8 µg/mL; linezolid was tested from 0.03-32 µg/mL.

Organisms: The test organisms as shown in Tables 97-101 consisted of clinical isolates from the Micromyx (MMX) repository and reference strains from the American Type Culture Collection (ATCC; Manassas, Va.), National Collection of Type Cultures (NCTC; Public Health England, Salisbury, UK), the Network on Antimicrobial Resistance in Staphylococcus aureus (NARSA; BEI Resources, Manassas, Va.), and the Centers for Disease Control and Prevention (CDC; Atlanta, Ga.). The test organisms were maintained frozen at −80° C. Prior to testing, the isolates were cultured on Tryptic Soy Agar with 5% sheep blood (BAP; Becton Dickson [BD]/BBL; Sparks, Md.; Lot Nos. 9080650 and 9108563) at 35° C. Relevant ATCC quality control (QC) organisms (Table 102) were included during testing in accordance with CLSI guidelines (3). Further details on the genetic characterization of the isolates where available can be found in Table 103.

Media: Cation-adjusted Mueller Hinton broth (CAMHB; BD; Lot No. 8190586) was used as the medium for testing (2, 3). For testing daptomycin, calcium was supplemented with 25 mg/mL $Ca^{2+}$, resulting in a final concentration of 50 mg/mL $Ca^{2+}$ (2, 3).

MIC Assay Procedure: MIC values were determined using a broth microdilution procedure described by CLSI (2, 3). Automated liquid handlers (Multidrop 384, Labsystems, Helsinki, Finland; Biomek 2000 and Biomek FX, Beckman Coulter, Fullerton Calif.) were used to conduct serial dilutions and liquid transfers.

To prepare the drug mother plates, which would provide the serial drug dilutions for the replicate daughter plates, the wells of columns 2 through 12 of standard 96-well microdilution plates (Costar 3795) were filled with 150 µl of the appropriate diluent for each row of drug. The test articles and comparator compounds (300 µl at 101× the highest concentration to be tested) were dispensed into the appropriate wells in column 1. The Biomek 2000 was then used to make 2-fold serial dilutions in the mother plates from column 1 through column 11. The wells of column 12 contained no drug and served as the organism growth control wells for the assay.

The daughter plates were loaded with 190 µL per well of RPMI using the Multidrop 384. The test panels were prepared on the Biomek FX instrument which transferred 2 µL of drug solution from each well of a mother plate to the corresponding well of each daughter plate in a single step.

A standardized inoculum of each test organism was prepared per CLSI methods to equal a 0.5 McFarland standard, followed by a dilution of 1:20. The plates were then inoculated with 10 µL of the diluted inoculum using the Biomek 2000 from low to high drug concentration resulting in a final concentration of approximately $5 \times 10^5$ CFU/mL.

Plates were stacked 3-4 high, covered with a lid on the top plate, placed into plastic bags, and incubated at 35° C. for 16 to 20 hr (vancomycin was read for S. aureus after 24 hr incubation time). The MIC was recorded as the lowest concentration of drug that inhibited visible growth of the organism.

Results and Discussion

As shown in Table 102, results for BisEDT and comparators were within CLSI established QC ranges against the relevant ATCC QC isolates, thus validating the susceptibility testing conducted during the study.

The activity of BisEDT, MB-2B, and MB-6, against the resistant Gram-negative bacilli are shown by species in Tables 97-100. BisEDT maintained potent activity with MIC values of 0.5-2 µg/mL across isolates with the exception of one isolate of P. aeruginosa (CDC 241) which had an MIC of 4 µg/mL (Table 99) and several isolates of K. pneumoniae with MIC values of 4-8 µg/mL (Table 98). The activity of BisEDT was not impacted by β-lactamase production or resistance to aminoglycosides (amikacin MIC ≥64 µg/mL), fluoroquinolones (levofloxacin MIC ≥2, 4, and 8≥64 for Enterobacteriaceae, P. aeruginosa, and A. baumannii, respectively).

Overall, MB-6 had MIC values that were either identical or within 2-fold of those observed with BisEDT; exceptions included select K. pneumoniae where MB-6 MIC values were lower than those of BisEDT. The activity of BisEDT and MB-6 was greater than that of MB-2B, particularly for P. aeruginosa and A. baumannii. The MIC values observed with BisEDT, MB-2B, and MB-6 against Gram-negative bacilli were comparable to those observed in prior studies (1, 4).

The activity of BisEDT, MB-2B, and MB-6 against VISA is shown in Table 101. BisEDT had potent MIC values of ≤0.06-0.25 µg/mL against these isolates. As with Gram-negative bacilli, the activity of BisEDT was comparable to that observed with MB-6 and was greater than that observed with MB-2B. Of note, two of the VISA isolates (NRS 13 and 27) from NARSA had vancomycin MIC values of 2 µg/mL, which indicated that during testing in this study they tested as vancomycin-susceptible. The other two isolates with vancomycin MIC values in the susceptible range (NRS 2 and 24) are heterogenous VISA (hVISA) for which vancomycin MIC values are known to vary. Resistance to levofloxacin and clindamycin (MIC values ≥4 µg/mL) was observed with all isolates except NRS 13 and did not impact BisEDT activity. Two of the isolates were also non-susceptible to daptomycin (NRS 13 and 22); all were susceptible to linezolid (MIC values ≤4 µg/mL). The activity observed with BisEDT in this study was comparable to that observed previously (1, 4).

In summary, BisEDT showed potent activity against genetically characterized β-lactam-resistant Gram-negative bacilli, the majority of which were MDR, and reference isolates of VISA. The activity of BisEDT was not impacted by resistance to β-lactams or any other class evaluated in this study. Finally, the activity of BisEDT and MB-6 was comparable against the evaluated bacteria and exceeded that observed with MB-2B.

TABLE 97

Activity of BisEDT, MB-2B, MB-6 and comparators against *Escherichia coli*

| Isolate | β-lactamase Type | MIC (µg/mL) | | | | | | | |
|---|---|---|---|---|---|---|---|---|---|
| | | BisEDT | MB-2B | MB-6 | CAZ | CAZ/CLAV | MEM | LVX | AMK |
| ATCC 35218 | ESBL | 1 | 2 | 1 | 0.12 | ≤0.06/4 | ≤0.008 | ≤0.008 | 1 |
| MMX 5755 | ESBL | 1 | 4 | 2 | >64 | 1/4 | 0.015 | 8 | 16 |
| MMX 5756 | ESBL | 1 | 2 | 1 | >64 | 0.5/4 | ≤0.008 | 4 | 64 |
| MMX 5758 | ESBL | 1 | 4 | 1 | 16 | 0.25/4 | ≤0.008 | 8 | 1 |
| CDC 451 | KPC | 1 | 2 | 1 | 64 | 16/4 | 1 | >8 | 4 |
| MMX 5745 | KPC | 1 | 4 | 2 | 32 | 16/4 | 2 | 8 | 0.5 |
| CDC 114 | ESBL/KPC | 2 | 2 | 2 | >64 | 64/4 | 2 | 4 | 1 |
| ATCC BAA-2471 | NDM | 1 | 2 | 2 | >64 | >64/4 | >8 | >8 | 64 |
| CDC 435 | NDM | 1 | 2 | 1 | >64 | >64/4 | >8 | >8 | >64 |
| CDC 503 | ESBL/NDM | 1 | 2 | 2 | >64 | >64/4 | 8 | >8 | >64 |
| CDC 118 | ESBL/NDM | 1 | 4 | 1 | >64 | >64/4 | 0.06 | 8 | >64 |

ATCC = American Type Culture Collection,
MMX = Micromyx,
CDC = Centers for Disease Control and Prevention,
ESBL = extended-spectrum β-lactamase,
KPC = *K. pneumoniae* carbapenemase,
NDM = New Delhi metallo-β-lactamase,
CAZ = ceftazidime,
CLAV = clavulanate,
MEM = meropenem,
LVX = levofloxacin,
AMK = amikacin

TABLE 98

Activity of BisEDT, MB-2B, MB-6 and comparators against *Klebsiella pneumoniae*

| Isolate | β-lactamase Type | MIC (µg/mL) | | | | | | | |
|---|---|---|---|---|---|---|---|---|---|
| | | BisEDT | MB-2B | MB-6 | CAZ | CAZ/CLAV | MEM | LVX | AMK |
| MMX 9029 | ESBL | 4 | 2 | 2 | 4 | 0.12/4 | 0.015 | 0.12 | 0.5 |
| CDC 112 | KPC | 2 | 4 | 2 | >64 | >64/4 | >8 | 4 | 16 |
| ATCC BAA-1705 | ESBL/KPC | 2 | 4 | 1 | >64 | >64/4 | 8 | >8 | 16 |
| CDC 113 | ESBL/KPC | 8 | 32 | 1 | >64 | >64/4 | >8 | 4 | 16 |
| CDC 115 | ESBL/KPC | 8 | 16 | 2 | >64 | >64/4 | >8 | >8 | 0.5 |
| CDC 120 | ESBL/KPC | 2 | 4 | 2 | >64 | 64/4 | >8 | >8 | 16 |
| CDC 126 | ESBL/KPC | 8 | 32 | 2 | 4 | 8 | 4 | 0.015 | 2 |
| CDC 129 | ESBL/KPC | 2 | 4 | 4 | >64 | >64/4 | 8 | >8 | 32 |
| CDC 135 | ESBL/VIM | 4 | 8 | 4 | >64 | >64/4 | 1 | >8 | 16 |
| CDC 138 | ESBL/NDM | 4 | 16 | 2 | >64 | >64/4 | >8 | >8 | >64 |
| CDC 158 | ESBL/NDM/OXA | 2 | 4 | 2 | >64 | >64/4 | >8 | 4 | 2 |

ATCC = American Type Culture Collection,
MMX = Micromyx,
CDC = Centers for Disease Control and Prevention,
ESBL = extended-spectrum β-lactamase,
KPC = *K. pneumoniae* carbapenemase,
NDM = New Delhi metallo-β-lactamase,
VIM = metallo-β-lactamase,
OXA = class D carbapenemases,
CAZ = ceftazidime,
CLAV = clavulanate,
MEM = meropenem,
LVX = levofloxacin,
AMK = amikacin

TABLE 99

Activity of BisEDT, MB-2B, MB-6 and comparators against *Pseudomonas aeruginosa*

| Isolate | β-lactamase Type | MIC (µg/mL) | | | | | | | |
|---|---|---|---|---|---|---|---|---|---|
| | | BisEDT | MB-2B | MB-6 | CAZ | CAZ/CLAV | MEM | LVX | AMK |
| CDC 356 | KPC | 1 | 4 | 1 | 64 | 64/4 | >8 | 0.12 | 2 |
| CDC 439 | IMP | 2 | 4 | 1 | >64 | >64/4 | >8 | 8 | >64 |
| CDC 444 | VIM | 1 | 4 | 1 | 32 | 32/4 | >8 | 8 | >64 |
| CDC 457 | VIM | 1 | 32 | 2 | >64 | 64/4 | >8 | >8 | 2 |
| CDC 231 | KPC/OXA | 2 | 16 | 2 | >64 | >64/4 | >8 | >8 | 8 |
| CDC 230 | VIM/OXA | 0.5 | 4 | 2 | 64 | 32/4 | >8 | 8 | >64 |
| CDC 241 | IMP/OXA | 4 | 32 | 8 | >64 | >64/4 | >8 | 8 | 32 |
| CDC 246 | NDM/OXA | 2 | 8 | 2 | >64 | >64/4 | >8 | >8 | >64 |
| CDC 250 | NDM/OXA | 2 | 8 | 2 | >64 | >64/4 | >8 | >8 | >64 |
| CDC 516 | KPC/AmpC | 1 | 4 | 1 | 64 | 64/4 | >8 | 0.25 | 2 |
| CDC 518 | KPC/AmpC | 1 | 4 | 1 | 32 | 32/4 | >8 | >8 | 16 |

CDC = Centers for Disease Control and Prevention,
KPC = *K. pneumoniae* carbapenemase,
NDM = New Delhi metallo-β-lactamase,
IMP = metallo-β-lactamase,
VIM = metallo-β-lactamase,
OXA = class D carbapenemases,
AmpC = class C cephalosporinase,
CAZ = ceftazidime,
CLAV = clavulanate,
MEM = meropenem,
LVX = levofloxacin,
AMK = amikacin

TABLE 100

Activity of BisEDT, MB-2B, MB-6 and comparators against *Acinetobacter baumannii*

| Isolate | β-lactamase Type | MIC (µg/mL) | | | | | | | |
|---|---|---|---|---|---|---|---|---|---|
| | | BisEDT | MB-2B | MB-6 | CAZ | CAZ/CLAV | MEM | LVX | AMK |
| NCTC 13304 | OXA | 0.5 | >16 | 0.5 | >64 | >64/4 | >8 | 1 | 0.5 |
| CDC 307 | OXA | 1 | 32 | 0.5 | 64 | 64/4 | 8 | 8 | >64 |
| CDC 311 | OXA | 1 | 32 | 0.5 | >64 | >64/4 | >8 | 2 | >64 |
| CDC 312 | OXA | 1 | 32 | 0.5 | >64 | >64/4 | 4 | 2 | 1 |
| CDC 273 | ESBL/OXA | 1 | 32 | 0.5 | 64 | 64/4 | >8 | >8 | >64 |
| CDC 274 | ESBL/OXA | 1 | 32 | 0.5 | >64 | >64/4 | >8 | 8 | 16 |
| CDC 275 | ESBL/OXA | 0.5 | 32 | 0.5 | >64 | >64/4 | >8 | 4 | >64 |
| CDC 277 | ESBL/OXA | 1 | >16 | 1 | >64 | >64/4 | >8 | 8 | 16 |
| CDC 284 | ESBL/OXA | 1 | >16 | 1 | 64 | 16/4 | >8 | 8 | 32 |
| CDC 308 | ESBL/OXA | 1 | 32 | 0.5 | 64 | 64/4 | 8 | 4 | >64 |
| CDC 313 | ESBL/OXA | 1 | 32 | 0.5 | >64 | >64/4 | >8 | 2 | 4 |

NCTC = National Collection of Type Cultures,
CDC = Centers for Disease Control and Prevention,
ESBL = extended-spectrum β-lactamase,
OXA = class D carbapenemases,
CAZ = ceftazidime,
CLAV = clavulanate,
MEM = meropenem,
LVX = levofloxacin,
AMK = amikacin

TABLE 101

Activity of BisEDT, MB-2B, MB-6 and comparators against vancomycin-intermediate *Staphylococcus aureus*

| Isolate | MIC (µg/mL) | | | | | | | |
|---|---|---|---|---|---|---|---|---|
| | BisEDT | MB-2B | MB-6 | VAN | DAP | CLI | LVX | LZD |
| NRS 1 (hVISA) | 0.12 | 1 | 0.12 | 4 | 1 | >8 | 4 | 1 |
| NRS 2 | ≤0.06 | 0.5 | ≤0.06 | 0.5 | 0.25 | >8 | 4 | 4 |
| NRS 3 | 0.25 | 2 | 0.25 | 8 | 1 | >8 | >8 | 1 |

TABLE 101-continued

Activity of BisEDT, MB-2B, MB-6 and comparators against vancomycin-intermediate *Staphylococcus aureus*

| | MIC (μg/mL) | | | | | | | |
|---|---|---|---|---|---|---|---|---|
| Isolate | BisEDT | MB-2B | MB-6 | VAN | DAP | CLI | LVX | LZD |
| NRS 22 | 0.25 | 2 | 0.25 | 4 | 2 | >8 | 8 | 1 |
| NRS 4 | 0.25 | 1 | 0.25 | 4 | 0.5 | >8 | 4 | 1 |
| NRS 13 | 0.12 | 1 | 0.12 | 2 | 2 | 0.06 | 0.12 | 2 |
| NRS 18 | 0.25 | 1 | 0.25 | 4 | 0.5 | >8 | 4 | 1 |
| NRS 24 (hVISA) | 0.25 | 1 | 1 | 2 | 0.5 | >8 | >8 | 2 |
| NRS 27 | 0.25 | 1 | 0.25 | 2 | 0.25 | >8 | 8 | 2 |

NRS = Network on Antimicrobial Resistance in *Staphylococcus aureus*,
MMX = Micromyx,
VISA = vancomycin-intermediate *S. aureus*,
hVISA = heterogenous vancomycin-intermediate *S. Aureus*,
VAN = vancomycin,
DAP = daptomycin,
CLI = clindamycin,
LVX = levofloxacin,
LZD = linezolid

TABLE 102

Activity of Bis-EDT, MB-2B, MB-6 and comparators against relevant ATCC QC organisms

| | | MIC (μg/mL) | | | | | | | |
|---|---|---|---|---|---|---|---|---|---|
| Organism | Isolate | BisEDT | MB-2B | MB-6 | CAZ | CAZ + CLAV | MEM | LVX | AMK |
| *E. coli* | ATCC 25922 | 0.5 (0.5-4)[1] | 2 | 1 | 0.25 (0.06-0.5) | 0.25/4 | ≤0.008 (0.008-0.06) | ≤0.008 (0.008-0.06) | 1 |
| | ATCC 35218 | 1 | 2 | 1 | 0.12 | ≤0.06/4 | ≤0.008 (0.008-0.06) | ≤0.008 | 1 |
| *K. pneumoniae* | ATCC BAA-1705 | 2 | 4 | 1 | >64 | >64/4 | 8 (8-64) | >8 | 16 |
| *P. aeruginosa* | ATCC 27853 | 1 (0.5-4) | 2 | 1 | 2 (1-4) | 2/4 | 0.25 (0.12-1) | 0.5 (0.5-4) | 2 (1-4) |

| | | MIC (μg/mL) | | | | | | | |
|---|---|---|---|---|---|---|---|---|---|
| Organism | Isolate | BisEDT | MB-2B | MB-6 | VAN | DAP | CLI | LVX | LZD |
| *S. aureus* | ATCC 29213 | 0.12 (0.12-1) | 1 | 0.12 | 0.5 (0.5-2) | 0.5 (0.12-1) | 0.25 (0.06-0.25) | 0.06 (0.06-0.5) | 4 (1-4) |

ATCC = American Type Culture Collection,
CAZ = ceftazidime,
CLAV = clavulanate,
MEM = meropenem,
LVX = levofloxacin,
AMK = amikacin,
VAN = vancomycin,
DAP = daptomycin,
CLI = clindamycin,
LVX = levofloxacin,
LZD = linezolid QC ranges in parentheses

TABLE 103

Available genetic characterization data on test isolates

| Organism | Isolate | Genetic Characterization Information |
|---|---|---|
| *E. coli* | ATCC 35218 | TEM-1 |
| | BAA-2471 | NDM-1 |
| | CDC 435 | NDM |
| | CDC 451 | KPC |
| | MMX 5745 | KPC, TEM, DFR |
| | MMX 5755 | SHV, TEM, OXA-1, AAD, ANT, SUL1, SUL2, GYR |
| | MMX 5756 | SHV, TEM, OXA-9, AAD, SUL2, GYR |
| | MMX 5758 | SHV, TEM, CTX-M-1, GYR |

TABLE 103-continued

Available genetic characterization data on test isolates

| Organism | Isolate | Genetic Characterization Information |
|---|---|---|
| | CDC 503 | CTX-M-15, NDM-1, OXA-181 |
| | CDC 114 | aadB, cmlA1, dfrA5, KPC-3, strA, strB, sul1, sul2, TEM-1B |
| | CDC 118 | aac(3)-IIa, catA1, CMY-6, dfrA29, NDM-1, OmpF, OXA-2, rmtC, strA, strB, sul1, TEM-1A |
| K. pneumoniae | BAA-1705 | KPC-2, TEM, SHV |
| | MMX 9029 | CTX-M1, SHV, TEM, AAC, SUL2 |
| | CDC 112 | aac(6'), aph(3'), aph(4), catA1, cmlA1, dfrA12, KPC-3, mph(A), oqxA, oqxA, oqxB, sul1, sul3 |
| | CDC 113 | aac(6')-Ib, aph(3')-Ia, aph(4)-Ia, catA1, cmlA1, dfrA12, KPC-3, mph(A), OmpK35, OmpK36, oqxA, oqxA, oqxB, SHV-11, sul1, sul3 |
| | CDC 115 | aph(3')-Ia, aph(4)-Ia, catA1, cmlA1, dfrA12, KPC-3, mph(A), OmpK35, oqxA, oqxA, oqxB, sul1, sul3, TEM-1A |
| | CDC 120 | aac(6')-33, aac(6')-Ib, aadA2, aadB, aph(3')-Ia, dfrA12, KPC-2, mph(A), OmpK35, oqxA, oqxA, oqxB, sul1, sul2, TEM-1D |
| | CDC 126 | aac(6')Ib-cr, catB3, dfrA1, fosA, KPC-2, OmpK36, oqxA, oqxA, OXA-1, sul1, TEM-1B |
| | CDC 129 | aac(6')-Ib, aadA2, aph(3')-Ia, catA1, dfrA12, KPC-3, mph(A), OmpK35, oqxA, oqxA, oqxB, sul1, TEM-1A |
| | CDC 135 | aac(3)-IIa, aac(6')-Ib, aph(3')-XV, catB2, dfrA14, OmpK35, oqxA, oqxA, OXA-9, SHV-12, sul1, TEM-1A, tet(D), VIM-1 |
| | CDC 138 | aadA2, ARR-3, CTX-M-15, dfrA12, dfrA14, mph(A), NDM-7, oqxA, oqxA, SHV-11, strA, strB, sul1, sul2, TEM-1B |
| | CDC 158 | aac(3)-IId, aac(6')Ib-cr, CTX-M-15, dfrA14, dfrA30, fosA, NDM-1, oqxA, oqxA, oqxB, OXA-1, strA, strB, sul2, TEM-1B, tet(B) |
| P. aeruginosa | CDC 439 | IMP |
| | CDC 444 | VIM |
| | CDC 457 | VIM |
| | CDC 356 | KPC |
| | CDC 230 | aac(3)-Id, aadA2, cmlA1, clfrB5, OXA-4, OXA-50, PAO, tet(G), VIM-2 |
| | CDC 231 | aac(6')-IIc, KPC-5, OXA-2, OXA-50, PAO |
| | CDC 241 | aac(6')-IIc, aadA7, catB7, IMP-1, OXA-101, OXA-50, OXA-9, PAO, sul1 |
| | CDC 246 | aadB, NDM-1, OXA-10, OXA-50, PAO, rmtD2, tet(G), VEB-1 |
| | CDC 250 | aadB, NDM-1, OXA-10, OXA-50, PAO, rmtD2, tet(G), VEB-1 |
| | CDC 516 | PDC-101; KPC-2 |
| | CDC 518 | PDC-103; KPC-2 |
| A. baumannii | NCTC 13304 | OXA-27 |
| | CDC 273 | aac(3)-IIa, ADC-25, aph(3')-Ic, aph(3')-VIa, OXA-23, OXA-66, strA, strB, sul2 |
| | CDC 274 | aac(3)-Ia, ADC-25, aph(3')-Ic, OXA-66, OXA-72, strA, strB, sul1, sul2, TEM-1D |
| | CDC 275 | ADC-25, aph(3')-Ic, armA, mph(E), msr(E), OXA-23, OXA-66, strA, strB, sul2, TEM-1D |
| | CDC 277 | aac(3)-IIa, OXA-24, OXA-65, strA, strB, sul2, TEM-1B |
| | CDC 284 | aac(3)-IIa, OXA-24, OXA-65, strA, strB, sul2, TEM-1B |
| | CDC 307 | ADC-25, aph(3')-Ic, armA, catB8, mph(E), msr(E), OXA-23, OXA-66, strA, strB, sul1, sul2 |
| | CDC 308 | ADC-25, armA, catB8, mph(E), msr(E), OXA-71, strA, strB, sul1, TEM-1D |
| | CDC 311 | ADC-25, aph(3')-Ic, armA, catB8, mph(E), msr(E), OXA-23, OXA-82, strA, strB, sul1 |
| | CDC 312 | aph(3')-Ic, catA1, OXA-69, sul2, tet(B) |
| | CDC 313 | aac(3)-Ia, aph(3')-Ic, catA1, OXA-23, OXA-69, TEM-1D, tet(A) |

References

1.) Beckman E, Wolfe C, Pillar C. In vitro Activity of Bismuth Thiols and Comparators Against Drug Resistant Gram-positive and -negative Bacteria and Yeast. Final Report 08-24-2016-Microbion 22. Micromyx, Kalamazoo, Mich. 2016.

2.) Clinical and Laboratory Standards Institute (CLSI). Methods for Dilution Antimicrobial Susceptibility Tests for Bacteria That Grow Aerobically; 11$^{th}$ ed. CLSI standard M07. CLSI, 950 West Valley Road, Suite 2500, Wayne, Pa. 19087 USA, 2018.

3.) CLSI. Performance Standards for Antimicrobial Susceptibility Testing; 29$^{th}$ ed. CLSI supplement M100. CLSI, 950 West Valley Road, Suite 2500, Wayne, Pa. 19087 USA, 2019.

4.) Schaadt R D, Peterson M, Sweeney D. In vitro Activity of Bismuth-1,2-ethanedithiol (BisEDT) Against Multiple Clinical Isolates of Gram-positive and -negative Bacteria. Final Report 08-08-2008-Microbion 2. Micromyx, Kalamazoo, Mich. 2008.

Example 13: Susceptibility Testing of Three Test Compounds Against Yeast (Candida spp.) and Mold (Aspergillus spp.)

Introduction

The in vitro activity of BisEDT and two additional bismuth-thiol investigational agents (MB-2B and MB-6) was determined for Candida spp. (C. albicans, C. glabrata, C. krusei, and C. auris) and Aspergillus spp. (A. niger, A. terreus, A. fumigatus and A. flavus). Comparators included amphotericin B, fluconazole, voriconazole, caspofungin and micafungin. Susceptibility was determined by broth microdilution conducted in accordance with guidelines from the Clinical and Laboratory Standards Institute (CLSI; 2,3). Material and Methods Test Compounds: The test agents BisEDT (MB-1-B3; Lot No. ED268-1-11-01), MB-2B, and MB-6 were shipped and stored at room temperature, in the dark, until assayed. The solvent and diluent for the test agents was DMSO (Sigma; St. Louis, Mo.; Lot No. SHBB9319V) and the prepared stock concentration was 6,464 µg/mL (101× the final test concentration for yeast and fungi). Comparator drugs are shown in Table 104 below:

TABLE 104

Comparator drugs

| Comparator Drug | Supplier | Lot No. | Solvent/Diluent | Working Stock Concentration (µg/mL) |
|---|---|---|---|---|
| Amphotericin B | Sigma | 086M4012V | DMSO | 6464 |
| Fluconazole | USP | H1l308 | DMSO | 6464 |
| Caspofungin | Sigma | 086M4750V | DMSO | 808 |
| Micafungin | Astellas | 023070 | DMSO | 808 |
| Voriconazole | USP | R032E0 | DMSO | 808 |

Microbion test compounds, amphotericin B, and fluconazole were evaluated over a concentration range of 0.06-64 µg/mL for yeast and mold. Caspofungin, micafungin, and voriconazole were tested from 0.008-8 µg/mL.

Organisms: The test organisms consisted of clinical isolates from the Micromyx (MMX) repository and reference strains from the American Type Culture Collection (ATCC, Manassas, Va.). The test organisms were maintained frozen at −80° C. Prior to testing, yeast were sub-cultured on Sabouraud Dextrose Agar (Becton, Dickson and Company; Sparks, Md.; Lot Nos. 9032625, 9074672) at 35° C. The molds were obtained from enumerated fungal stocks previously prepared at Micromyx and stored in a 0.1% TWEEN® saline solution, at 4° C., until use. C. krusei ATCC 6258, C. parapsilosis ATCC 22019, A. fumigatus ATCC MYA-3626, and A. flavus ATCC 204304 were included for purposes of quality control (4, 5).

Media: The medium employed for the testing of the yeast and mold isolates was RPMI 1640 from Hyclone Laboratories (Logan, Utah; Lot No. AC10257966A) buffered with MOPS from EMD Millipore (Burlington, Mass.; Lot No. 3173588) (2, 3).

MIC Assay Procedures: MIC values were determined using a broth microdilution procedure described by CLSI (2, 3). Automated liquid handlers (Multidrop 384, Labsystems, Helsinki, Finland; Biomek 2000 and Biomek FX, Beckman Coulter, Fullerton Calif.) were used to conduct serial dilutions and liquid transfers.

To prepare the drug mother plates, which would provide the serial drug dilutions for the replicate daughter plates, the wells of columns 2 through 12 of standard 96-well microdilution plates (Costar 3795) were filled with 150 µl of DMSO for each row of drug. The test articles and comparator compounds (300 µl at 101× the highest concentration to be tested) were dispensed into the appropriate wells in column 1. The Biomek 2000 was then used to make 2-fold serial dilutions in the mother plates from column 1 through column 11. The wells of column 12 contained no drug and served as the organism growth control wells for the assay.

The daughter plates were loaded with 190 µL per well of RPMI using the Multidrop 384. The daughter plates were prepared on the Biomek FX instrument which transferred 2 µL of drug solution from each well of a mother plate to the corresponding well of each daughter plate in a single step.

A standardized inoculum of each organism was prepared per CLSI methods (2, 3). For the yeast, colonies were picked from the streak plate and a suspension was prepared in saline to equal a 0.5 McFarland standard. This suspension was diluted 1:100 in RPMI resulting in a final concentration of approximately $0.5\text{-}2.5\times10^3$ CFU/mL in the assay. For the molds, based on the previously determined spore count (CFU/mL) from a spore suspension of each Aspergillus spp. isolate, the suspension was diluted in RPMI such that a final concentration of approximately $0.2\text{-}2.5\times10^4$ CFU/mL was achieved in the assay. The inoculum for each organism was dispensed into sterile reservoirs divided by length (Beckman Coulter), and the Biomek 2000 was used to inoculate the plates. Daughter plates were placed on the Biomek 2000 work surface reversed so that inoculation took place from low to high drug concentration. The Biomek 2000 delivered 10 µL of standardized inoculum into each well. DMSO was present at a final concentration of 1% in the test wells.

Plates were stacked four high, covered with a lid on the top plate, placed into plastic bags, and incubated at 35° C. The Candida spp. and Aspergillus isolates were read after a 24 hr incubation and again at 48 hr.

The microplates were viewed from the bottom using a plate viewer. For each mother plate, an un-inoculated solubility control plate was observed for evidence of drug precipitation. For yeast, the $MIC_0$ was reported as the lowest concentration of drug that completely inhibited visible growth of the organism for Microbion test articles, amphotericin B, and voriconazole; the lowest concentration that showed 50% inhibition relative to the growth control was reported as the $MIC_2$ for all Microbion test articles, micafungin, caspofungin, and fluconazole. For molds, MIC values were reported as the lowest concentration at which visible growth was inhibited, and minimum effective concentrations (MECs) were reported for caspofungin, micafungin and the Microbion test agents as the lowest concentration where the growth shifted to a small, rounded, compact hyphal form at the bottom of the well as compared to the hyphal growth seen throughout the medium in the growth control well. MECs were only reported where observed.

Results and Discussion

As shown in Table 110, results for BisEDT and comparators were within CLSI established QC ranges against the relevant ATCC QC isolates with the exception of amphotericin B at 48 hr against C. krusei ATCC 6258. In this instance, amphotericin B was within the QC range at 24 hr for the same isolate and was within the QC range at 48 hr for C. parapsilosis ATCC 22019, A. flavus ATCC 204304, and A. fumigatus MYA-3626. These results validate the susceptibility testing conducted during the study.

The activity of BisEDT, MB-2B, and MB-6, against yeast are shown by species in Tables 105-108. BisEDT maintained potent activity with 50% inhibition ($MIC_2$ values) observed from 0.25-1 µg/mL across species and 100% inhibition ($MIC_0$ values) observed from 0.5-2 µg/mL for all species except C. albicans, where $MIC_0$ values were 1-8 µg/mL. The activity of BisEDT was not impacted by resistance to echinocandins or azole anti-fungal agents and was notably maintained against C. auris for which multi-drug resistance and azole resistance is particularly an issue (6). The activity of MB-2B and MB-6 was similar to that of BisEDT, with MIC values identical or within 2-fold those of BisEDT. The MIC values observed with BisEDT, MB-2B, and MB-6 against yeast were comparable to those observed in a prior study (1).

The activity of BisEDT, MB-2B, and MB-6 against Aspergillus spp. is shown in Table 109. Overall, BisEDT resulted in complete inhibition at 24 hr with $MIC_0$ values of 2-8 µg/mL for most isolates. However, no complete inhibition was observed with *A. flavus* MMX 7935 ($MIC_0$ of >64 µg/mL), and an $MIC_0$ of 0.5 µg/mL was observed against *A. terreus* MMX 8229. After 48 hr of incubation, complete inhibition by BisEDT was less commonly observed across the tested isolates but in instances where $MIC_0$ values were not evident, MEC values were apparent and these values were typically consistent with the $MIC_0$ values reported at 24 hr. As with yeast, the activity of BisEDT was comparable to that observed with MB-2B and MB-6. The activity observed among the comparators against the *Aspergillus* spp. was typically more potent than BisEDT, MB-2B, and MB-6 with the exception of fluconazole which, as expected, was inactive.

In summary, BisEDT showed potent activity against both *Candida* spp., including the notoriously difficult to treat *C. auris*, and *Aspergillus* spp. The activity of BisEDT against yeast was not impacted by azole or echinocandin resistance. Finally, the activity of BisEDT, MB-2B, and MB-6 were comparable against the evaluated yeast and mold.

TABLE 105

Activity of BisEDT, MB-2B, MB-6 and comparators against *Candida albicans*

| | | Test agent and activity (µg/mL) at 24 hr | | | | | | | | | |
|---|---|---|---|---|---|---|---|---|---|---|---|
| | | BisEDT | | MB-2B | | MB-6 | | AMP B | FLU | VORI | CASP | MICA |
| Isolate No. | Type | $MIC_2$ | $MIC_0$ | $MIC_2$ | $MIC_0$ | $MIC_2$ | $MIC_0$ | $MIC_0$ | $MIC_2$ | $MIC_2$ | $MIC_2$ | $MIC_2$ |
| ATCC 90028 | Susceptible | 0.5 | 4 | 0.5 | 2 | 0.5 | 2 | 0.25 | 0.25 | ≤0.008 | 0.06 | 0.03 |
| ATCC 204276 | MICA-R | 0.5 | 1 | 0.5 | 1 | $1^a$ | 1 | 0.25 | 0.25 | ≤0.008 | 0.25 | 4 |
| ATCC MYA-2732 | FLU-R, VORI-I | 1 | 2 | 1 | 2 | 1 | 2 | 0.25 | 16 | 0.5 | 0.06 | 0.03 |
| MMX 7067 | FLU-R, VORI-R | 1 | 2 | 0.5 | 1 | 0.5 | 1 | 0.25 | >64 | >8 | 0.06 | 0.03 |
| MMX 7424 | CASP-R, MICA-R | 1 | 4 | 1 | 2 | 1 | 2 | 0.25 | 0.5 | ≤0.008 | 8 | 4 |
| MMX 7053 | Susceptible | 0.5 | 1 | 0.5 | 1 | 0.5 | 1 | 0.12 | 0.12 | ≤0.008 | 0.06 | 0.06 |
| MMX 7445 | FLU-R, VORI-R | 1 | 8 | 1 | 2 | 1 | 2 | 0.12 | >64 | >8 | $0.06^a$ | 0.03 |
| MMX 7430 | Susceptible | 1 | 8 | 0.5 | 1 | 0.25 | 0.5 | 0.25 | 0.5 | ≤0.008 | 0.06 | 0.03 |
| MMX 7437 | FLU-I | 1 | 8 | 1 | 2 | 1 | 2 | 0.25 | 4 | 0.12 | 0.06 | 0.03 |
| MMX 7403 | Susceptible | 0.5 | 2 | 0.5 | 2 | 0.25 | 2 | 0.25 | 1 | ≤0.008 | 0.06 | 0.03 |

$MIC_2$ = 50% inhibition,
$MIC_0$ = complete inhibition,
AMP B = amphotericin B,
FLU = fluconazole,
VORI = voriconazole,
CASP = caspofungin,
MICA = micafungin,
I = intermediate,
R = resistant
$^a$insufficient growth at 24 hr to determine 50% inhibitory endpoint, result after 48 hr incubation reported
*there are no AMP B CLSI breakpoints for yeast (4)

TABLE 106

Activity of BisEDT, MB-2B, MB-6 and comparators against *Candida glabrata*

| | | Test agent and activity (µg/mL) | | | | | | | | | |
|---|---|---|---|---|---|---|---|---|---|---|---|
| | | BisEDT | | MB-2B | | MB-6 | | AMP B | FLU | VORI | CASP | MICA |
| Isolate No. | Type | $MIC_2$ | $MIC_0$ | $MIC_2$ | $MIC_0$ | $MIC_2$ | $MIC_0$ | $MIC_0$ | $MIC_2$ | $MIC_2$ | $MIC_2$ | $MIC_2$ |
| ATCC 90030 | Susceptible | 0.5 | 1 | 0.5 | 1 | 0.5 | 1 | 0.25 | 8 | 0.12 | 0.12 | 0.06 |
| ATCC MYA-2950 | Susceptible | 0.5 | 1 | 0.5 | 1 | 0.5 | 1 | 0.12 | 8 | 0.12 | 0.12 | 0.03 |
| MMX 7103 | CASP-R, MICA-R | 0.5 | 1 | 0.5 | 1 | 0.5 | 1 | 0.25 | 4 | 0.12 | >8 | 8 |
| MMX 7307 | CASP-R, MICA-R, FLU-R | 0.5 | 1 | 0.5 | 1 | 0.5 | 1 | 0.25 | >64 | 4 | >8 | 8 |
| MMX 7285 | CASP-R, MICA-R | 0.25 | 0.5 | 0.25 | 0.5 | 0.25 | 0.5 | 0.25 | 32 | 1 | 0.5 | 0.5 |
| MMX 7093 | FLU-R | 0.5 | 1 | 0.5 | 1 | 1 | 2 | 0.25 | 64 | 2 | 0.12 | 0.06 |
| MMX 7101 | FLU-R | 0.5 | 1 | 0.5 | 1 | 0.5 | 1 | 0.25 | 64 | 2 | 0.12 | 0.06 |
| MMX 7087 | Susceptible | 0.5 | 1 | 0.5 | 1 | 0.5 | 1 | 0.12 | 1 | 0.03 | 0.12 | 0.03 |
| MMX 7549 | Susceptible | $0.5^a$ | 0.5 | 0.5 | 1 | 0.5 | 1 | 0.25 | 4 | 0.06 | 0.06 | 0.06 |
| MMX 7111 | Susceptible | 0.5 | 1 | 0.5 | 1 | 0.5 | 1 | 0.25 | 2 | 0.06 | 0.12 | 0.06 |

$MIC_2$ = 50% inhibition,
$MIC_0$ = complete inhibition,
AMP B = amphotericin B,
FLU = fluconazole,
VORI = voriconazole,
CASP = caspofungin,
MICA = micafungin,
I = intermediate,
R = resistant
*there are no AMP B CLSI breakpoints for yeast and there are no VORI breakpoints for *C. glabrata* (4)

TABLE 107

Activity of BisEDT, MB-2B, MB-6 and comparators against *Candida krusei*

| | | Test agent and activity (μg/mL) | | | | | | | | | | |
|---|---|---|---|---|---|---|---|---|---|---|---|---|
| | | BisEDT | | MB-2B | | MB-6 | | AMP B | FLU | VORI | CASP | MICA |
| Isolate No. | Type | $MIC_2$ | $MIC_0$ | $MIC_2$ | $MIC_0$ | $MIC_2$ | $MIC_0$ | $MIC_0$ | $MIC_2$ | $MIC_2$ | $MIC_2$ | $MIC_2$ |
| ATCC 14243 | Susceptible | 0.5 | 1 | 1 | 2 | 0.5 | 1 | 0.25 | 16 | 0.06 | 0.012 | 0.25 |
| ATCC 6258 | MICA-I | 0.5 | 1 | 1 | 2 | 0.5 | 1 | 0.5 | 16 | 0.12 | 0.25 | 0.5 |
| MMX 7125 | Susceptible | 0.5 | 1 | 1 | 2 | 0.5 | 1 | 0.5 | 32 | 0.25 | 0.25 | 0.25 |
| MMX 7128 | Susceptible | 0.5 | 1 | 1 | 2 | 1 | 2 | 0.5 | 16 | 0.12 | 0.25 | 0.25 |
| MMX 7141 | Susceptible | 0.5 | 1 | 1 | 2 | 1 | 2 | 0.25 | 16 | 0.12 | 0.25 | 0.25 |
| MMX 7153 | MICA-R | 0.5 | 1 | 1 | 2 | 0.5 | 1 | 0.5 | 32 | 0.25 | 0.25 | 1 |
| MMX 7155 | Susceptible | 0.5 | 1 | 1 | 2 | 0.5 | 1 | 0.25 | 32 | 0.25 | 0.25 | 0.25 |
| MMX 7563 | Susceptible | 0.5 | 1 | 1 | 2 | 0.5 | 1 | 0.5 | 32 | 0.25 | 0.12 | 0.25 |
| ATCC 96685 | Susceptible | 0.25 | 0.5 | 0.25 | 0.5 | 0.25 | 0.5 | 0.5 | 32 | 0.5 | 0.12 | 0.25 |
| MMX 9878 | MICA-I, VORI-I | 0.5 | 1 | 0.5 | 1 | 0.5 | 1 | 0.5 | 64 | 1 | 0.25 | 0.5 |

$MIC_2$ = 50% inhibition,
$MIC_0$ = complete inhibition,
AMP B = amphotericin B,
FLU = fluconazole,
VORI = voriconazole,
CASP = caspofungin,
MICA = micafungin,
I = intermediate,
R = resistant
*there are no AMP B CLSI breakpoints for yeast and there are no FLU breakpoints for *C. krusei* (4)

TABLE 108

Activity of BisEDT, MB-2B, MB-6 and comparators against *Candida auris*

| | | Test agent and activity (μg/mL) | | | | | | | | | | |
|---|---|---|---|---|---|---|---|---|---|---|---|---|
| | | BisEDT | | MB-2B | | MB-6 | | AMP B | FLU | VORI | CASP | MICA |
| Isolate No. | Type | $MIC_2$ | $MIC_0$ | $MIC_2$ | $MIC_0$ | $MIC_2$ | $MIC_0$ | $MIC_0$ | $MIC_2$ | $MIC_2$ | $MIC_2$ | $MIC_2$ |
| MMX 9862 | Susceptible | 0.5 | 2 | 0.5 | 1 | 0.5 | 1 | 0.25 | 2 | 0.03 | 0.12 | 0.12 |
| MMX 9863 | FLU-R, VORI-R[c] | $1^a$ | 1 | $1^a$ | 1 | 1 | 2 | 0.12 | >64 | >8 | $0.12^b$ | 0.5 |
| MMX 9864 | FLU-R, VORI-R | 0.5 | 1 | $1^a$ | 1 | $1^a$ | 1 | 0.25 | >64 | 2 | $0.25^b$ | 0.5 |
| MMX 9865 | FLU-R, VORI-R | $1^a$ | 1 | $1^a$ | 1 | 1 | 2 | 0.25 | >64 | 8 | $0.25^b$ | 0.25 |
| MMX 9866 | FLU-R, VORI-R | 1 | 2 | $1^a$ | 1 | 1 | 2 | 0.5 | >64 | 8 | $0.12^b$ | 0.5 |
| MMX 9867 | FLU-R, VORI-R | 1 | 2 | 1 | 2 | 1 | 2 | 0.5 | >64 | 8 | 0.12 | 0.5 |
| MMX 9868 | FLU-R, VORI-R | $1^b$ | $1^a$ | ND | 1 | 1 | 4 | 0.25 | >64 | >8 | 0.25 | 0.25 |
| MMX 9869 | FLU-R, VORI-R | $1^b$ | 2 | 1 | 2 | 1 | 4 | 1 | >64 | 2 | 0.25 | 0.25 |
| MMX 9870 | FLU-R, VORI-R | 1 | 2 | 1 | 2 | 1 | 2 | 1 | >64 | 4 | 0.25 | 0.5 |
| MMX 9871 | Susceptible | $1^a$ | 1 | $1^a$ | 1 | 1 | 2 | 1 | >64 | 1 | $0.25^b$ | 0.5 |

$MIC_2$ = 50% inhibition,
$MIC_0$ = complete inhibition,
AMP B = amphotericin B,
FLU = fluconazole,
VORI = voriconazole,
CASP = caspofungin,
MICA = micafungin,
Azole-R = azole-resistant,
ND = not determined (no $MIC_2$ was apparent)
[a]insufficient growth at 24 hr to determine 50% inhibitory endpoint, result after 48 hr incubation reported
[b]eagle effect observed (clear $MIC_2$ endpoint but regrowth at higher test concentrations potentially due to inducible resistance or compound precipitation in vitro)
[c]based on breakpoints published by Lockhart et al., 2017 (6); CLSI breakpoints have not been established for *C. auris*

TABLE 109

Activity of BisEDT, MB-2B, MB-6 and comparators against *Aspergillus* spp.

| | | Test agent and activity (μg/mL) | | | | | | |
|---|---|---|---|---|---|---|---|---|
| | | BisEDT | MB-2B | MB-6 | AMP B | FLU | VORI | CASP | MICA |
| Organism | Isolate No. | $MIC_0$ 24/48 hr | $MIC_0$ 24/48 hr | $MIC_0$ 24/48 hr | $MIC_0$ | $MIC_2$ | $MIC_0$ | MEC | MEC |
| *A. fumigatus* | ATCC MYA-3626 | 4/8 | 4/8 | 2/4 | 1 | >64 | 0.5 | 0.06 | 0.03 |
| | ATCC 204305 | $8/8^a$ | $4/8^a$ | $8/4^a$ | 1 | >64 | 0.5 | 0.25 | 0.25 |
| | MMX 5934 | $4/8^a$ | $8/8^a$ | $2/4^a$ | 1 | >64 | 0.25 | 0.12 | 0.06 |

TABLE 109-continued

Activity of BisEDT, MB-2B, MB-6 and comparators against *Aspergillus* spp.

| | | Test agent and activity (µg/mL) | | | | | | | |
|---|---|---|---|---|---|---|---|---|---|
| Organism | Isolate No. | BisEDT MIC$_0$ 24/48 hr | MB-2B MIC$_0$ 24/48 hr | MB-6 MIC$_0$ 24/48 hr | AMP B MIC$_0$ | FLU MIC$_2$ | VORI MIC$_0$ | CASP MEC | MICA MEC |
| | MMX 5938 | —/2$^b$ | —/2$^b$ | —/1$^b$ | 1 | >64 | 0.25 | 0.12$^b$ | ≤0.008$^b$ |
| | MMX 5939 | 4/8$^a$ | 4/8$^a$ | 2/4$^a$ | 1 | >64 | 2 | 0.12 | 0.06 |
| *A. flavus* | ATCC 204304 | 4/8$^a$ | 4/4$^a$ | 4/4$^a$ | 1 | >64 | 2 | 0.06 | 0.12 |
| | ATCC 22546 | 2/4 | 1/2 | 1/2 | 1 | >64 | 1 | 0.06 | ≤0.008 |
| | MMX 7935 | >64/8$^a$ | 32/4$^a$ | 8/8 | 1 | >64 | 0.5 | 0.03 | ≤0.008 |
| *A. niger* | ATCC 29508 | —/2$^b$ | —/2$^b$ | —/2$^b$ | 0.25 | >64 | 0.5 | 0.06$^b$ | ≤0.008$^b$ |
| *A. terreus* | MMX 8229 | 0.5/1 | 0.5/1 | 0.25/1 | 0.25 | >64 | 0.25 | 0.12$^b$ | ≤0.008$^b$ |

MIC$_0$ = complete inhibition,
MEC = minimum effective concentration,
AMP B = amphotericin B,
FLU = fluconazole,
VORI = voriconazole,
CASP = caspofungin,
MICA = micafungin
$^a$result shown at 48 hr is the MEC, complete inhibition (MIC$_0$) not observed at this timepoint
$^b$result reported for 48 hr only, insufficient growth for 24 hr read
*there are no CLSI breakpoints for *Aspergillus* spp. (5)

TABLE 110

Activity of Bis-EDT, MB-2B, MB-6 and comparators against relevant ATCC QC organisms

| Organism | Test Agent | QC Range 24 hr | QC Range 48 hr | MIC 24 hr | MIC 48 hr |
|---|---|---|---|---|---|
| *E. coli* ATCC 25922 | BisEDT | 0.5-4 | — | 0.5$^a$ | — |
| | MB-2B | — | — | 2$^a$ | — |
| | MB-6 | — | — | 0.5$^a$ | — |
| | Amphotericin B | — | — | >64 | — |
| | Fluconazole | — | — | >64 | — |
| | Voriconazole | — | — | >64 | — |
| | Caspofungin | — | — | >64 | — |
| | Micafungin | — | — | >64 | — |
| *S. aureus* ATCC 29213 | BisEDT | 0.12-1 | — | 0.5$^a$ | — |
| | MB-2B | — | — | 1$^a$ | — |
| | MB-6 | — | — | 1$^a$ | — |
| | Amphotericin B | — | — | >64 | — |
| | Fluconazole | — | — | >64 | — |
| | Voriconazole | — | — | >64 | — |
| | Caspofungin | — | — | >64 | — |
| | Micafungin | — | — | >64 | — |
| *C. parapsilosis* ATCC 22019 | BisEDT | — | — | 0.5/1$^b$ | 1/2$^b$ |
| | MB-2B | — | — | 1/2$^b$ | 1/2$^b$ |
| | MB-6 | — | — | 1/2$^b$ | 1/4$^b$ |
| | Amphotericin B | 0.25-2 | 0.5-4 | 0.5 | 0.5 |
| | Fluconazole | 0.5-4 | 1-4 | 1 | 2 |
| | Voriconazole | 0.015-0.12 | 0.03-0.25 | 0.12 | 0.12 |
| | Caspofungin | 0.25-1 | 0.5-4 | 0.25 | 0.5 |
| | Micafungin | 0.5-2 | 0.5-4 | 0.5 | 2 |
| *C. krusei* ATCC 6258 | BisEDT | — | — | 0.5/1$^b$ | 1/2$^b$ |
| | MB-2B | — | — | 1/2$^b$ | 1/4$^b$ |
| | MB-6 | — | — | 0.5/1$^b$ | 1/4$^b$ |
| | Amphotericin B | 0.5-2 | 1-4 | 0.5 | 0.5 |
| | Fluconazole | 8-64 | 16-128 | 16 | 32 |
| | Voriconazole | 0.06-0.5 | 0.12-1 | 0.12 | 0.5 |
| | Caspofungin | 0.12-1 | 0.25-2 | 0.25 | 0.25 |
| | Micafungin | 0.12-0.5 | 0.12-0.5 | 0.5 | 0.5 |
| *A. flavus* ATCC 204304 | BisEDT | — | — | 4 | 8$^c$ |
| | MB-2B | — | — | 4 | 8$^c$ |
| | MB-6 | — | — | 4 | 4$^c$ |
| | Amphotericin B | — | 0.5-4 | 0.5 | 1 |
| | Fluconazole | — | — | >64 | >64 |
| | Voriconazole | — | 0.5-4 | 0.12 | 2 |
| | Caspofungin | — | — | 0.12 (MEC) | 0.06 (MEC) |
| | Micafungin | — | — | 0.06 (MEC) | 0.008 (MEC) |

TABLE 110-continued

Activity of Bis-EDT, MB-2B, MB-6 and comparators against relevant ATCC QC organisms

| Organism | Test Agent | QC Range 24 hr | QC Range 48 hr | MIC 24 hr | MIC 48 hr |
|---|---|---|---|---|---|
| *A. fumigatus* ATCC MYA-3626 | BisEDT | — | — | 4 | 8 |
| | MB-2B | — | — | 4 | 8 |
| | MB-6 | — | — | 2 | 4 |
| | Amphotericin B | — | 0.5-4 | 0.5 | 1 |
| | Fluconazole | — | — | >64 | >64 |
| | Voriconazole | — | 0.25-1 | 0.25 | 0.5 |
| | Caspofungin | — | — | 0.06 (MEC) | 0.06 (MEC) |
| | Micafungin | — | — | 0.03 (MEC) | 0.008 (MEC) |

References:

1.) Beckman E, Wolfe C, Pillar C. In vitro Activity of Bismuth Thiols and Comparators Against Drug Resistant Gram-positive and -negative Bacteria and Yeast. Final Report 08-24-2016-Microbion 22. Micromyx, Kalamazoo, Mich. 2016.
2.) Clinical and Laboratory Standards Institute (CLSI). *Reference Method for Broth Dilution Antifungal Susceptibility Testing of Yeasts.* $4^{th}$ ed. CLSI standard M27. CLSI, 940 West Valley Road, Suite 1400, Wayne, Pa. 19087-1898 USA, 2017.
3.) CLSI. *Reference Method for Broth Dilution Antifungal Susceptibility Testing of Filamentous Fungi; Approved Standard.* $3^{rd}$ ed. CLSI standard M38. CLSI, 940 West Valley Road, Suite 1400, Wayne, Pa. 19087-1898 USA, 2017.
4.) CLSI. *Performance Standards for Antifungal Susceptibility Testing of Yeasts.* $1^{st}$ ed. CLSI supplement M60. CLSI, 940 West Valley Road, Suite 1400, Wayne, Pa. 19087-1898 USA, 2017.
5.) CLSI. *Performance Standards for Antifungal Susceptibility Testing of Filamentous Fungi; Approved Standard.* $1^{st}$ ed. CLSI supplement M61. CLSI, 940 West Valley Road, Suite 1400, Wayne, Pa. 19087-1898 USA, 2017.
6.) Lockhart S R, Etienne K A, Vallabhaneni S, Farooqi J, Chowdhary A, Govender N, et al. Simultaneous Emergence of Multi drug-Resistant *Candida auris* on 3 Continents Confirmed by Whole-Genome Sequencing and Epidemiological Analyses. Clin Infect Dis 2017; 64:134-140.

Example 14: Studies on Processing Conditions on BisEDT Particle Size Distribution It was observed that careful control of the reaction temperature and the rate of 1,2 ethanedithiol addition had pronounced impact on the BisEDT particle size distribution. Representative syntheses are shown below for BisEDT synthesized at 20° C. with a 1.25 hour addition of 1,2-ethane via syringe pump and BisEDt synthesized at 15° C. with a 1 hour addition of 1,2-ethane via syringe pump. Table 111 below shows that temperature conditions play a critical role in particle size distribution, with processing temperatures in the range of 20-30° C. providing BisEDT particle size distribution that are both small and uniform in particle size (such as a D90 below 2 microns).

Representative synthesis of BisEDT at 20° C. with 1.25 hour addition of thiol via syringe pump, and polypropylene cloth for filtration BisEDT synthesis was performed on 10-g scale. To a 1-L jacketed reactor was charged USP water (480 mL, 48 vol), followed by 70% HNO3 (34 mL, 3.4 vol). A solution of bismuth subnitrate (10 g, 6.84 mmols) in water (43 mL, 4.3 vol) and 70% HNO3 (14 mL, 1.4 vol) was added at 20° C. The reaction mixture was cooled to 15° C. for addition of 95% Ethanol. The 95% ethanol (180 mL, 18 vol) was then added slowly. (Ethanol addition is exothermic, temperature reached 22° C.). The temperature was then adjusted back to 20° C. This was followed by dropwise addition of 1,2 ethanedithiol (4.3 mL, 7.5 mmols in 95% ethanol in 94 mL, 9.4 vol) over a period of 1.25 hour with the batch temperature at 20° C. during which time it turned into a yellow suspension. The reaction was stirred at 20° C. overnight. The reaction mixture was filtered through polypropylene cloth and washed with 95% ethanol (45 mL, 4.5 vol). The wet cake was charged back to the reactor and slurried in 95% ethanol (380 mL, 38 vol) for two hours at 20° C. The suspension was then filtered (same cloth) and washed with 95% ethanol (30 mL, 3 vol). The wet cake was again slurried in 95% EtOH (170 mL, 17 vol) at 20° C., filtered (same cloth), and washed with 95% ethanol (30 mL, 3 vol). The wet cake was then slurried in acetone (170 mL, 17 vol) at 20° C. overnight, followed by filtration (same cloth) and acetone wash (20 mL, 2 vol). The acetone (170 ml, 17 vol) treatment was repeated on the solids and stirred for 2 hours. The suspension was filtered (same cloth) and washed with acetone (30 mL, 3 vol) and died at 45° C. and dried at 45° C. (18 hours) to provide canary yellow solid (10.81 g 91.0%).

Representative synthesis of BisEDT at 15° C. with 1 hour addition of thiol via syringe pump, and polypropylene cloth for filtration: The synthesis BisEDT was performed on 10-g scale, temperature profile was studied with data logger. Ethane dithiol was added at 15° C. over 1 hour via syringe pump and the filtration was performed using PP filter cloth. To a 1-L jacketed reactor was charged USP water (480 mL, 48 vol) and cooled to 15° C., followed by 70% HNO3 (34 mL, 3.4 vol). A solution of bismuth subnitrate (10 g, 6.84 mmols) in water (43 mL, 4.3 vol) and 70% HNO3 (14 mL, 1.4 vol) was added at the same temperature. The 95% ethanol (180 mL, 18 vol) was then added slowly. (Ethanol addition is exothermic, temperature reached 22.5° C.). It was then allowed to cool to 15° C. This was followed by dropwise addition of 1,2 ethanedithiol (4.3 mL, 7.5 mmols in 95% ethanol in 94 mL, 9.4 vol) over an hour with the batch temperature at 15° C. The reaction was allowed to stir at 15° C. overnight. The reaction mixture was filtered through polypropylene cloth and washed with 95% ethanol (45 mL, 4.5 vol). The wet cake was charged back to the reactor and slurried in 95% ethanol (380 mL, 38 vol) for two hours at 20° C. The suspension was then filtered (same cloth) and washed with 95% ethanol (30 mL, 3 vol). The wet cake was again slurried in 95% EtOH (170 mL, 17 vol) at 20° C., filtered (same cloth), and washed with 95% ethanol (30 mL, 3 vol). The wet cake was then slurried in acetone (170 mL, 17 vol) at 20° C. overnight, followed by filtration (same cloth) and acetone wash (20 mL, 2 vol). The acetone (170 ml, 17 vol) treatment was repeated on the solids and stirred for 2 hours. The suspension was filtered (same cloth) and washed with acetone (30 mL, 3 vol) and died at 45° C. and dried at 45° C. (18 hours) to provide canary yellow solid (10.43 g 87.8%).

TABLE 111

Particle Size Distribution of BisEDT samples

| Sample | D (10) μm | D (50) μm | D (90) μm | D [4,3] μm | Conditions |
|---|---|---|---|---|---|
| 1 | 0.80 | 2.4 | 5.9 | 2.9 | Dalton Synthesis Conditions |
| 2 | 0.58 | 1.7 | 3.9 | 2.0 | Dalton Synthesis Conditions |
| 3 | 0.59 | 1.9 | 4.5 | 2.3 | 30° C., 5 h addition of 1,2-ethane dithiol via addition funnel |
| 4 | 0.44 | 1.48 | 3.1 | 1.7 | 30° C., 4 hour addition of 1,2-ethane dithiol via syringe pump |
| 5 | 0.33 | 0.72 | 1.6 | 0.86 | 20° C., 1 h addition of 1,2-ethane dithiol via addition funnel |
| 6 | 0.34 | 0.87 | 1.8 | 0.98 | 20° C., 4 h addition of 1,2-ethane dithiol via addition funnel |
| 7 | 0.39 | 1.3 | 1.6 | 1.4 | 20° C., 1 hour addition of 1,2-ethane dithiol via syringe pump. Sample slurried in EtOH. Cloth filtration |
| 8 | 0.36 | 1.0 | 1.8 | 1.0 | 20° C., 1 hour addition of 1,2-ethane dithiol via syringe pump. Sample slurried in MeOH. Cloth filtration |
| 9 | 0.67 | 1.0 | 1.9 | 1.1 | 20° C., 1 hour addition of 1,2-ethane dithiol via syringe pump. Sample slurried in Abs. MeOH. Cloth filtration |
| 10 | 0.36 | 0.88 | 1.7 | 0.97 | 20° C., 1 hour addition of 1,2-ethane dithiol via syringe pump. Sample slurried in IPA. Cloth filtration |
| 11 | 0.38 | 1.2 | 2.4 | 1.4 | 15° C. 1.5 hour addition of 1,2-ethane dithiol via syringe pump. Cloth filtration |
| 12 | 0.37 | 1.2 | 2.4 | 1.3 | 20° C., 1.25 hour addition of 1,2-ethane via syringe pump |
| 13 | 0.36 | 0.98 | 2.1 | 1.2 | 10° C., 1 h addition of 1,2-ethane dithiol via syringe pump |
| 14 | 0.36 | 1.0 | 2.1 | 1.2 | 10° C. 1 hour addition of 1,2-ethane dithiol via syringe pump. Cloth filtration |
| 15 | 0.32 | 0.72 | 1.6 | 0.86 | 10° C., 4 hours addition of 1,2-ethane dithiol via syringe pump. Cloth filtration. |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

The invention claimed is:

1. A method of treating, managing or lessening the severity of cystic fibrosis (CF) symptoms and infections in a subject, the method comprising administering to the subject an aerosol comprising a plurality of dispersed liquid droplets, wherein the liquid droplets comprise a bismuth-thiol (BT) composition that comprises bismuth-1,2-ethanedithiol (BisEDT) microparticles suspended therein, the BisEDT microparticles having a D90 of less than about 2 μm as measured by laser diffraction, and wherein at least 70% of the liquid droplets have a mass median aerodynamic diameter (MMAD) from about 0.4 μm to about 5 μm as measured by cascade impaction or laser time of flight.

2. The method of claim 1, wherein at least 80% of the dispersed liquid droplets have a MMAD from about 0.7 μm to about 4 μm.

3. The method of claim 1, wherein at least 90% of the dispersed liquid droplets have a MMAD from about 0.9 μm to about 3 μm.

4. The method of claim 1, wherein the BT composition comprises BisEDT at a concentration greater than about 0.1 mg/mL, about 0.05% to about 1.0% of polysorbate 80, about 0.05 mM to 40 mM of sodium chloride, and optionally about 2 mM to 20 mM of sodium phosphate at about pH 7.4.

5. The method of claim 1, wherein when the aerosolized composition comprising BisEDT is deposited to the lung region, the BisEDT has an average half-life of about 4 days.

6. The method of claim 1, wherein the subject has at least one pulmonary infection containing one or more bacterial pathogens and/or fungal pathogens.

7. The method of claim 6, wherein the method comprises at least one of: (i) reducing initial formation of a bacterial biofilm; (ii) impairing growth of a bacterial biofilm; (iii) reducing reformation of the bacterial biofilm.

8. The method of claim 6, wherein the one or more pathogens are selected from *Haemophilus influenzae, Staphylococcus aureus, Staphylococcus warneri Staphylococcus lugdunensis, Staphylococcus epidermidis, Streptococcus milleri/anginous, Streptococcus pyogenes*, non-tuberculosis mycobacteria, *Mycobacterium tuberculosis, Burkholderia* spp., *Achromobacter xylosoxidans, Stenotrophomonas maltophilia, Alcaligenes xylosoxidans, Haemophilus pittmaniae, Serratia marcescens, Candida albicans*, drug resistant *Candida albicans, Candida glabrata, Candida krusei, Candida guilliermondii, Candida auris, Candida tropicalis, Aspergillus niger, Aspergillus terreus, Aspergillus fumigatus, Aspergillus flavus, Morganella morganii, Inquilinus limosus, Bdellovibrio bacteriovorus, Vampirovibrio chlorellavorus, Cupriadidus metallidurans, Cupriavidus pauculus, Cupriavidus respiraculi, Exophilia dermatitidis, Herbaspirillum frisingense, Herbaspirillum seropedicae, Neisseria gonorrhoeae*, New Delhi metallo-beta-lactamase 1 positive *E. coli*, Vancomycin-resistant *E. faecium*, Vancomycin-resistant *E. faecalis, E. faecium, E. faecalis*, Clindamycin-resistant *S. agalactiae, S. agalactiae, Bacteroides fragilis, Clostridium difficile, Streptococcus pneumonia, Moraxella catarrhalis, Haemophilus haemolyticus, Haemophilus parainfluenzae, Chlamydophilia pneumoniae, Mycoplasma pneumoniae, Atopobium, Sphingomonas, Saccharibacteria, Leptotrichia, Capnocytophaga, Oribacterium, Aquabacterium, Lachnoanaerobaculum, Campylobacter, Acinetobacter; Agrobacterium; Bordetella; Brevundimonas; Chryseobacterium; Delftia; Enterobacter; Klebsiella; Pandoraea; Pseudomonas; Ralstonia*, and *Prevotella*.

9. The method of claim 8, wherein the one or more pathogens are non-tuberculosis mycobacteria.

10. The method of claim 1, wherein when the aerosolized composition comprising BisEDT is deposited to a lung region, the BisEDT has an average half-life of more than 2 days.

11. A method of treating, managing or lessening the severity of symptoms and infections associated with one or more pulmonary diseases or infections in a subject, the method comprising administering to the subject an aerosol comprising a plurality of dispersed liquid droplets, wherein the liquid droplets comprise a bismuth-thiol (BT) composition that comprises BisEDT microparticles suspended therein, the BisEDT microparticles having a D90 of less than about 2 μm as measured by laser diffraction, and wherein at least 70% of the liquid droplets have a MMAD from about 0.4 μm to about 5 μm as measured by cascade impaction or laser time of flight.

12. The method of claim 11, wherein the one or more pulmonary diseases or infections are not the result of or associated with cystic fibrosis.

13. The method of claim 12, wherein the pulmonary infection is bronchiectasis infection, pneumonia, valley fever, allergic bronchopulmonary aspergillosis, ventilator acquired pneumonia, hospital acquired pneumonia, community acquired pneumonia, ventilator associated tracheobronchitis, lower respiratory tract infection, non-tuberculous Mycobacteria (NTM), anthrax, legionellosis, pertussis, bronchitis, Bronchiolitis, chronic obstructive pulmonary disease associated infection, and post-lung transplantation.

14. The method of claim 13, wherein the pulmonary infection is NTM.

15. The method of claim 8, wherein
the species of *Pseudomonas* is selected from the group consisting of *Pseudomonas aeruginosa, Pseudomonas mendocina, Pseudomonas pseudoalcaligenes, Pseudomonas putida*, and *Pseudomonas stutzeri;*
the species of *Pandoraea* is selected from the group consisting of *Pandoraea sputorum, Pandoraea apista, Pandoraea pnomenusa, Pandoraea sputorum, Pandoraea norimbergensis*, and *Pandoraea pulmonicola;*
the species of *Ralstonia* is selected from the group consisting of *Ralstonia mannitolilytica, Ralstonia insidiosa*, and *Ralstonia pickettii;*
the species of *Acinetobacter* is *Acinetobacter baumanni;*
the species of *Bordetella* is *Bordetella bronchiseptica;*
the species of *Enterobacter* is *Enterobacter cloaca;*
the species of *Klebsiella* is *Klebsiella pneumoniae*; and
the species of *Delftia* is *Delftia acidivordans*.

16. The method of claim 1, wherein administering the BT composition is via inhalation, orally or nasally, using an aerosol device.

17. The method of claim 1, wherein upon administration of the aerosolized composition to the subject, at least 15% of the dose is deposited on the lung.

18. The method of claim 1, wherein upon administration of the aerosolized composition to the subject, at least 60% of the dose is deposited on the lung.

19. The method of claim 11, wherein upon administration of the aerosolized composition to the subject, at least 15% of the dose is deposited on the lung.

20. The method of claim 11, wherein upon administration of the aerosolized composition to the subject, at least 60% of the dose is deposited on the lung.

21. The method of claim 11, wherein at least 80% of the dispersed liquid droplets have a MMAD from about 0.7 μm to about 4 μm.

22. The method of claim 11, wherein at least 90% of the dispersed liquid droplets have a MMAD from about 0.9 μm to about 3 μm.

* * * * *